US011781124B2

(12) United States Patent
Chang et al.

(10) Patent No.: US 11,781,124 B2
(45) Date of Patent: Oct. 10, 2023

(54) RECOMBINANT POLYNUCLEOTIDE SEQUENCE FOR PRODUCING ASTAXANTHIN AND USES THEREOF

(71) Applicant: ACADEMIA SINICA, Taipei (TW)

(72) Inventors: Jui-Jen Chang, Taipei (TW); Caroline Thia, Taipei (TW); Hao-Yeh Lin, Taipei (TW); Yu-Ju Lin, Taipei (TW); Chieh-Chen Huang, Taipei (TW); Wen-Hsiung Li, Taipei (TW)

(73) Assignee: ACADEMIA SINICA, Taipei (TW)

( * ) Notice: Subject to any disclaimer, the term of this patent is extended or adjusted under 35 U.S.C. 154(b) by 506 days.

(21) Appl. No.: 17/094,623

(22) Filed: Nov. 10, 2020

(65) Prior Publication Data

US 2021/0071153 A1 Mar. 11, 2021

Related U.S. Application Data

(60) Division of application No. 16/200,269, filed on Nov. 26, 2018, now Pat. No. 10,865,397, which is a continuation of application No. 15/353,372, filed on Nov. 16, 2016, now abandoned, which is a continuation of application No. PCT/US2015/031273, filed on May 16, 2015.

(60) Provisional application No. 61/994,828, filed on May 16, 2014.

(51) Int. Cl.

| | |
|---|---|
| ***C12N 9/14*** | (2006.01) |
| ***C12P 23/00*** | (2006.01) |
| ***C12N 15/81*** | (2006.01) |

(52) U.S. Cl.

CPC ............. *C12N 9/14* (2013.01); *C12N 15/815* (2013.01); *C12P 23/00* (2013.01)

(58) Field of Classification Search

None

See application file for complete search history.

(56) References Cited

U.S. PATENT DOCUMENTS

| | | | |
|---|---|---|---|
| 2011/0252501 | A1 | 10/2011 | Abad et al. |
| 2012/0142082 | A1 | 6/2012 | Sharpe et al. |

FOREIGN PATENT DOCUMENTS

| | | | |
|---|---|---|---|
| DE | 19916140 | A1 | 10/2000 |
| DE | 10238980 | A1 | 3/2004 |
| WO | WO2005019461 | A2 | 3/2005 |

OTHER PUBLICATIONS

Jui-Jen Chang, et al., "PGASO: A synthetic biology tool for engineering a cellulolytic yeast", Biotechnology for Biofuels, Jul. 27, 2012; 5(1):53, 12 pgs.

Ken Ukibe, et al., "Metabolic Engineering of *Saccharomyces cerevisiae* for Astaxanthin Production and Oxidative Stress Tolerance", *Applied And Environmental Microbiology*, Nov. 2009, vol. 75, No. 22, pp. 7205-7211.

Soren Gassel, et al., "Genetic engineering of the complete carotenoid pathway towards enhanced astaxanthin formation in Xanthophyllomyces dendrorhous staiting from a high-yield mutant", *Appl Ivficrohiol Biotechnol* (2014) 98:345-350.

Lohr, M., et al. ("Genome-based examination of chlorophyll and carotenoid biosynthesis in Chlamydomonas reinhardtii." Plant Physiol. 138:490-515(2005) (Year: 2005).

Li Y., Huang et al. (Glucose sensing and the mitochondrial alternative pathway are involved in the regulation of astaxanthin biosynthesis in the dark-grown Chiarella zofingiensis (Chlorophyceae). Planta 228:735-743 (2008) (Year: 2008).

Visser, Hans "Metabolic engineering of the astaxanthin-biosynthetic pathway of Xanthophyllomyces dendrorhous" Mini Review FEMS Yeast Research 4 (2003) 221-231.

*Primary Examiner* — Kagnew H Gebreyesus

(74) *Attorney, Agent, or Firm* — Muncy, Geissler, Olds & Lowe, P.C.

(57) ABSTRACT

Disclosed herein are recombinant polynucleotide sequences, vectors, host cells and methods for producing astaxanthin. The recombinant polynucleotide sequence is designed to provide a higher level of astaxanthin precursors via a shorter metabolic pathway, and thereby attains higher level of end products (e.g., astaxanthin) with desired stereoisomeric form and/or esterified form.

18 Claims, 72 Drawing Sheets

Specification includes a Sequence Listing.

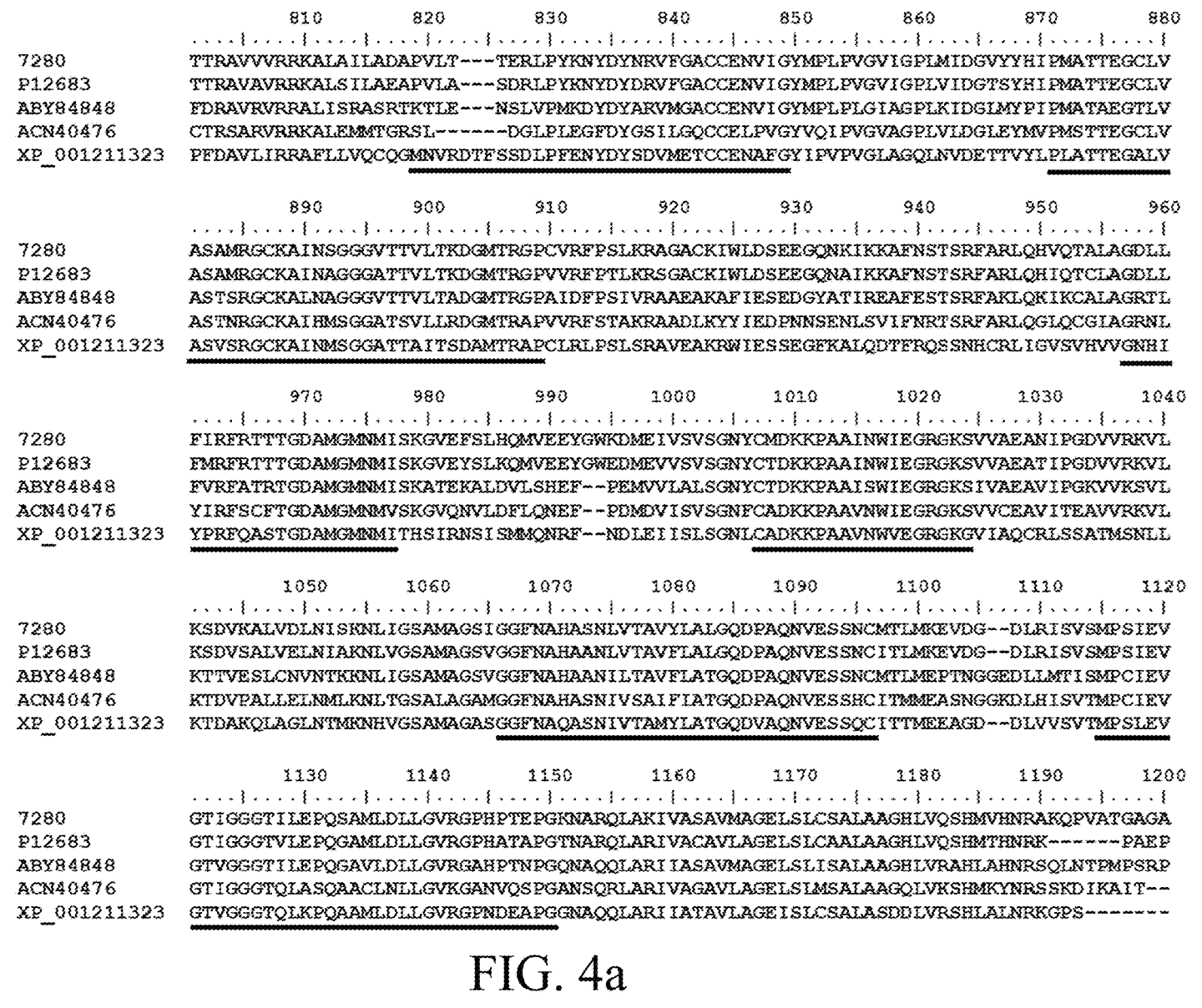

```
                     810       820       830       840       850       860       870       880
7280          TTRAVVVRRKALAILADAPVLT---TERLPYKNYDYNRVFGACCENVIGYMPLPVGVIGPLMIDGVYYHIPMATTEGCLV
P12683        TTRAVAVRRKALSILAEAPVLA---SDRLPYKNYDYDRVFGACCENVIGYMPLPVGVIGPLVIDGTSYHIPMATTEGCLV
ABY84848      FDRAVRVRRALISRASRTKTLE---NSLVPMKDYDYARVMGACCENVIGYMPLPLGIAGPLKIDGLMYPIPMATAEGTLV
ACN40476      CTRSARVRRKALEMMTGRSL------DGLPLEGFDYGSILGQCCELPVGYVQIPVGVAGPLVLDGLEYMVPMSTTEGCLV
XP_001211323  PFDAVLIRRAFLLVQCQGMNVRDTFSSDLPFENYDYSDVMETCCENAFGYIPVPVGLAGQLNVDETTVYLPLATTEGALV

                     890       900       910       920       930       940       950       960
7280          ASAMRGCKAINSGGGVTTVLTKDGMTRGPCVRFPSLKRAGACKIWLDSEEGQNKIKKAFNSTSRFARLQHVQTALAGDLL
P12683        ASAMRGCKAINAGGGATTVLTKDGMTRGPVVRFPTLKRSGACKIWLDSEEGQNAIKKAFNSTSRFARLQHIQTCLAGDLL
ABY84848      ASTSRGCKALNAGGGVTTVLTADGMTRGPAIDFPSIVRAAEAKAFIESEDGYATIREAFESTSRFAKLQKIKCALAGRTL
ACN40476      ASTNRGCKAIHMSGGATSVLLRDGMTRAPVVRFSTAKRAADLKYYIEDPNNSENLSVIFNRTSRFARLQGLQCGIAGRNL
XP_001211323  ASVSRGCKAINMSGGATTAITSDAMTRAPCLRLPSLSRAVEAKRWIESSEGFKALQDTFRQSSNHCRLIGVSVHVVGNHI

                     970       980       990      1000      1010      1020      1030      1040
7280          FIRFRTTTGDAMGMNMISKGVEFSLHQMVEEYGWKDMEIVSVSGNYCMDKKPAAINWIEGRGKSVVAEANIPGDVVRKVL
P12683        FMRFRTTTGDAMGMNMISKGVEYSLKQMVEEYGWEDMEVVSVSGNYCTDKKPAAINWIEGRGKSVVAEATIPGDVVRKVL
ABY84848      FVRFATRTGDAMGMNMISKATEKALDVLSHEF--PEMVVLALSGNYCTDKKPAAISWIEGRGKSIVAEAVIPGKVVKSVL
ACN40476      YIRFSCFTGDAMGMNMVSKGVQNVLDFLQNEF--PDMDVISVSGNFCADKKPAAVNWIEGRGKSVVCEAVITEAVVRKVL
XP_001211323  YPRFQASTGDAMGMNMITHSIRNSISMMQNRF--NDLEIISLSGNLCADKKPAAVNWVEGRGKGVIAQCRLSSATMSNLL

                    1050      1060      1070      1080      1090      1100      1110      1120
7280          KSDVKALVDLNISKNLIGSAMAGSIGGFNAHASNLVTAVYLALGQDPAQNVESSNCMTLMKEVDG--DLRISVSMPSIEV
P12683        KSDVSALVELNIAKNLVGSAMAGSVGGFNAHAANLVTAVFLALGQDPAQNVESSNCITLMKEVDG--DLRISVSMPSIEV
ABY84848      KTTVESLCNVNTKKNLIGSAMAGSVGGFNAHAANILTAVFLATGQDPAQNVESSNCMTLMEPTNGGEDLLMTISMPCIEV
ACN40476      KTDVPALLELNMLKNLTGSALAGAMGGFNAHASNIVSAIFIATGQDPAQNVESSHCITMMEASNGGKDLHISVTMPCIEV
XP_001211323  KTDAKQLAGLNTMKNHVGSAMAGASGGFNAQASNIVTAMYLATGQDVAQNVESSQCITTMEEAGD--DLVVSVTMPSLEV

                    1130      1140      1150      1160      1170      1180      1190      1200
7280          GTIGGGTILEPQSAMLDLLGVRGPHPTEPGKNARQLAKIVASAVMAGELSLCSALAAGHLVQSHMVHNRAKQPVATGAGA
P12683        GTIGGGTVLEPQGAMLDLLGVRGPHATAPGTNARQLARIVACAVLAGELSLCAALAAGHLVQSHMTHNRK------PAEP
ABY84848      GTVGGGTILEPQGAVLDLLGVRGAHPTNPGQNAQQLARIIASAVMAGELSLISALAAGHLVRAHLAHNRSQLNTPMPSRP
ACN40476      GTIGGGTQLASQAACLNLLGVKGANVQSPGANSQRLARIVAGAVLAGELSIMSALAAGQLVKSHMKYNRSSKDIKAIT--
XP_001211323  GTVGGGTQLKPQAAMLDLLGVRGPNDEAPGGNAQQLARIIATAVLAGEISLCSALASDDLVRSHLAINRKKGPS-------
```

FIG. 4a

1: PXXXXDYXXXXXXCCEXXXGYXXXPXGXXG

2:PXXTXEGXLVASXXRGCKAXXXXGGXTXXX
XXDXMTRXP

3: GXXXXXRFXXXTGDAMGMNM

4: CXDKKPAAXXWXEGRGK

5:GGFNAXAXNXXXAXXXAXGQDXAQNVES
SXC

6:MPXXEVGTXGGGTXLXXQXAXLXLLGVXG
XXXXXPG

FIG. 4b

```
                    10        20        30        40        50        60        70        80
           ....|....|....|....|....|....|....|....|....|....|....|....|....|....|....|....|
AAY33921   -------------------------------------------------MDYANILTAIPLEFTPQDDIVLLEPYHYLGK
NP_624521  MRTTESEKGLRMPGLPPMVAPPAEQVDDPVTATDAANAVDAVLRGVLDERLRHCRAVDPLFARELADRLAALTARGGKRL
BAB99565   -----------------MKDVSLSSFDAHDLDLDKFPEVVRDRLTQFLDAQELTIADIGAPVTDAVAHLRSFVLNGGKRI
NP_696587  ------------MCSSNPVDKLLGMCTTANNREIIEPRIIQLVRELTAAPATDEVADALKPVMEQVVDQAASSSQGGKRL

                    90       100       110       120       130       140       150       160
           ....|....|....|....|....|....|....|....|....|....|....|....|....|....|....|....|
AAY33921   NPGKEIRSQLIEAFNYWLDVKKEDLEVIQNVVGMLHTASLLMDDVEDSSVLRRGSPVAHLIYGIPQTINTANYVYFLAYQ
NP_624521  RTAFAHCGWRAAGG----SGDATAVLRTGAALELLQACALVHDDVMDGSVQRRGAPALHVDLARGHWAAGMHGSSESFGT
BAB99565   RPLYAWAGFLAAQGHKNSSEKLESVLDAAASLEFIQACALIHDDIIDSSDTRRGAPTVHRAVEADHRANNFEGDPEHFGV
NP_696587  RALLALDAFDILAGDVTPDRRD-AMIDLACAIEVFQTAALVHDDIIDESDLRRGKPSAHHALEQAVH-------SGAIGR

                   170       180       190       200       210       220       230       240
           ....|....|....|....|....|....|....|....|....|....|....|....|....|....|....|....|
AAY33921   EIFKLRPTPIPMPVIPPSSASLQSSVSSASSSSSASSENGGTSTPNSQIPFSKDTYLDKVITDEMLSLHRGQGLELFWRD
NP_624521  SAAVLTGDLALAWADDLLTETALGTPHGPRLHGEWRAMRTEMVAGQYRDLHAQAARSSGVDEA----L------------
BAB99565   SVSILAGDMALVWAEDMLQDSGLSAEALARTRDAWRGMRTEVIGGQLLDIYLESHANESVELA----D------------
NP_696587  GLGLMLGDILATACIEITRRSASRLPNTDALNEAFLTMQREVEIGQVLDLAVEMTPLSNPEALANASL------------

                   250       260       270       280       290       300       310       320
           ....|....|....|....|....|....|....|....|....|....|....|....|....|....|....|....|
AAY33921   SLTCPSEEEYVKMVLGKTGGLFRIAVRLMMAKSECDIDFVQLVNLISIYFQIRDDYMNLQSSEYAHNKNFAEDLTEGKFS
NP_624521  -----AIATLKSALYTVARPLALGAVLAGAADGDALEALRAAGRCAGLAFQLRDDLLGAFGDPALTGKPADDDLRSRKLT
BAB99565   -----SVNRFKTAAYTIARPLHLGASIAGGSPQLID-ALLHYGHDIGIAFQLRDDLLGVFGDPAITGKPAGDDIREGKRT
NP_696587  -----NVFRWKTASYTTIAPLLLALLAAGESPDQARHCALAVGRPLGLAFQLADDLLDVVGSSRNTGKPVGGDIREGKRT
```

FIG. 5a

1 : LXXDDXXDXSXXRRGXPXXH

2 : FQXXDD

FIG. 5b

```
                  10        20        30        40        50        60        70        80
CAB51949    -----------------------PSPDPLVTDHYFYMRALSLLITPPTMLLAALSGEYAFDWKSGRAKSTIA-AIMIPTV
XP_762434   PSTPARRPLAPFAVATCVVCFVLGLQASVPATHTYYFGMISWWSSMPLALLLWGSIDFVRNMGVGAGFIPFAISVLGPTL
NP_344223   ----------------------------MEIFKPDYIMIDSMIFFPTLILS----FLIKRNYVK----LLKSIGIVSP-I
YP_024312   ----------------------------MDITHFYYFIILSFIFFPVLGISLTNEFKKVRNYRA----LLYAMLFTDP-V

                  90       100       110       120       130       140       150       160
CAB51949    YLIWVDYVAVGQDSWSINDEKIVGWRLGGVLPIEEAMFFLLTNLMIVLGLSACDHTQALYLLHGRTIYGNKKMPSSFPLI
XP_762434   YLWSSDIYALRRGTWHINQATSLNIFPIPDLPIEEMLFFLVTNVILVSACFTFDRCVAICRLSAPD-HQPPLSPSYLPLG
NP_344223   YLFW-DFLATWRNSWTFNPKYVAGIYVI-DLPIEEVMFFLVTPFATLLIF---DFVMGKVRDKEVK-WVPKVVCVAIPLL
YP_024312   YIVW-DSLSVTYHVWTFNKKYITGIMVY-NLPVEEILFFFVVPFSTFLIYESIDYIKNDSFISKTS-RIKKIMFIIAILF

                 170       180       190       200       210       220       230       240
CAB51949    TPPVLSLFF--------SSRPYS----SQPKRDLELAVKLLEKKSRSFFVASAGFPSEVRERLVGLYAFCRVTDDLIDSP
XP_762434   SLATYTKLWAAFVRSDRSSLPTSCASASVEPQDLSASLQVLRAASKSFNAASLLLPWDLRTDLGCLYAFCRVADDLVDDH
NP_344223   LLTLPFVYNYSYTFIDLVYLIMSLIVSLLIGRNLLASRNFWIFMGLSY-IPFLVFDYFLTSDPVVIYGSHSIVGIRFITI
YP_024312   ILNAIYFYSYIYMLLASVFTAFIILLTLKIMPSLYRSSNYWLFIIIMY-IPFIVFDHFLTSLPVFTYGVHAIINIRILSI

                 250       260       270       280       290       300       310       320
CAB51949    EVSSNPHA-TIDMVSDFLTLLFGPPL-----HPSQPDKILSSPLLPPSHPSRPTGMYPLPPPPSLSPAELVQFLTERV--
XP_762434   AQELQAKAKNLDVVRDIVDAVYADSIVDRKQHLSTPIGERLRILLASAALSDKIKQDTRAAATSIAP--LTQYIPKRLWY
NP_344223   PIEDFIYSFSMITFYTVFYIRGNSLWMKQK--------------------------------------------------
YP_024312   PVEEFIYVYSLMNFYALFYNIYKKRSNKDELKFIVNYPLRIK--------------------------------------
                                                                   Lycopene cyclase domain
                 330       340       350       360       370       380       390       400
CAB51949    PVQYHFAFRLLAKLQGLIPRYPLDEL--LRGYTTDLIFPLSTEAVQARKTPIETTADLLDYGLCVAGSVAELLVYVSWAS
XP_762434   EMLQGYSADLRFQHQDARQRTRLQSMDDLVEYSQCVAGVVGEMCIRVILGRCGSTVPLDLEVDRKIALRASKTIEQSINV
NP_344223   --------------------------------------------------------------------------------
YP_024312   --------------------------------------------------------------------------------
```

FIG. 7a

1: YXXWXDXXXXXXXXWXXN

2: PXXXXXFF

FIG. 7b

```
                 250       260       270       280       290       300       310       320
             ....|....|....|....|....|....|....|....|....|....|....|....|....|....|....|....|
CAB51949     MIVLGLSACDHTQALYLLHGRTIYGNKKMPSSFPLITPPVLSLFFSSRPYSSQPKRDLELAVKLLEKKSRSFFVASAGFP
NP_279693    MLCRSALYCWHP-GTPSRGAMIAVGDGSTPQPLLYSPTLARPRVMDGRQSHQPTASDREWCHSAVQDVSRTFALTIDALE
NP_681887    ----------------------------------MRVGVNPPMIQMVLENPVSVKDAECFCQEILPQVSRTFALSIRFLP
ZP_00089878  ----------------------------------------MLESQTALAIESSTTSADAYQNAILSKVSRTFALTIPQLP
```

Trans-Isoprenyl Diphosphate Synthases

```
                 330       340       350       360       370       380       390       400
             ....|....|....|....|....|....|....|....|....|....|....|....|....|....|....|....|
CAB51949     SEVRERLVGLYAFCRVTDDLIDSPEVSSNPHATIDMVSDFLTLLFGPPLHPSQPDKILSSPLLPPSHPSRPTGMYPLPPP
NP_279693    EPMATRICVGYLLCRVADTVEDATAMPPTEQAQL---LETYDAALDPDCGTTVAEFQAAVGDHVPSEPN-----------
NP_681887    GNLGRAVLVAYLICRIADTVEDDPVASIAAKTAL---LDHLLQCFD---SPALANSYGETARGVQGEP------------
ZP_00089878  PLLRRAVTNAYLLCRIADTIEDEPAFSAEEKRRY---EDAFIDAVTGRIAPQYFSTELASRFSTETSE------------

                 410       420       430       440       450       460       470       480
             ....|....|....|....|....|....|....|....|....|....|....|....|....|....|....|....|
CAB51949     PSLSPAELVQFLTERVPVQYHFAFRLLAKLQGLIPRYPLDELLRGYTTDLIFPLSTEAVQARKTPIETTADLLDYGLCVA
NP_279693    ---ADWRVVANTTRVVS-----AFESLDDAAKAAIRPTVREMATGMAS-----FVQRYADAGGLRIQSPTELEEYCWYVA
NP_681887    ---AHVQLVKHTGIVFT-----LYRSLPRTSQQHVQRWVSEMVHGMKK-----FINLYPN--GIRIQTLAEYKEYCYYVA
ZP_00089878  ---AERDLVSQLPLVLQ-----VTNSLKPAQRMAIVNCLKVMSHGMHD-----FQRNVGQ--H-GLETLCDMDCYCYCVA
```

Trans-Isoprenyl Diphosphate Synthases

```
                 490       500       510       520       530       540       550       560
             ....|....|....|....|....|....|....|....|....|....|....|....|....|....|....|....|
CAB51949     GSVAELLVYVSWASAPSQVPATIEEREAVLVASREMGTALQLVNIARDIKGDAT-EGRFYLPLSFFGLRDESKLAIPTDW
NP_279693    GTVGELVTELLARDAPS------DAAAAMRENARSFALLLQLVNVAKDVRPDYEEENNVYLPQEWLDDHDLAPEDVADPE
NP_681887    GTVGYLLTDLWHEHSPS---IGADEYQVLLKRCAAFGEALQTVNILKDIAWDAEHENSIYIPNESLILQGSSHQTLLSAE
ZP_00089878  GVVGEMLTELLIDFDPA---L-ASQRDPLMRLAISFGQGLQMTNILKD-QWEDYRRGVCWLPQDVFARYGVRLEELQAGR

                 570       580       590       600       610       620       630       640
             ....|....|....|....|....|....|....|....|....|....|....|....|....|....|....|....|
CAB51949     TEPRPQDFDKLLSLSPSSTLPSSNASESFRFEWKTYSLPLVAYAEDLAKHSYKGIDRLPTEVQAG--MRAACASYLLIGR
NP_279693    HAGRVASVVERVTDRARGYVADAQRWLEVMPTSQGNTLAAWAVPFLLAVGTMRELGNRPADVVREGDVKVDREEVHAVIG
NP_681887    HLQQNHAAIKELIALAWHDLDEAQAYLLSVPKAAIPIRLFCVLPLLFAYATLRELTHSTAMLQPGGGVKISRAEVKSLMV
ZP_00089878  QDANYMSALTELIGVAHAHLRDALEYTLMIPNRHSGFRRFCLWSIGLAVLTLRKLQQNPHF-SAGEQVKVSRKAVAYTIA
```

FIG. 7c

1: YXXCRXXDXXXD

2: YXXXVAGXVXXXXXXXXXXXXP

FIG. 7d

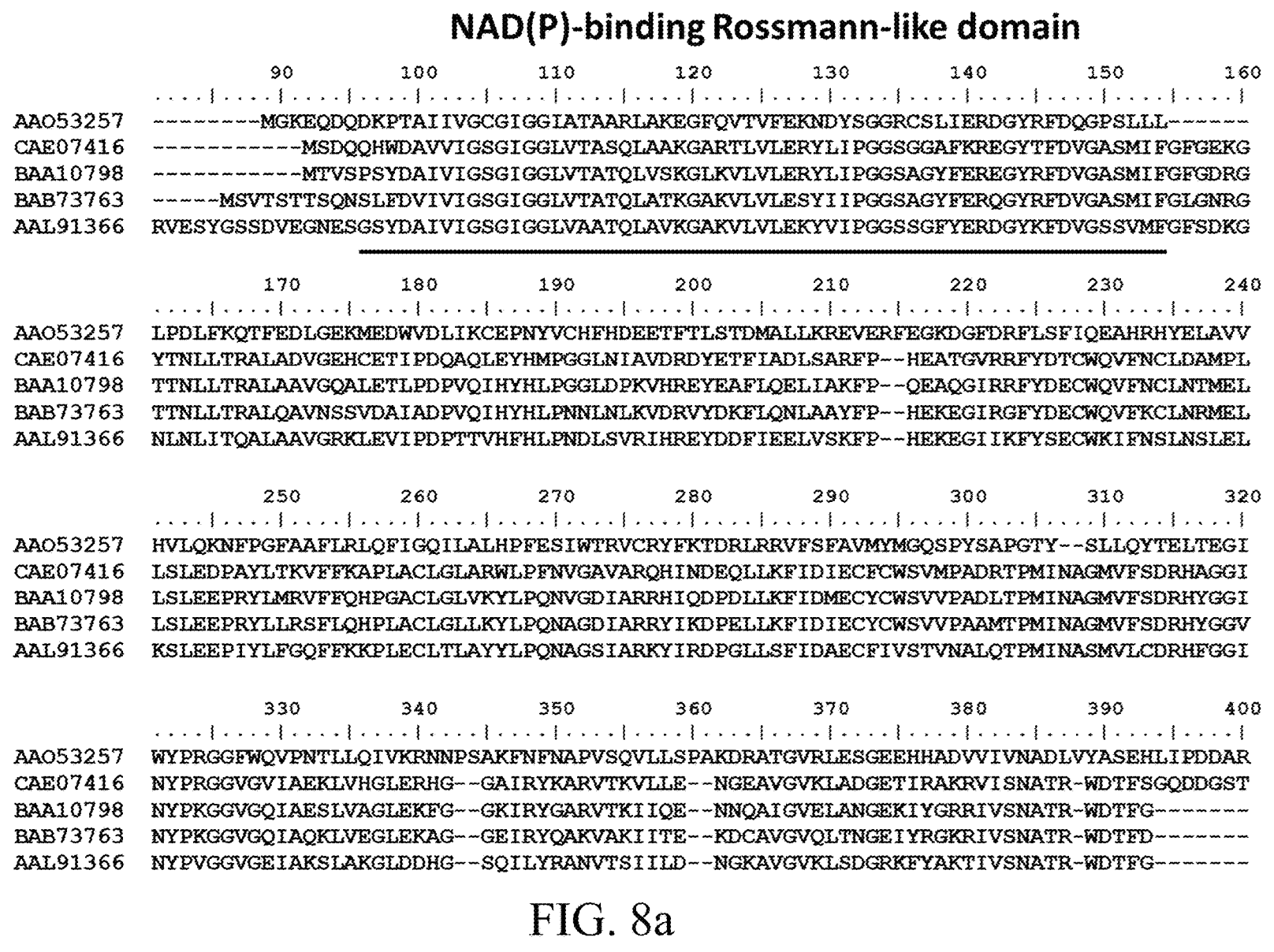

NAD(P)-binding Rossmann-like domain

```
                   90        100       110       120       130       140       150       160
           ....|....|....|....|....|....|....|....|....|....|....|....|....|....|....|....|
AAO53257   --------MGKEQDQDKPTAIIVGCGIGGIATAARLAKEGFQVTVFEKNDYSGGRCSLIERDGYRFDQGPSLLL------
CAE07416   -----------MSDQQHWDAVVIGSGIGGLVTASQLAAKGARTLVLERYLIPGGSGGAFKREGYTFDVGASMIFGFGEKG
BAA10798   -----------MTVSPSYDAIVIGSGIGGLVTATQLVSKGLKVLVLERYLIPGGSAGYFEREGYRFDVGASMIFGFGDRG
BAB73763   -----MSVTSTTSQNSLFDVIVIGSGIGGLVTATQLATKGAKVLVLESYIIPGGSAGYFERQGYRFDVGASMIFGLGNRG
AAL91366   RVESYGSSDVEGNESGSYDAIVIGSGIGGLVAATQLAVKGAKVLVLEKYVIPGGSSGFYERDGYKFDVGSSVMFGFSDKG

                  170       180       190       200       210       220       230       240
           ....|....|....|....|....|....|....|....|....|....|....|....|....|....|....|....|
AAO53257   LPDLFKQTFEDLGEKMEDWVDLIKCEPNYVCHFHDEETFTLSTDMALLKREVERFEGKDGFDRFLSFIQEAHRHYELAVV
CAE07416   YTNLLTRALADVGEHCETIPDQAQLEYHMPGGLNIAVDRDYETFIADLSARFP--HEATGVRRFYDTCWQVFNCLDAMPL
BAA10798   TTNLLTRALAAVGQALETLPDPVQIHYHLPGGLDPKVHREYEAFLQELIAKFP--QEAQGIRRFYDECWQVFNCLNTMEL
BAB73763   TTNLLTRALQAVNSSVDAIADPVQIHYHLPNNLNLKVDRVYDKFLQNLAAYFP--HEKEGIRGFYDECWQVFKCLNRMEL
AAL91366   NLNLITQALAAVGRKLEVIPDPTTVHFHLPNDLSVRIHREYDDFIEELVSKFP--HEKEGIIKFYSECWKIFNSLNSLEL

                  250       260       270       280       290       300       310       320
           ....|....|....|....|....|....|....|....|....|....|....|....|....|....|....|....|
AAO53257   HVLQKNFPGFAAFLRLQFIGQILALHPFESIWTRVCRYFKTDRLRRVFSFAVMYMGQSPYSAPGTY--SLLQYTELTEGI
CAE07416   LSLEDPAYLTKVFFKAPLACLGLARWLPFNVGAVARQHINDEQLLKFIDIECFCWSVMPADRTPMINAGMVFSDRHAGGI
BAA10798   LSLEEPRYLMRVFFQHPGACLGLVKYLPQNVGDIARRHIQDPDLLKFIDMECYCWSVVPADLTPMINAGMVFSDRHYGGI
BAB73763   LSLEEPRYLLRSFLQHPLACLGLLKYLPQNAGDIARRYIKDPELLKFIDIECYCWSVVPAAMTPMINAGMVFSDRHYGGV
AAL91366   KSLEEPIYLFGQFFKKPLECLTLAYYLPQNAGSIARKYIRDPGLLSFIDAECFIVSTVNALQTPMINASMVLCDRHFGGI

                  330       340       350       360       370       380       390       400
           ....|....|....|....|....|....|....|....|....|....|....|....|....|....|....|....|
AAO53257   WYPRGGFWQVPNTLLQIVKRNNPSAKFNFNAPVSQVLLSPAKDRATGVRLESGEEHHADVVIVNADLVYASEHLIPDDAR
CAE07416   NYPRGGVGVIAEKLVHGLERHG--GAIRYKARVTKVLLE--NGEAVGVKLADGETIRAKRVISNATR-WDTFSGQDDGST
BAA10798   NYPKGGVGQIAESLVAGLEKFG--GKIRYGARVTKIIQE--NNQAIGVELANGEKIYGRRIVSNATR-WDTFG-------
BAB73763   NYPKGGVGQIAQKLVEGLEKAG--GEIRYQAKVAKIITE--KDCAVGVQLTNGEIYRGKRIVSNATR-WDTFD-------
AAL91366   NYPVGGVGEIAKSLAKGLDDHG--SQILYRANVTSIILD--NGKAVGVKLSDGRKFYAKTIVSNATR-WDTFG-------
```

FIG. 8a

GXGIGGXXXAXXLXXXGXXXXVXE
XXXXXGGXXXXXXRXGYXFDXGXS

FIG. 8b

```
                  10        20        30        40        50        60        70        80
          ....|....|....|....|....|....|....|....|....|....|....|....|....|....|....|....|
AAY20974  -------------MFILVLLTGALGLAAFSWASIAFFSLYLAPRRSSLYNLQGPNHTNYFTGNFLDILSARTG-EEHAKY
Q08477    MPQLSLSSLGLWPMAASPWLLLLLVGASWLLARILAWTYTFYDNCCRLRCFPQPPKRNWFLGHLGLIHSSEEGLLYTQSL
P33274    MSQLSLSWLGLGPEVAFPWQTLLLFGASWILAQILTQIYAAYRNFRRLRGFPQPPKRNWLMGHVGMVTPTEQGLKELTRL
P11707    ------------MDLIFSLETWVLLAASLVLLYLYGTSTHGLFKKMGIPGPTPLPFIGTILEYRKG--IWDFDIECRKKY
P33270    ----------------MFVLIYLLIAISSLLAYLYHRNFN-YWNRRGVPHDAPHPLYGNMVGFRKNRVMHDFFYDYYNKY

                  90       100       110       120       130       140       150       160
          ....|....|....|....|....|....|....|....|....|....|....|....|....|....|....|....|
AAY20974  REKYGSTLRFAGIAGAPVLNSTDPKVFNHVMKE--AYDYPKPGMAARVLRIATGDGVVTAEGEAHKRHRRIMIPSLSAQA
Q08477    ACTFGDMCCWWVGPWHAIVRIFHPTYIKPVLFAPAAIVPKDK-VFYSFLKPWLGDGLLLSAGEKWSRHRRMLTPAFHFNI
P33274    VGTYPQGFLMWIGPMVPVITLCHSDIVRSILNASAAVALKDV-IFYTILKPWLGDGLLVSAGDKWSRHRRMLTPAFHFNI
P11707    -GKMWGLFDG----RQPLMVITDPDMIKTVLVKECYSVFTNRRSF--GPVGFMKKAVSISEDEDWKRVRTLLSPTFTSGK
P33270    -RKSGFPFVGFYFLHKPAAFIVDTQLAKNILIKD-FSNFADRGQFHNGRDDPLTQHLFNLDGKKWKDMRQRLTPTFTSGK

                 170       180       190       200       210       220       230       240
          ....|....|....|....|....|....|....|....|....|....|....|....|....|....|....|....|
AAY20974  VKSMVPIFLEKGMELVDKMMEDAAEKDMAVGESAGEKKATRLETEGVDVKDWVGRATLDVMALAGFDYKSDSLQNKTNEL
Q08477    LKPYMKIFNE--SVNIMHAKWQLLASE---------------GSARLDMFEHISLMTLDSLQKCVFSFDSHCQEKPSEYI
P33274    LKPYVKIFND--STNIMHAKWKRLISE---------------GSSRLDMFEHVSLMTLDSLQKCVFSFDSNCQEKSSEYI
P11707    LKEMLPIIAQYGDVLVKNLRQE---AE---------------KGKPVDLKEIFGAYSMDVITGTSFGVNIDSLRNPQDPF
P33270    MKFMFPTVIKVSEEFVKVITEQVPAAQ---------------NGAVLEIKELMARFTTDVIGTCAFGIECNTLRTPVSDF

                 250       260       270       280       290       300       310       320
          ....|....|....|....|....|....|....|....|....|....|....|....|....|....|....|....|
AAY20974  YVAFVGLTDGFAPTLDSFKAIMWDFVPYFRTMKRRHEIPLTQGLAVSRRVGIELMEQKKQAVLGSASDQAVDKKDVQGRD
Q08477    AAILELSALVTKRHQQILLYIDFLY-YLTPDGQRFRRAC--------RLVHDFTDAVIQERRRTLPSQGVDDFLQAKAKS
P33274    AAILELSALVAKRHQQPLLFMDLLY-NLTPDGMRFHKAC--------NLVHEFTDAVIRERRRTLPDQGLDEFLKSKAKS
P11707    VKNVRRLLKFSFFDPLLLSITLFPFLTPIFEALHISMFP--------KDVMDFLKTSVEKIKDDRLKDKQKRRVDFLQLM
P33270    -RTMGQKVFTDMRHGKLLTMFVFSF-PKLASRLRMRMMP--------EDVHQFFMRLVNDTIALRERENFKRN-DFMNLL
```

FIG. 10a

```
                330       340       350       360       370       380       390       400
         ....|....|....|....|....|....|....|....|....|....|....|....|....|....|....|....|
AAY20974 ILSLLVRANIAANLPESQKLSDEEVLAQISNLLFAGYETSSTVLTWMFHRLSEDKAVQDKLREEICQIDTDMP----TLD
Q08477   KTLDFIDVLLLSKDEDGKKLSDEDIRAEADTFMFEGHDTTASGLSWVLYHLAKHPEYQERCRQEVQELLKDREPKEIEWD
P33274   KTLDFIDVLLLTKDEDGKELSDEDIRAEADTFMFEGHDTTASGLSWILYNLANDPEYQERCRQEVQELLRDRDPEEIEWD
P11707   INSQNSKEI-----DSHKALDDIEVVAQSIIILFAGYETTSSTLSFIMHLLATHPDVQQKLQEEIDTLLPNKE-L-ATYD
P33270   IELKQKGRVTLDNGEVIEGMDIGELAAQVFVFYVAGFETSSSTMSYCLYELAQNQDIQDRLRNEIQTVLEEQEGQ-LTYE

                410       420       430       440       450       460       470       480
         ....|....|....|....|....|....|....|....|....|....|....|....|....|....|....|....|
AAY20974 ELNALPYLEAFVKESLRLDPPSPYANRECLKDEDFIPLAEPVIGRDGSVINEVRITKGTMVMLPLFNINRSKFIYGEDAE
Q08477   DLAQLPFLTMCIKESLRLHPPVPAVSRCCTQDIVLPDG--RVI------------PKGIICLISVFGTHHNPAVW-PDPE
P33274   DLAQLPFLTMCIKESLRLHPPVTVISRCCTQDILLPDG--RTI------------PKGIICLISIFGIHHNPSVW-PDPE
P11707   TLVKMEYLDMVVNETLRLYPIAGRLERVCKKDVDING---TFI------------PKGTIVMMPTYALHRDPQHW-TEPD
P33270   SIKAMTYLNQVISETLRLYTLVPHLERKALNDYVVPGHEKLVI------------EKGTQVIIPACAYHRDEDLY-PNPE

                490       500       510       520       530       540       550       560
         ....|....|....|....|....|....|....|....|....|....|....|....|....|....|....|....|
AAY20974 EFRPERWLEDVTDSLNSIEAPYGHQASFISGPRACFGWRFAVAEMKAFLFVTLRRVQFEPIISHPEYEHITLIISRPRIV
Q08477   VYDPFRFDPKNIKERSPLA-----FIPFSAGPRNCIGQAFAMAEMKVVLGLTLLRFR--VL----PDHTEPRR--KPELV
P33274   VYNPFRFDPENIKDSSPLA-----FIPFSAGPRNCIGQTFAMSEMKVALALTLLRFR--LL----PDDKEPRR--QPELI
P11707   EFRPERFSKKNKDNINPYI-----YHPFGAGPRNCLGMRFALMNIKLALVRLMQNFSFKLC----KETQVPLKLGKQGLL
P33270   TFDPERFSPEKVAARESVE-----WLPFGDGPRNCIGMRFGQMQARIGLAQIISRFRVSVC----DTTEIPLKYSPMSIV
```

FIG. 10b

1:RXXXXPXXXXXXXK

2:GXXTXXXXXXXXXXXLXXXXXXQXXXXXE

3:FXXGPRXCXGXXFXXXXXXXXL

FIG. 10c

```
                        10        20        30        40        50        60        70        80
              ....|....|....|....|....|....|....|....|....|....|....|....|....|....|....|....|
ACI43097      --MATLSDLVILLLGALLALGFYNKDRLLGSSSSSASTTSGSSAATANGSKPTYSNGNGNAFKGDPRDFVARMKDQKKRL
XP_001731494  --MAGITLWLVAGLVGLITV-FILRNTLFKSQEVA-------EPIEEDD--------------GDGSNFVERLELQKKRI
XP_762420     --MASQLDLFVLGLGGLLAVLYLFRDSLFGGAKDTGSKLANGAPLAATD--------------QGGADFVSKLKSQNKRI
Q00141        MAQLDTLDLVVLAVLLVGSVAYFTKGTYWAVAKDPYASTGPAMNGAAKA--------------GKTRNIIEKMEETGKNC
NP_596046     ---MKTYEYVLLVIILILSLCYFIYNNFLNKPKAP----------ERRV--------------VATDSIVELMEAEKLTA

                        90       100       110       120       130       140       150       160
              ....|....|....|....|....|....|....|....|....|....|....|....|....|....|....|....|
ACI43097      AVFYGSQTGTAEEYATRIAKEAKSRFGVSSLVCDIEEYDFEKLDQVPEDCAIVFCMATYGEGEPTDNAVQFIEMISQDDP
XP_001731494  VIFFGSQTGTAEEYAIRIAREVKSRYGTSPLVVDPEPEEFDKLDLLPENCVAVFVMATYGEGEPTDNAVAMMDFLKSPDV
XP_762420     AIFYGSQTGTAEEYATKLAKEAKARFGTSSLVLDPEEYEFDKLDQMPQDTVAVFVMATYGEGEPTDNAVGLMEFIENESP
Q00141        VIFYGSQTGTAEDYASRLAKEGSQRFGLKTMVADLEEYDYENLDQFPEDKVAFFVLATYGEGEPTDNAVEFYQFFTGDDV
NP_596046     AVFFGSQTGTAEDFAYRFSTEAKANFNLTNMVFDLENYDLTDLDNFDRSKLLVFFLATYGEGEPTDNAEAFLQLLEGDDT

                       170       180       190       200       210       220       230       240
              ....|....|....|....|....|....|....|....|....|....|....|....|....|....|....|....|
ACI43097      EFSEGS----T-LDGLKYVVFGLGNKTYEQYNVVGRQLDARLTALGATRVGERGEGDDDKS-MEEDYLAWKDDMFAALAT
XP_001731494  AFTNGS----T-LENLHYVAFGLGNRTYEYFNEAIRQLDARLLELGAHRIGERGEGDDEKG-LEEDYLAWKDPMFEELAA
XP_762420     EFSNGS----ERLENLNYVIFGLGNRTYEHFNAVARKLDARLQSLGAKRIGERGEGDDDKS-MEEDYLAWKDSMFEALAT
Q00141        AFESASA-DEKPLSKLKYVAFGLGNNTYEHYNAMVRQVDAAFQKLGPQRIGSAGEGDDGAGTMEEDFLAWKEPMWAALSE
NP_596046     VFSSGKGIEDTPFEGIRYAIFGLGNHTYEYYNAMAKKVDAAMTRLGATRVGNLGLGDDAAGMLEEDYLQWKDDTLPEIGK
```

Flavodoxin

FIG. 11a

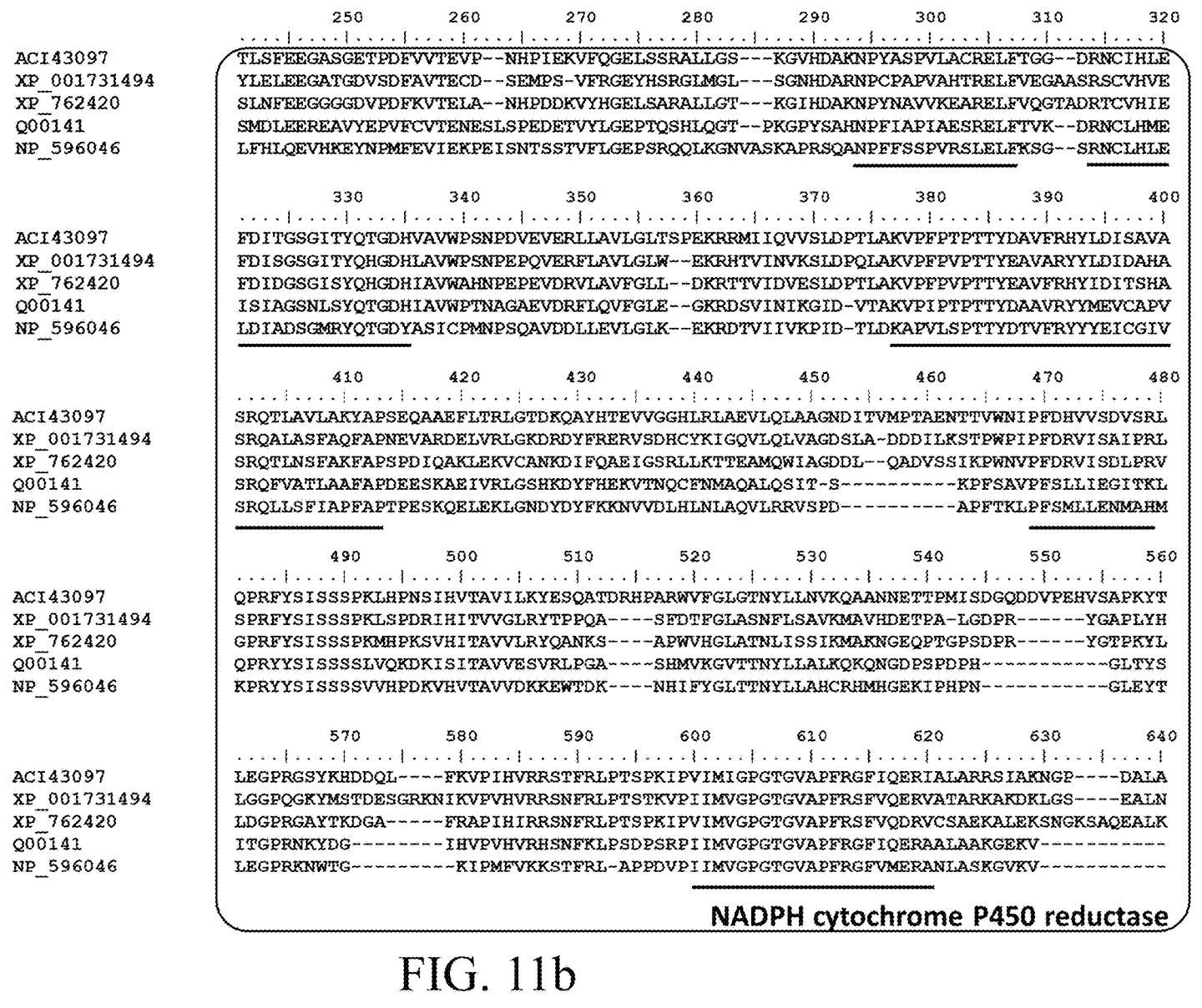

```
                         250       260       270       280       290       300       310       320
ACI43097      TLSFEEGASGETPDFVVTEVP--NHPIEKVFQGELSSRALLGS---KGVHDAKNPYASPVLACRELFTGG--DRNCIHLE
XP_001731494  YLELEEGATGDVSDFAVTECD--SEMPS-VFRGEYHSRGLMGL---SGNHDARNPCPAPVAHTRELFVEGAASRSCVHVE
XP_762420     SLNFEEGGGGDVPDFKVTELA--NHPDDKVYHGELSARALLGT---KGIHDAKNPYNAVVKEARELFVQGTADRTCVHIE
Q00141        SMDLEEREAVYEPVFCVTENESLSPEDETVYLGEPTQSHLQGT--PKGPYSAHNPFIAPIAESRELFTVK--DRNCLHME
NP_596046     LFHLQEVHKEYNPMFEVIEKPEISNTSSTVFLGEPSRQQLKGNVASKAPRSQANPFFSSPVRSLELFKSG--SRNCLHLE

                         330       340       350       360       370       380       390       400
ACI43097      FDITGSGITYQTGDHVAVWPSNPDVEVERLLAVLGLTSPEKRRMIIQVVSLDPTLAKVPFPTPTTYDAVFRHYLDISAVA
XP_001731494  FDISGSGITYQHGDHLAVWPSNPEPQVERFLAVLGLW--EKRHTVINVKSLDPQLAKVPFPVPTTYEAVARYYLDIDAHA
XP_762420     FDIDGSGISYQHGDHIAVWAHNPEPEVDRVLAVFGLL--DKRTTVIDVESLDPTLAKVPFPVPTTYEAVFRHYIDITSHA
Q00141        ISIAGSNLSYQTGDHIAVWPTNAGAEVDRFLQVFGLE--GKRDSVINIKGID-VTAKVPIPTPTTYDAAVRYYMEVCAPV
NP_596046     LDIADSGMRYQTGDYASICPMNPSQAVDDLLEVLGLK--EKRDTVIIVKPID-TLDKAPVLSPTTYDTVFRYYYEICGIV

                         410       420       430       440       450       460       470       480
ACI43097      SRQTLAVLAKYAPSEQAAEFLTRLGTDKQAYHTEVVGGHLRLAEVLQLAAGNDITVMPTAENTTVWNIPFDHVVSDVSRL
XP_001731494  SRQALASFAQFAPNEVARDELVRLGKDRDYFRERVSDHCYKIGQVLQLVAGDSLA-DDDILKSTPWPIPFDRVISAIPRL
XP_762420     SRQTLNSFAKFAPSPDIQAKLEKVCANKDIFQAEIGSRLLKTTEAMQWIAGDDL--QADVSSIKPWNVPFDRVISDLPRV
Q00141        SRQFVATLAAFAPDEESKAEIVRLGSHKDYFHEKVTNQCFNMAQALQSIT-S----------KPFSAVPFSLLIEGITKL
NP_596046     SRQLLSFIAPFAPTPESKQELEKLGNDYDYFKKNVVDLHLNLAQVLRRVSPD----------APFTKLPFSMLLENMAHM

                         490       500       510       520       530       540       550       560
ACI43097      QPRFYSISSSPKLHPNSIHVTAVILKYESQATDRHPARWVFGLGTNYLLNVKQAANNETTPMISDGQDDVPEHVSAPKYT
XP_001731494  SPRFYSISSSPKLSPDRIHITVVGLRYTPPQA----SFDTFGLASNFLSAVKMAVHDETPA-LGDPR------YGAPLYH
XP_762420     GPRFYSISSSPKMHPKSVHITAVVLRYQANKS----APWVHGLATNLISSIKMAKNGEQPTGPSDPR------YGTPKYL
Q00141        QPRYYSISSSSLVQKDKISITAVVESVRLPGA----SHMVKGVTTNYLLALKQKQNGDPSPDPH-----------GLTYS
NP_596046     KPRYYSISSSSVVHPDKVHVTAVVDKKEWTDK----NHIFYGLTTNYLLAHCRHMHGEKIPHPN-----------GLEYT

                         570       580       590       600       610       620       630       640
ACI43097      LEGPRGSYKHDDQL----FKVPIHVRRSTFRLPTSPKIPVIMIGPGTGVAPFRGFIQERIALARRSIAKNGP----DALA
XP_001731494  LGGPQGKYMSTDESGRKNIKVPVHVRRSNFRLPTSTKVPIIMVGPGTGVAPFRSFVQERVATARKAKDKLGS----EALN
XP_762420     LDGPRGAYTKDGA-----FRAPIHIRRSNFRLPTSPKIPVIMVGPGTGVAPFRSFVQDRVCSAEKALEKSNGKSAQEALK
Q00141        ITGPRNKYDG--------IHVPVHVRHSNFKLPSDPSRPIIMVGPGTGVAPFRGFIQERAALAAKGEKV-----------
NP_596046     LEGPRKNWTG---------KIPMFVKKSTFRL-APPDVPIIMVGPGTGVAPFRGFVMERANLASKGVKV-----------
```

NADPH cytochrome P450 reductase

FIG. 11b

1:FXGSQTGTAEXXAXXXXXE

2:EXXXXXXLDXXXXXXXXXFXXATYGEGEPTDNA

3:YXXFGLGNXTYEXXNXXXXXXDAXXXXLGXXRXGXXGXGDD

4:EEDXLXWK

FIG. 11c

1:NPXXXXXXXXXELF

2:RXCXHXEXXIXXSXXXYQXGD

3:KXPXXXPTTYXXXXRXYXXXXXXXSRQXXXXXAXXAP

4:PFXXXXXXXXXXXPRXYSISSS

5:PXIMXGPGTGVAPFRXFXXXR

FIG. 11d

```
                          90        100       110       120       130       140       150       160
                 ....|....|....|....|....|....|....|....|....|....|....|....|....|....|....|....|
XP_001698699     SDLGGIAVAVTVIALWATLFVYGLWFVKLPWALKVGETATSWATIAAVFFSLEFLYTGLFITTHDAMHGTIALRNRRLND
BAB74888         LSSTIRDDKNINKGIFIACFILFLWAISLILLLSIDTSIIHKSLLGIAMLWQTFLYTGLFITAHDAMHGVVYPKNPRINN
NP_924674        LAEGVITHKNDSSGLWWALVIIGLWIFSFAAALRLPIGELSLQAVIGVVILRTFLHTGLFITAHDAMHRTVFPANHRIND
ABB25938         VATKAAQARHQRQSLILAALIGSAWIITFVISMLINVNVWSSSAILGFILLRSFLHTGLFIVAHDAMHHSLAPLNENLNN
CAE07883         ANEFSPQAL---KGLALAGLIGSAWLLSLGLSYTLPLDQTPGLLIGSLILLRAFLHTGLFIVAHDSMHASLVPGHPGLNR

                         170       180       190       200       210       220       230       240
                 ....|....|....|....|....|....|....|....|....|....|....|....|....|....|....|....|
XP_001698699     FLGQLAISLYAWFDYSVLHRKHWEHHNHTGEPRVDPDFHRGNP-NLAVWFAQFMVSYMTLSQ-----FLKIAVWSNLLLL
BAB74888         FIGKLTLILYGLLPYKDLLKKHWLHHGHPGTDL-DPDYYNGHPQNFFLWYLHFMKSYWRWTQ----IFGLVMIFHGLKNL
NP_924674        WLGTAAVGLYAFMPYRELLIKHQLHHRFPATGK-DPDYHDGEHSGFFQWYLKFMKDYMESRNTPFLIAGMAVVFGVCTWL
ABB25938         NIGRLCLFLYAGLSYKSCSKNHSLHHRYPESAA-DPDFHSIQNSKPINWYFRFLSNYLDAKQFCILTIVWLLLLQITSSV
CAE07883         WIGKVYLLVYAGLSYERCSRNHRRHHLAPETFQ-DPDYQRCTNNNILDWYVHFMGNYLGMRQLLNLSCLWLALIIILNGSD

                         250       260       270       280       290       300       310       320
                 ....|....|....|....|....|....|....|....|....|....|....|....|....|....|....|....|
XP_001698699     AGAPLANQLLFMTAAPILSAFRLFYYGTYVPHHPEKGHTGAMPWQVSRTSSASRLQSFLTCYHFDLHWEHHRWPYAPWWE
BAB74888         VHIPENNLIIFWMIPSILSSVQLFYFGTFLPHKKLEG--GYTNPHCARSIPLPLFWSFVTCYHFGYHKEHHEYPQLPWWK
NP_924674        MGVPLVNLALFWLLPLVLSSLQLFYFGTYLPHRQPDG--GYRNRHRATSNRLSSFWSFVSCYHFGYHWEHHEYPLVPWHR
ABB25938         NPNAAENIIIFCPIPLIISSIQLFFVGTCLPHQITRK---EAGRQRPRSLSLHPLLSFAACYHFGYHLEHHLNPSTPWFK
CAE07883         LPAQIMHLLLFSVLPLIISSCQLFLVGTWLPHRRGAT---TRPGVTTRSLALHPALSFAACYNFGYHREHHESPSTPWFQ

                         330       340       350       360       370       380       390       400
                 ....|....|....|....|....|....|....|....|....|....|....|....|....|....|....|....|
XP_001698699     LPKCRQIARGAALAPGPLPVPAAAAATAATAAAAAAATGSPAPASRAGSASSASAAASGFGSGHSGSVAAQPLSSLPLLS
BAB74888         LPEAHKISL-----------------------------------------------------------------------
NP_924674        LPEARR--------------------------------------------------------------------------
ABB25938         LPNLRVASLQREQAKIKHSH------------------------------------------------------------
CAE07883         LPQLRNESFT----------------------------------------------------------------------
```

FIG. 14a

1: FLXTGLFIXXHDXMH

2:DPDXXXXXXXXXXWXXXFXXXY

3:FXXXXXXXSXXXLFXXGTXXPH

4:SFXXCYXFXXHXEHHXXPXXP
WXXLP

FIG. 14b

```
                       10        20        30        40        50        60        70        80
               ....|....|....|....|....|....|....|....|....|....|....|....|....|....|....|....|
XP_001698698   MMLASRPAVALGARAQPQVLRPTLVPRPGMVS----NLRLQPVKVADPIVASETSQVMEAPQ-EKKLSEFELKRLE----
ABS50237       MQTVFQPSSVWHLRNRHVLGDRTCVPCRTSLSTCRHAVRLVRANVAETQATPTTSQMLEEVHDESHAASASSQIFELAVK
Q9SPK6         MLSKLQSISV-KARRVELARDIT----RPKVCLHAQRCSLVRLRVAAPQTEEALGTVQAAGAGDEHSADVALQQLDRAIA

                       90       100       110       120       130       140       150       160
               ....|....|....|....|....|....|....|....|....|....|....|....|....|....|....|....|
XP_001698698   ---RKQQRAQEAATYKFSAIAATVLVLSIAVVATYYRFAWHFAEDGDLPVDEMAATLLLVFGGMFGMEMYARFAHKVLWH
ABS50237       TSIKRQQRNRQQLTYQGSAIAASLGVGALAVAATHYKFSYHMPSESPFPWLDMAGTLALVIGGVFGMEMWARYAHKALWH
Q9SPK6         E--RRARRKREQLSYQAAAIAASIGVSGIAIFATYLRFAMHMTVGGAVPWGEVAGTLLLVVGGALGMEMYARYAHKAIWH

                      170       180       190       200       210       220       230       240
               ....|....|....|....|....|....|....|....|....|....|....|....|....|....|....|....|
XP_001698698   DFEPGWALHKSHHEPRTGPFELNDIYAVANALPAMALCAYGFFTPHVIGGVCFGAGLGITLFGIAYMFFHDGLVHRRFPV
ABS50237       DFQPGWALHKSHHEPRIGPFEANDIFAVINAVPAFSLCLYGFLTPNLVGSLCFGAGLGITLFGIMYMFIHDGLVHKRFPV
Q9SPK6         ESPLGWLLHKSHHTPRTGPFEANDLFAIINGLPAMLLCTFGFWLPNVLGAACFGAGLGITLYGMAYMFVHDGLVHRRFPT

                      250       260       270       280       290       300
               ....|....|....|....|....|....|....|....|....|....|....|....|....
XP_001698698   GPIANLPYMKRIMVAHQIHHTNKFGGVPFGMFLGVQELEAVPGGKEELDKLMADLEAREAAAAKAAGSS
ABS50237       GPIAQMPAMKRVAIAHKLHHSEKYGGVPWGMFFGPQELEAI-GAGPELDRLCAELDSKSS---------
Q9SPK6         GPIAGLPYMKRLTVAHQLHHSGKYGGAPWGMFLGPQELQHIPGAAEEVERLVLELDWSKR---------
```

FIG. 15a

1:HXXXXXXXPXXXXAXTLXLVXGGXXGMEMXARXAHKXXWHXXXXGWXLHKSHHXPRXG
PFE

2:PAXXLCXXGFXXPXXXGXXCFGAGLGITLXGXXYMFXHDGLVHXRFPXGPIAXXPX
MKRXXXAHXXHHXXKXGGXP

FIG. 15b

RECOMBINANT POLYNUCLEOTIDE SEQUENCE FOR PRODUCING ASTAXANTHIN AND USES THEREOF

CROSS REFERENCE TO RELATED APPLICATIONS

This application is a divisional application of U.S. application Ser. No. 16/200,269, filed Nov. 26, 2018, which is Continuation of U.S. application Ser. No. 15/353,372, filed on Nov. 16, 2016, which is a Continuation of International Application No. PCT/US2015/031273, filed on May 16, 2015, which claims priority of U.S. Provisional Application No. 61/994,828 filed on May 16, 2014. The entire contents of all of which are hereby incorporated by reference.

BACKGROUND OF THE INVENTION

1. Field of the Invention

The present disclosure relates to biosynthesis of astaxanthin. More particularly, the disclosed invention relates to the biosynthesis of astaxanthin or its precursors or derivatives.

2. Description of Related Art

Carotenoids are light harvesting pigments that protect the photosynthetic apparatus from photo-oxidative damage under excessive light. In humans, carotenoids, which are the precursor of vitamin A and may function as antioxidants, can stimulate the immune system and can provide protection against a broad range of human diseases, including cancer. In nature, there are many kinds of carotenoids, including astaxanthin, lycopene, β-carotene, echinenone, canthaxanthin, and zeaxanthin. The red carotenoid astaxanthin possesses higher antioxidant activity than other carotenoids, so it has a great commercial potential for use in aquaculture, pharmaceutical, cosmetics, and food industries.

Astaxanthin (3,3'-dihydroxy-β-carotene-4,4'-dione) (FIG. 1) is a carotenoid pigment which confers a characteristic coloration to some birds, crustaceans and salmon. It is thought that an upset in the oxidative balance can contribute to rheumatoid arthritis, heart disease, Parkinson's disease, Alzheimer's disease, cancer, and stroke. This super antioxidant carotenoid is over 500 times stronger in antioxidative potency than vitamin E and 10 times stronger than other carotenoids. Many studies have shown that astaxanthin has health-promoting effects in the prevention and treatment of various diseases, such as cancer, chronic inflammatory diseases, metabolic syndromes, diabetes, diabetic nephropathy, cardiovascular diseases, gastrointestinal diseases, liver diseases, neurodegenerative diseases, eye diseases, skin diseases, exercise-induced fatigue, male infertility, $HgCl_2$-induced acute renal failure, immune support, and reduction in the risk of atherosclerosis.

Astaxanthin is one of the best-selling products in the carotenoid market. Astaxanthin made from chemical synthesis has the major share of the market, and its commercial use is mainly as a feed additive for salmon and trout farming. Synthetic astaxanthin is produced using petrochemicals. While synthetic and natural astaxanthins have essentially the same chemical formula, the molecular properties are different, and it is this difference that provides for the natural astaxanthin's safe and effective antioxidant properties. Moreover, chemically synthesized astaxanthin is not legal in the pharmacy market for three reasons:

First, the geometric isomer form affects the absorption of synthetic astaxanthin. As the chemical synthetic astaxanthin with the configuration Z form (cis-isomeric) cannot be absorbed by animals, the U.S. Food and Drug Administration (FDA) has banned it (Table 1). In comparison, the configuration in natural astaxanthin is 98% configuration E (trans-isomer) (Table 1).

TABLE 1

The geometric isomers and stereoisomers isomers of astaxanthin from different sources.

| | | | Optical isomers (%) | | | Geometrical isomers (%) | |
|---|---|---|---|---|---|---|---|
| Astaxanthin source | Concentration | Derivation | 3S, 3'S | 3R, 3'S | 3R, 3'R | All-trans | Cis |
| Synthetic sources | — | 100% free | 25 | 50 | 25 | 65-75 | 25-30 |
| *Haematococcus pluvialis* | 1-4% | Esterified | 100 | — | — | 59 | 41 |
| *Xanthophyllomyces dendrorhous* | 0.5% | 100% free | — | — | 100 | 95.5 | 4.5 |
| Plant (GEM) | 0.2% | — | V | — | — | V | — |
| *Escherichia coli* (GEM) | 0.14% | — | V | — | — | V | — |
| *Saccharomyces cerevisiae* (GEM) | 0.004% | Esterified | V | — | — | V | — |

GEM: genetically engineered microorganism

Second, various astaxanthin isomers have been characterized on the basis of the configuration of the two hydroxyl groups on the molecule. As each molecule has two chiral centers in C-3 and C-3', astaxanthin may have three configurational isomers, including two enantiomers (3R, 3'R and 3S, 3'S) and a mesoform (3R, 3'S) (FIG. 1). The 3S, 3'S stereoisomer has higher antioxidant activity than the 3R, 3'R stereoisomer, while no antioxidant activity has been found for the 3R, 3'S mesoform. Synthetic astaxanthin is a mixture of the (3S, 3'S), (3R, 3'S), and (3R, 3'R) isomers with approximately the ratios of 1:2:1, whereas the 3S, 3'S stereoisomer is the main form found in algae (Table 1).

Third, synthetic astaxanthin in its free form is particularly susceptible to oxidation. Indeed, astaxanthin in nature is either conjugated with proteins or esterified with one or two fatty acids to form a monoester and diester forms, and these esterified molecules are also more easily absorbed by the human body. Natural astaxanthin produced from algae, such as *Haematococcus pluvialis*, has been shown to be a far more potent free radical scavenger and antioxidant than synthetic astaxanthin. Synthetic products can only be used as a part of fish feed.

Astaxanthin has been considered a potential functional food and pharmaceutical component because of its expanding medical potential and has been increasingly used as a feed and food pigment in the aquaculture industry. Since natural astaxanthin, especially 3S, 3'S stereoisomer esterified astaxanthin, has an advantage over synthetic products, establishing the carotenoid pathway in a suitable host to produce astaxanthin is of scientific and industrial interest. Although the carotenoid biosynthetic pathway has been studied (FIGS. 2*a* and 2*b*), it is not trivial to demonstrate the cell factory principle for producing the ideal astaxanthin (3S, 3'S stereoisomer esterified astaxanthin). Many hosts, such as salmon, shrimp, green alga, plants, *Phaffia rhodozyma*, engineered microorganisms, have been reported to accumulate different isomers of astaxanthin and its derivatives in the cell. However, all of them have different limitations for astaxanthin production, such as low concentration in cold-water fish and shrimp, unexpected ketolation in all plant systems, lower antioxidant-activity end products in *Xanthophyllomyces dendrorhous*, and huge land and long culturing time by green algae culturing. Furthermore, it is difficult to control the specific carotenoid end products production and their ratios, even through an induction approach or mutagenesis improvement.

In view of the foregoing, there exists a need for a novel approach to the biosynthesis of astaxanthin.

SUMMARY

The following presents a simplified summary of the disclosure. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The specific aim of the present invention is to provide a recombinant polynucleotide sequence, a vector, a host cell and a method for use in the biosynthesis of astaxanthin, a precursor or a derivative thereof. Based on the antioxidant efficacy of the astaxanthin and/or its precursor or derivative, the present invention also provides a method for improving the tolerance of a host cell to a stress, and a method of enhancing the productivity of a host in producing ethanol or baccatin III.

In one aspect, the present disclosure is directed to a recombinant polynucleotide sequence for producing astaxanthin, a precursor or a derivative thereof, in a host cell. The recombinant polynucleotide sequence comprises four gene cassettes: (1) a first gene cassette that comprises a first promoter operatively linked to a first nucleic acid sequence, which encodes a geranylgeranyl pyrophosphate synthase (GGPP synthase); (2) a second gene cassette that comprises a second promoter operatively linked to a second nucleic acid sequence, which encodes a 3-hydroxy-3-methylglutaryl-coenzyme A reductase (HMG-CoA reductase); (3) a third gene cassette that comprises a third promoter operatively linked to a third nucleic acid, which encodes a phytoene desaturase; and (4) a fourth gene cassette that comprises a fourth promoter operatively linked to a fourth nucleic acid sequence, which encodes a bi-functional enzyme (hereinafter, phytoene synthase/lycopene cyclase) that possesses the function of phytoene synthase and lycopene cyclase. The 3'-end of each gene cassettes in the recombinant polynucleotide sequence is homologous to the 5'-end of the next gene cassette downstream therefrom.

According to one embodiment of the present disclosure, the first nucleic acid sequence is a crtE gene that comprises the sequence of SEQ ID NO: 1, the second nucleic acid sequence is a HMG1 gene that comprises the sequence of SEQ ID NO: 2, the third nucleic acid sequence is a crtI gene that comprises the sequence of SEQ ID NO: 3, and the fourth nucleic acid sequence is a crtYB gene that comprises the sequence of SEQ ID NO: 4.

According to certain embodiments of the present disclosure, the astaxanthin is 3S, 3'S-astaxanthin. According to other embodiments of the present disclosure, the astaxanthin is 3R, 3'R-astaxanthin.

According to one embodiment, the precursor of astaxanthin is geranylgeranyl-pyrophosphate (GGPP), phenicoxanthin, lycopene, echinenone, canthaxanthin, phytoene, zeaxanthin, β-cryptoxanthin, or β-carotene. According to another embodiment, the derivative of astaxanthin is an astaxanthin monoester or an astaxanthin diester.

In some embodiments of the present disclosure, the recombinant polynucleotide sequence comprises six gene cassettes, which are (1) a first gene cassette that comprises a first promoter operatively linked to a first nucleic acid sequence, which encodes a GGPP synthase; (2) a second gene cassette that comprises a second promoter operatively linked to a second nucleic acid sequence, which encodes a HMG-CoA reductase; (3) a third gene cassette that comprises a third promoter operatively linked to a third nucleic acid, which encodes a phytoene desaturase; and (4) a fourth gene cassette that comprises a fourth promoter operatively linked to a fourth nucleic acid sequence, which encodes a phytoene synthase/lycopene cyclase; (5) a fifth gene cassette that comprises a fifth promoter operatively linked to a fifth nucleic acid sequence which encodes a β-carotene hydroxylase; and (6) a sixth gene cassette that comprises a sixth promoter operatively linked to a sixth nucleic acid sequence, which encodes a β-carotene ketolase. The 3'-end of each gene cassettes in the recombinant polynucleotide sequence is homologous to the 5'-end of the next gene cassette downstream therefrom.

According to one embodiment of the present disclosure, the fifth nucleic acid sequence is a chYb gene that comprises any of the sequence of SEQ ID NO: 5, 6, or 7, and the sixth nucleic acid sequence is a bkt gene that comprises the sequence of SEQ ID NO: 8.

According to the embodiment of the present disclosure, each of the first to sixth promoters is selected from the group consisting of, a ScGapDH promoter, KlGapDH promoter, ScPGK promoter, KlPGK promoter, KlADHI promoter, ScADHI promoter, KlADH4 promoter, ScADH4 promoter, KlLac4 promoter and ICL promoter. Preferably, the first to sixth promoters are different from one another.

In other embodiments of the present disclosure, the recombinant polynucleotide sequence comprises six gene cassettes, which are (1) a first gene cassette that comprises a first promoter operatively linked to a first nucleic acid sequence, which encodes a GGPP synthase; (2) a second gene cassette that comprises a second promoter operatively linked to a second nucleic acid sequence, which encodes a HMG-CoA reductase; (3) a third gene cassette that comprises a third promoter operatively linked to a third nucleic acid, which encodes a phytoene desaturase; and (4) a fourth gene cassette that comprises a fourth promoter operatively linked to a fourth nucleic acid sequence, which encodes a phytoene synthase/lycopene cyclase; (5) a seventh gene cassette that comprises a seventh promoter operatively linked to a seventh nucleic acid sequence, which encodes a P450 reductase; and (6) an eighth gene cassette that comprises an eighth promoter operatively linked to an eighth nucleic acid sequence, which encodes a β-carotene oxygenase. The 3'-end of each gene cassettes in the recombinant polynucleotide sequence is homologous to the 5'-end of the next gene cassette downstream therefrom.

According to one embodiment of the present disclosure, the seventh nucleic acid sequence is a crtR gene that comprises the sequence of SEQ ID NO: 9, and the eighth nucleic acid sequence is a crtS gene that comprises the sequence of SEQ ID NO: 10.

According to another embodiment of the present disclosure, each of the first, second, third, fourth, seventh, and eighth promoters is selected from the group consisting of ScGapDH promoter, KlGapDH promoter, ScPGK promoter, KlPGK promoter, KlADHI promoter, ScADHI promoter, KlADH4 promoter, ScADH4 promoter, KlLac4 promoter and ICL promoter. Preferably, the promoters are different from one another.

In certain embodiments of the present disclosure, the recombinant polynucleotide sequence further comprises a marker gene cassette that comprises a marker promoter operatively linked to a marker gene.

The second aspect of the present disclosure is directed to a recombinant vector for producing astaxanthin, a precursor or a derivative thereof, in a host cell. The vector comprises a recombinant polynucleotide sequence according to the above-mentioned aspect/embodiment(s) of the present disclosure, and a control sequence operably linked thereto for expressing the recombinant polynucleotide sequence.

The third aspect of the present disclosure pertains to a host cell for producing astaxanthin, a precursor or a derivative thereof, in which the host cell comprises the recombinant polynucleotide sequence or the vector according to the above-discussed aspect(s)/embodiment(s) of the present disclosure. For different recombinant polynucleotide sequences or vectors comprised in the host cell, the produced astaxanthin may be 3S, 3'S-astaxanthin or 3R, 3'R-astaxanthin. The precursor of astaxanthin may be geranylgeranyl-pyrophosphate (GGPP), phenicoxanthin, lycopene, echinenone, canthaxanthin, phytoene, zeaxanthin, β-cryptoxanthin, or β-carotene. The derivative of astaxanthin may be an astaxanthin monoester or an astaxanthin diester.

In optional embodiments, the host cell is a eukaryotic cell or a prokaryotic cell.

In the fourth aspect, the present disclosure is directed to a method for producing astaxanthin, a precursor or a derivative thereof. According to further embodiments, the method comprises the step of cultivating the host cell according to the above-mentioned aspect/embodiment(s) in a medium, in which the medium may be a medium that comprises a material selected from the group consisting of glucose, galactose, glycerol, and fatty acid so as to produce astaxanthin or a precursor or a derivative thereof. In one specific embodiment, the medium comprises 0.5-40% glycerol. In another specific embodiment, the medium comprises 0.001-5% fatty acid, such as octanoic acid.

The fifth aspect of the present disclosure pertains to a method for improving the tolerance of a host cell to a stress. The method comprises introducing the present recombinant polynucleotide sequence and/or vector into the host cell. According to one embodiment, the stress to the host is caused by being exposed to ethanol, butanol, UV exposure, furfural, or a drug precursor, such as 10-deacetyl baccatin III (10 DB).

In a further aspect, the present disclosure is directed to a method of improving the productivity of a host cell in producing ethanol or baccatin III, comprising introducing the present recombinant polynucleotide sequence and/or vector into the host cell.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description in light of the accompanying drawings, where:

FIG. 4*a* is a sequence alignment data that depicts the conserved region of HMG-CoA reductases, in which the catalytic domains 1-6 are marked with underlines; 7208 represents the HMG-CoA reductase derived from *Kluveromyces marxianus*, P12683 represents the HMG-CoA reductase derived from *Saccharomyces cerevisiae*, ACN40476 represents the HMG-CoA reductase derived from *Picea sitchensis*, XP 001211323 represents the HMG-CoA reductase derived from *Aspergillus terreus*, and ABY84848 represents the HMG-CoA reductase derived from *Ganoderma lucidum* according to one example of the present disclosure;

FIG. 4*b* is a schematic diagram that depicts the conserved residues within the catalytic domains 1-6 of HMG-CoA reductase, in which the conserved residues are highlighted with underlines according to one example of the present disclosure;

FIG. 5*a* is a sequence alignment data that depicts the conserved region of geranylgeranyl pyrophosphate (GGPP) synthases, in which the catalytic domains 1-2 are marked with underlines; AAY33921 represents the GGPP synthase derived from *Xanthophyllomyces dendrorhous*, NP_624521 represents the GGPP synthase derived from *Streptomyces coelicolor*, BAB99565 represents the GGPP synthase derived from *Corynebacterium glutamicum*, ZP_00056752 represents the GGPP synthase derived from *Thermobifida fusca*, and NP_696587 represents the GGPP synthase derived from *Bifidobacterium longum* according to another example of the present disclosure;

FIG. 5*b* is a schematic diagram that depicts the conserved residues within the catalytic domains 1-2 of GGPP synthase, in which the conserved residues are highlighted with underlines according to another example of the present disclosure;

Figure 7B:
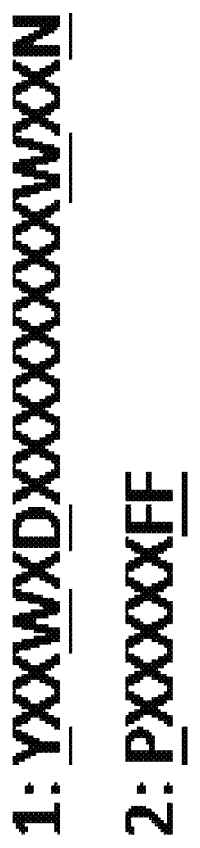

FIG. 7*a* is a sequence alignment data that depicts the conserved region of lycopene cyclase domain, in which the catalytic domains 1-2 are marked with underlines;

Figure 9:
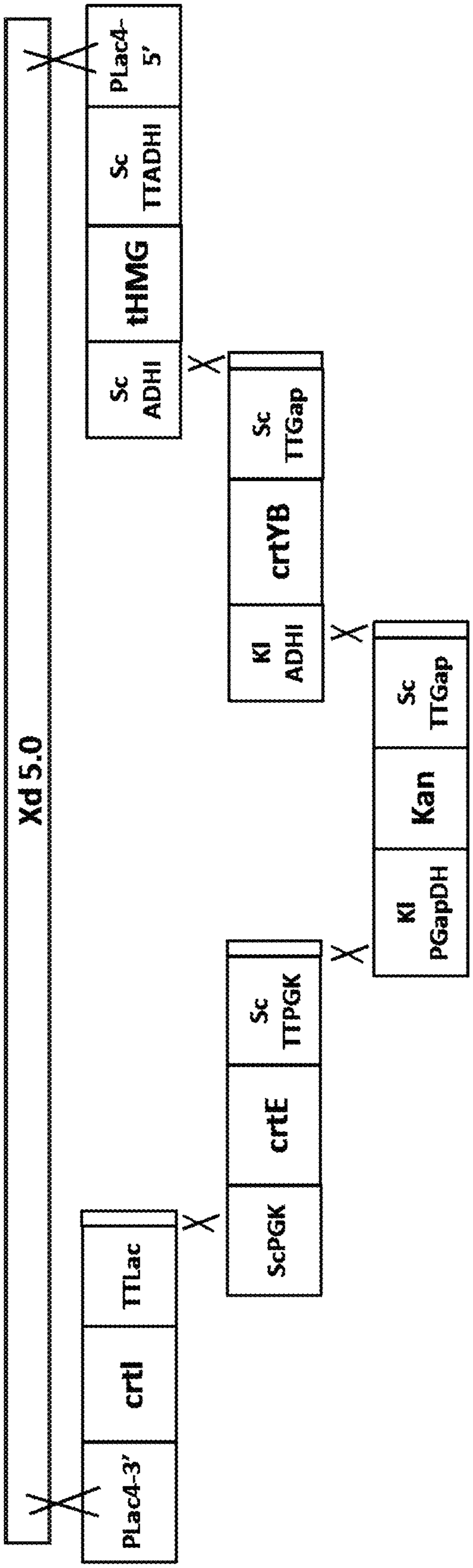
Figure 12:
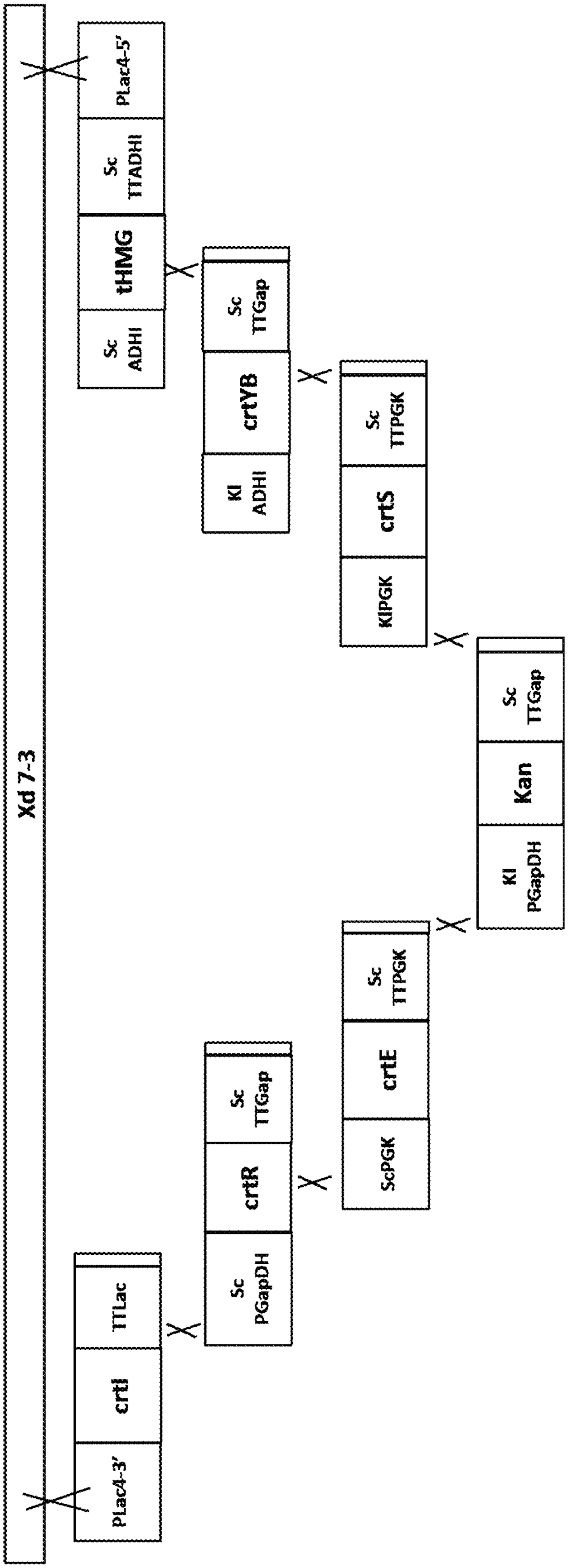
Figure 13A:
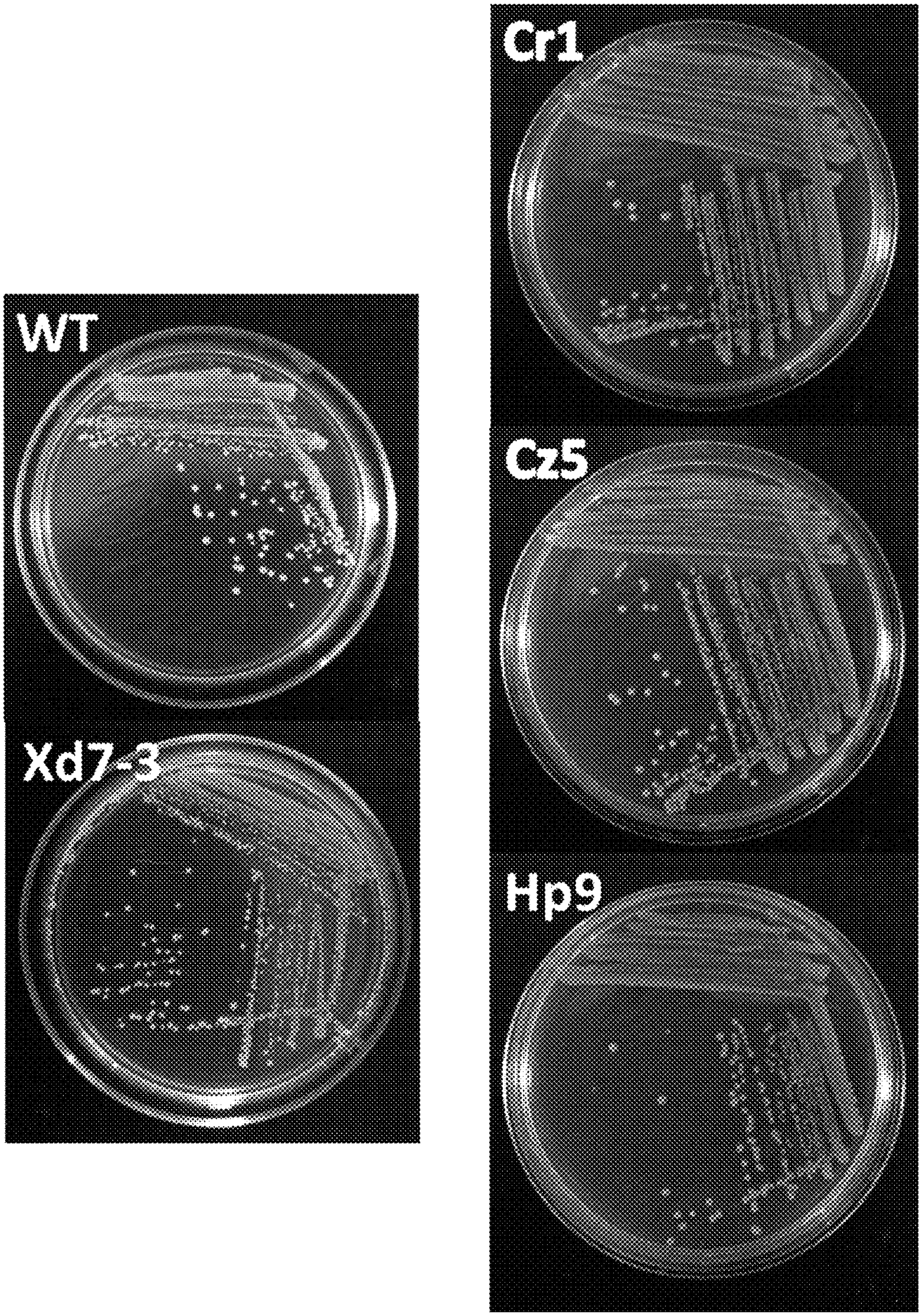
Figure 13B:
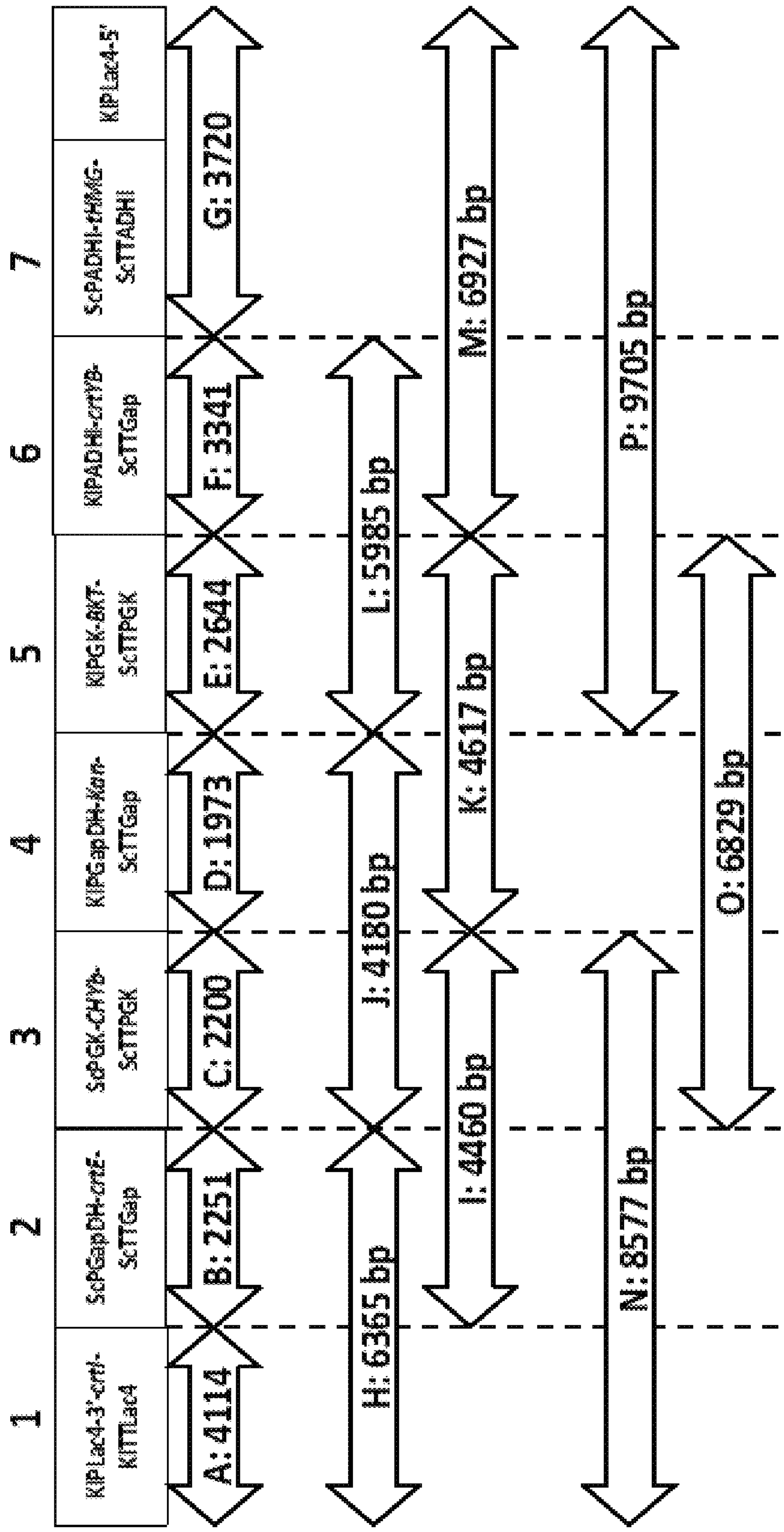
Figure 13C:
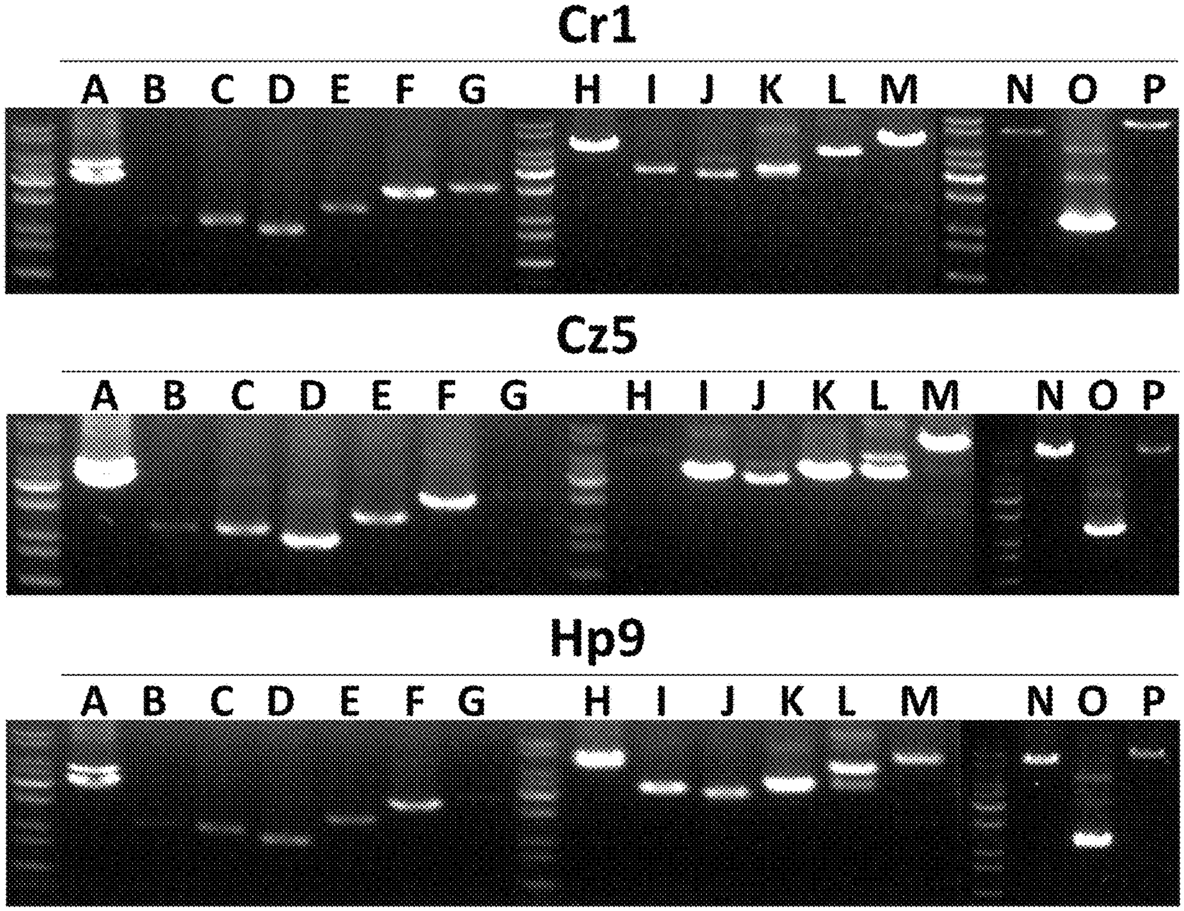
Figure 16A:
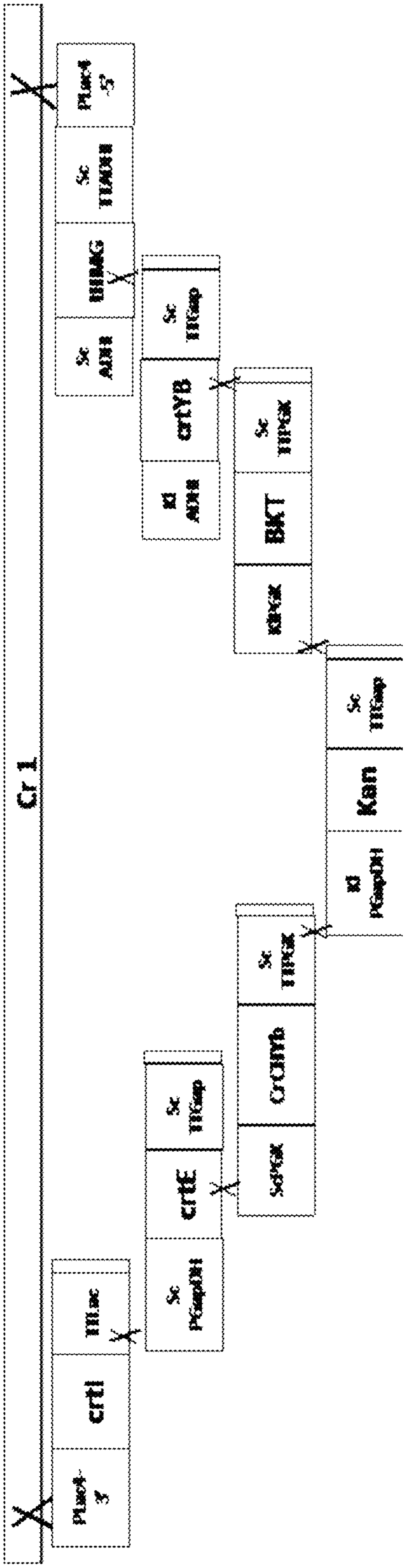
Figure 16B:
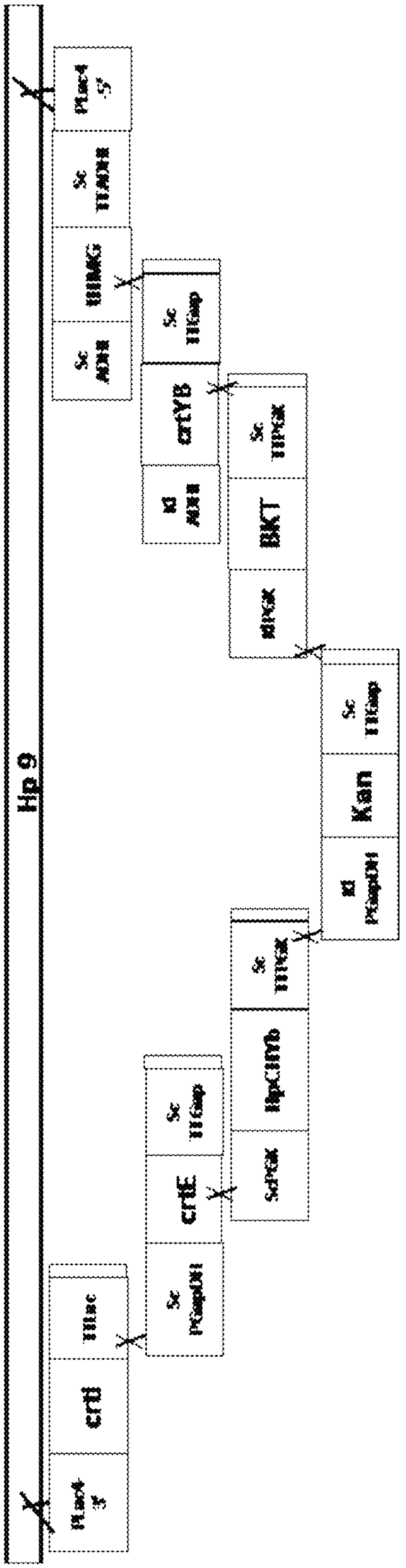
Figure 16C:
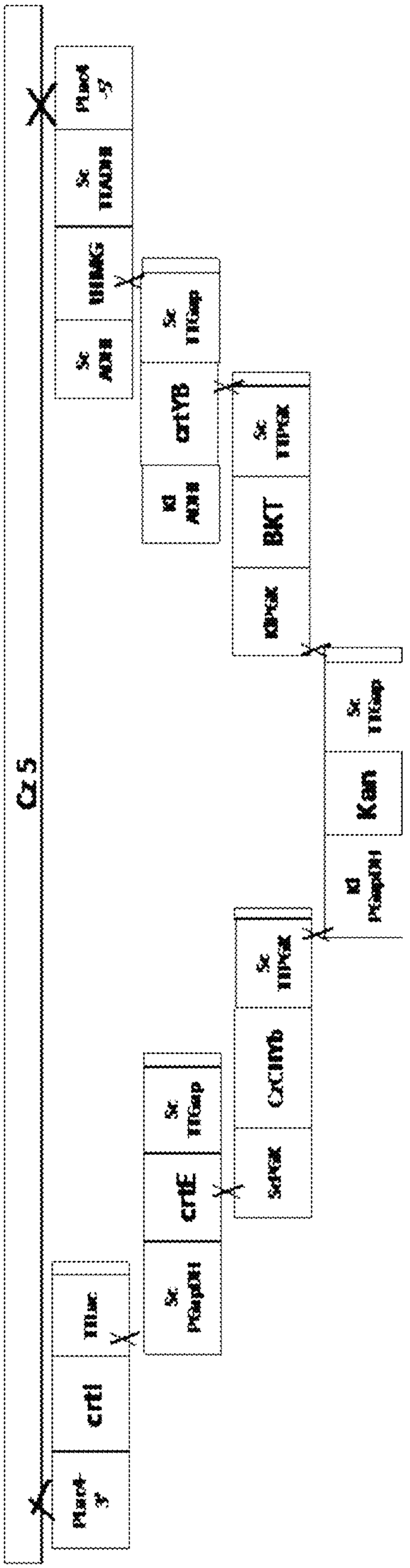
Figure 17A:
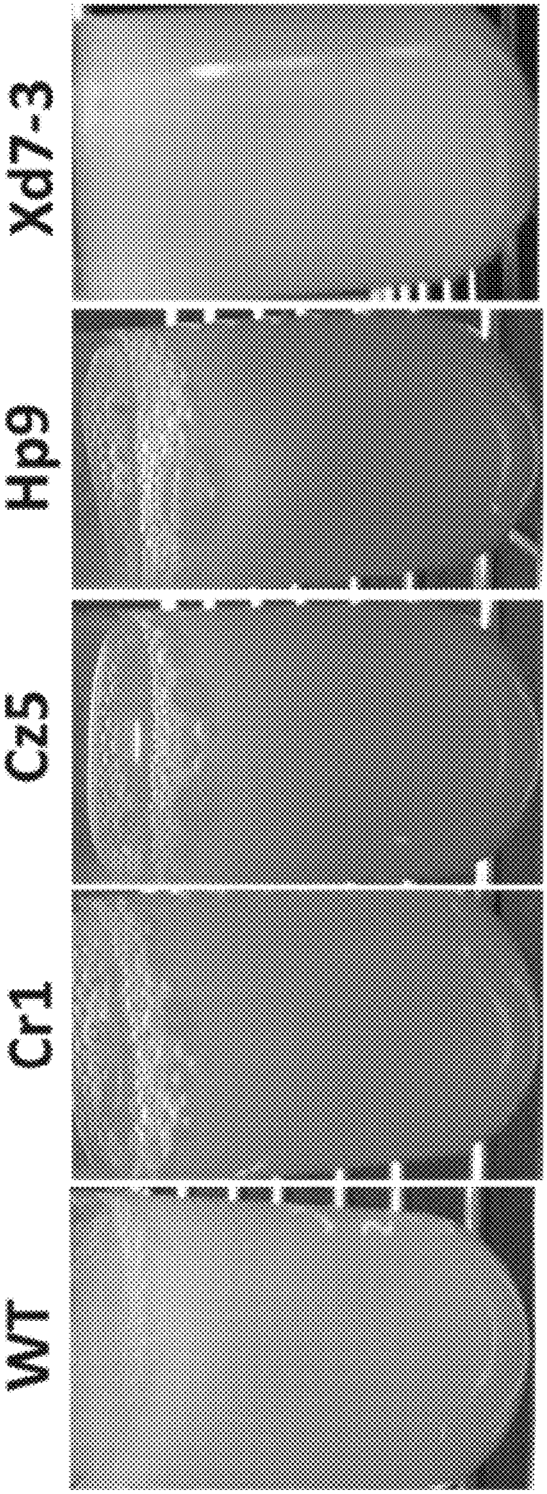
Figure 17B:
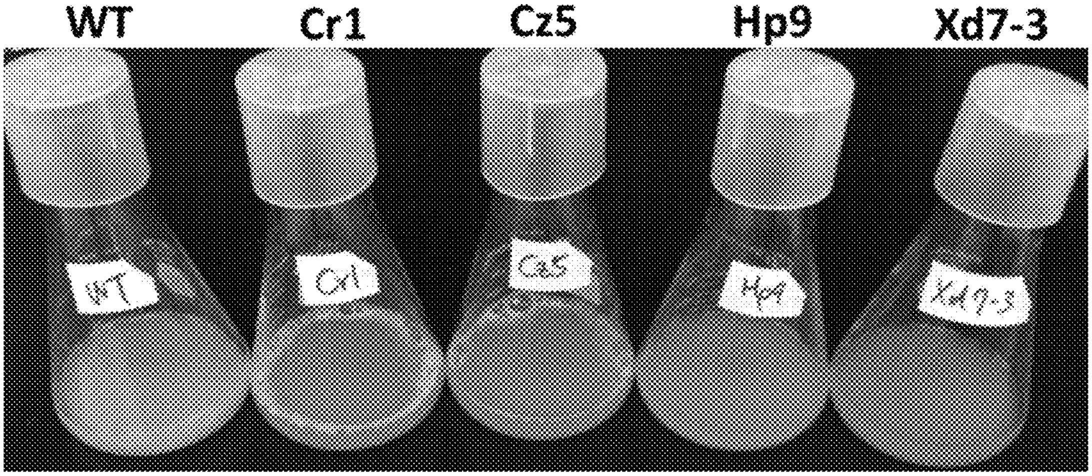
Figure 17C:
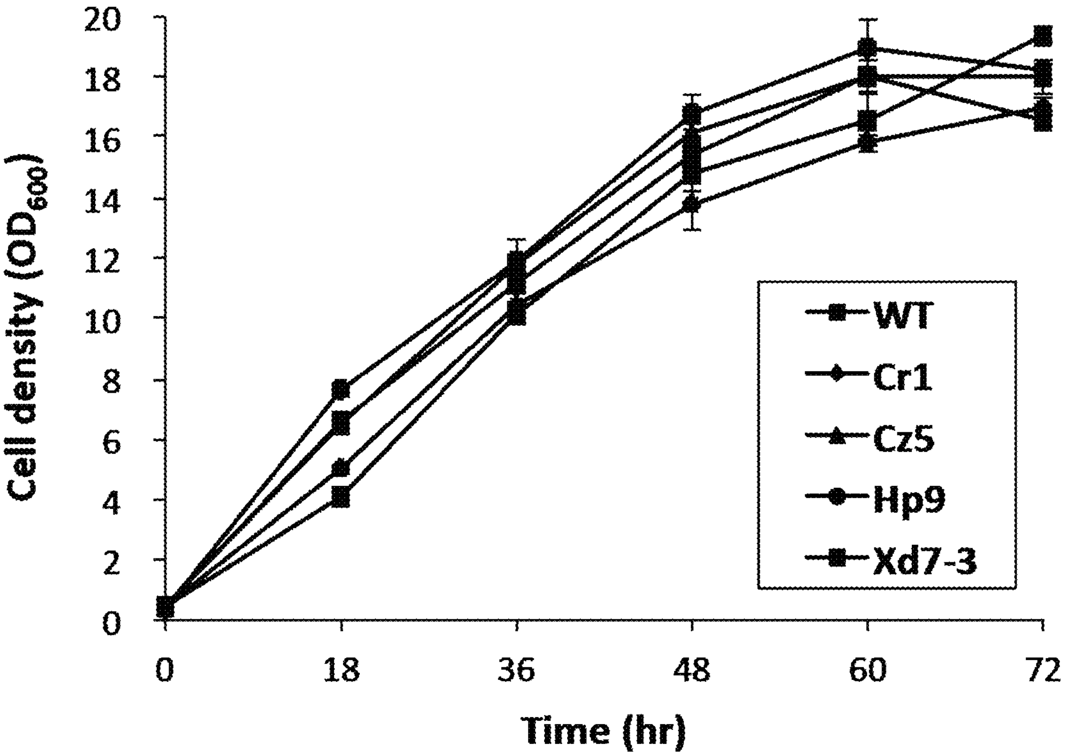
Figure 17D:
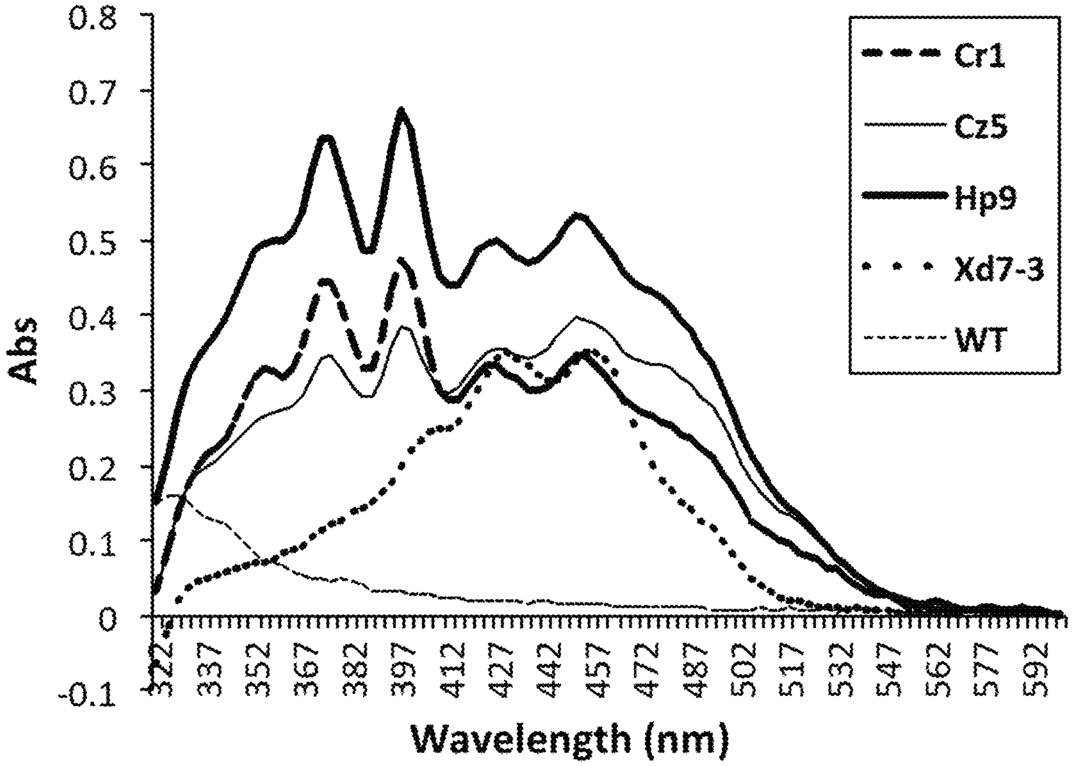
Figure 18A:
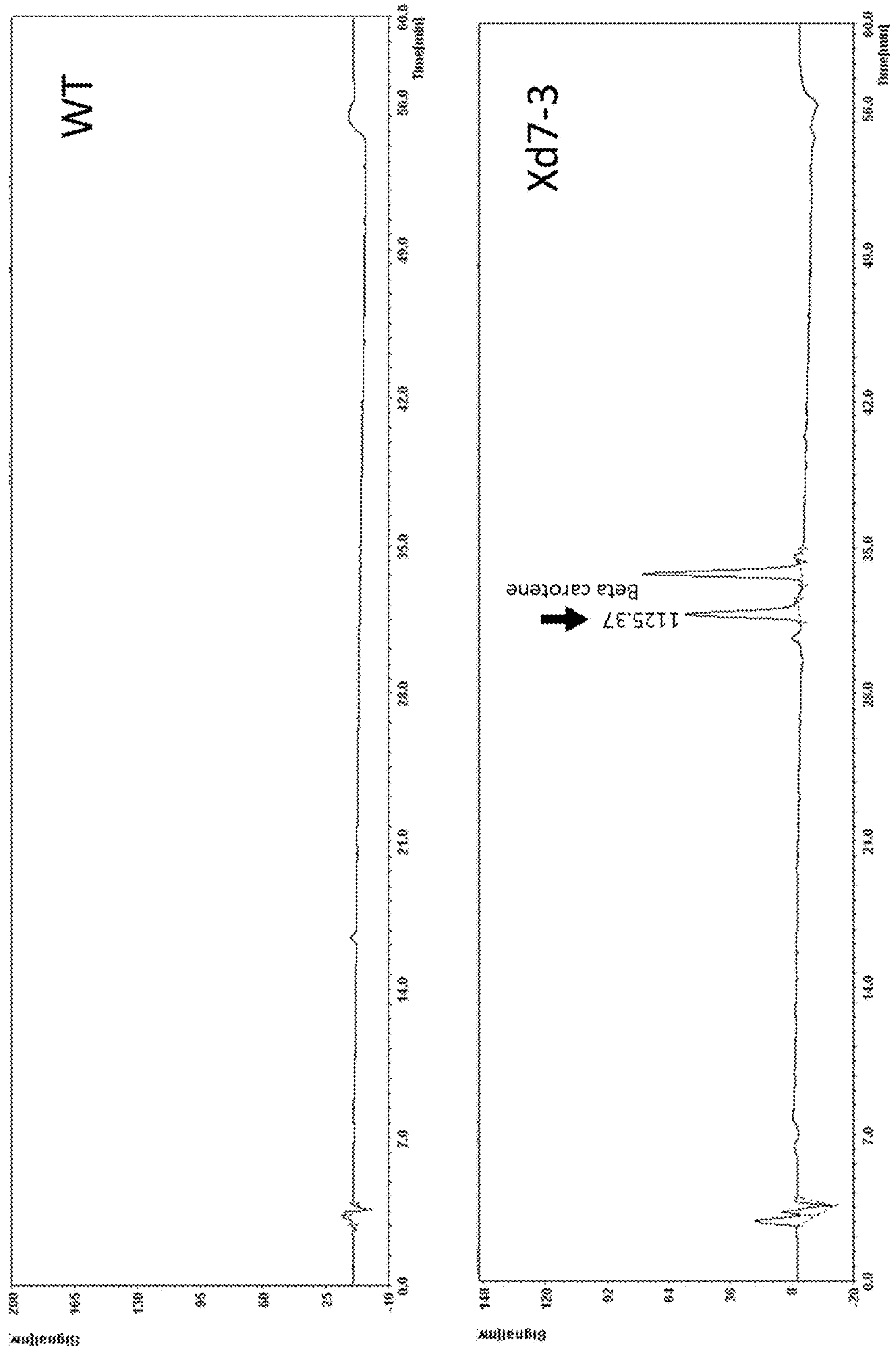
Figure 18B:
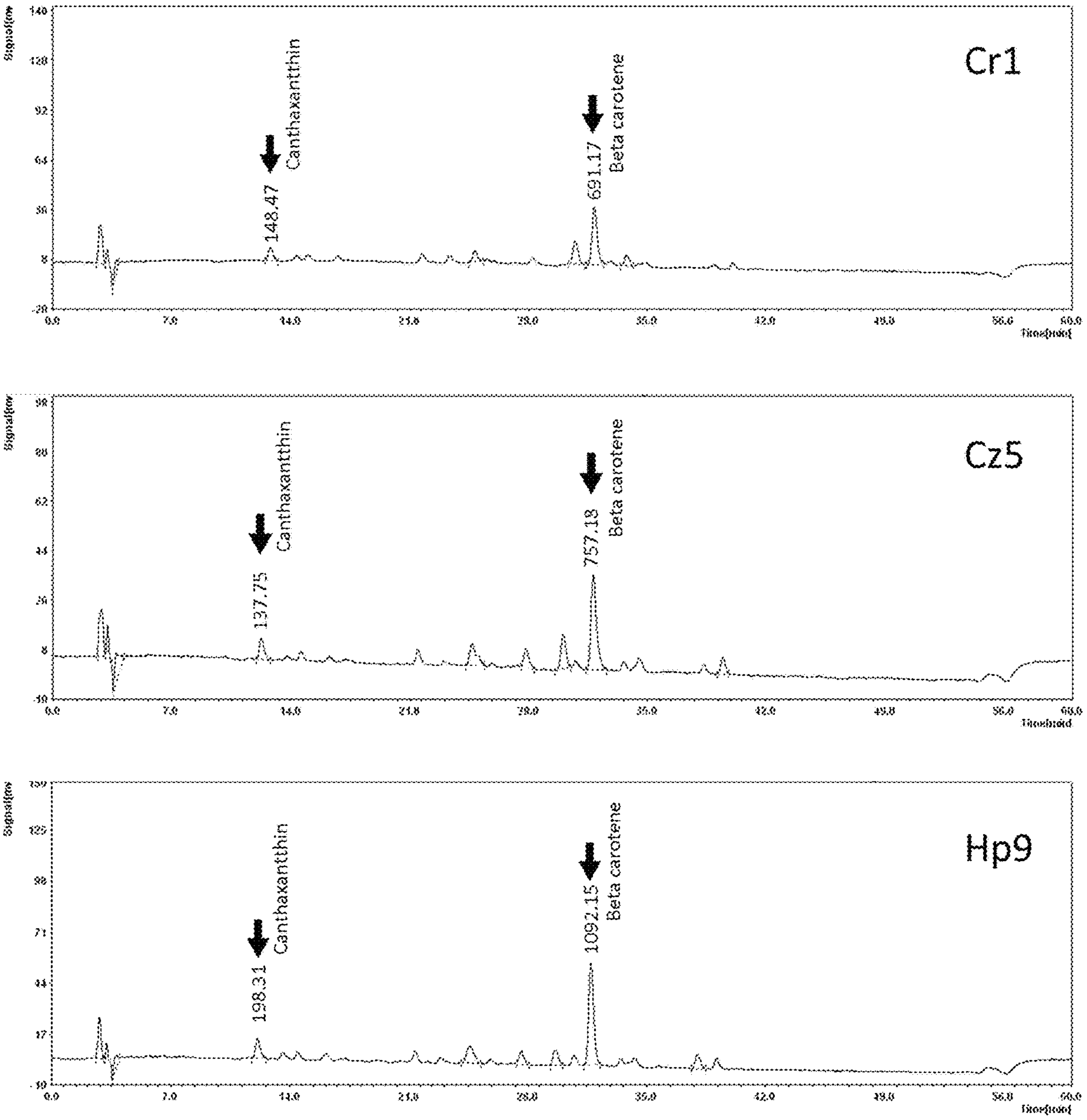
Figure 19A:
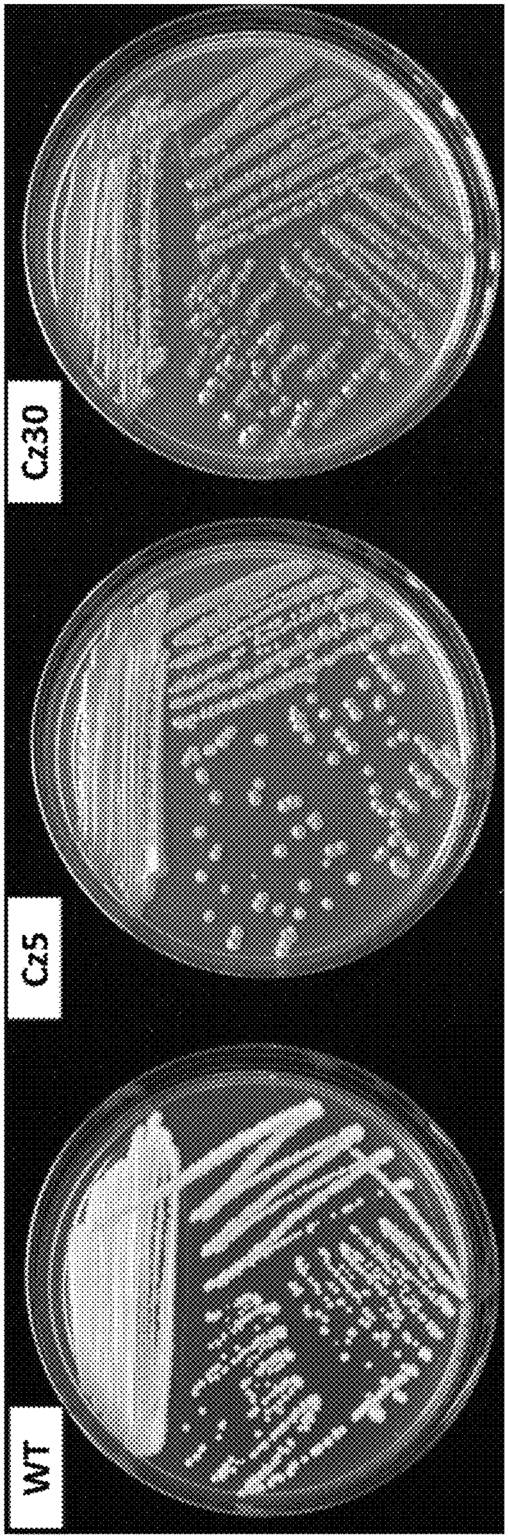
Figure 19B:
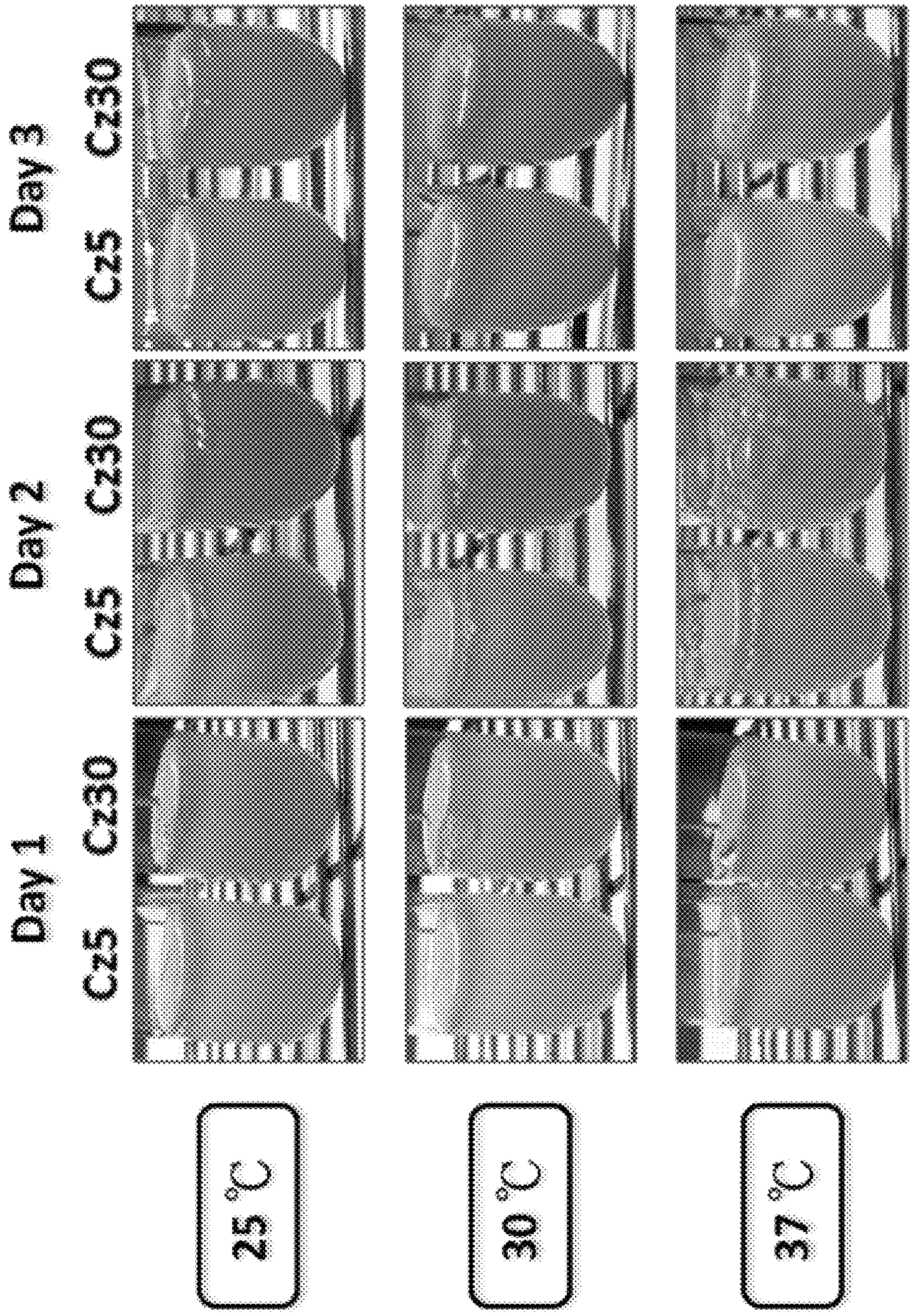
Figure 19C:
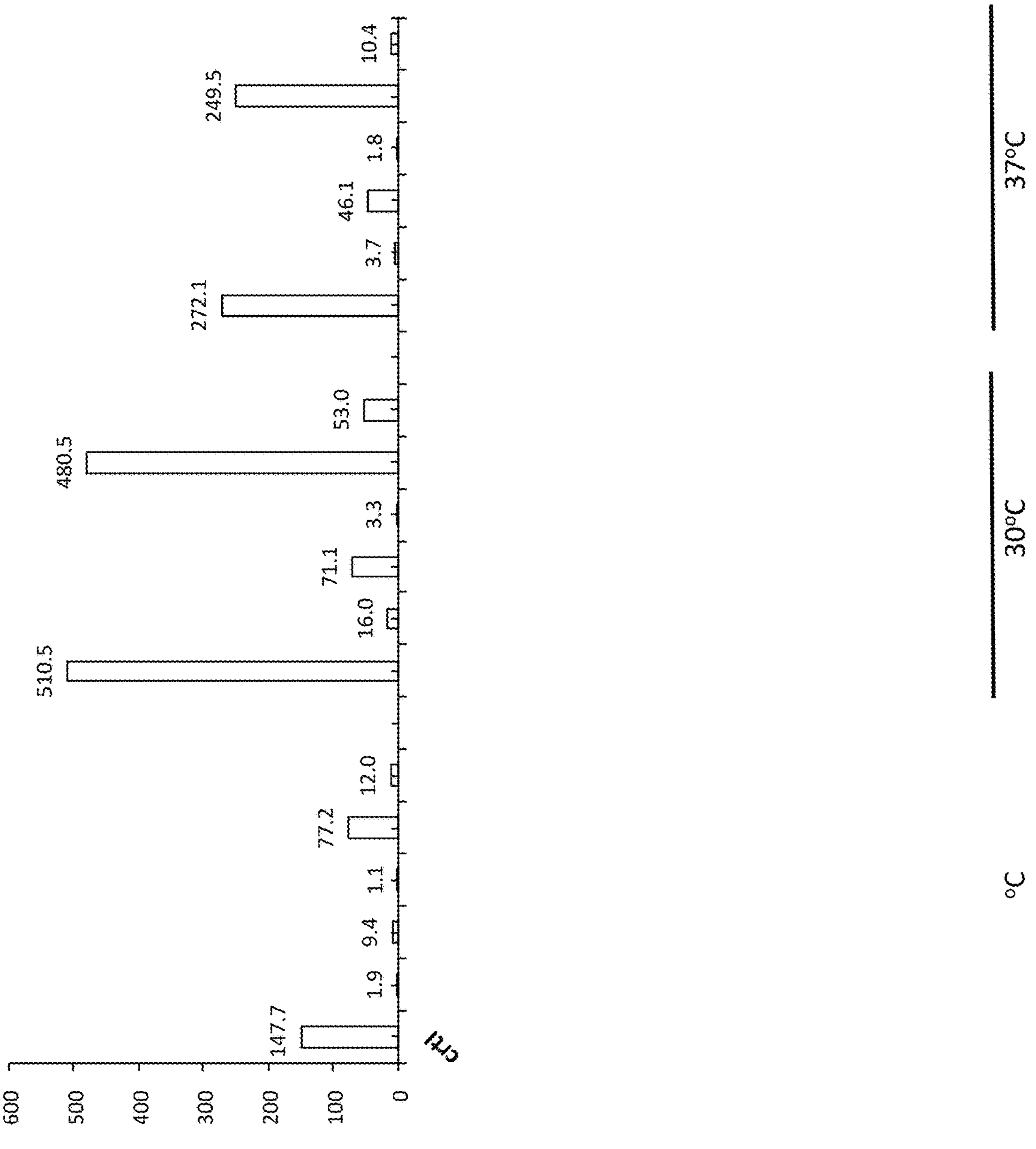
Figure 20A:
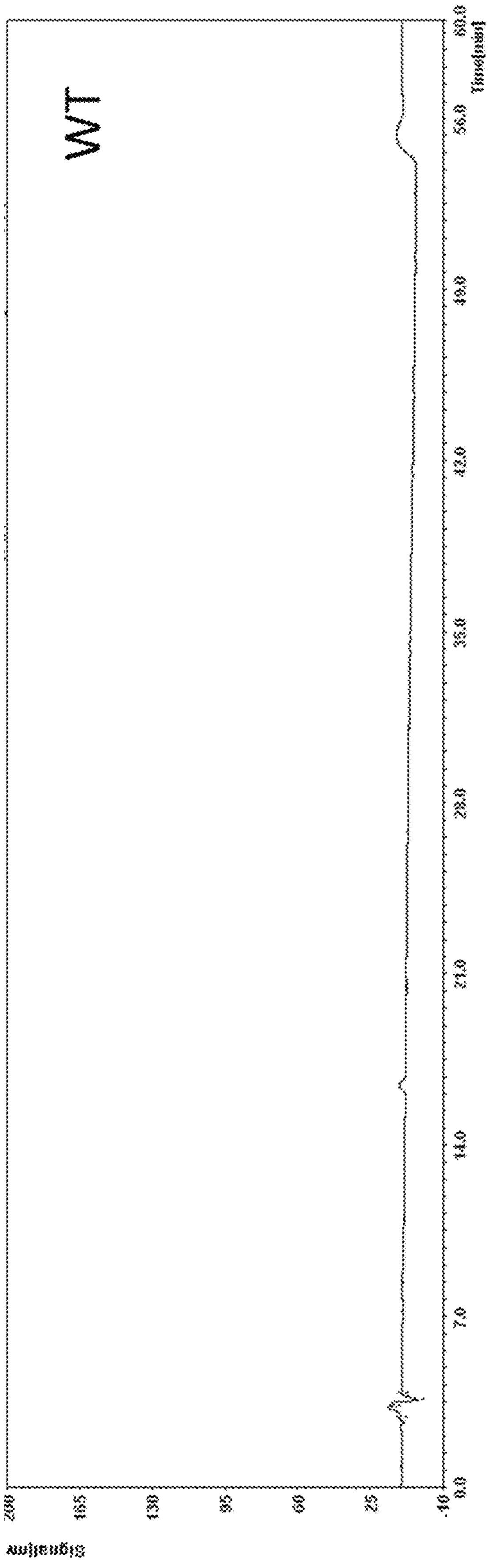
Figure 20B:
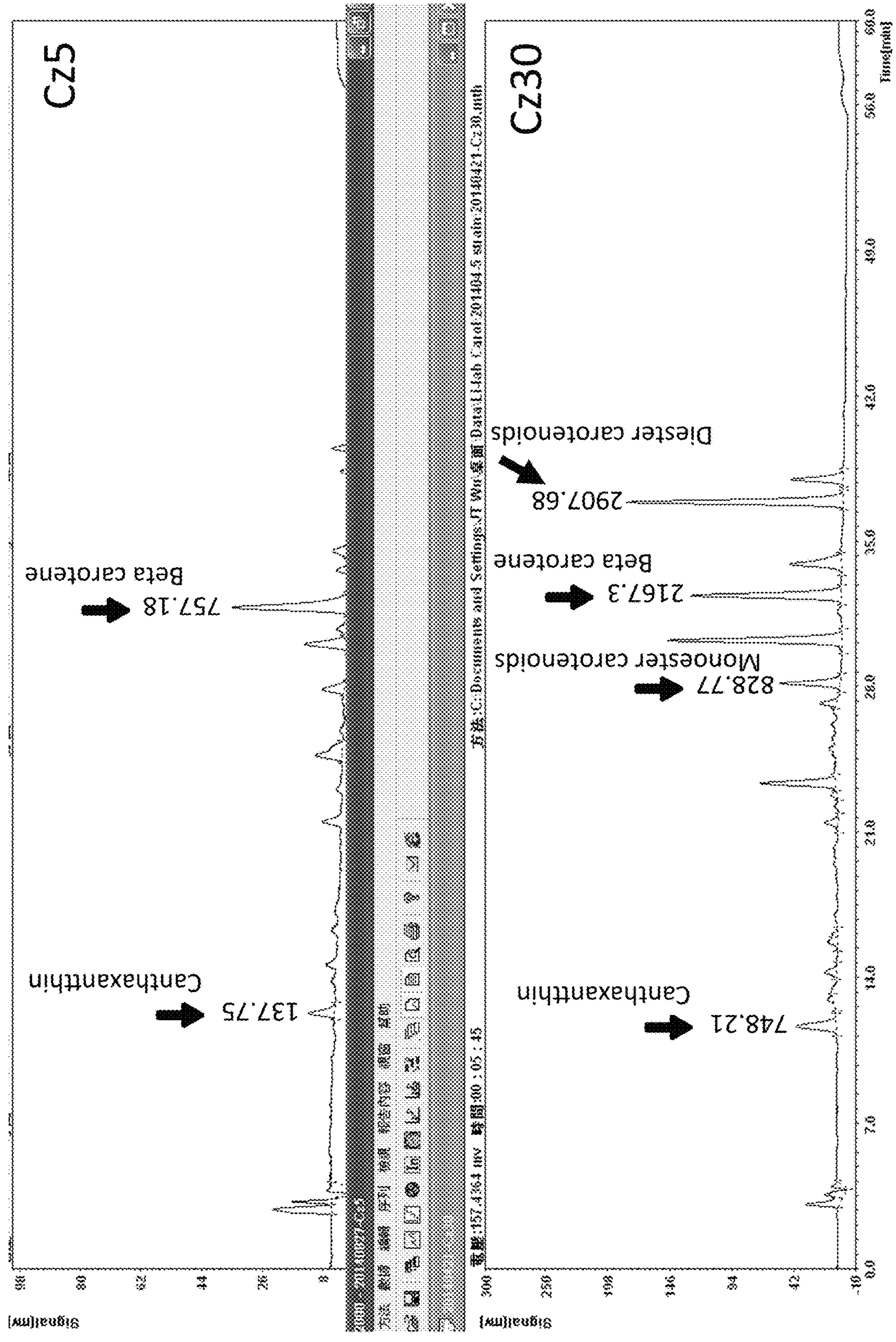
Figure 21A:
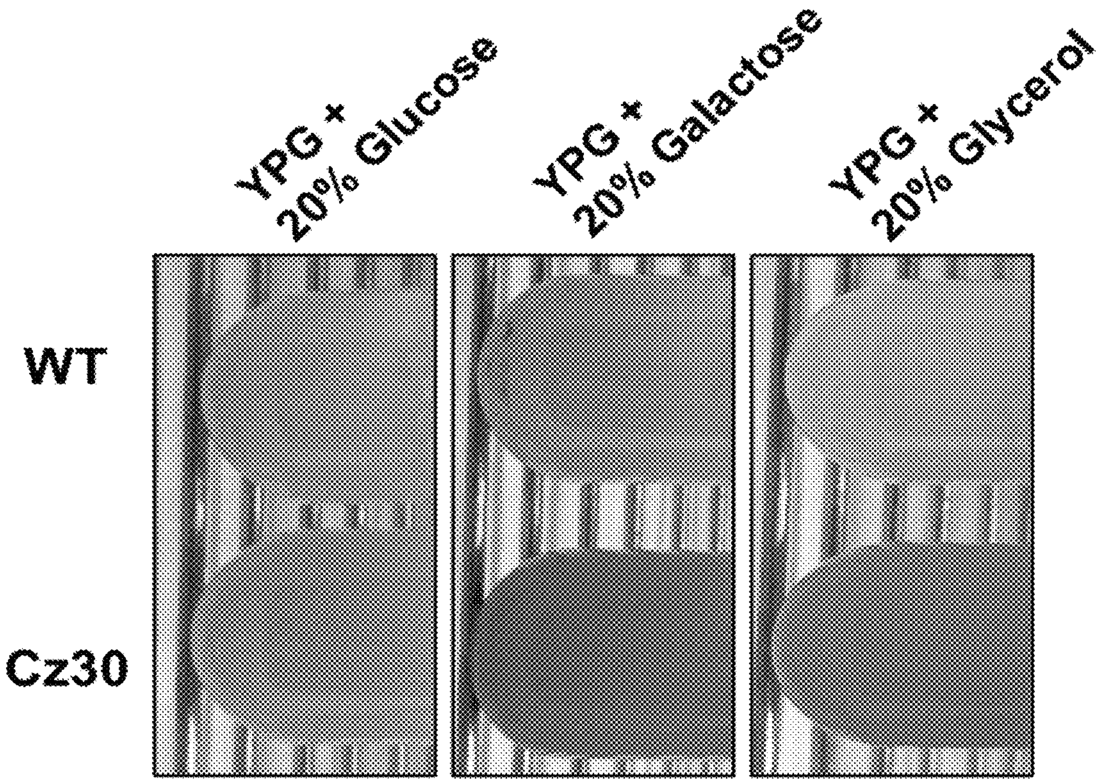
Figure 21B:
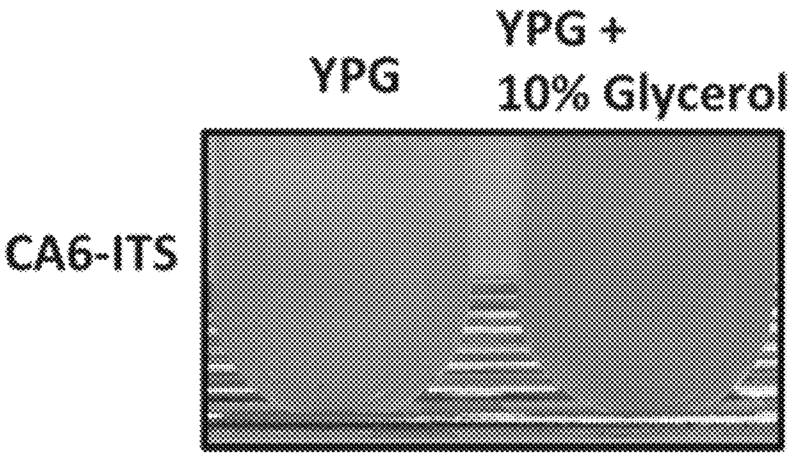
Figure 22:
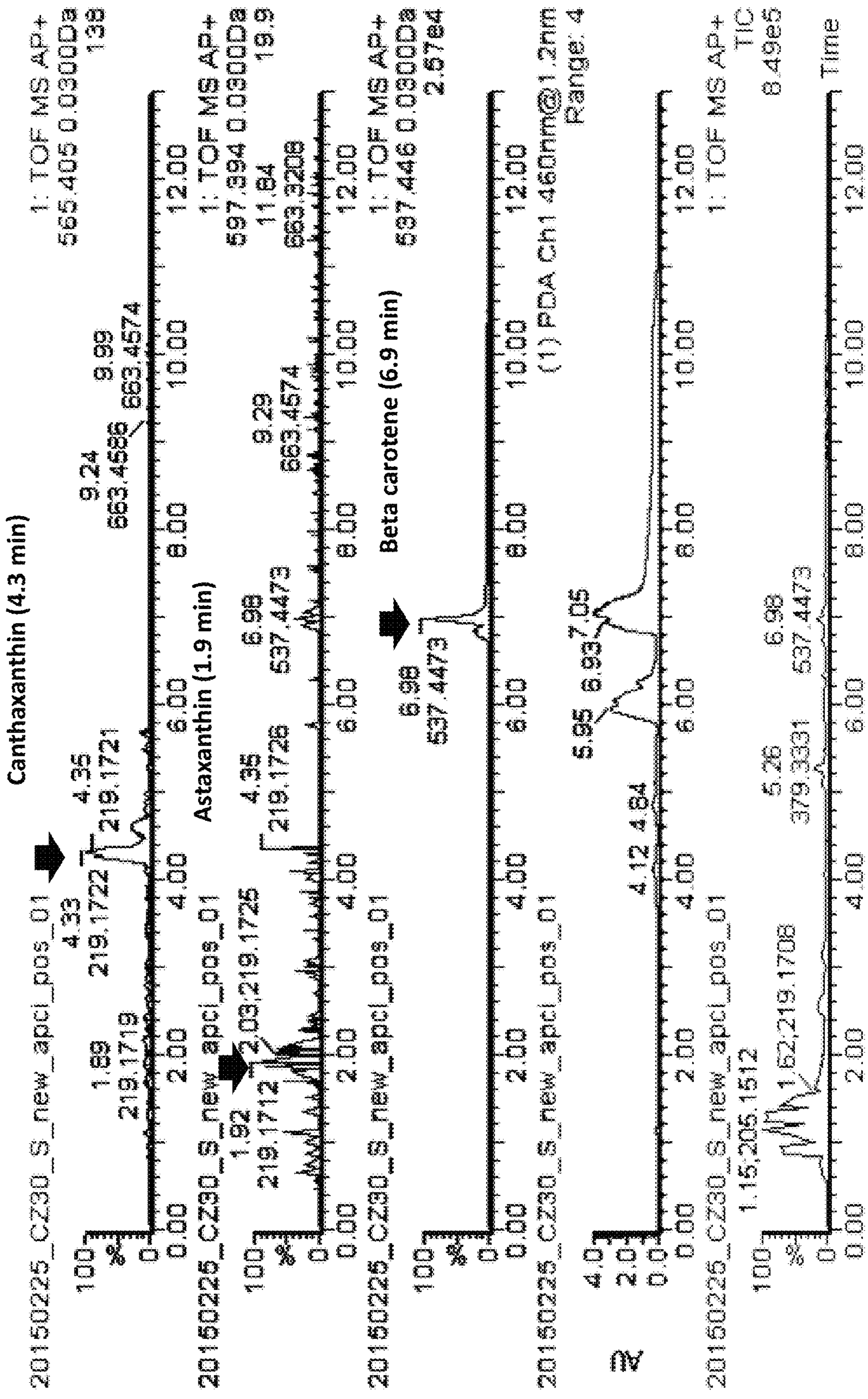
Figure 23A:
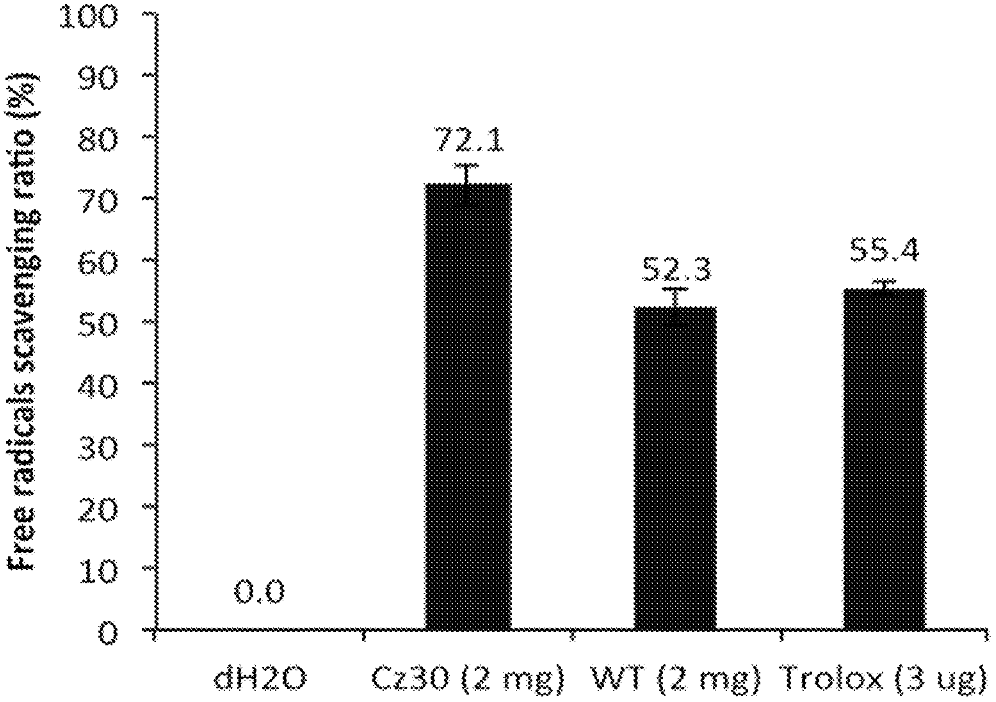
Figure 23B:
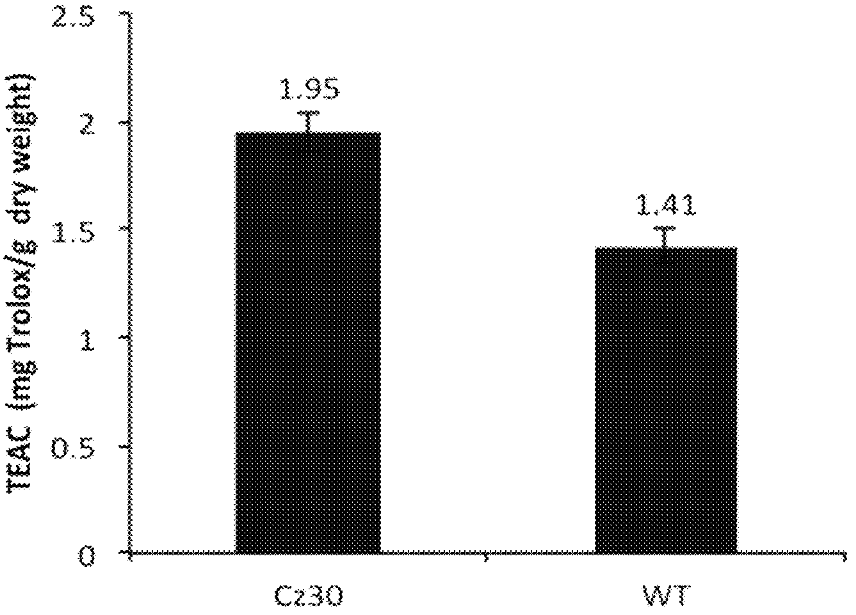
Figure 24A:
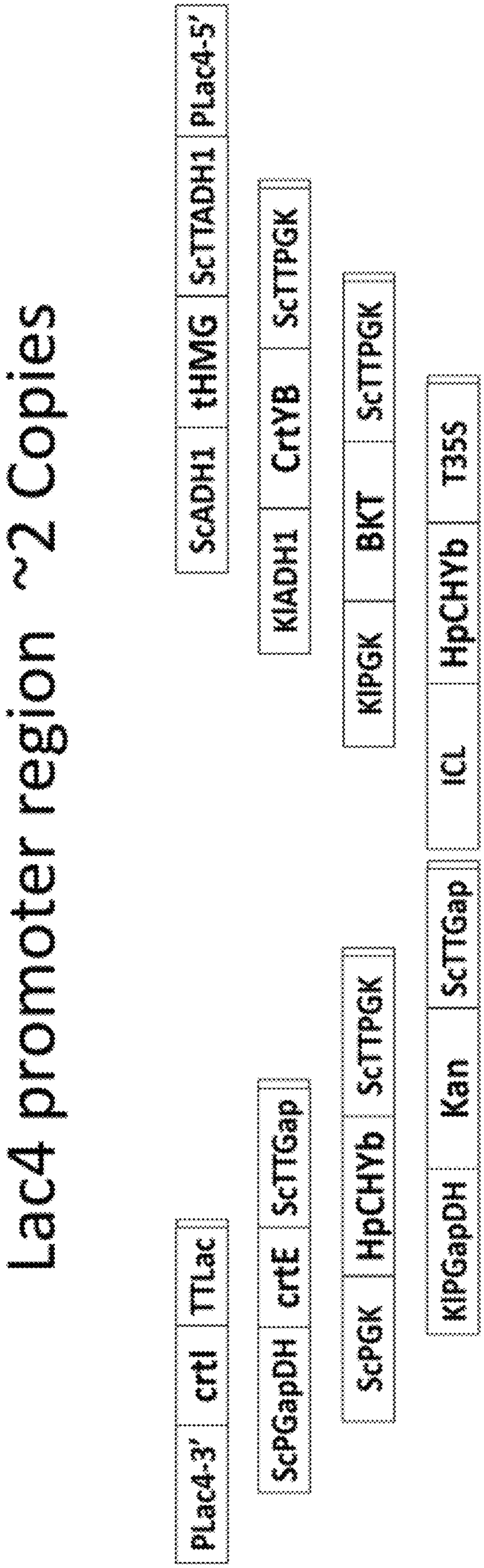
Figure 24B:
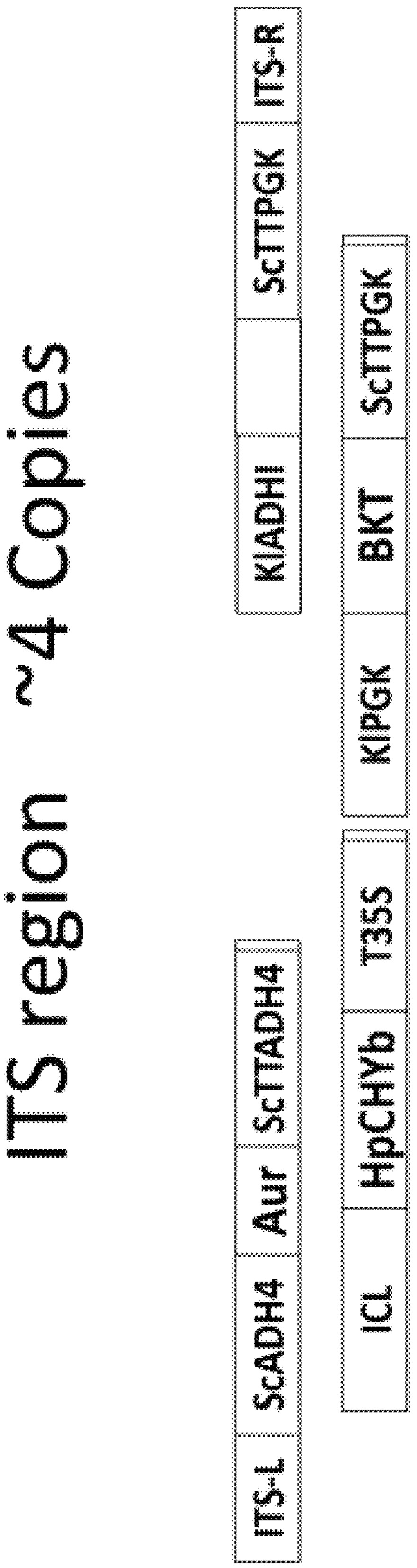
Figure 24C:
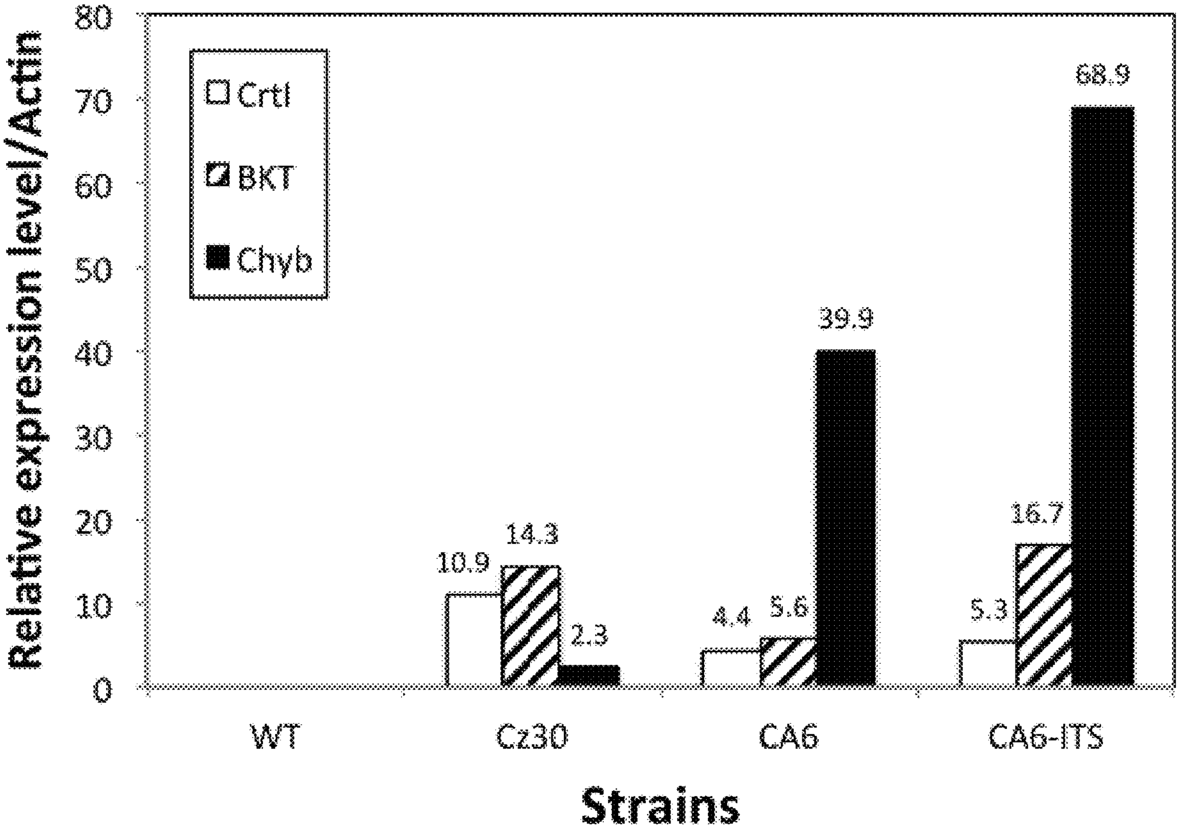
Figure 24D:
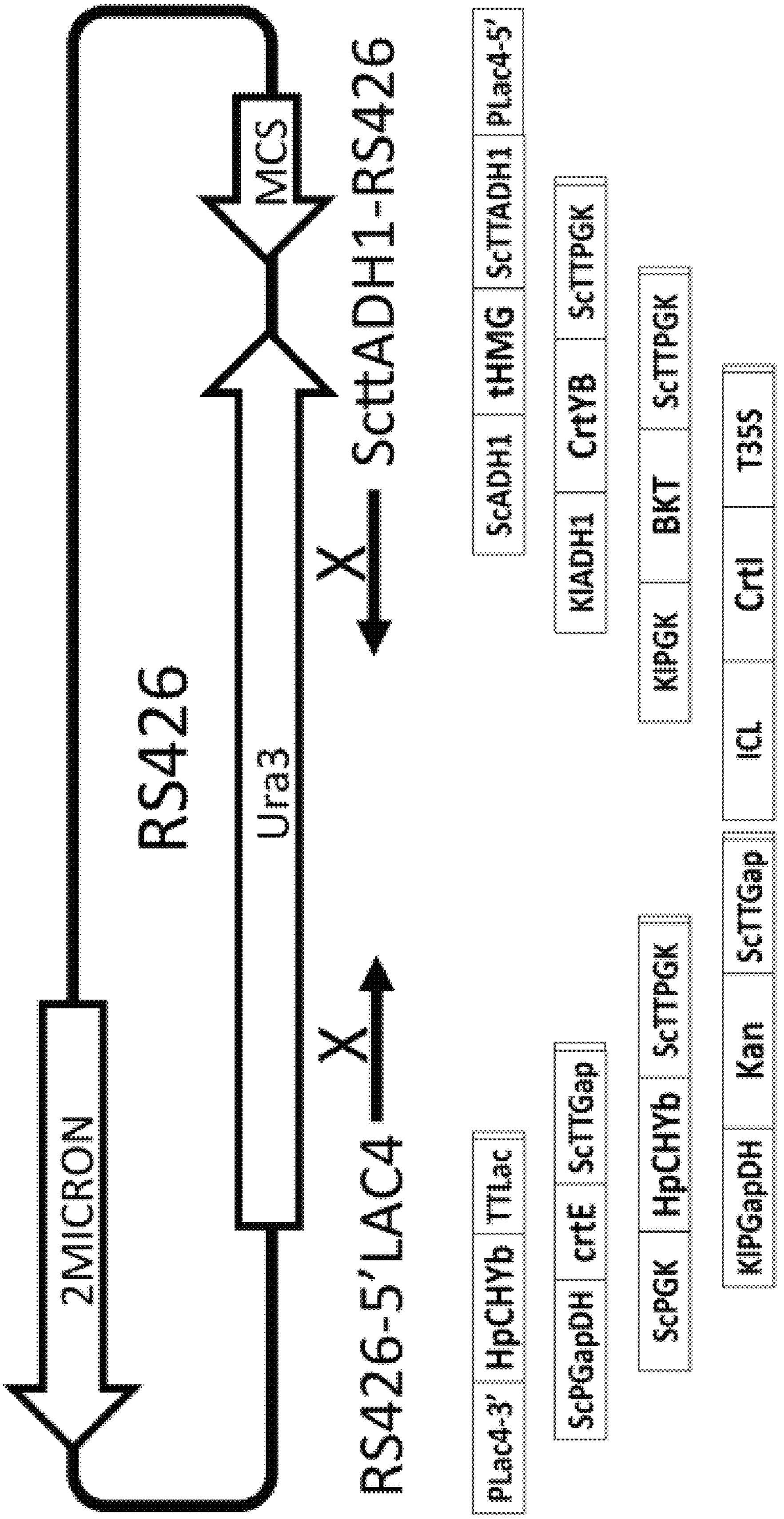
Figure 24E:
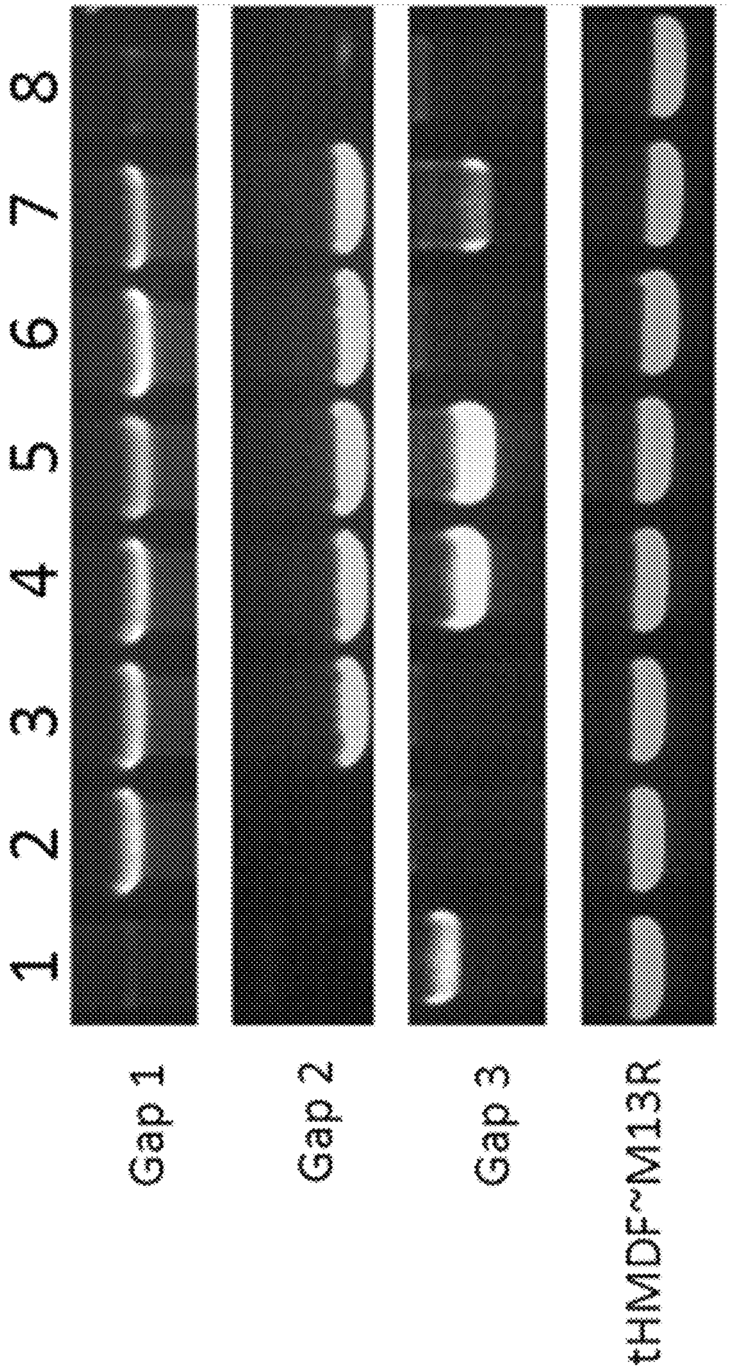
Figure 24F:
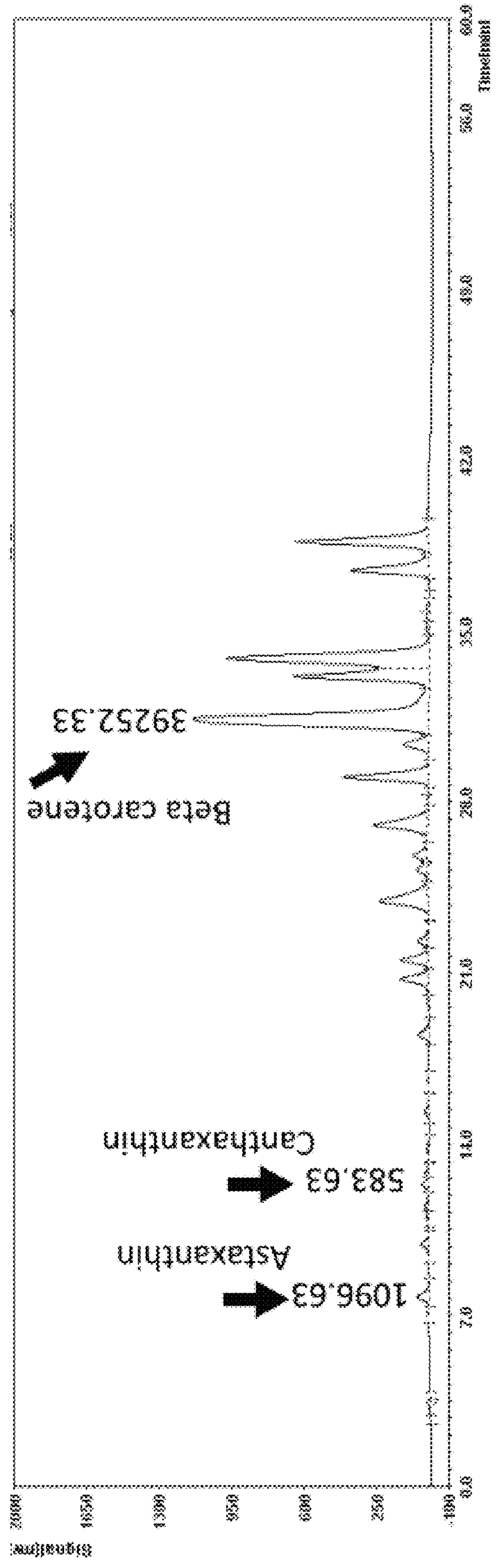
Figure 25A:
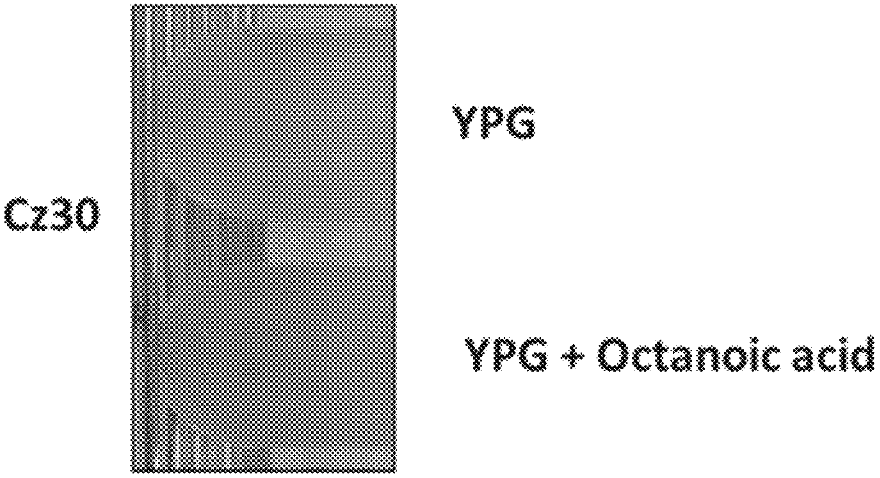
Figure 25B:
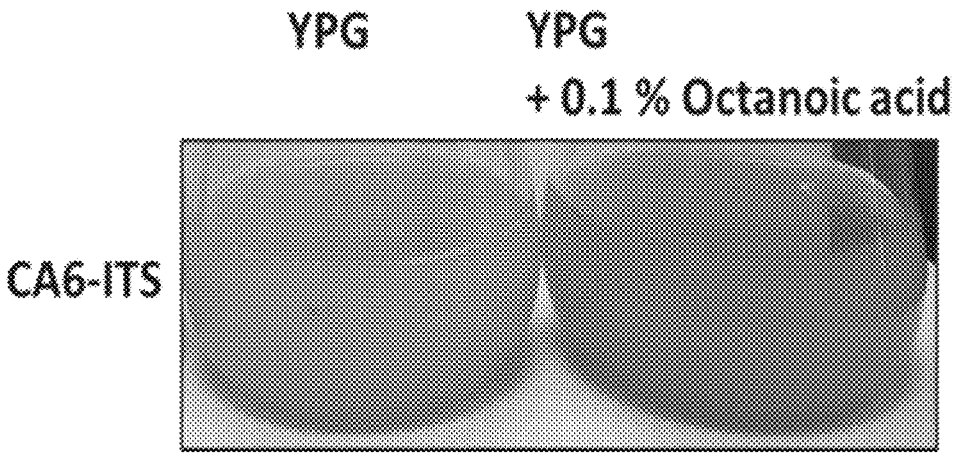
Figure 26A:
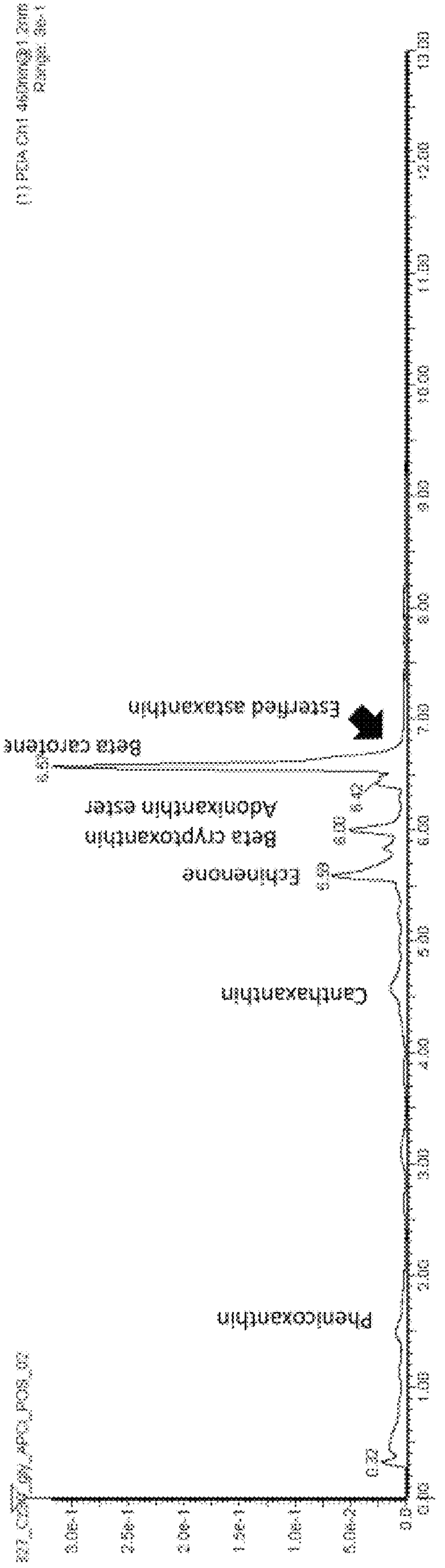
Figure 26B:
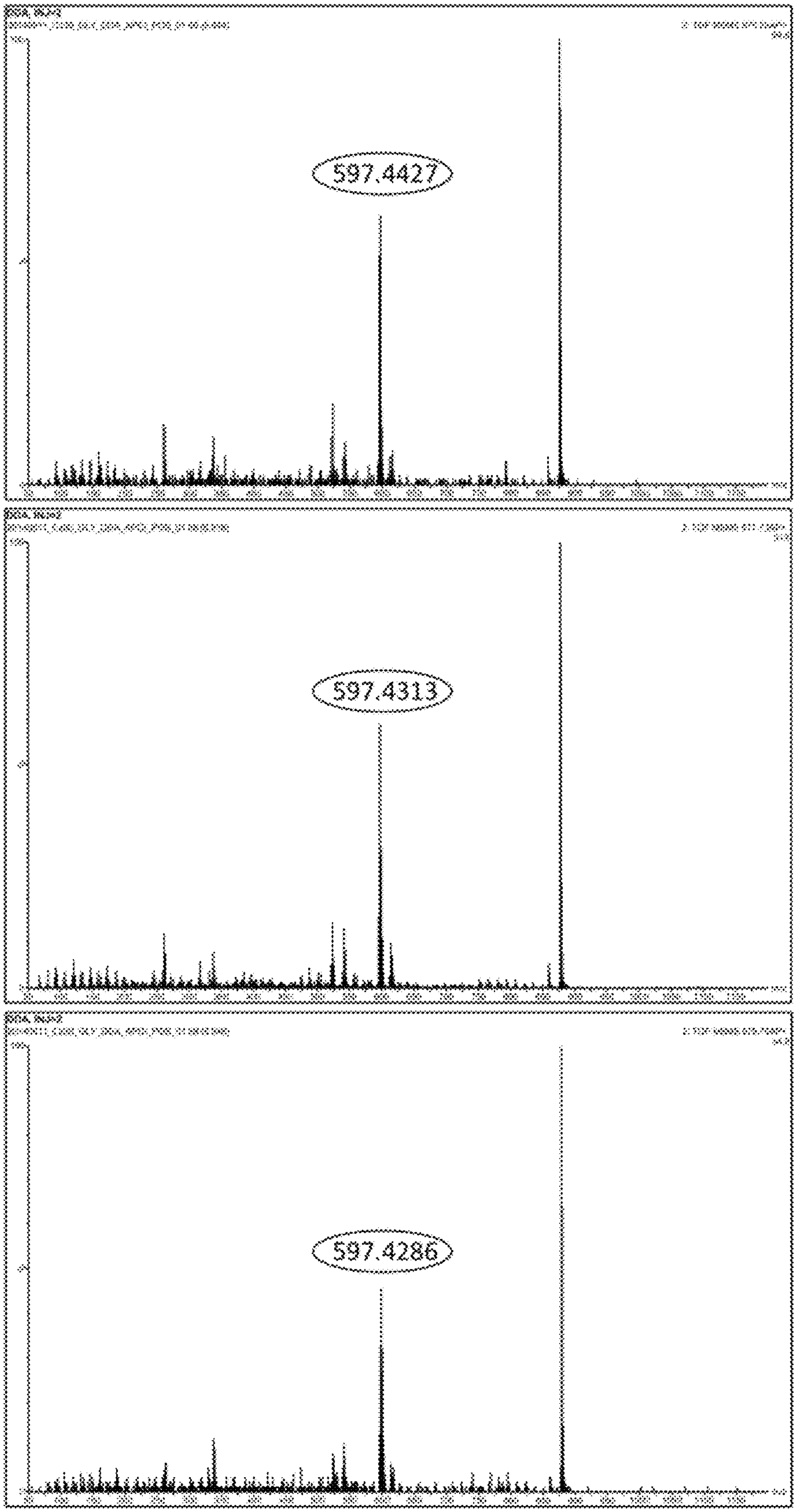
Figure 28A:
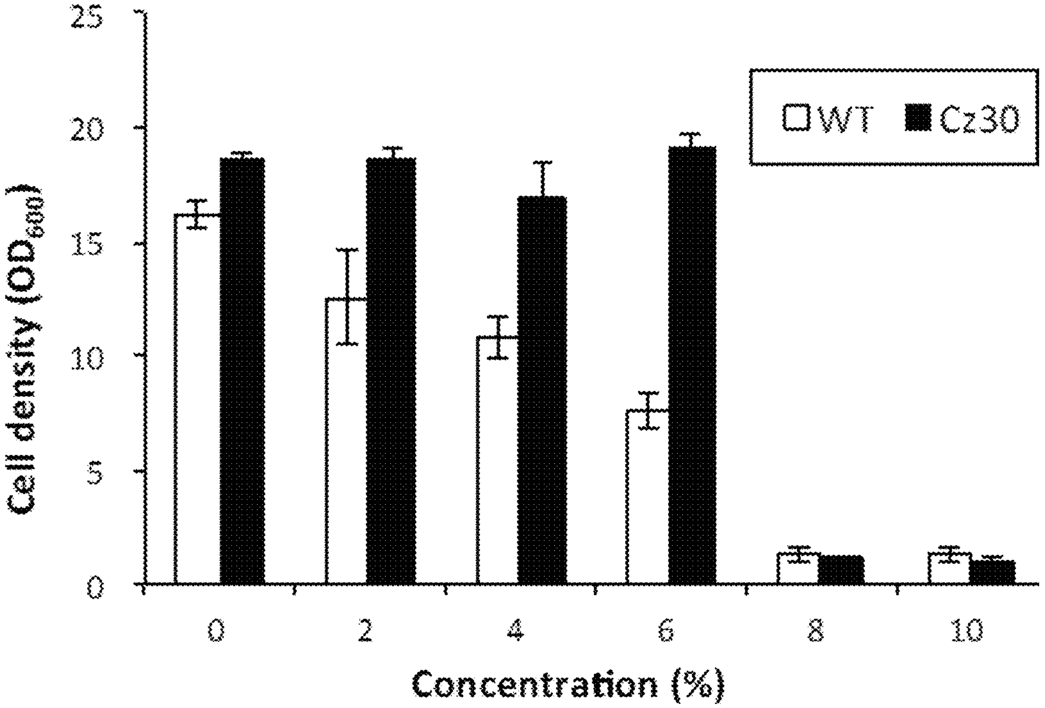
Figure 28B:
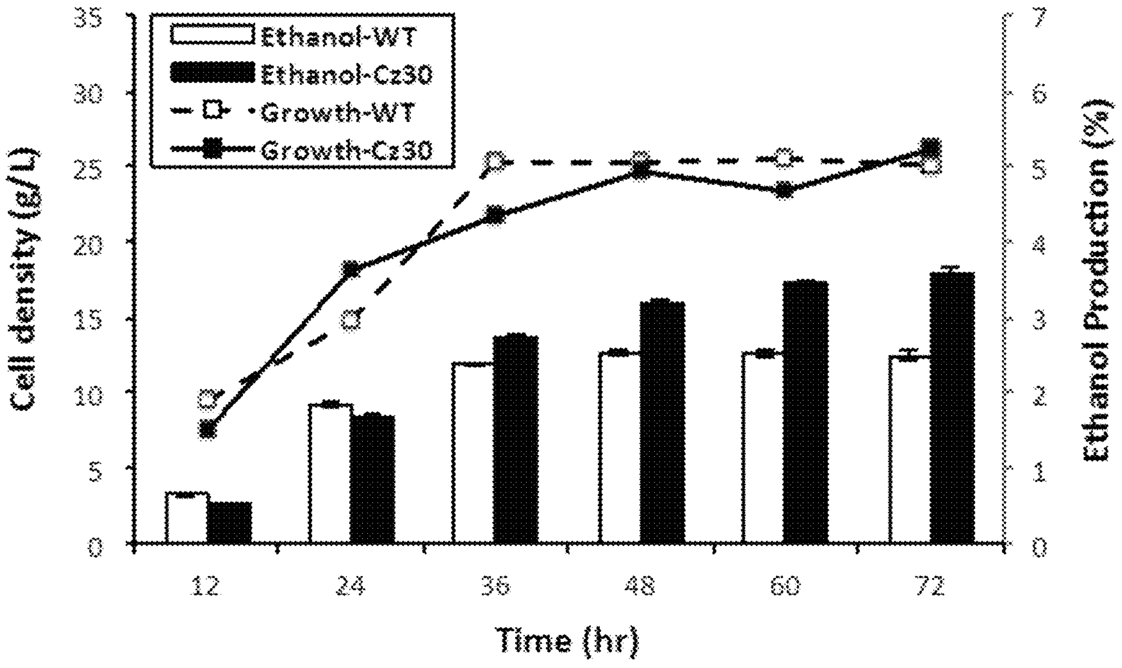
Figure 29A:
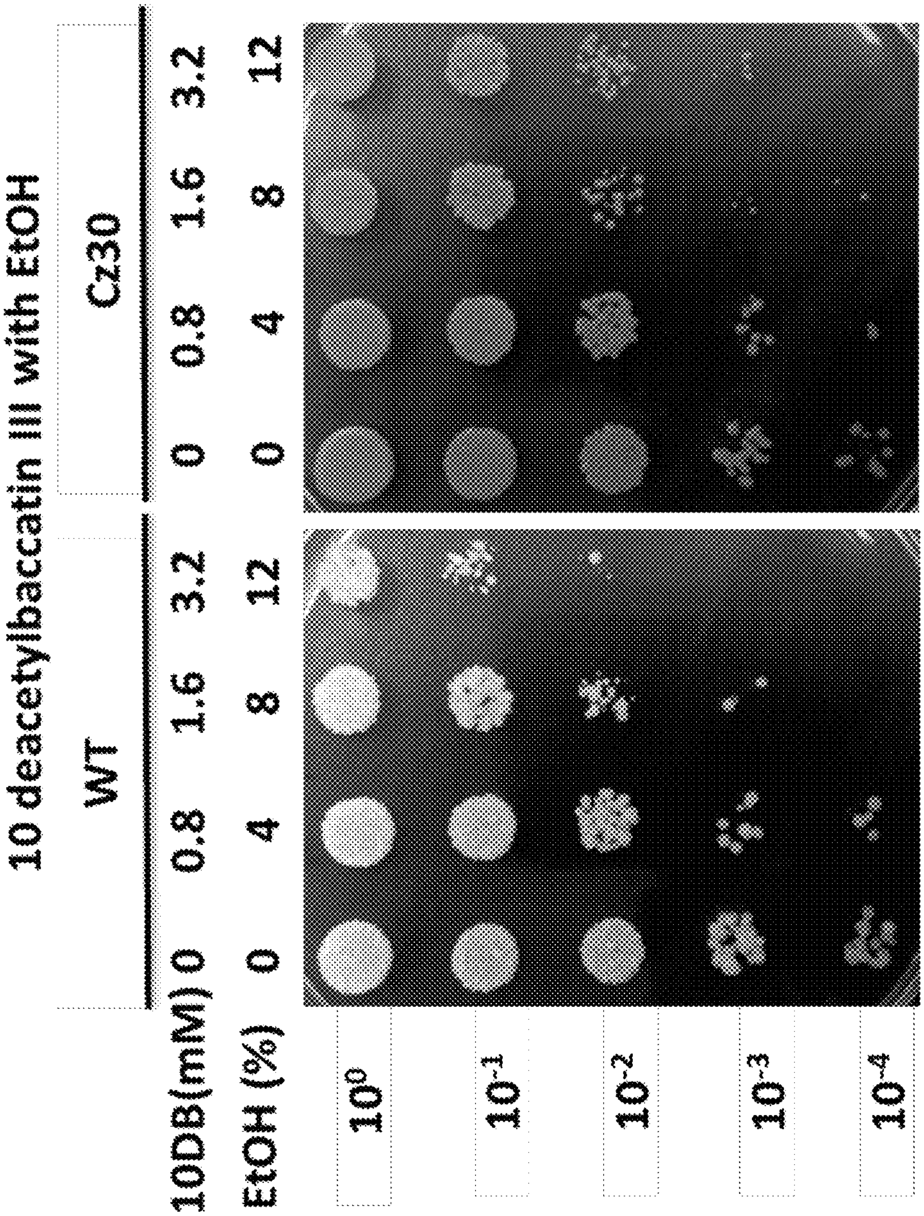
Figure 29B:
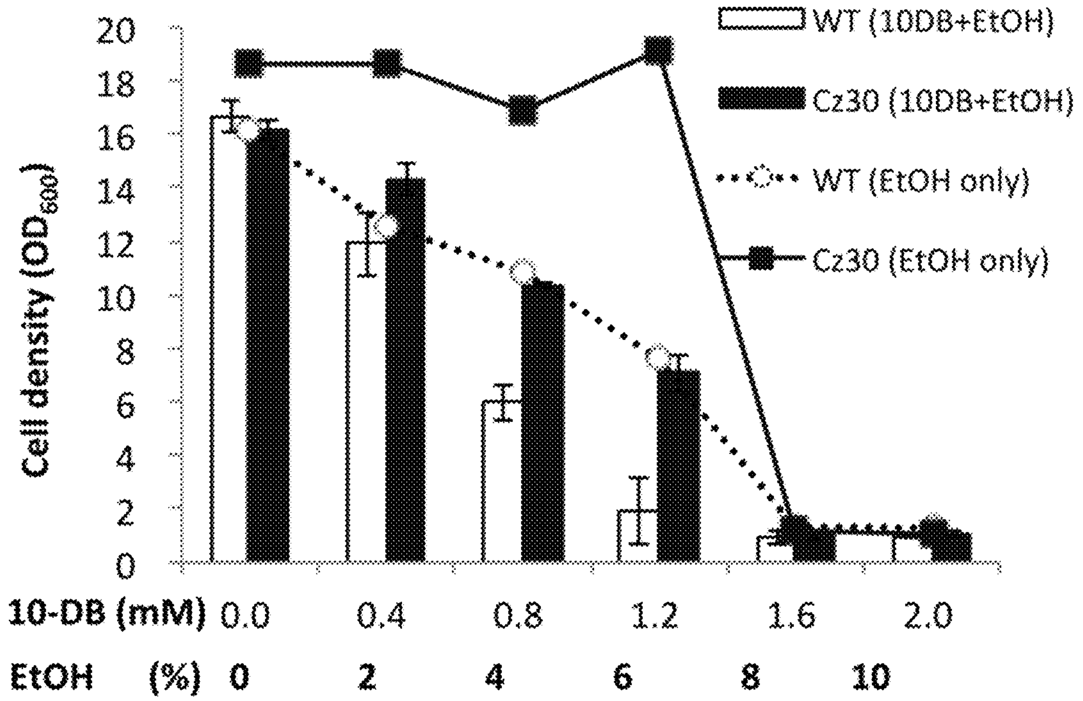
Figure 30A:
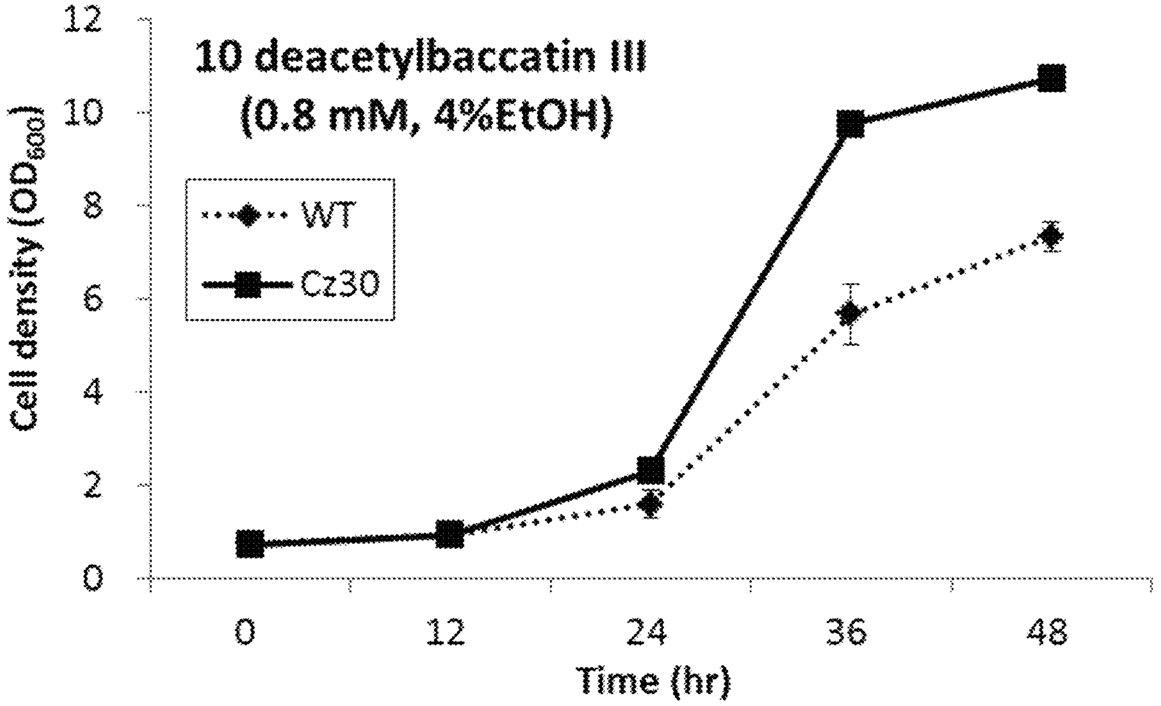
Figure 30B:
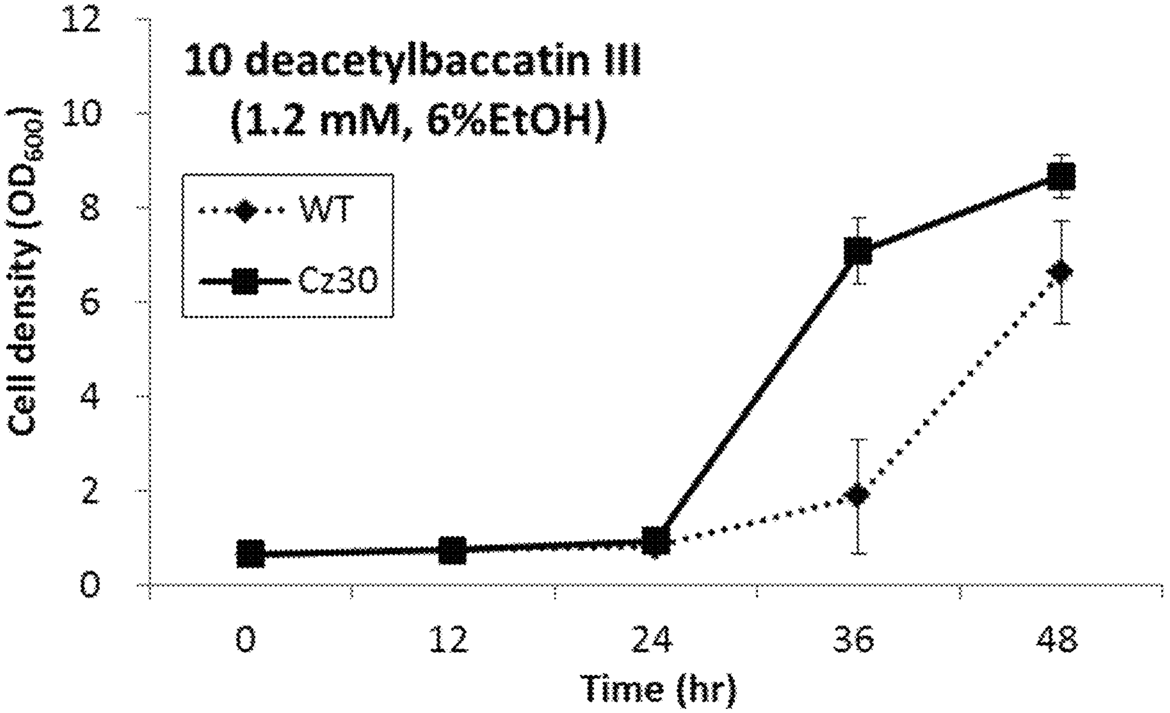
Figure 31:
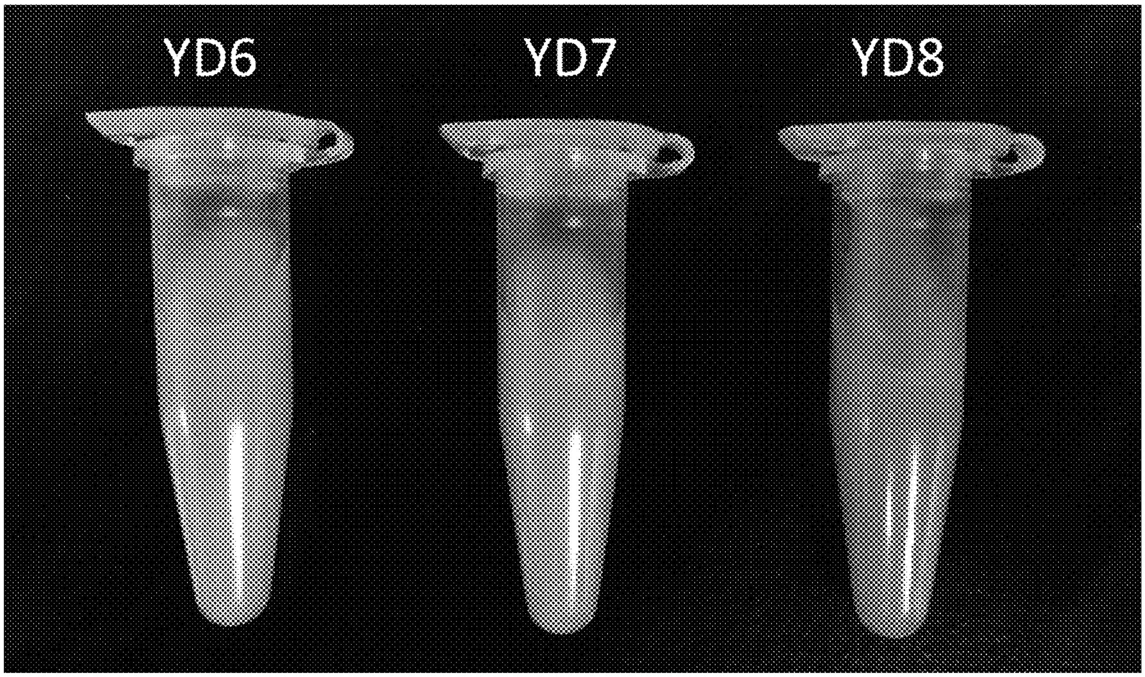

CAB51949 represents the lycopene cyclase derived from *Xanthophyllomyces dendrorhous*, XP_762434 represents the lycopene cyclase derived from *Ustilago maydis* 521, NP_344223 represents the lycopene cyclase derived from *Sulfolobus solfataricus* P2, and YP_024312 represents the lycopene cyclase derived from *Picrophilus torridus* DSM 9790 according to one example of the present disclosure;

FIG. 7*b* is a schematic diagram that depicts the conserved residues within the catalytic domains 1-2 of lycopene cyclase domain, in which the conserved residues are highlighted with underlines according to one example of the present disclosure;

FIG. 7*c* is a sequence alignment data that depicts the conserved region of trans-isoprenyl diphosphate synthases, in which the catalytic domains 1-2 are marked with underlines; CAB51949 represents the trans-isoprenyl diphosphate synthase derived from *Xanthophyllomyces dendrorhous*, NP_279693 represents the trans-isoprenyl diphosphate synthase derived from *Halobacterium* sp. NRC-1, NP_681887 represents the trans-isoprenyl diphosphate synthase derived from *Thermosynechococcus elongatus* BP-1, and ZP_00089878 represents the trans-isoprenyl diphosphate synthase derived from *Azotobacter vinelandii* according to one example of the present disclosure;

FIG. 7*d* is a schematic diagram that depicts the conserved residues within the catalytic domains 1-2 of trans-isoprenyl diphosphate synthase, in which the conserved residues are highlighted with underlines according to one example of the present disclosure;

FIG. 8*a* is a sequence alignment data that depicts the conserved region of phytoene desaturases, in which the NAD(P)-binding Rossmann-like domain is marked with underline; AAO53257 represents the phytoene desaturase derived from *Xanthophyllomycesene desatura*; CAE07416 represents the phytoene desaturase derived from *Synechococcus* sp. WH 8102, BAA10798 represents the phytoene desaturase derived from *Synechocystis* sp. PCC 6803, BAB73763 represents the phytoene desaturase derived from *Nostoc* sp. PCC 7120, and AAL91366 represents the phytoene desaturase derived from *Solanum lycopersicum* according to another example of the present disclosure;

FIG. 8*b* is a schematic diagram that depicts the conserved residues within the NAD(P)-binding Rossmann-like domain of phytoene desaturase, in which the conserved residues are highlighted with underlines according to another example of the present disclosure;

FIG. 9 is a schematic diagram that depicts a genetically engineered strain Xd 5.0 comprising the recombinant polynucleotide sequence, which comprises 5 gene cassettes (abbreviated as crtI-crtE-Kan-crtYB-tHMG1) according to one example of the present disclosure;

FIGS. 10*a* and 10*b* are sequence alignments data that depict the conserved region of β-carotene oxygenases, in which the catalytic domains 1-3 are marked with underlines; AAY33921 represents the β-carotene oxygenase derived from *Xanthophyllomyces dendrorhous*; Q08477 represents the β-carotene oxygenase derived from *Homo sapiens*, P33274 represents the β-carotene oxygenase derived from *Rattus norvegicus*, P11707 represents the β-carotene oxygenase derived from *Oryctolagus cuniculus*, and P33270 represents the β-carotene oxygenase derived from *Drosophila melanogaster* according to another example of the present disclosure;

FIG. 10*c* is a schematic diagram that depicts the conserved residues within the catalytic domains 1-3 of β-carotene oxygenase, in which the conserved residues are highlighted with underlines according to another example of the present disclosure;

FIGS. 11*a* and 11*b* are sequence alignment data that depict the conserved region of P450 reductases, in which the flavodoxin domains (FIG. 11*a*) and the NADPH cytochrome p450 reductase domains (FIG. 11*b*) are respectively marked with underlines; ACI43097 represents the P450 reductase derived from *Xanthophyllomyces dendrorhous*, Q00141 represents the P450 reductase derived from *Aspergillus niger*, NP_596046 represents the P450 reductase derived from *Schizosaccharomyces pombe*, XP_001731494 represents the P450 reductase derived from *Malassezia globosa* CBS 7966, and XP_762420 represents the P450 reductase derived from *Ustilago maydis* 521 according to one example of the present disclosure;

FIG. 11*c* is a schematic diagram that depicts the conserved residues within the flavodoxin domains 1-4 of P450 reductase, in which the conserved residues are highlighted with underlines according to one example of the present disclosure;

FIG. 11*d* is a schematic diagram that depicts the conserved residues within the NADPH cytochrome p450 reductase domains 1-5, in which the conserved residues are highlighted with underlines according to one example of the present disclosure;

FIG. 12 is a schematic diagram that depicts a genetically engineered strain Xd 7-3 comprising the recombinant polynucleotide sequence, which comprises 7 gene cassettes (abbreviated as crtI-crtR-crtE-Kan-crtS-crtYB-tHMG1) according to one example of the present disclosure;

FIG. 13*a* are photographs that respectively depict the phenotype of the agar plate culturing of specified strains, in which all the strains were selected with a 10 generation sub-culturing according to another example of the present disclosure;

FIG. 13*b* is a schematic diagram that depicts the scheme used to construct the recombinant polynucleotide sequence according to another example of the present disclosure;

FIG. 13*c* are the photographs of gel electrophoresis that respectively depict the DNA segments extracted from the specified strains followed by amplification via colony PCR assay according to one example of the present disclosure;

FIG. 14*a* is a sequence alignment data that depicts the conserved region of β-carotene ketolases, in which the catalytic domains 1-4 are marked with underlines; XP_001698699 represents the β-carotene ketolase derived from *Chlamydomonas reinhardtii*, BAB74888 represents the β-carotene ketolase derived from *Nostoc* sp. PCC 7120, NP_924674 represents the β-carotene ketolase derived from *Gloeobacter violaceus* PCC 7421, ABB25938 represents the β-carotene ketolase derived from *Synechococcus* sp. CC9902, and CAE07883 represents the β-carotene ketolase derived from *Synechococcus* sp. WH 8102 according to another example of the present disclosure;

FIG. 14*b* is a schematic diagram that depicts the conserved residues within the catalytic domains 1-4 of β-carotene ketolase, in which the conserved residues are highlighted with underlines according to another example of the present disclosure;

FIG. 15*a* is a sequence alignment data that depicts the conserved region of β-carotene hydroxylase, in which the catalytic domains 1-2 are outlined by red rectangle borders; XP_001698698 represents the β-carotene hydroxylase derived from *Chlamydomonas reinhardtii*, ABS50237 represents the β-carotene hydroxylase derived from *Chromochloris zofingiensis*, and Q9SPK6 represents the β-carotene hydroxylase derived from *Haematococcus pluvialis* according to one example of the present disclosure;

FIG. 15*b* is a schematic diagram that depicts the conserved residues within the catalytic domains 1-2 of β-carotene hydroxylase, in which the conserved residues are highlighted in red according to one example of the present disclosure;

FIG. 16*a* is a schematic diagram that depicts a genetically engineered strain Cr1 comprising the recombinant polynucleotide sequence, which comprises 7 gene cassettes (i.e., crtI-crtE-CrChYb-Kan-CrBKT-crtYB-tHMG1) according to one example of the present disclosure;

FIG. 16*b* is a schematic diagram that depicts a genetically engineered strain Hp9 comprising the recombinant polynucleotide sequence, which comprises 7 gene cassettes (i.e., crtI-crtE-HpChYb-Kan-CrBKT-crtYB-tHMG1) according to another example of the present disclosure;

FIG. 16*c* is a schematic diagram that depicts a genetically engineered strain Cz5 comprising the recombinant polynucleotide sequence, which comprises 7 gene cassettes (i.e., crtI-crtE-CzChYb-Kan-CrBKT-crtYB-tHMG1) according to still another example of the present disclosure;

FIG. 17*a* are photographs that respectively depict the broth containing specified strains according to one example of the present disclosure;

FIG. 17*b* are photographs that respectively depict the broth containing specified strains according to another example of the present disclosure;

FIG. 17*c* is a line chart that depicts the growth curve of specified strains according to one example of the present disclosure;

FIG. 17*d* is a line chart that depicts the full-spectrum UV/V of total carotenoids measured by spectrophotometry assay according to one example of the present disclosure;

FIGS. 18*a* and 18*b* present the high-performance liquid chromatography (HPLC) results of specified strains determined by HPLC spectrometry assay under UV450 nm, in which 1 indicates free-form canthaxanthin, 6 indicates free-form β-carotene, and 2, 3, 4, 5, 7, and 8 indicate unknown peaks according to another example of the present disclosure;

FIG. 19*a* are photographs that respectively depict the colonies of specified strains according to one example of the present disclosure;

FIG. 19*b* are photographs that respectively depict the broth containing specified strains under different temperatures according to one example of the present disclosure;

FIG. 19*c* are histograms that depict the gene expression according to one example of the present disclosure;

FIGS. 20*a* and 20*b* present the HPLC results of specified strains determined by HPLC spectrometry assay under UV450 nm according to one example of the present disclosure;

FIG. 21*a* is a photograph that depicts the broth containing specified strains and components according to another example of the present disclosure;

FIG. 21*b* is a photograph that depict the broth containing CA6-ITS strain and specified components according to another example of the present disclosure;

FIG. 22 presents the liquid chromatography-mass spectrometry (LC/MS) analysis under UV460 nm with saponification treatment according to one example of the present disclosure;

FIG. 23*a* is a histogram that depicts the free radicals scavenging ratio of specified strains, in which the ratio is determined by antioxidant capacity assay using ABTS substrate according to one example of the present disclosure;

FIG. 23*b* is a histogram that depicts the result of Trolox equivalent antioxidant capacity (TEAC) assay according to one example of the present disclosure;

FIG. 24*a* is a schematic diagram that depicts the recombinant polynucleotide sequence that comprises 8 gene cassettes according to one example of the present disclosure;

FIG. 24*b* is a schematic diagram that depicts the internal transcribed spacer (ITS) region of CA6-ITS strain that comprises 7 gene cassettes according to one example of the present disclosure;

FIG. 24*c* is a histogram that depicts the relative gene expression of specified genes that are respectively extracted from specified strains followed by analysis via reverse transcription polymerase chain reaction (RT-PCR) according to example of the present disclosure;

FIG. 24*d* is a schematic diagrams that depicts a high copy number plasmid RS426 comprising the present recombinant polynucleotide sequence according to another example of the present disclosure;

FIG. 24*e* is a photograph that depicts the result of electrophoresis according to one example of the present disclosure;

FIG. 24*f* presents the HPLC data of the astaxanthin produced by CA6-ITS strain according to one example of the present disclosure;

FIGS. 25*a* and 25*b* are photographs that depict the broth containing specified strains and components according to another example of the present disclosure;

FIG. 26*a* presents the ultra-performance liquid chromatography (UPLC) result measured by LC MS/MS analysis under UV460 nm according to one example of the present disclosure;

FIG. 26*b* presents the MS/MS result measured by LC MS/MS analysis under UV460 nm according to another example of the present disclosure;

FIGS. 27*a*, 27*b*, 27*c* and 27*d* are photographs that reveal the colonies of wild-type and Cz30 strains respectively treated with UV exposure (FIG. 27*a*), furfural (FIG. 27*b*), ethanol (FIG. 27*c*), and isobutanol (FIG. 27*d*) according to one example of the present disclosure;

FIG. 28*a* is a histogram that depicts the cell densities of wild-type and Cz30 strains respectively treated with different ethanol concentration according to another example of the present disclosure;

FIG. 28*b* is the data that depicts the cells densities and ethanol production of wild-type and Cz30 strains cultivated in YPG medium containing 20% galactose, in which left y axis represents the cells density, the right y axis represents the ethanol production, and the x axis represents the time dimension according to another example of the present disclosure;

FIG. 29*a* are photographs that reveal the colonies of wild-type and Cz30 strains respectively treated with specified concentration of 10 deacetylbaccatin III (10 DB), which is dissolved in specified concentration of ethanol, according to one example of the present disclosure;

FIG. 29*b* is a histogram that depicts the cell densities of wild-type and Cz30 strains respectively treated with specified concentrations of 10 DB according to one example of the present disclosure;

FIGS. 30*a* and 30*b* are line charts that depict the growth curves of wild-type and Cz30 strains respectively treated with 0.8 mM 10 DB dissolved in 4% ethanol (FIG. 30*a*), and 1.2 mM 10 DB dissolved in 6% ethanol (FIG. 30*b*); and FIG. 31 is a photograph that depicts the bio-conversion of 10 DB in specified strains.

In accordance with common practice, the various described features/elements are not drawn to scale but instead are drawn to best illustrate specific features/elements relevant to the present invention.

DETAILED DESCRIPTION OF THE INVENTION

The detailed description provided below in connection with the appended drawings is intended as a description of the present example and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skills in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skills in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "control sequence" refers to polynucleotide sequences which are necessary to affect expression of coding sequences to which they are operably linked. The nature of such control sequences differs depending upon the host organism. In prokaryotes, control sequences generally include promoters, ribosomal binding sites, and terminators. In eukaryotes control sequences generally include promoters, terminators and enhancers or silencers. The term "control sequence" is intended to include, at a minimum, all components the presence of which are necessary for the expression of coding sequences, and may also include additional advantageous components and which determines when, how much and where a specific gene is expressed. In certain embodiments, the term "control sequence" includes the regulatory components other than the specified promoters.

Reference herein to a "promoter" is to describe a synthetic or fusion molecule or derivative, which confers, activates or enhances expression of a nucleic acid sequence in a cell, tissue or organ.

"Nucleic acid sequence", "polynucleotide" or "nucleic acid" can be used interchangeably and are understood to mean, according to the present disclosure, either a double-stranded DNA, a single-stranded DNA or a product of transcription of said DNA (e.g., RNA molecule). It should also be understood that the present disclosure does not relate to genomic polynucleic acid sequences in their natural environment or natural state. The nucleic acid, polynucleotide, or nucleic acid sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

The term "sequence identity" as used herein refers to the sequence relationships between two or more nucleic acids or amino acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. In some embodiments, two sequences have the same total number of nucleotides or amino acids. The aligned sequences can be analyzed by any method familiar with one skilled artisan, including GAP, BESTFIT, BLAST, FASTA, and TFASTA.

Figure 1:
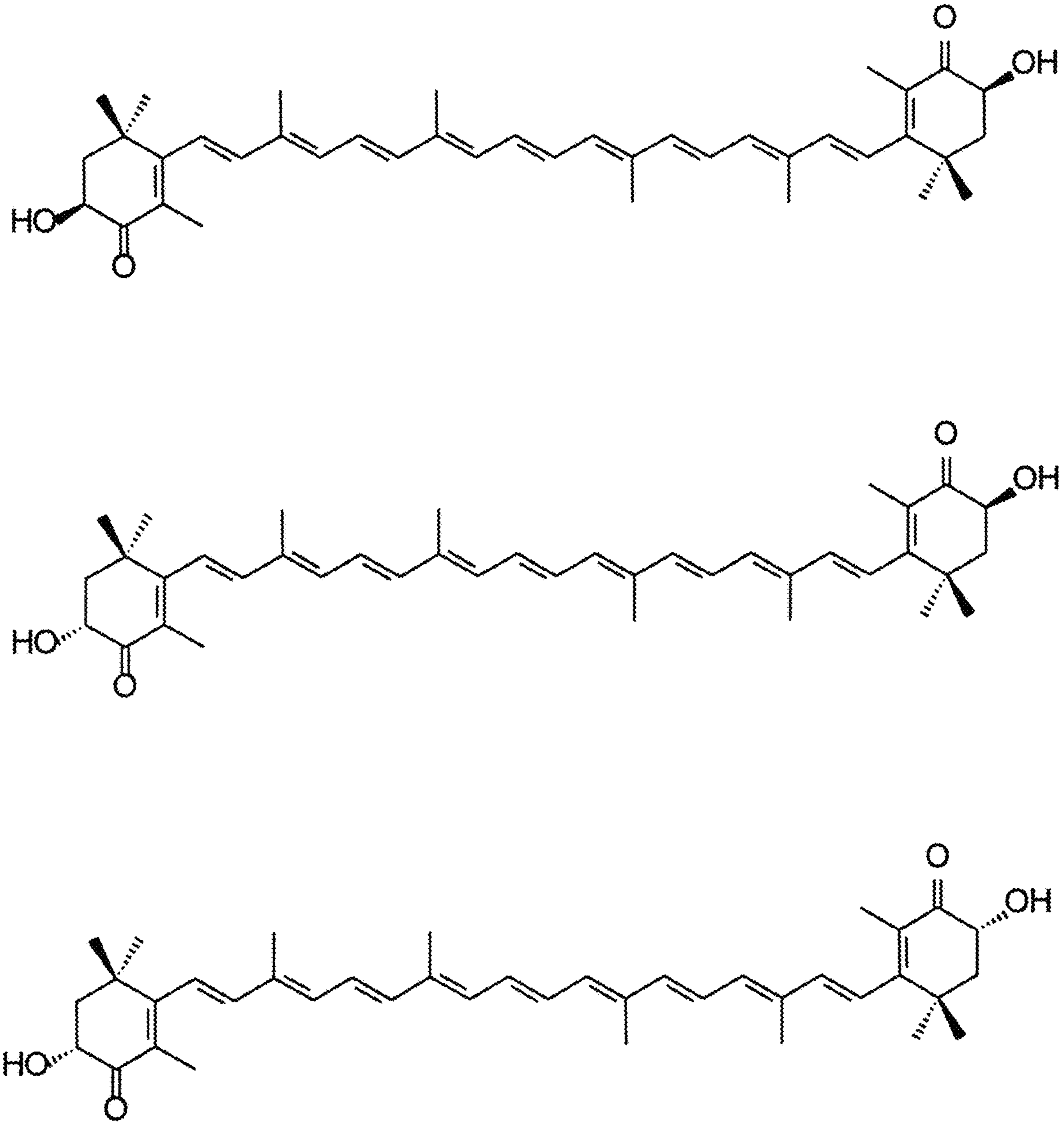
FIG. 1 are drawings that respectively depict the chemical structures of 3S, 3'S astaxanthin (upper panel), 3R, 3'R astaxanthin (middle panel), and 3R, 3'S astaxanthin (lower panel)
Figure 2A:
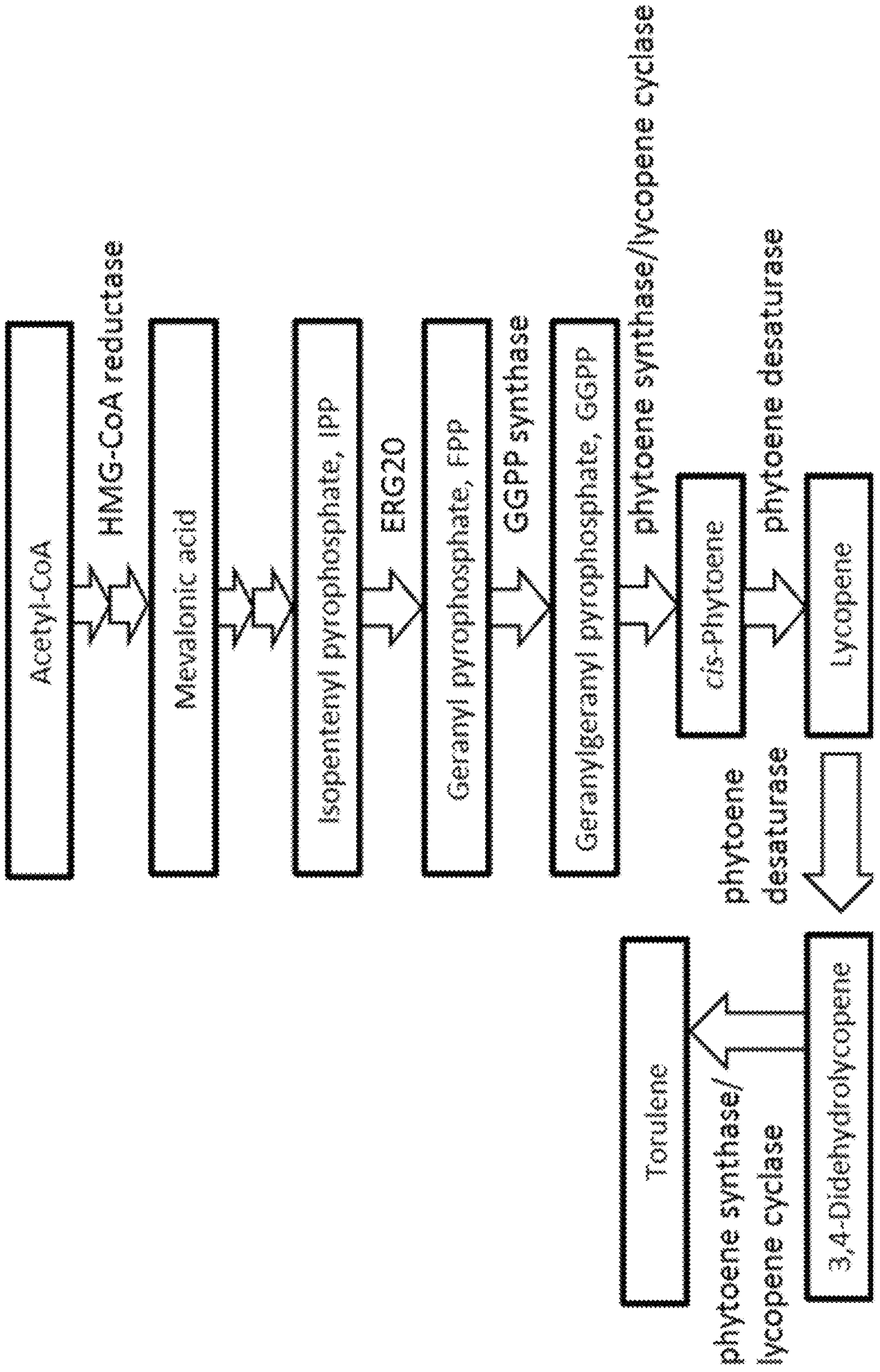
FIGS. 2*a* and 2*b* are schematic diagrams that depict the carotenoid biosynthetic pathway.
Figure 2B:
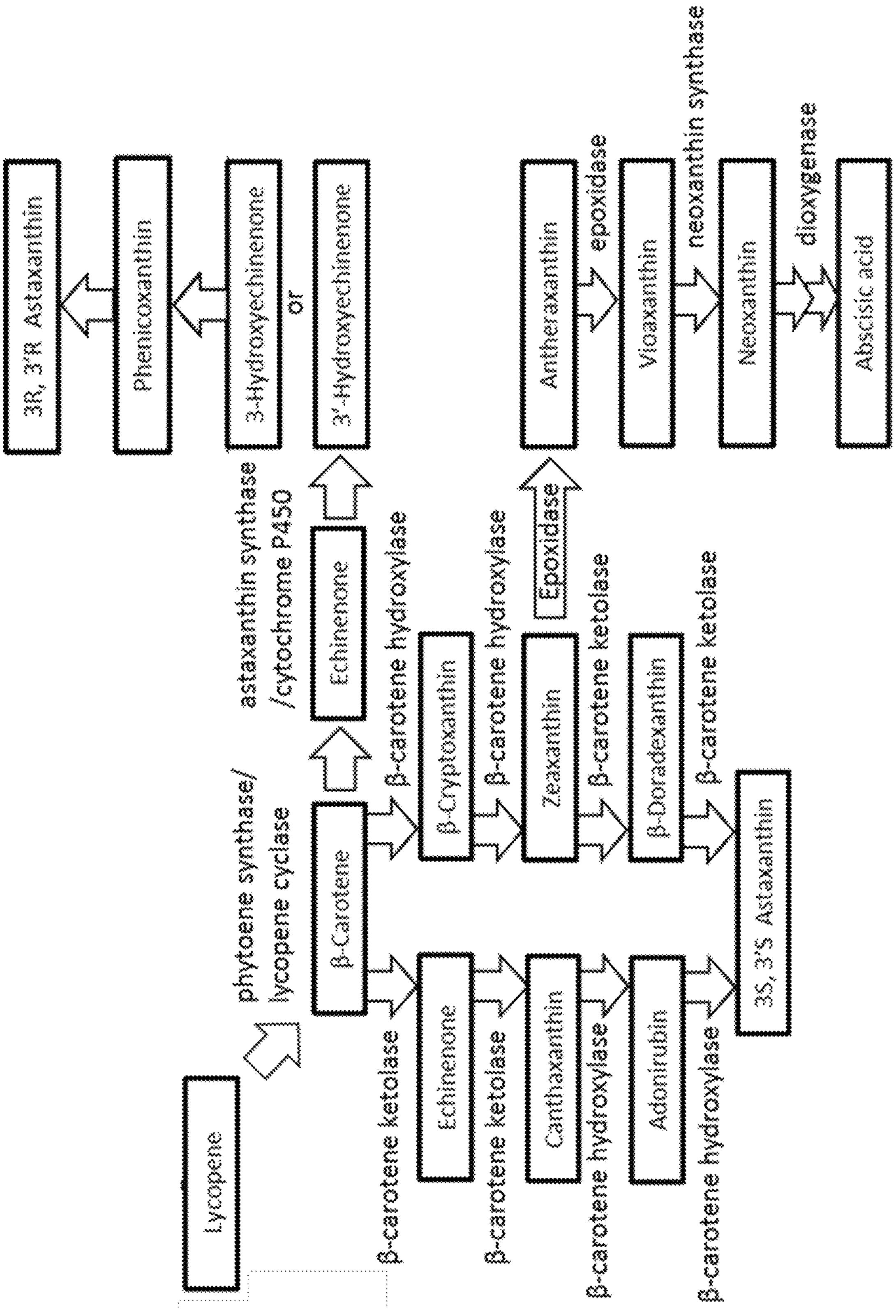
Figure 3A:
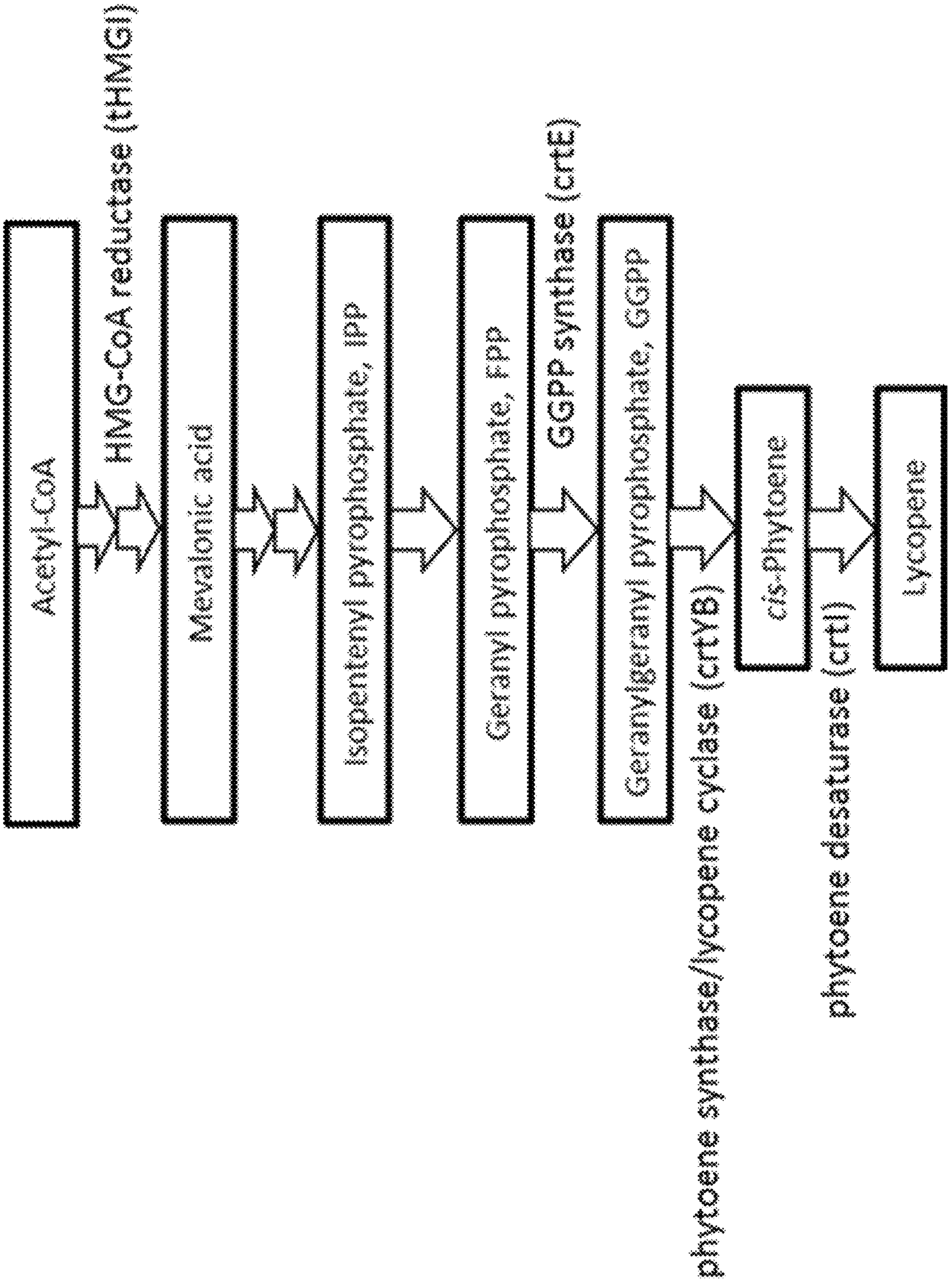
FIGS. 3*a* and 3*b* are schematic diagrams that depict the designer biosynthetic pathway of 3S, 3'S astaxanthin.
Figure 3B:
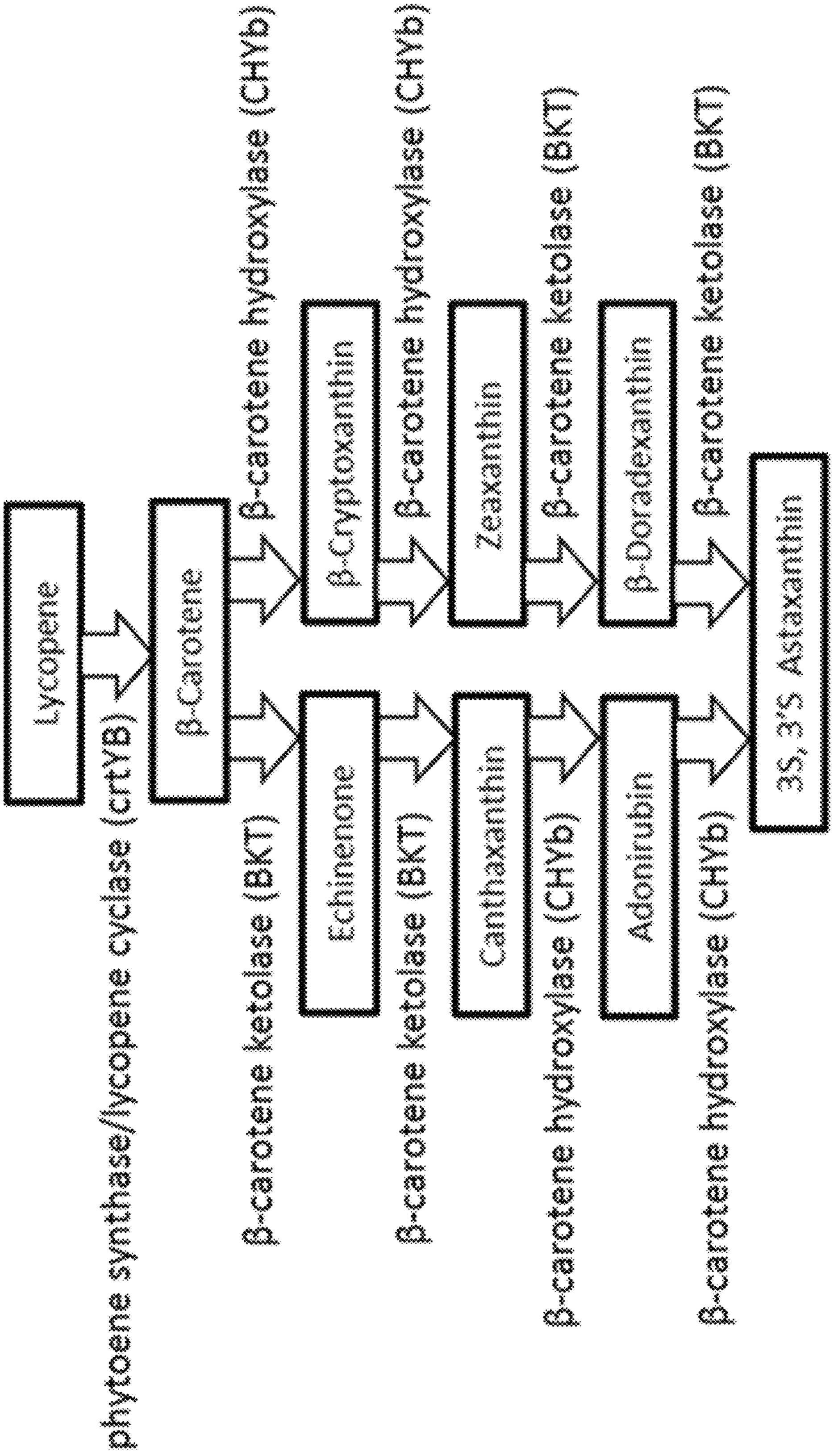

As discussed above, current technologies for astaxanthin biosynthesis have many limitations and cannot economically compete with chemical synthesis. On the other hand, although many astaxanthins are cheaply produced by chemical synthesis, the production process causes high environmental pollution, and its product cannot be easily preserved or easily absorbed by the human body, and is not well accepted by food and pharmaceutical markets. In view of the foregoing, the present invention aims at providing an approach (FIGS. 3*a* and 3*b*) so as to efficiently and massively produce the astaxanthin or its precursor or derivative in a host cell. Compared with the conventional method (e.g., the production by engineered microorganism) and chemical synthesis, the present approach is characterized by 4 advantages: (1) higher precursor synthesis, (2) shorter metabolic pathway, (3) correct structure of end products, and (4) ester-form protection.

Specifically, the present disclosure provide a recombinant polynucleotide sequence that encodes several polypeptides that regulate the biosynthesis of astaxanthin; a vector comprising the present recombinant polynucleotide sequence; a host cell comprising the present recombinant polynucleotide sequence and/or vector; and accordingly, a method of using the host cell to biosynthesize astaxanthin, its precursors or derivatives. Based on the antioxidant efficacy of the thus produced astaxanthin and/or its precursors or derivatives, the present disclosure also provides a method for improving the tolerance of a host cell to a stress; as well as a method for improving the productivity of a host cell in producing ethanol or a drug precursor, such as baccatin III.

The thus produced astaxanthin may be 3S, 3'S-astaxanthin or 3R, 3'R-astaxanthin. The precursor of astaxanthin may be geranylgeranyl-pyrophosphate (GGPP), phenicoxanthin, lycopene, echinenone, canthaxanthin, phytoene, zeaxanthin, β-cryptoxanthin, or β-carotene. The derivative of astaxanthin may be an astaxanthin monoester or an astaxanthin diester.

1. Recombinant Polynucleotide Sequence

The first aspect of the present disclosure is directed to a recombinant polynucleotide sequence, which is constructed by a Promoter-based Gene Assembly and Simultaneous Overexpression (PGASO) technique (Chang et al., 2012). The PGASO technique is a cloning strategy that employs overlapping polynucleotides for recombinatorial assembly of gene cassettes with individual promoters; and accordingly, multiple gene cassettes can be inserted in a pre-designated order into the genome of a cell. Briefly, each gene cassette contains 2 parts: (1) the gene sequence linked, at the 5' end, to a promoter sequence, and (2) a sequence at the 3' end of the gene cassette that is identical to the 5' end of the adjacent cassette. A portion of the 5'-end of the promoter sequence for the first gene cassette and a portion of the 3'-end of the second gene cassette are homologous to a predetermined site in the host genome in order to facilitate site-specific insertion. Preferably, the promoter sequences in each gene cassettes are different from each other. The sequence at the 3'-end of a gene cassette, however, should be homologous to a portion of the promoter sequence in the adjacent downstream gene cassette. When the gene cassettes are introduced into the cells, they will join together in the pre-designated order via homologous recombination between the pairs of overlapping and promoter sequences, and thereby are inserted into the genome via homologous recombination at the promoter sequence of the first and the 3'-end of the last gene cassette.

All the following recombinant polynucleotide sequences are constructed based on the concept of the PGASO technique.

1.1 A Recombinant Polynucleotide Sequence Comprising Two Gene Cassettes

According to one embodiment of the present disclosure, the present recombinant polynucleotide sequence comprises two gene cassettes. The first gene cassette comprises a first nucleic acid sequence driven by a first promoter, in which the first nucleic acid sequence encodes a geranylgeranyl pyrophosphate (GGPP) synthase, an enzyme catalyzing the formation of GGPP from geranyl pyrophosphate (FPP). The second gene cassette comprises a second nucleic acid sequence driven by a second promoter, in which the second nucleic acid sequence encodes a 3-hydroxy-3-methylglutaryl-coenzyme A (HMG-CoA) reductase, which catalyzes the formation of mevalonic acid from acetyl-CoA. Based on the strategy of the PGASO technique, the 3'-end of one gene cassette is homologous to the 5'-end of another gene cassette downstream thereto. Thus, when the two gene cassettes are introduced into the host cell, they would be assembled to constitute the recombinant polynucleotide sequence For example, in one embodiment of the present disclosure, the sequence at the 3'-end of the first gene cassette is homologous to a portion of the second promoter. The constructed recombinant polynucleotide sequence, structurally, comprises two gene cassettes, that is, the first and second gene cassettes, from 5'-end to 3'-end.

Optionally, the recombinant polynucleotide sequence might further comprise a marker cassette, which comprises a marker promoter and a marker gene operatively linked to the marker promoter. According to another embodiment, the sequence of the 3'-end of the first gene cassette is homologous to a portion of the marker promoter, while the sequence of the 3'-end of the marker cassette is homologous to a portion of the second promoter. Thus, after the homologous recombination, the marker cassette is located between the first and second gene cassettes.

To produce the GGPP synthase, the first nucleic acid sequence is a crtE gene or a fragment thereof, which can be derived from the crtE gene of *Xanthophyllomyces dendrorhous, Streptomyces coelicolor, Corynebacterium glutamicum, Thermobifida fusca*, or *Bifidobacterium longum*. In one specific embodiment, the first nucleic acid sequence is derived from the catalytic domain of crtE gene of *Xanthophyllomyces dendrorhous*, and comprises the sequence of SEQ ID NO: 1.

To produce HMG-CoA reductase, the second nucleic acid sequence is a HMG1 gene or a fragment thereof, which can be derived from the HMG1 gene of *Kluveromyces marxianus, Saccharomyces cerevisiae, Picea sitchensis, Aspergillus terreus*, or *Ganoderma lucidum*. In one embodiment, the second nucleic acid sequence is derived from the catalytic domain of HMG1 gene of *Kluveromyces marxianus*. It is known that the truncated HMG-CoA reductase (tHMG1) causes a reduction in the feedback inhibition and thus improves the downstream GGPP accumulation in yeast. Accordingly, in one specific example, the second nucleic acid sequence is a tHMG1 and comprises the sequence of SEQ ID NO: 2.

The maker gene can be a screening marker gene (e.g., fluorescent gene, 3-glucuronidase gene, and LacZ gene) or a selection marker gene (e.g., antibiotic resistance gene). According to one embodiment of the present disclosure, the marker gene is an antibiotic resistance gene, such as the KanMX marker gene that confers kanamycin/geneticin (G418)/neomycin resistance, or the AUR1-C gene that confers aureobasidin A (AbA) resistance to the host.

Examples for suitable promoters that may be used to respectively drive the expression of the first, second, and marker nucleic acid sequences/genes include, but are limited to ScGapDH promoter, KlGapDH promoter, ScPGK promoter, KlPGK promoter, KlADHI promoter, ScADHI promoter, KlADH4 promoter, ScADH4 promoter, KlLac4 promoter and ICL promoter. Preferably, each of the nucleic acids or gene cassettes in the recombinant polynucleotide sequence is driven by a promoter that is different from one another. In one embodiment, the first promoter is KlLac4 promoter, the second promoter is ScADHI promoter, and the marker promoter is KlGapDH promoter.

1.2 A Recombinant Polynucleotide Sequence Comprising Four Gene Cassettes

According to another embodiment of the present disclosure, the present recombinant polynucleotide sequence comprises four gene cassettes. Specifically, in addition to the first and second gene cassettes that respectively express the GGPP synthase and HMG-CoA reductase as described above in section 1.1, the recombinant polynucleotide sequence may further comprise a third and a fourth gene cassette. The third gene cassette comprises a third nucleic acid sequence driven by a third promoter, in which the third nucleic acid sequence encodes a phytoene desaturase, an enzyme that catalyzes the formation of lycopene from cis-phytoene. The fourth gene cassette comprises a fourth nucleic acid driven by a fourth promoter, in which the fourth nucleic acid sequence encodes a bi-functional enzyme (hereinafter, phytoene synthase/lycopene cyclase), which possesses the respective functions of phytoene synthase and lycopene cyclase; both enzymes play a role in catalyzing the conversion from lycopene to β-carotene.

The four gene cassettes as described herein are assembled in accordance with the strategy of the PGASO technique. That is, the 3'-end of each gene cassette is homologous to the 5'-end of the next gene cassette downstream thereto. For example, in one embodiment of the present disclosure, the sequence at the 3'-end of the third gene cassette is homologous to a portion of the first promoter; the sequence of the 3'-end of the first gene cassette is homologous to a portion of the fourth promoter; and the sequence of the 3'-end of the fourth gene cassette is homologous to a portion of the second promoter. The four gene cassettes would spontaneously assemble in vivo and produce the recombinant polynucleotide sequence, which comprises the third gene cassette, the first gene cassette, the fourth gene cassette, and the second gene cassette, in sequence, from 5'-end to 3'-end.

Optionally, the recombinant polynucleotide sequence might further comprise the marker cassette comprising a marker promoter and a marker gene operatively linked to the marker promoter. The recombinant polynucleotide sequence comprising the marker cassette is constructed in a similar manner by use of the PGASO method; and hence, detailed description thereof is omitted for the sake of brevity. According to one embodiment of the present disclosure, the marker cassette is located between the first gene cassette and the fourth gene cassette.

To produce the phytoene desaturase, the third nucleic acid sequence is a crtI gene or a fragment thereof, which can be derived from *Xanthophyllomyces dendrorhous, Xanthophyllomycesene desatura, Synechococcus* sp. WH 8102, *Synechocystis* sp. PCC 6803, *Nostoc* sp. PCC 7120, or *Solanum lycopersicum*. In one specific embodiment, the third nucleic acid sequence is derived from the catalytic domain of the crtI gene of *Xanthophyllomyces dendrorhous*, and comprises the sequence of SEQ ID NO: 3.

To construct the bi-functional enzyme with respective functions of a phytoene synthase and a lycopene cyclase, the fourth nucleic acid sequence is constructed to comprise a crtYB gene or a fragment thereof, which can be derived from *Xanthophyllomyces dendrorhous, Ustilago maydis* 521, *Sulfolobus solfataricus* or *Picrophilus torridus*. In one specific embodiment, the fourth nucleic acid sequence is derived from the catalytic domain of the crtYB gene of *Xanthophyllomyces dendrorhous*, and comprises the sequence of SEQ ID NO: 4.

The maker gene can be a screening marker gene or a selection marker gene. According to one embodiment of the present disclosure, the marker gene is an antibiotic resistance gene KanMX.

Examples for suitable promoters that may be used to respectively drive the expression of the first, second, third, fourth, and marker nucleic acid sequences/genes include, but are not limited to, ScGapDH promoter, KlGapDH promoter, ScPGK promoter, KlPGK promoter, KlADHI promoter, ScADHI promoter, KlADH4 promoter, ScADH4 promoter, KlLac4 promoter and ICL promoter. Preferably, each of the nucleic acids in the recombinant polynucleotide sequence is driven by a different promoter. In one embodiment, the first promoter is the ScPGK promoter, the second promoter is the ScADHI promoter, the third promoter is the KlLac4 promoter, the fourth promoter is the KlADHI promoter, and the marker promoter is the KlGapDH promoter.

1.3 A Recombinant Polynucleotide Sequence Comprising Six Gene Cassettes for Expressing 3S, 3'S-Astaxanthin According to another embodiment of the present disclosure, the recombinant polynucleotide sequence comprises six gene cassettes for the purpose of producing 3S, 3'S-astaxanthin. Specifically, in addition to the first to fourth gene cassettes that respectively express the GGPP synthase, HMG-CoA reductase, phytoene desaturase, and phytoene synthase/lycopene cyclase as described above in section 1.2, the recombinant polynucleotide sequence may further comprise additional two gene cassettes that respectively express the β-carotene hydroxylase and β-carotene ketolase. Both the β-carotene hydroxylase and β-carotene ketolase are necessary for the conversion of β-carotene to 3S, 3'S-astaxanthin. More specifically, the fifth gene cassette comprises a fifth nucleic acid sequence driven by a fifth promoter, in which the fifth nucleic acid sequence encodes a β-carotene hydroxylase. The sixth gene cassette comprises a sixth nucleic acid sequence driven by a sixth promoter, in which the sixth nucleic acid sequence encodes a β-carotene ketolase.

Similarly, the recombinant polynucleotide sequence comprising 6 gene cassettes is also constructed based on the strategy of the PGASO technique, in which the 3'-end of each gene cassette is homologous to the 5'-end of the next gene cassette downstream thereto. For example, in one specific example, the sequence at the 3'-end of the third gene cassette is homologous to a portion of the first promoter; the sequence of the 3'-end of the first gene cassette is homologous to a portion of the fifth promoter; the sequence of the 3'-end of the fifth gene cassette is homologous to a portion of the sixth promoter; the sequence of the 3'-end of the sixth gene cassette is homologous to a portion of the fourth promoter; and the sequence of the 3'-end of the fourth gene cassette is homologous to a portion of the second promoter. Once being introduced into a host cell, the six gene cassettes would spontaneously assemble to produce the recombinant polynucleotide sequence, which comprises the third gene cassette, the first gene cassette, the fifth gene cassette, the sixth gene cassette, the fourth gene cassette, and the second gene cassette, in sequence, from 5'-end to 3'-end.

Still optionally, the recombinant polynucleotide sequence may further comprise a marker gene cassette, which comprises a marker gene driven by a marker promoter. In the embodiment, the constructed marker cassette is located between the fifth gene cassette and the sixth gene cassette.

To produce the β-carotene hydroxylase, the fifth nucleic acid sequence is constructed to comprise a chYb gene or a fragment thereof which can be derived from *Chlamydomonas reinhardtii, Chlorella zofingiensis*, or *Haematococcus pluvialis*. In one embodiment, the fifth nucleic acid sequence is derived from the catalytic domain of the chYb gene of *Chlamydomonas reinhardtii*, and comprises the sequence of SEQ ID NO: 5. In another embodiment, the fifth nucleic acid sequence is derived from the catalytic domain of the chYb gene of *Chlorella zofingiensis*, and comprises the sequence of SEQ ID NO: 6. In still another embodiment, the fifth nucleic acid sequence is derived from the catalytic domain of the chYb gene of *Haematococcus pluvialis*, and comprises the sequence of SEQ ID NO: 7.

To produce the β-carotene ketolase, the sixth nucleic acid sequence is constructed to comprise a bkt gene or a fragment thereof which can be derived from *Chlamydomonas reinhardtii, Nostoc* sp. PCC 7120*, Gloeobacter violaceus* PCC 7421*, Synechococcus* sp. CC9902, or *Synechococcus* sp.

WH 8102. In one specific embodiment, the sixth nucleic acid sequence is derived from the catalytic domain of the bkt gene of *Chlamydomonas reinhardtii*, and comprises the sequence of SEQ ID NO: 8.

The maker gene can be a screening marker gene or a selection marker gene as described above. According to one embodiment of the present disclosure, the marker gene is an antibiotic resistance gene KanMX.

Examples of suitable promoters that may be used to respectively drive the expression of the first to sixth nucleic acid sequences and the marker gene, include, but are not limited to ScGapDH promoter, KlGapDH promoter, ScPGK promoter, KlPGK promoter, KlADHI promoter, ScADHI promoter, KlADH4 promoter, ScADH4 promoter, KlLac4 promoter and ICL promoter. Preferably, each of the nucleic acids in the recombinant polynucleotide sequence is driven by a promoter that is different from one another. In one embodiment, the first promoter is the ScGapDH promoter, the second promoter is the ScADHI promoter, the third promoter is the KlLac4 promoter, the fourth promoter is the KlADHI promoter, the fifth promoter is the ScPGK promoter, the sixth promoter is the KlPGK promoter, and the marker promoter is the KlGapDH promoter.

1.4 A Recombinant Polynucleotide Sequence Comprising Six Gene Cassettes for Expressing 3R, 3'R-Astaxanthin The present invention also provides a recombinant polynucleotide sequence that is designed to massively produce 3R, 3'R-astaxanthin in the host cell. According to some embodiments of the present disclosure, the recombinant polynucleotide sequence for producing 3R, 3'R-astaxanthin comprises six gene cassettes, in which the first four gene cassettes respectively express the GGPP synthase, HMG-CoA reductase, phytoene desaturase, and phytoene synthase/lycopene cyclase as described above in section 1.2, whereas the last two gene cassettes (hereinafter, the seventh gene cassette and the eighth gene cassette) respectively express the P450 reductase and β-carotene oxygenase, which are known to play a critical role in catalyzing the formation of 3R, 3'R-astaxanthin from β-carotene. Specifically, the seventh gene cassette comprises a seventh nucleic acid sequence driven by a seventh promoter, in which the seventh nucleic acid sequence encodes a P450 reductase. The eighth gene cassette comprises an eighth nucleic acid sequence driven by an eighth promoter, in which the eighth nucleic acid sequence encodes a β-carotene oxygenase.

Similarly, the recombinant polynucleotide sequence for producing 3R, 3'R-astaxanthin is constructed in accordance with the concept of the PGASO strategy, in which the 3'-end of each gene cassette is homologous to the 5'-end of the next gene cassette downstream thereto. For example, according to one embodiment, the sequence at the 3'-end of the third gene cassette is homologous to a portion of the seventh promoter; the sequence of the 3'-end of the seventh gene cassette is homologous to a portion of the first promoter; the sequence of the 3'-end of the first gene cassette is homologous to a portion of the eighth promoter; the sequence of the 3'-end of the eighth gene cassette is homologous to a portion of the fourth promoter; and the sequence of the 3'-end of the fourth gene cassette is homologous to a portion of the second promoter. As the homologous sequences between the gene cassettes render the in vivo homologous recombination, the seven gene cassettes would be assembled to produce the recombinant polynucleotide sequence, which comprises the third gene cassette, the seventh gene cassette, the first gene cassette, the eighth gene cassette, the fourth gene cassette, and the second gene cassette, in sequence, from 5'-end to 3'-end.

Optionally, the recombinant polynucleotide sequence for producing 3R, 3'R-astaxanthin may further comprise a marker gene cassette, which comprises a marker gene driven by a marker promoter. In one preferred embodiment, the marker cassette is located between the first gene cassette and the eighth gene cassette.

To produce the P450 reductase, the seventh nucleic acid sequence is constructed to comprise a crtR gene or a fragment thereof, which can be derived from *Xanthophyllomyces dendrorhous, Aspergillus niger, Schizosaccharomyces pombe, Malassezia globosa* CBS 7966, or *Ustilago maydis* 521. In one specific embodiment, the seventh nucleic acid sequence is derived from *Xanthophyllomyces dendrorhous*, and comprises the sequence of SEQ ID NO: 9.

To produce β-carotene oxygenase, the eighth nucleic acid sequence is constructed to comprise a crtS gene or a fragment thereof, which can be derived from *Xanthophyllomyces dendrorhous, Homo sapiens, Rattus norvegicus, Oryctolagus cuniculus*, or *Drosophila melanogaster*. In one embodiment, the eighth nucleic acid sequence is derived from *Xanthophyllomyces dendrorhous*, and comprises the sequence of SEQ ID NO: 10.

The maker gene can be a screening marker gene or a selection marker gene. According to one embodiment of the present disclosure, the marker gene is an antibiotic resistance gene KanMX.

Examples for suitable promoters that may be used to respectively drive the expression of the first, second, third, fourth, seventh, eighth, and marker nucleic acid sequences/genes include, but are not limited to, ScGapDH promoter, KlGapDH promoter, ScPGK promoter, KlPGK promoter, KlADHI promoter, ScADHI promoter, KlADH4 promoter, ScADH4 promoter, KlLac4 promoter and ICL promoter. Preferably, each of the nucleic acids in the recombinant polynucleotide sequence is driven by a promoter that is different from one another. In one embodiment, the first promoter is the ScPGK promoter, the second promoter is the ScADHI promoter, the third promoter is the KlLac4 promoter, the fourth promoter is the KlADHI promoter, the seventh promoter is the ScGapDH promoter, the eighth promoter is the KlPGK promoter, and the marker promoter is the KlGapDH promoter. All the promoters listed above are constitutive yeast promoters that are actively in all circumstances and can efficiently drive the gene expression in the yeast cells.

According to some embodiments of the present disclosure, each of the promoters mentioned in section 1.1 to 1.4 (i.e., the first, second, third, fourth, fifth, sixth, seven, eighth, and marker promoter) comprises a specific nucleotide sequence. In one specific example, the KlLac4 promoter comprises a nucleotide sequence of SEQ ID NO: 63; the ScGapDH promoter comprises a nucleotide sequence of SEQ ID NO: 64; the ScPGK promoter comprises a nucleotide sequence of SEQ ID NO: 65; the KlGapDH promoter comprises a nucleotide sequence of SEQ ID NO: 66; the KlPGK promoter comprises a nucleotide sequence of SEQ ID NO: 67; the KlADHI promoter comprises a nucleotide sequence of SEQ ID NO: 68; and the ScADHI promoter comprises a nucleotide sequence of SEQ ID NO: 69.

As would be appreciated, each of the promoters used to drive the expression of respective gene cassettes as described in section 1.1 to 1.4 (i.e., the first, second, third, fourth, fifth, sixth, seven, eighth, and marker gene cassette) may be replaced by other constitutive promoters that drive the gene expression in different species other than yeast, so that the gene cassettes can be efficiently expressed in prokaryotic host cells (e.g., bacterial host cell) or other eukaryotic host cells (e.g., the mammalian cell). Suitable promoters that may be used to drive gene expression in prokaryotic host cells include, but are not limited to, T3 promoter, T5 promoter, T7 promoter, trp promoter, lac promoter, tac promoter (a hybrid of trp and lac promoter), lac-derived promoter, araBAD promoter, recA promoter, proU promoter, cst-1 promoter, tatA promoter, cadA promoter, nar promoter, cspA promoter, SP6 promoter, Rhamnose promoter, and phoA promoter. The promoters suitable for driving gene expression in mammalian cells may be selected from the group consisting of SV40 early promoter, Rous sarcoma virus promoter, adenovirus major late promoter, human cytomegalovirus (CMV) immediate early promoter, murine stem cell virus (MSCV) promoter, virus's internal promoter Ubiquitin C (UbC) promoter, elongation factor-1 alpha (EF-1 alpha) promoter, phosphoglycerate kinase (PGK) promoter, and CMV early enhancer/chicken β actin (CAG) promoter.

In addition to the PGASO technique, the gene cassettes described in section 1.1 to 1.4 (i.e., the first, second, third, fourth, fifth, sixth, seven, eighth, and marker gene cassette) can be assembled by other suitable methods known to any skilled artisan, such as proper restriction enzymes, and Gateway cloning system, as long as the preferred products (i.e., 3 S, 3'S-astaxanthin or 3R, 3'R-astaxanthin) are produced.

If different construction strategy was used, the gene cassettes described in section 1.1 to 1.4 (i.e., the first, second, third, fourth, fifth, sixth, seven, eighth, and marker gene cassette) can be assembled in different sequences and/or orders. Accordingly, the assembled product may be different from the present recombinant polynucleotide sequence in the sequences of gene cassettes comprised therein via employing different overlapping/homologous polynucleotides for recombinatorial assembly. Alternatively, different restriction enzymes may be used to generate the desired gene cassettes. Thus, the polynucleotide sequence comprising the present gene cassettes with different assembly sequences is also within the scope of the present disclosure.

The order of the assembled recombinant polynucleotide sequence can be confirmed and analyzed by any method commonly used in laboratory or clinical research. For example, the order can be analyzed by gene sequencing, restriction enzyme digestion, or long-PCR assay. According to one embodiment of the present disclosure, the order of the recombinant polynucleotide sequence is analyzed by long-PCR assay. Generally, long-PCR assay is a technique used to amplify extremely long PCR products (up to 40 kb DNA), which can be exerted by commercially available kits in accordance with the instruction manual.

2. Vector Comprising the Present Recombinant Polynucleotide Sequence

The second aspect of the present disclosure pertains to a vector that comprises the recombinant polynucleotide sequence according to the above-mentioned aspect/embodiment(s) of the present disclosure, and a control sequence operably linked to the recombinant polynucleotide sequence.

The control sequence exists for the purpose of facilitating the expression of the recombinant polynucleotide sequence in various types of host cells. Accordingly, the control sequence may comprise different elements (e.g., promoter, ribosomal binding site/RBS, enhancer/silencer, and terminator) therein. For example, to be expressed in yeast cells, the control sequence would comprise an autonomously replicating sequence (ARS) that contains the origin of replication in the yeast genome, in which the ARS contains four regions (A, B1, B2, and B3), named in order of their effects on plasmid stability. The A-Domain is highly conserved, and any mutation abolishes the function of origin of replication. Mutations in the B1, B2, and B3 regions would diminish, but not prevent the function of the origin replication. Generally, the replication origin of the control sequence for the initiation of vector replication in the yeast cell consists of an essential DNA sequence (i.e., the ARS consensus sequence, ACS) that recruits replication proteins.

To be expressed in prokaryotic host cells, the control sequence may comprise a replication origin (ori), and an operon. Typically, the replication origin can be an oriC, which is derived from the genome of *Escherichia coli* (*E. coli*), or a pUC, which is derived from pBR322 (a plasmid of *E. coli*) and comprises two mutations. The operon is used to regulate the expression of promoter; the example of suitable operon includes, but is not limited to, lac operon, trp operon, and Tn10-derived tetracycline resistance (Tet) operon.

To be expressed in mammalian cells, the control sequence may comprise a replication origin, and an enhancer/silencer. The replication origin for initiating the replication of a vector in the mammalian cells can be a SV40 origin derived from the genome of the SV40 virus, or an oriC derived from the genome of a mammalian cell. Enhancer is a short (50-1500 bp) region of DNA generally cis-acting, located upstream or downstream of the gene it regulates where it can be bound with proteins (activators) to activate the transcription of gene(s); while silencer is a DNA sequence located upstream or downstream of the gene it regulates where it is capable of binding transcription factors (repressors) to repress the transcription of gene(s).

The present recombinant polynucleotide sequence can be operably linked to the control sequence by any method known to a skilled artisan. For example, the linkage can be exerted by proper restriction enzymes, Gateway cloning system, or homologous recombination.

According to one embodiment of the present disclosure, the present recombinant polynucleotide sequence is operably linked to the control sequence by homologous recombination. Specifically, the present recombinant polynucleotide sequence is co-transformed with the control sequence into a yeast cell, in which the 5'-end and 3'-end of recombinant polynucleotide sequence are respectively homologous to the 3'-end and 5'-end of a marker gene within the control sequence. Thus, the gene cassettes comprised in the recombinant polynucleotide sequence can be spontaneously assembled into the control sequence in vivo. In one specific embodiment, the control sequence is a plasmid pRS426, and the marker gene is URA3 gene.

According to one embodiment of the present disclosure, the control sequence is a high-copy-number plasmid vector. Thus, after the homologous recombination, the present recombinant polynucleotide sequence could be highly expressed in the yeast cells.

3. Host Cells for Expressing the Present Recombinant Polynucleotide Sequence

The third aspect of the present disclosure is directed to a host cell, which is employed to express the recombinant polynucleotide sequences, and thereby producing astaxanthin, a precursor and/or a derivative thereof. In some embodiments, the host cell is transfected with the vector of section 2, which comprises the recombinant polynucleotide sequences of sections 1.1, 1.2, 1.3, or 1.4.

The astaxanthin thus produced may be 3S, 3'S-astaxanthin or 3R, 3'R-astaxanthin. The precursor of astaxanthin may be geranylgeranyl-pyrophosphate, phenicoxanthin, lycopene, echinenone, canthaxanthin, phytoene, zeaxanthin, β-cryptoxanthin, or β-carotene. The derivative of astaxanthin may be an astaxanthin monoester or an astaxanthin diester.

The present recombinant polynucleotide sequence and/or vector can be introduced into the host cell by the method known to a skilled artisan. Specifically, the method for introducing the exogenous DNA and/or vector into a prokaryotic host cell (e.g., bacterial host cell) commonly used in the relevant field includes chemical treatment (such as incubating the host cell in a solution containing divalent cations, then followed by a heat treatment), and electroporation (such as briefly treating the host cell with an electric field that creates holes in the cell membrane).

To introduce the exogenous DNA and/or vector into a yeast cell, any of the following treatments may be used, which include, but are not limited to, enzyme treatment (treating the host cell with enzymes to degrade the cell wall), chemical treatment (exposing the host cell to alkali cations), electroporation, and glass bead agitation. According to one embodiment of the present disclosure, the present recombinant polynucleotide sequence and/or vector is introduced into the yeast cell via electroporation.

As to introducing the exogenous DNA and/or vector into a eukaryotic host cell (e.g., the mammalian cell), the host cell may be treated by chemicals (such as, calcium phosphate, highly branched organic compound/dendrimer, liposome, and cationic polymers), electroporation, cell squeezing (gently squeezing cell membrane), sonoporation (inducing pore formation in cell membrane by high-intensity ultrasound), optical transfection (generating a tiny hole in cell membrane by highly focused laser), impalefection (DNA bound to a surface of a nanofiber that is inserted into a cell), gene gun (DNA coupled to a nanoparticle of an inert solid that is then “shot” directly into the target cell's nucleus), magnetofection/magnet assisted transfection (using magnetic force to deliver DNA into target cells), and/or viral method/viral transduction (using viruses as a carrier to delivery DNA into target cells).

Accordingly, the host cell suitable for expressing astaxanthin, a precursor and/or a derivative thereof can be prokaryotic (e.g., bacterial cell), or eukaryotic (e.g., yeast cell and mammalian cell). According to one preferred embodiment of the present disclosure, the host cell is a yeast cell.

According to some embodiments, the host cell is a yeast cell that is selected from the group consisting of *Kluveromyces marxianus, Candida boidinii, Aspergillus terreus, Pichia pastoris, Hansenula polymorpha, Klyveromyces lactis, Arxula adeninivorans, Yarrowia lipolytica, Schizosaccharomyces pombe, Saccharomyces cerevisiae, Kluyveromyces marxianus, Lecanicillium, Galactomyces, Geotrichum, Scopulariopsis, Fusarium, Cyberlindnera, Debaryomyces, Dekkera, Hanseniaspora, Kazachstania, Lachancea, Metschnikowia, Pichia, Torulopsis, Schwanniomyces, Starmerella, Trigonopsis, Wickerhamomyces, Zygosaccharomyces, Zygotorulaspora, Lachancea, Torulaspora, Neurospora, Aspergillus, Penicillium, Sporendonema, Cystofilobasidium, Guehomyces, Mucor, Rhizopus, Escherichia coli, Bifidobacterium, Brevibacterium, Corynebacterium, BrachYbacterium, Microbacterium, Arthrobacter, Kocuria, Micrococcus, Propionibacterium, Streptomyces, Bacillus, Carnobacterium, Enterococcus, Tetragenococcus, Lactobacillus, Pediococcus, Leuconostoc, Oenococcus, Weissella, Macrococcus, Staphylococcus, Lactococcus, Streptococcus, Acetobacter, Gluconacetobacter, Hafnia, Halomonas*, and *Zymomonas* cell. In one specific embodiment, the host cell is *Kluyveromyces marxianus.*

According to one embodiment of the present disclosure, the host cell may comprise one or more copies of the present gene cassette/recombinant polynucleotide sequence/vector described above in sections 1 and 2, so as to efficiently produce astaxanthin, a precursor and/or a derivative thereof.

Since toxic intermediate products generated during the fermentation process commonly used for the mass production of proteins from the cultivated host cells, the astaxanthin/astaxanthin precursor/astaxanthin derivative produced by the present recombinant polynucleotide sequence/vector may protect the host cells from being damaged by any toxic intermediates during the fermentation process.

According to embodiments of the present disclosure, the thus produced astaxanthin, a precursor, and/or a derivative thereof exhibits anti-oxidation activity that renders the host cell tolerant to a stress. The stress may be caused from the host cell being exposed to ethanol, butanol, UV exposure, furfural, and/or the precursor of an anticancer drug. In one specific example, the host cell is tolerant to a precursor of an anticancer drug, 10-deacetyl baccatin III (10 DB), which gives rise to the anticancer drug, paclitaxel. The tolerance of the host cell to different stresses can be evaluated by various methods, depending on the experimental purpose. For example, the tolerance can be evaluated by the measurement of colony number, cell growth, cell density, or gene expression.

4. Methods for Producing Astaxanthin, its Precursors, or Derivatives

The fourth aspect of the present disclosure pertains to a method of producing astaxanthin, a precursor and/or a derivative thereof. The method comprises cultivating the host cell as described in section 3 in a medium (e.g., a yeast extract-peptone-glycerol (YPG) medium) that comprises a material selected from the group consisting of glucose, galactose, glycerol, fatty acid, and/or a combination thereof. In one embodiment, the medium comprises glycerol. In another embodiment, the medium comprises glucose. In still another embodiment, the medium comprises galactose. In further still another embodiment, the medium comprises fatty acid, such as octanoic acid.

The concentration of glucose, galactose, or glycerol sufficient to induce the expression of gene cassettes within the hose cell is about 0.5-40% (mass concentration, w/w); that is, the concentration can be 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, or 40% by weight; while the concentration of fatty acid sufficient to induce the expression of gene cassettes within the hose cell is about 0.001%-5% (mass concentration, w/w); that is the concentration can be 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, or 5% by weight.

Preferably, the concentration of glucose, galactose, or glycerol used to induce the expression of gene cassettes within the hose cell is about 5-30%; while the concentration of fatty acid used to induce the expression of gene cassettes within the hose cell is about 0.005-0.5%.

According to some embodiments of the present disclosure, the medium comprises one component selected from the group consisting of glucose, galactose, glycerol, and fatty acid. In one embodiment, the medium comprises 20% glucose. In another embodiment, the medium comprises 20% galactose. In still another embodiment, the medium comprises 0.01-0.1% fatty acid. In one preferred embodiment, the medium comprises 10-20% glycerol.

As would be appreciated, the medium may comprises at least two components selected from the group consisting of glucose, galactose, glycerol, and fatty acid so as to efficiently induce the expression of gene cassettes within the hose cell.

According to embodiments of the present disclosure, the temperature suitable for the host cell to produce the astaxanthin is in the range of about 18° C.-42° C.; for example, the temperature can be 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., or 42° C. In one embodiment, the temperature is 30° C. In another embodiment, the temperature is 37° C. According to one preferred example, the temperature is 25° C.

The expression of the present recombinant polynucleotide sequence/vector in a host may be evaluated by various methods known in the art. For example, the expression can be detected by direct visualization and/or photography of the color of colony and/or broth containing the present host. Or, the expression can be analyzed by measuring the cell growth, cell density, gene expression, high-performance liquid chromatography (HPLC) analysis, or liquid chromatography-mass spectrometry (LC/MS) analysis.

According to some embodiments of the present disclosure, the method further comprises the step of isolating the thus produced astaxanthin, its precursors and/or derivatives directly from the host cell or the medium. In one embodiment, the astaxanthin is directly isolated from the host cell by extracting the expressed protein from the yeast cell, such as by autolysis (mixing the yeast cell with toluene/ammonium hydroxide followed by incubating the mixture at room temperature for 24-48 hours), homogenization (by the use of homogenizer, French press, or Manton-Gaulin homogenizer), glass bead vortexing (disrupting the yeast cell by agitation with glass beads), enzymatic lysis (digesting the cell wall by zymolase or lyticase), freezing and grinding (freeze the cells directly in liquid nitrogen and ground the frozen cells to a powder using a mortar and pestle), and chemical treatment (such as by treating the host cell with SDS, and/or acetone). According to one embodiment of the present disclosure, the astaxanthin is extracted from the yeast cell by treating the host cell with acetone. According to another embodiment, the astaxanthin is extracted from the host cell by lyophilization, followed by methanol treatment.

According to some embodiments of the present disclosure, the astaxanthin thus produced is 3S, 3'S-astaxanthin or 3R, 3'R-astaxanthin.

According to one embodiment, the product of the present method is a precursor of astaxanthin, which may be GGPP, phenicoxanthin, lycopene, echinenone, canthaxanthin, β-cryptoxanthin, zeaxanthin, phytoene, or β-carotene.

According to other embodiments, the product of the present method is a derivative of astaxanthin, which may be an astaxanthin monoester or an astaxanthin diester.

According to embodiments of the present disclosure, the astaxanthin and/or the precursor or derivative thereof thus produced possesses antioxidation activity, and can be used as an antioxidant. The antioxidation activity can be evaluated by any in vitro and/or in vivo method known to any person skilled in the art. For example, the method suitable for evaluating in vitro antioxidation activity may be 1, 1-diphenyl-2-picrylhydrazyl (α,α-diphenyl-β-picrylhydrazyl; DPPH) scavenging activity, hydrogen peroxide scavenging ($H_2O_2$) assay, nitric oxide scavenging activity, peroxynitrite radical scavenging activity, Trolox equivalent antioxidant capacity (TEAC) method/ABTS radical cation decolorization assay, total radical-trapping antioxidant parameter (TRAP) method, ferric reducing-antioxidant power (FRAP) assay, superoxide radical scavenging activity (SOD), hydroxyl radical scavenging activity, hydroxyl radical averting capacity (HORAC) method, oxygen radical absorbance capacity (ORAC) method, reducing power method (RP), phosphomolybdenum method, ferric thiocyanate (FTC) method, thiobarbituric acid (TBA) method, DMPD (N,N-dimethyl-p-phenylene diamine dihydrochloride) method, β-carotene linoleic acid method/conjugated diene assay, xanthine oxidase method, cupric ion reducing antioxidant capacity (CUPRAC) method, or metal chelating activity. The method for determining the in vivo antioxidation activity includes, but is not limited to, ferric reducing ability of plasma, reduced glutathione (GSH) estimation, glutathione peroxidase (GSHPx) estimation, glutathione-S-transferase (GST), superoxide dismutase (SOD) method, catalase (CAT), γ-glutamyl transpeptidase activity (GGT) assay, glutathione reductase (GR) assay, lipid peroxidation (LPO) assay, and LDL assay. According to one embodiment of the present disclosure, the Trolox equivalent antioxidant capacity (TEAC) method/ABTS radical cation decolorization assay is employed to measure the antioxidation activity of the produced astaxanthin, or the precursor or derivative thereof.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Gene Synthesis

The bkt gene of *Chlamydomonas reinhardtii*, the chYb gene of *Chlamydomonas reinhardtii* (i.e., CrChYb gene), the chYb gene of *Chromochloris zofingiensis* (i.e., CzChYb gene), and the chYb gene of *Haematococcus pluvialis* (i.e., HpChYb gene) were respectively synthesized by the GeneArt® Gene Synthesis (GENEART, Germany). All the synthesized gene sequences were subjected to multi-parameter gene optimization by GeneOptimizer® Process based on the codon usage of the host, *Xanthophyllomyces dendrorhous.*

Accordingly, the synthesized bkt gene had an amino acid sequence of SEQ ID NO: 8; the synthesized CrChYb gene had an amino acid sequence of SEQ ID NO: 5; the synthesized CzChYb gene had an amino acid sequence of SEQ ID NO: 6; and the synthesized HpChYb gene had an amino acid sequence of SEQ ID NO: 7.

Gene Cloning

The crtE gene, the truncated HMG1 gene (tHMG1 gene), the crtI gene, the crtYB gene, the crtR gene, and the crtS gene were respectively amplified from *Xanthophyllomyces dendrorhous* and *Kluyveromyces marxianus* by PCR. The primers used to clone each gene and the sequence identification number (SEQ ID NO) of each cloning gene were listed in Table 2.

TABLE 2

| Primers for cloning and the cloning sequence | | | |
|---|---|---|---|
| Gene | Species | Primer for gene cloning (SEQ ID NO) | Gene sequence (SEQ ID NO) |
| crtE | *Xanthophyllomyces dendrorhous* | 11, 12 | 1 |
| tHMG1 | *Kluyveromyces marxianus* | 13, 14 | 2 |
| crtI | *Xanthophyllomyces dendrorhous* | 15, 16 | 3 |
| crtYB | *Xanthophyllomyces dendrorhous* | 17, 18 | 4 |
| crtR | *Xanthophyllomyces dendrorhous* | 19, 20 | 9 |
| crtS | *Xanthophyllomyces dendrorhous* | 21, 22 | 10 |

The KlLac4 promoter was amplified by PCR via primers of SEQ ID NOs: 70, 71, 72, and 73; the amplified KlLac4 promoter had a nucleotide sequence of SEQ ID NO: 63. The ScGapDH promoter was amplified by PCR via primers of SEQ ID NOs: 74, 75, 76, and 77; the amplified ScGapDH promoter had a nucleotide sequence of SEQ ID NO: 64. The ScPGK promoter was amplified by PCR via primers of SEQ ID NOs: 82, 83, 84, and 85; the amplified ScPGK promoter had a nucleotide sequence of SEQ ID NO: 65. The KlGapDH promoter was amplified by PCR via primers of SEQ ID NOs: 86, 87, 88, and 89; the amplified KlGapDH promoter had a nucleotide sequence of SEQ ID NO: 66. The KlPGK promoter was amplified by PCR via primers of SEQ ID NOs: 90, 91, 92, and 93; the amplified KlPGK promoter had a nucleotide sequence of SEQ ID NO: 67. The KlADHI promoter was amplified by PCR via primers of SEQ ID NOs: 94, 95, 96, and 97; the amplified KlADHI promoter had a nucleotide sequence of SEQ ID NO: 68. The ScADHI promoter was amplified by PCR via primers of SEQ ID NOs: 78, 79, 80, and 81; the amplified ScADHI promoter had a nucleotide sequence of SEQ ID NO: 69.

To facilitate the following construction of recombinant polynucleotide sequences, the amplified promoters were respectively cloned into the plasmid pUC18 plasmid by the restriction enzymes SalI and EcoRI.

Gene Cassette Assembly

Consecutive gene cassettes containing overlapping 55 bp regions on the border were used for recombinant gene assembly. The gene cassettes were assembled by fusion PCR via use of the TaKaRa Ex Taq system. The reaction mixture contained 0.2 mM of each primer (respectively described below), 0.25 mM of each deoxynucleoside triphosphate, 1×PCR buffer with 2 mM $MgCl_2$, 2 μL of DNA and 2.5 U of Ex Taq DNA polymerase. PCR reaction was carried out at 94° C. for 1 min followed by annealing temperature from 58° C. to 53° C. for 1 min, and 72° C. for optimized period for 10 cycles.

Yeast Culture for Optimal Condition

To find the optimal condition for carotenoid production, the engineered yeasts were cultivated in YPG medium (1% BactoDifco-Yeast Extract, 2% BactoDifco-Peptone, 2% Merck-D(+)-Galactose) respectively at 25° C., 30° C., and 37° C. for 3 days. To test the utilization of carbon source for cell growth, the engineered yeasts were cultivated in YPG medium with the addition of 20% glucose, 20% galactose, or 20% glycerol.

Yeast Transformation and Clone Screening

The yeast cells were incubated in 5 ml of YPG medium (1% BactoDifco-Yeast Extract, 2% BactoDifco-Peptone, 2% Merck-D(+)-Glucose) at 30° C. with shaking at 200 rpm for 16 hr. The gene cassettes were co-transformed into *Klyveromyces lactis* (*K. lactis* Protein Expression Kit, New England Biolabs) so as to express these exogenous genes in yeast cells. When the gene cassettes were amplified by HiFi-PCR (polymerase chain reaction with high fidelity enzyme, PrimeSTAR MAX DNA Polymerase, TaKaRa) and introduced into the cells in one step, they joined together in the predesignated order via homologous recombination between the pairs of overlapping and promoter sequences. Then, they were inserted into the genome via homologous recombination at the promoter sequence of the first and the 3' end of the last gene cassette. The neomycin phosphotransferase gene essential for G418 resistance (Kan MX) was used as a marker gene for clone screening. The target DNA fragments in 10 μl volume with an equal molar ratio of each fragment were mixed with 40 μl of competent cells. The electroporation was performed (1.0 kV, 400Ω, and 25 μF capacitance) using a BioRad system (GenePluserXcell™, Bio-Rad, Hercules, Calif.) with an aluminum cuvette (2 mm). The cells were spread onto YPG plates (1% BactoDifco-Yeast Extract, 2% BactoDifco-Peptone, and 2% Merck-galactose) containing G418 (200 μg/ml).

To confirm the presence of each fragment, each isolated colony was digested in QucikExtract™ DNA Extraction Solution (EPICENTRE, Madison, Wis.) to remove yeast cell wall. A Long-PCR method (EmeraldAmp MAX PCR Master Mix, TaKaRa) were used for checking the order of these gene cassettes with gene specific checking primers (SEQ ID NOs: 23-36), and a high throughput colonies screening were accomplished by an automatic electrophoresis analysis system (Fragment Analyzer™ Automated CE System, Advanced Analytical Technologies).

Reverse Transcription-Polymerase Chain Reaction (RT-PCR) Assay

The genomic DNA was purified from yeast cells using a DNA Isolation Kit III (DNA Isolation Kit III, Roche). The template mRNA was purified from yeast cells using RNeasy mini kits (Qiagen, Chatsworth, Calif.). The cDNA synthesis was conducted using a reverse transcription kit (SuperScript™ II kit, Invitrogen). A real-time qPCR analysis can be employed for checking the driving strength of these promoters in the same strain, and the relative transcription profiles between these promoters will be established under different culturing temperatures. The relative quantification of each gene was carried out via the Universal Probe Library Set (UPLS, LightCyclerW 480 Probes Master, Roche) with a specific primer pair (the amplicon size is 100 to 150 bp) on a LightCycler (LightCycler 480, Roche), following the protocol of the manufacturer. The primers used to analyze the gene expression in the RT-PCT assay was listed in Table 3.

TABLE 3

| The primers for RT-PCR assay. | | |
|---|---|---|
| Primer name | SEQ ID NO | Sequence |
| crtE-UPL#1-F | 37 | CGAGATGCTTTCCCTCCATA |
| crtE-UPL#1-R | 38 | TTCGCTAGGACACGTCAGACT |
| crtI-UPL#155-F | 39 | CCGATCCTTCCTTTTACGTG |
| crtI-UPL#155-R | 40 | CGGCACAAGAATGACGATAG |
| crtR-UPL#41-F | 41 | ACGTCGTCTCTGACGTTTCC |
| crtR-UPL#41-R | 42 | TTGGGTGAAGTTTCGGAGAA |
| crtS-UPL#149-F | 43 | GGATGTTCAAGGTCGGGATA |
| crtS-UPL#149-R | 44 | CGGACAGCTTTTGAGATTCAG |

TABLE 3-continued

The primers for RT-PCR assay.

| Primer name | SEQ ID NO | Sequence |
|---|---|---|
| crtYB-UPL#34-F | 45 | CACTGATCTTATCTTTCCCTTATCG |
| crtYB-UPL#34-R | 46 | GTGGTCTCGATAGGCGTCTT |
| tHMG-UPL#119-F | 47 | TTCTGCTATGGCGGGTTC |
| tHMG-UPL#119-R | 48 | GCTGTAACCAAATTCGAAGCA |
| CrBKT-UPL#159-F | 49 | GCTGCTGCAACTGGTTCAC |
| CrBKT-UPL#159-R | 50 | GCACTAGCGGAACTAGCAGAA |
| CrChYb-UPL#48-F | 51 | TTCTTTCACGATGGATTGGTC |
| CrChYb-UPL#48-R | 52 | TGTATGGTAAGTTGGCGATAGG |
| CZChYb-UPL#157-F | 53 | CGCCCACAAATTACACCATT |
| CZChYb-UPL#157-R | 54 | TCCGAAAAACATACCCCAAG |
| HpChYb#139-F | 55 | AACGACTTGTTCGCAATCATTA |
| HpChYb#139-R | 56 | CCCAACACGTTTGGCAAC |
| Kan-UPL#144-F | 57 | AGACTAAACTGGCTGACGGAAT |
| Kan-UPL#144-R | 58 | CATCAGGAGTACGGATAAAATGC |
| Actin-UPL#9-F | 59 | GCGTAGATTGGAACAACGTG |
| Actin-UPL#9-R | 60 | AGAACTACCGGTATTGTGTTGGA |
| alg9-UPL#132-F | 61 | CAATCAATGGCCCGTATCAT |
| alg9-UPL#132-R | 62 | TGTCTCAGAAGCACAGTTTGG |

Antioxidant Capacity Assay 2,2'-azino-bis(3-ethylbenzothiazoline-6-sulphonic acid) (ABTS) is frequently used by the food industry and agricultural researchers to measure the antioxidation capacities of foods. In this assay, ABTS is converted to its radical cation by addition of sodium persulfate. This radical cation is blue in color and absorbs light at 734 nm. The ABTS radical cation is reactive towards most antioxidants. During this reaction, the blue ABTS radical cation is converted back to its colorless neutral form. The reaction may be monitored spectrophotometrically. This assay is often referred to as the Trolox equivalent antioxidant capacity (TEAC) assay. The reactivities of the various antioxidants tested are compared to that of Trolox, which is a water-soluble analog of vitamin E. For functional confirmation, an antioxidant capacity assay of the cell was done with the ABTS substrate reaction. After 72 hours culturing in YPG medium at 25° C., the cells were lyophilized and the pigments in the cell were extracted by methanol for analysis.

High Performance Liquid Chromatography (HPLC) Analysis

Three-day-cultivated cells were collected and washed with deionized water. The cell pellet was lyophilized in a freeze drier. Carotenoids were extracted from the dried cells with acetone for reverse-phase high-performance liquid chromatography (HPLC) analysis. To carry out the analyses a Jasco HPLC instrument was employed including a PU-2089 Quaternary Pump and an 870-UV intelligent UV-VIS detector. HPLC separation and quantization were performed on a Nomura Chemical Develosil C30-UG Column (3 μm, ID 4.6 mm×L 250 mm–UG17346250W) using methanol/MTBE/water (81:15:4) and methanol/MTBE/water (7:90:3) as mobile phases. The flow rate employed was 1 ml/min and the chromatograms were recorded at 460 nm.

Ethanol Production Assay

The production of ethanol was analyzed by gas chromatography (Shimazdu, GC-14, Japan) with a flame ionization detector (FID) and a stainless steel column (80/120 Carbopack B/6.6% Carbowax, 2 m×2 mm), with nitrogen as mobile gas. The running condition included heating of the column from 80 to 150° C. at a ramp rate of 4° C. per min, an injection temperature of 180° C., and a detection temperature of 250° C. Each fermentation experiment and the subsequent analysis were repeated three times.

Example 1 Construction of Recombinant Polynucleotide Sequence

1.1 crtE-Kan-tHMG1

Geranylgeranyl-pyrophosphate (GGPP) is an important precursor for the biosynthesis of medical compounds, such as carotenoids, gibberellins, tocopherols, chlorophylls, terpenes and terpenoids, in many organisms. HMG-CoA reductase (encoded by HMG1 gene) and GGPP synthase (encoded by crtE gene) are two important intermediates in the HMG-CoA reductase pathway. It has been demonstrated that expressing the truncated HMG-CoA reductase (tHMG1) could cause a reduction in the feedback inhibition and thus improves the downstream GGPP accumulation in the yeast. Accordingly, a recombinant polynucleotide sequence crtE-Kan-tHMG1 was constructed to comprise a crtE gene and a HMG1 gene. The neomycin phosphotransferase gene essential for G418 resistance (Kan) was used as a marker gene for clone screening.

Figure 5B:
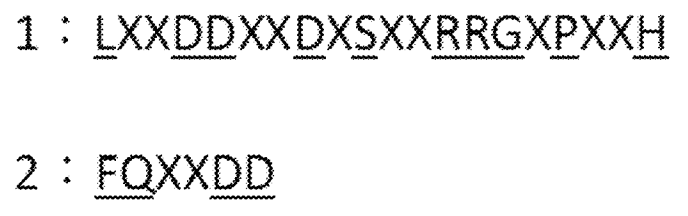

The amino acid sequence of HMG-CoA reductases and GGPP synthase derived from different host cell were analyzed by BLAST analysis (FIGS. 4*a* and 5*a*). Based on the predicted amino acid sequences of the functional domain (FIGS. 4*b* and 5*b*), the genes were cloned or synthesized with optimized codon usage for the expression host, and then constructed as designer gene cassettes with respective promoters.

In practice, the crtE gene amplified by PCR via primers of SEQ ID NOs: 11 and 12 was first assembled with the KlLac4 promoter in the plasmid pUC18 by the restriction enzymes AgeI and NcoI, and then amplified by PCR via primers of SEQ ID NOs: 23 and 24 so as to produce the KlLac4-crtE gene cassette. The Kan gene amplified by PCR with the primers of SEQ ID NOs: 94 and 95 was assembled with the KlGapDH promoter in the plasmid pUC18 by the restriction enzymes AgeI and NcoI, and then amplified by PCR with the primers of SEQ ID NOs: 25 and 26 to produce the KlGapDH-Kan gene cassette, in which the nucleotide sequence of SEQ ID NO: 25 was partly complementary to the nucleotide sequence of SEQ ID NO: 24 (i.e., AGTATGGTAACGACCGTACAGGCAA vs. TTGCCTGTACGGTCGTTACCATACT); and thus, the 5'-end of the KlGapDH-Kan gene cassette was homologous to the 3'-end of the KlLac4-crtE gene cassette. The tHMG1 gene amplified by PCR via primers of SEQ ID NOs: 13 and 14 was assembled with the ScADHI promoter in the plasmid pUC18 by the restriction enzymes AgeI and NcoI, and then amplified by PCR using the primers of SEQ ID NOs: 27 and 28 to produce the ScADHI-tHMG1 gene cassette, in which the nucleotide sequence of SEQ ID NO: 27 was partly complementary to the nucleotide sequence of SEQ ID NO: 26 (i.e., GTGTACAATATGGACTTCCTCTTTTC vs. GAAAAGAGGAAGTCCATATTGTACAC); and accordingly, the 5'-end of the ScADHI-tHMG1 gene cassette was homologous to the 3'-end of the KlGapDH-Kan gene cassette.

Figure 6:
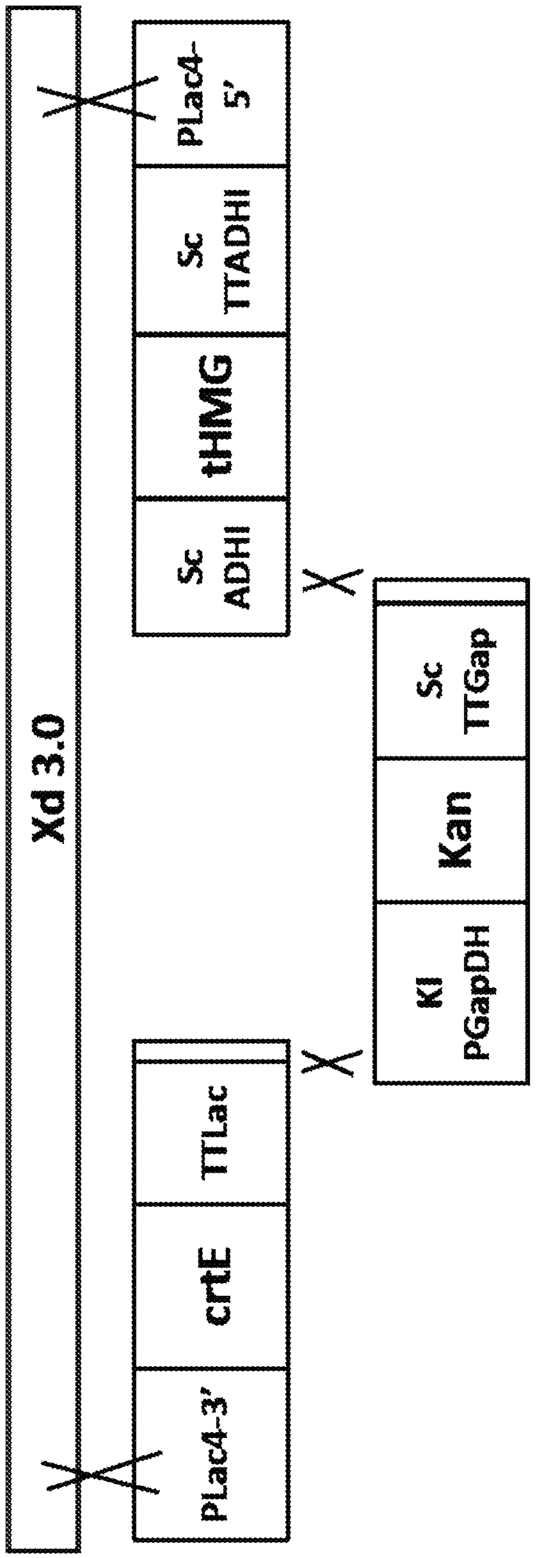
FIG. 6 is a schematic diagram that depicts a genetically engineered strain Xd 3.0 comprising the recombinant polynucleotide sequence, which comprises 3 gene cassettes (abbreviated as crtE-Kan-tHMG1) according to one example of the present disclosure.

Based on the homologous sequences between the KlLac4-crtE gene cassette and the KlGapDH-Kan gene cassette, and the homologous sequences between the KlGapDH-Kan gene cassette and the ScADHI-tHMG1 gene cassette, when the three gene cassettes were co-transformed into *Kluyveromyces marxianus*, they spontaneously assembled to produce the recombinant polynucleotide sequence crtE-Kan-tHMG1 (as summarized in FIG. 6 and Table 4). The engineered strain that comprised the recombinant polynucleotide sequence crtE-Kan-tHMG1 was designated as Xd3.0.

TABLE 4

Gene cassettes of crtE-Kan-tHMG1

| Gene cassette | SEQ ID NOs for Primers for assembling gene cassette | Homologous sequence |
|---|---|---|
| KlLac4-crtE | 23, 24 | the sequence of 3'-end of KlLac4-crtE is homologous to that of 5'-end of KlGapDH-Kan |
| KlGapDH-Kan | 25, 26 | |
| ScADHI-tHMG1 | 27, 28 | the sequence of 3'-end of KlGapDH-Kan is homologous to that of 5'-end of ScADHI-tHMG1 |

1.2 crtI-crtE-Kan-crtYB-tHMG1

β-carotene, the most well-known provitamin A carotenoid, has been used to treat various disorders such as erythropoietic protoporphyria. It has also been used to reduce the risk of breast cancer in women before menopause, and the risk of age-related macular degeneration (AMD). β-carotene is an important midstream precursor for the production of downstream carotenoids, and the crtY (phytoene synthase) gene, the crtI (phytoene desaturase) gene and the crtB (lycopene cyclase) are the important intermediates in the β-carotene biosynthesis pathway. Accordingly, a recombinant polynucleotide sequence crtI-crtE Kan-crtYB-tHMG1 was constructed in Example 1.2 that comprised a crtI gene, a crtE gene, a crtYB gene (encoding a bi-functional enzyme of phytoene synthase and lycopene cyclase), a tHMG1 gene, and a Kan marker gene.

The amino acid sequence of the lycopene cyclase domain, the trans-Isoprenyl diphosphate synthase, and the NAD(P)-binding Rossmann-like domain were respectively analyzed by BLAST analysis (FIGS. 7*a*, 7*c* and 8*a*). Based on the predicted amino acid sequences of the functional domain (FIGS. 7*b*, 7*d* and 8*b*), the genes were cloned or synthesized with optimized codon usage for the expression host, and then constructed as designer gene cassettes with individual promoters.

With a similar construction strategy as described in Example 1.1, the crtI gene amplified by PCR using the primers of SEQ ID NOs: 15 and 16 was first assembled with the KlLac4 promoter in pUC18 by the restriction enzymes AgeI and NcoI, and then amplified by PCR using the primers of SEQ ID NOs: 23 and 29 to produce the KlLac4-crtI gene cassette. The crtE gene amplified by PCR using the primers of SEQ ID NOs: 11 and 12 was assembled with the ScPGK promoter in pUC18 by the restriction enzymes AgeI and NcoI, and then amplified by PCR with the primers of SEQ ID NOs: 30 and 24 to produce the ScPGK-crtE gene cassette. The Kan gene amplified by PCR with the primers of SEQ ID NOs: 94 and 95 was assembled with the KlGapDH promoter in pUC18 by the restriction enzymes AgeI and NcoI, and then amplified by PCR with the primers of SEQ ID NOs: 25 and 31 to produce the KlGapDH-Kan gene cassette. The crtYB gene amplified by PCR with the primers of SEQ ID NOs: 17 and 18 was assembled with the KlADHI promoter in pUC18 by the restriction enzymes AgeI and NcoI, and then amplified by PCR with the primer of SEQ ID NOs: 32 and 26 to produce the KlADHI-crtYB gene cassette. The tHMG1 gene amplified by PCR with the primers of SEQ ID NOs: 13 and 14 was assembled with the ScADHI promoter in pUC18 by the restriction enzymes XhoI and NotI, and then amplified by PCR with the primers of SEQ ID NOs: 27 and 28 to produce the ScADHI-tHMG1 gene cassette.

With the homologous sequences between each of the gene cassettes, when the five gene cassettes were co-transformed into *Kluyveromyces marxianus*, they spontaneously assembled to produce the recombinant polynucleotide sequence crtI-crtE Kan-crtYB-tHMG1 (as summarized in FIG. 9 and Table 5). The engineered strain that comprised the recombinant polynucleotide sequence crtI-crtE-Kan-crtYB-tHMG1 was designated as Xd5.0.

TABLE 5

Gene cassettes of crtI-crtE-Kan-crtYB-tHMG1

| Gene cassette | SEQ ID NOs for Primer for assembling gene cassette | Homologous sequence |
|---|---|---|
| KlLac4-crtI | 23, 29 | the sequence of 3'-end of KlLac4-crtE is homologous to that of 5'-end of ScPGK-crtE |
| ScPGK-crtE | 30, 24 | |
| KlGapDH-Kan | 25, 31 | the sequence of 3'-end of ScPGK-crtE is homologous to that of 5'-end of KlGapDH-Kan |
| KlADHI-crtYB | 32, 26 | the sequence of 3'-end of KlGapDH-Kan is homologous to that of 5'-end of KlADHI-crtYB |
| ScADHI-tHMG1 | 27, 28 | the sequence of 3'-end of KlADHI-crtYB is homologous to that of 5'-end of ScADHI-tHMG1 |

1.3 crtI-crtR-crtE-Kan-crtS-crtYB-tHMG1

For converting the β-carotene intermediate to astaxanthin, two downstream astaxanthin synthase genes, crtS (β-carotene oxygenase) and crtR (P450 reductase), were introduced into the *Kluyveromyces marxianus* host. In the Example 1.3, a recombinant polynucleotide sequence crtI-crtR-crtE-Kan-crtS-crtYB-tHMG1 was constructed that comprised a crtI gene, a crtR gene, a crtE gene, a crtS gene, a crtYB gene (encoding a bi-functional enzyme that possess the respective functions of a phytoene synthase and a lycopene cyclase), a tHMG1 gene, and a Kan marker gene.

The conserved domain regions of β-carotene oxygenase and P450 reductase were determined as the catalytic domain (FIGS. 10*a* and 11*a*). Further, the conserved residues in each conserved domain were also analyzed (FIGS. 10*b*, 11*b*, and 11*c*). The codon used to construct the recombinant polynucleotide sequence crtI-crtR-crtE-Kan-crtS-crtYB-tHMG1 was based on the analysis result. With the similar PGASO construction strategy, the crtI gene amplified by PCR using the primers of SEQ ID NOs: 15 and 16 was assembled with the KlLac4 promoter in pUC18 by the restriction enzymes AgeI and NcoI, and then amplified by PCR using the primers of SEQ ID NOs: 23 and 33 to produce the KlLac4-crtI gene cassette. The crtR gene amplified by PCR using the primers of SEQ ID NOs: 19 and 20 was assembled with the ScGapDH promoter in pUC18 by the restriction enzymes SfiI and NcoI, and then amplified by PCR using the primers of SEQ ID NOs: 34 and 29 to produce the ScGapDH-crtR gene cassette. The crtE gene amplified by PCR using the primers of SEQ ID NOs: 11 and 12 was assembled with the ScPGK promoter in pUC18 by the restriction enzymes AgeI and NcoI, and then amplified by PCR using the primers of SEQ ID NOs: 30 and 24 to produce the ScPGK-crtE gene cassette. The Kan gene amplified by PCR with the primers of SEQ ID NOs: 98 and 99 was assembled with the KlGapDH promoter in pUC18 by the restriction enzymes AgeI and NcoI, and then amplified by PCR using the primers of SEQ ID NOs: 25 and 35 to produce the KlGapDH-Kan gene cassette. The crtS gene amplified by PCR using the primers of SEQ ID NOs: 21 and 22 was assembled with the KlPGK promoter in pUC18 by the restriction enzymes AgeI and NcoI, and then amplified by protein PCR using the primers of SEQ ID NOs: 36 and 31 to produce the KlPGK-crtS gene cassette. The crtYB gene amplified by PCR with the primers of SEQ ID NOs: 17 and 18 was assembled with the KlADHI promoter in pUC18 by the restriction enzymes AgeI and NotI, and then amplified by PCR using the primer of SEQ ID NOs: 32 and 26 to produce the KlADHI-crtYB gene cassette. The tHMG1 gene amplified by PCR with the primers of SEQ ID NOs: 13 and 14 was assembled with the ScADHI promoter in pUC18 by the restriction enzymes NotI and XhoI, and then amplified by PCR using the primers of SEQ ID NOs: 27 and 28 to produce the ScADHI-tHMG1 gene cassette.

When the seven gene cassettes were co-transformed into *Kluyveromyces marxianus*, they spontaneously assembled to produce the recombinant polynucleotide sequence crtI-crtR-crtE-Kan-crtS-crtYB-tHMG1 based on the homologous sequences between gene cassettes (as summarized in FIG. 12 and Table 6). The engineered strain that comprised the recombinant polynucleotide sequence crtI-crtR-crtE-Kan-crtS-crtYB-tHMG1 was designated as Xd7-3.

TABLE 6

Gene cassettes of crtI-crtR-crtE-Kan-crtS-crtYB-tHMG1

| Gene cassette | SEQ ID NOs for Primers for assembling gene cassette | Homologous sequence |
|---|---|---|
| KlLac4-crtl | 23, 33 | |
| ScGapDH-crtR | 34, 29 | the sequence of 3'-end of KlLac4-crtE is homologous to that of 5'-end of ScGapDH-crtR |
| ScPGK-crtE | 30, 24 | the sequence of 3'-end of ScGapDH-crtR is homologous to that of 5'-end of ScPGK-crtE |
| KlGapDH-Kan | 25, 35 | the sequence of 3'-end of ScPGK-crtE is homologous to that of 5'-end of KlGapDH-Kan |
| KlPGK-crtS | 36, 31 | the sequence of 3'-end of KlGapDH-Kan is homologous to that of 5'-end of KlPGK-crtS |
| KlADHI-crtYB | 32, 26 | the sequence of 3'-end of KlPGK-crtS is homologous to that of 5'-end of KlADHI-crtYB |
| ScADHI-tHMG1 | 27, 28 | the sequence of 3'-end of KlADHI-crtYB is homologous to that of 5'-end of ScADHI-tHMG1 |

This engineered strain Xd7-3 should be able to produce the red carotenoids, 3R, 3'R astaxanthin stereoisomer. However, Xd7-3 exhibited the cell color changes by yellow carotenoids (β-carotene and zeaxanthin) accumulation (FIG. **13*a*** and Table 7). It is speculated that the enzyme efficiency of β-carotene oxygenase and P450 reductase from *Xanthophyllomyces dendrorhous* might not be good enough, or/and the promoter strength of ScPGapDH might be too low.

TABLE 7

The carotenoids concentration of the engineered strains, WT, Xd7-3, Cr1, Cz5, and Hp9.

| | Specific amount (μg/g [dw]) of carotenoids[a] | | | | |
|---|---|---|---|---|---|
| Carotenoid | Cr1 | Cz5 | Hp9 | Xd7-3 | WT |
| β-carotene | 59.6 ± 2.3 (1) | 93.9 ± 3 (1.6) | 224.4 ± 9.9 (3.8) | 244.7 ± 5.1 (4.1) | —[b] |
| Canthaxanthin | 18.4 ± 3.6 (1.4) | 12.8 ± 1.9 (1) | 39.8 ± 2.7 (3.1) | — | — |

[a]The data are averages of three independent cultures. The n-fold increases in carotenoid production levels compared to that of strain which is lowest (the value for strain is set at 1).

[b]—, not detected.

1.4 crtI-crtE-ChYb-Kan-CrBKT-crtYB-tHMG1

In order to produce the 3S, 3'S astaxanthin stereoisomer, two additional astaxanthin synthase genes, bkt (encoding β-carotene ketolase) and chYb (encoding β-carotene hydroxylase), were introduced into *Kluyveromyces marxianus*.

To construct the recombinant polynucleotide sequence crtI-crtE-ChYb-Kan-CrBKT-crtYB-tHMG1, the amino acid sequences of the conserved regions of β-carotene ketolase were first analyzed (FIG. 14*a*), in which the conserved residues in each conserved region were illustrated in FIG. 14*b*. Based on the analysis result, the gene was cloned or synthesized with optimal codon usage for the expression host, and then constructed as designer gene cassettes with the KlPGK promoter.

Furthermore, to select the other key enzymatic genes in the astaxanthin biosynthesis pathway, the chYb genes from the three different algae, *C. reinhardtii* (CrChYb), Ch. *zofingiensis* (CZChYb), and *H. pluvialis* (HpChYb), were also cloned and used to construct designer gene cassettes with the ScPGK promoter. As described above, the conserved domain region was determined (FIG. 15); the gene was cloned or synthesized with optimal codon usage for the expression in the host.

The recombinant polynucleotide sequence crtI-crtE-ChYb-Kan-CrBKT-crtYB-tHMG1 was constructed by the method similar to that for constructing crtE-Kan-tHMG1 or crtI-crtE-Kan-crtYB-tHMG1, in which the ChYb gene can be the CrChYb gene, the CzChYb gene, or the HpChYb gene. Briefly, the amplified crtI gene fragment was assembled with the KlLac4 promoter in pUC18 via the restriction enzymes AgeI and NcoI, and then amplified by PCR using the primers of SEQ ID NOs: 23 and 33 to produce the KlLac4-crtI gene cassette. The amplified crtE gene fragment was assembled with the ScGapDH promoter in pUC18 via the restriction enzymes AgeI and NcoI, and then amplified by PCR with the primers of SEQ ID NOs: 34 and 29 to produce the ScGapDH-crtE gene cassette. The ChYb gene (i.e., CrChYb gene, CzChYb gene, or HpChYb gene) was assembled with the ScPGK promoter in pUC18 by the restriction enzymes XhoI and NotI, and then amplified by PCR with the primers of SEQ ID NOs: 30 and 24 to produce the ScPGK-ChYb gene cassette. The Kan gene was assembled with the KlGapDH promoter in pUC18 by the restriction enzymes AgeI and NcoI, and then amplified by PCR with the primers of SEQ ID NOs: 25 and 35 to produce the KlGapDH-Kan gene cassette. The BKT gene was assembled with the KlPGK promoter in pUC18 by the restriction enzymes XhoI and NotI, and then amplified by protein PCR with the primers of SEQ ID NOs: 36 and 31 to produce the KlPGK-BKT gene cassette. The crtYB gene was assembled with the KlADHI promoter in pUC18 by the restriction enzymes AgeI and NotI, and then amplified by PCR with the primer of SEQ ID NOs: 32 and 26 to produce the KlADHI-crtYB gene cassette. The tHMG1 gene was assembled with the ScADHI promoter in pUC18 by the restriction enzymes XhoI and NotI restriction enzyme sites, and then amplified by PCR with the primers of SEQ ID NOs: 27 and 28 to produce the ScADHI-tHMG1 gene cassette.

With the similar concept, the homologous sequences between each gene cassette render the homologous recombination of the seven gene cassettes in the host cell *Kluyveromyces marxianus* so as to produce the recombinant polynucleotide sequence crtI-crtE-ChYb-Kan-CrBKT-crtYB-tHMG1, in which the ChYb can be CrChYb, HpChYb, or CzChYb (as summarized in FIG. 16 and Table 8).

TABLE 8

Gene cassettes of crtI-crtE-ChYb-Kan-CrBKT-crtYB-tHMG1

| Gene cassette | SEQ ID NOs for Primers for assembling gene cassette (forward vs. reverse) | Homologous sequence |
|---|---|---|
| KlLac4-crtI | 23, 33 | the sequence of 3'-end of KlLac4-crtE is homologous to that of 5'-end of ScGapDH-crtE |
| ScGapDH-crtE | 34, 29 | |
| ScPGK-ChYb | 30, 24 | the sequence of 3'-end of ScGapDH-crtE is homologous to that of 5'-end of ScPGK-ChYb |
| KlGapDH-Kan | 25, 35 | the sequence of 3'-end of ScPGK-ChYb is homologous to that of 5'-end of KlGapDH-Kan |
| KlPGK-BKT | 36, 31 | the sequence of 3'-end of KlGapDH-Kan is homologous to that of 5'-end of KlPGK-BKT |
| KlADHI-crtYB | 32, 26 | the sequence of 3'-end of KlPGK-BKT is homologous to that of 5'-end of KlADHI-crtYB |
| ScADHI-tHMG1 | 27, 28 | the sequence of 3'-end of KlADHI-crtYB is homologous to that of 5'-end of ScADHI-tHMG1 |

The produced recombinant polynucleotide sequences (i.e., crtI-crtE-CrChYb-Kan-CrBKT-crtYB-tHMG1, (crtI-crtE-HpChYb-Kan-CrBKT-crtYB-tHMG1, and (crtI-crtE-CzChYb-Kan-CrBKT-crtYB-tHMG1) were respectively introduced into the *Kluyveromyces marxianus* genome (FIG. 16). The engineered strain that comprised the recombinant polynucleotide sequence crtI-crtE-HpChYb-Kan-CrBKT-crtYB-tHMG1 was designated as Hp9; the engineered strain that comprised the recombinant polynucleotide sequence crtI-crtE-CrChYb-Kan-CrBKT-crtYB-tHMG1 was designated as Cr1; and the engineered strain that comprised the recombinant polynucleotide sequence crtI-crtE-CzChYb-Kan-CrBKT-crtYB-tHMG1 was designated as Cz5.

Example 2 Characterization of Engineered Strain that Comprised Recombinant Polynucleotide Sequence of Example 1.4

The characteristic of the engineered strains Cr1, Cz5, and Hp9 constructed in Example 1.4 were examined in Example 2. The expression of gene cassettes and the productivity of carotenoids were first verified in Example 2.1, while the optimal condition for the host cell to express the carotenoids were determined in Example 2.2.

2.1 Expression of Recombinant Polynucleotide Sequence of Example 1.4

After sub-culturing for 10 generations, the stable clones, Cr1, Cz5, and Hp9, were selected. According to the data in FIG. 13*a* and Table 7, HpChYb might possess a stronger β-carotene hydroxylase activity than CrChYb and CZChYb. To verify the order of these gene cassettes in each clone, a long-PCR method (EmeraldAmp MAX PCR Master Mix, TaKaRa) and electrophoresis analysis were used. The data indicated that each of these stable clones possessed the designed gene cassettes in the corrected order (FIGS. 13*b* and 13*c*).

A 50 ml batch fermentation culture was employed to compare these engineered strains in the optimal culturing condition. After 3 days culturing, the growth curve data indicated that the Hp9 and Cz5 strains grew slightly faster than any of the WT strain, the Cr1 strain, and the Xd7-3 strain (FIG. 17*c*). These strains, especially Hp9, exhibited a significant change in the color of the cultured medium, turning from the control cream color into red or deep orange color (FIGS. 17*a* and 17*b*).

To quantify the carotenoids in the cell, acetone was employed to extract these pigments from the yeast culture. The full-spectrum UV/V spectrophotometry was used to estimate the total amount of carotenoids; in which the free form pure carotenoid compounds, including β-carotene, astaxanthin, canthaxanthin, and zeaxanthin, were used as the four standards. Based on the analysis results, all the carotenoid compounds had an absorption spectrum between 400 nm and 530 nm (data not shown). The carotenoids extracted from all of these engineered strains (Xd7-3, Cr1, Cz5, and Hp9) also possessed an absorption spectrum between 400 nm and 530 nm, except the WT strain (FIG. 17*d*).

HPLC was used to analyze the compositions of the thus produced carotenoids, and each of the free form carotenoid compounds could be separated by their respective retention times. For example, astaxanthin may be separated at 7.8 min, zeaxanthin at 9.7 min, canthaxanthin at 12.8 min, and β-carotene at 32 min. After quantifying the concentration of β-carotene by interpolating from a standard curve, it was estimated that each engineered strains, including Xd7-3, Cr1, Cz5 and Hp9 strains could respectively accumulate 244.7, 59.6, 93.9 and 224.4 μg/g of β-carotene. The data also indicated that the Hp9 strain could produce β-carotene 3.8-folds faster than the Cr1 strain. Furthermore, except the WT strain and the Xd7-3 strain, all the engineered strains that possessed algal bkt and chyb genes could accumulate canthaxanthin in the cells as well; in which about 18.4, 12.8, and 39.8 μg/g of canthaxanthin were respectively found in the Cr1, Cz5, and Hp9 strains (Table 7). The data also indicated that the Hp9 strain could produce canthaxanthin 3.1 times faster than the Cz5 strain.

The algal β-carotene hydroxylase gene Crchyb from *Chlamydomonas reinhardtii*, Czchyb from *Chlorella zofingiensis*, or Hpchyb from *Haematococcus pluvialis* and six other carotenoid-synthesis pathway genes were co-integrated into the genome of the yeast host *Kluyveromyces marxianus*. Each of these three algal genes exhibited a higher efficiency to convert β-carotene to downstream carotenoids than the fungal genes from *Phaffia rhodozyma*. Furthermore, the strain having Hpchyb displayed a higher carotenoid productivity than the strains integrated with Crchyb or Czchyb, indicating that Hpchyb is more efficient than Crchyb and Czchyb. Taken together, these results suggest that β-carotene hydroxylase plays a crucial role in the biosynthesis of carotenoids.

Further, according to the HPLC spectrometry assay under UV450 nm (FIGS. 18*a* and 18*b*), each engineered strains of the present example exhibited a peak of free-form canthaxanthin (peak 1), a peak of free-form β-carotene (peak 6), and some unknown peaks (peaks 2, 3, 4, 5, 7, and 8). Thus, these engineered strains should be able to produce the carotenoids and their derivatives, such as zeaxanthin, 3S, 3'S astaxanthin stereoisomer, and/or their esterified derivatives.

2.2 Characterizing the Optimal Expression Condition of the Recombinant Polynucleotide Sequence of Example 1.4

In the present example, the optimal condition for expressing carotenoids and their derivatives by the engineered strains established in Example 1.4 was determined, in which the optimal temperature was evaluated in Example 2.2.1, while the optimal culture medium was verified in Example 2.2.2.

2.2.1 Optimal Temperature

To increase the carotenoids productivity of the present vector, one more copy of the vector was integrated into the Cz5 strain; the generated strain was then designated as the Cz30 strain. Compared with the Cz5 strain, the Cz30 strain produced a stronger red color change (FIG. 19*a*).

To evaluate the optimal condition for carotenoid production, Cz5 and Cz30 were separately cultivated in YPG medium at 25° C., 30° C., and 37° C. After culturing for 3 days, the broth (contained either Cz5 or Cz30) cultivated at 25° C. or 30° C. was in red color, while the broth (contained either Cz5 or Cz30) cultivated at 37° C. remained in white color (FIG. 19*b*). Besides, only Cz30 exhibited a significant color change at 25° C. after being cultivated for 2 days. The data indicated that 25° C. was the optimal temperature for carotenoid production, and Cz30 had a higher productivity than that of Cz5.

Since the Cz30 strain exhibited a significantly stronger red color change, as compared with that of the Cz5 strain, the gene expression profiles of Cz30 were examined under different culturing temperatures. All samples were harvested after being cultured for 48 hours, and the mRNA was extracted from each sample for real time PCR assay. As the data illustrated in FIG. 19*c*, the expression levels of all transformed genes were much higher in Cz30 than in Cz5 in all of the conditions investigated; the data was consistent with the observation that Cz30 produced more carotenoids, and exhibited a stronger red color. Further, the results also indicated that the expression levels of all transformed genes were higher at 30° C. than at 25° C. or 37° C. As 25° C. produced the strongest red color, the data implied that 25° C. was the optimal condition for the enzyme reactions (FIG. 19*c*).

Since the phytoene desaturase (encoded by crtI) and the β-carotene ketolase (encoded by BKT) are the crucial enzymes in the production of 3S, 3'S-astaxanthin, two stronger promoters, i.e., pLac4 and pKlPGK, were used to drive these two genes. Accordingly, it was expected that the expression levels of the CHI and CrBKT genes would be higher than those of the other genes (FIG. 19*c*).

The HPLC spectrometry assay further confirmed that the engineered Cz30 strain accumulated higher amounts of β-carotene, canthaxanthin, and esterified astaxanthin derivatives (i.e., monoester carotenoids and diester carotenoids) in the pathway (FIGS. 20*a* and 20*b*).

Accordingly, the date indicated that compared with the Cz5 strain, the Cz30 strain had a higher productivity of carotenoid; further, the data also demonstrated that 25° C. was the optimal temperature for carotenoid production.

2.2.2 Optimal Culture Medium

To investigate the carbon source for cell growth, the wild type *Kluyveromyces marxianus* (WT) and the engineered strain Cz30 were separately cultivated in YPG medium with the addition of 20% glucose, 20% galactose, or 20% glycerol. After culturing at 25° C. for 2 days, the broth of WT cells was in white color, whereas the broth of Cz30 exhibited yellow (glucose), orange (galactose), or red (glycerol) color (FIG. 21*a*). These data indicated that Cz30 produced and accumulated different combinations of carotenoids in the cell, depending on the added component in the culture medium (i.e., glucose, galactose, or glycerol). The differences in cell color between different carbon sources might be caused by the accumulation of different concentrations of carotenoids in the cell; or it could be due to the synthesis of different types of carotenoids, such as yellow carotenoids (β-carotene and zeaxanthin) and pinkish-red carotenoids (canthaxanthin, astaxanthin, and other esterified astaxanthin derivatives) (FIG. 21*a*). However, the discoloration of the host cells was observed after being cultured for 5 days, except when 20% glycerol was added.

All of the engineered Cz5 and Cz30 samples cultivated with glycerol were harvested after culturing for 48 hours and 72 hours, and their mRNAs were extracted for real time PCR assay. It was found that the expression level of the CzBKT gene was higher than that of the HpCHYB at 48 hours at 25° C., 30° C. or 37° C., as expected from the designed gene cassettes for the cantaxanthin production (Table 9). Furthermore, the expression level of the HpCHYB gene was higher than that of the CzBKT gene at 72 hours, for the conversion of cantaxanthin to astaxanthin (Table 9).

TABLE 9

The relative gene expression levels of the engineered strains with 20% glycerol added YPG medium.

| | | Relative RNA expression level | | | | |
|---|---|---|---|---|---|---|
| | | 25° C. | | 30° C. | | 37° C. |
| Strain | time | chyb | bkt | chyb | bkt | chyb | bkt |
| Cz5 | 48 hr | 1 | 15.14 | 1.93 | 15.79 | 6.71 | 12.07 |
| | 120 hr | 2.43 | — | 2.93 | — | 7.93 | — |
| Cz30 | 48 hr | 1.29 | 12.79 | 4.07 | 7.79 | 4.64 | 23.5 |
| | 120 hr | 7.29 | — | 3.86 | — | 7.21 | — |

(1) The n-fold increases in RNA expression levels compared to that of strain which is lowest (the value for strain is set at 1)
(2) —: non-detectable Based on the results of the LC spectrometry assay, the Cz30 cultivated in the present of 20% glycerol accumulated higher amounts of β-carotene and canthaxanthin, compared with those cultivated in the present of 20% galactose (Table 10). After the saponification treatment, LC/MS analysis was employed to confirm the identities of the produced compounds, and the data indicated that the carotenoids thus produced included β-carotene, canthaxanthin, and astaxanthin (FIG. 22).

Interestingly, the Cz30 cell cultivated in glycerol, which is the byproduct of the bio-diesel industry, exhibited a significant red color change, as compared with culturing in other carbon sources, indicating the potential use of Cz30 for the development of a green industry. Moreover, the broth of Cz30 remained in red color after being cultured for 5 days in 20% glycerol, although the relationship between glycerol metabolism and carotenoid esterification is still not clear.

The carotenoids were extracted from WT and Cz30 strain, and the antioxidant ability of the thus produced carotenoids was determined by use of the ABTS substrate reaction. After culturing in YPG medium at 25° C. for 72 hours, the host cells were lyophilized and the pigments in the cells were extracted by methanol. The extract of Cz30 exhibited a higher free radical scavenging capacity (72.1%) than that of WT (52.3%) (FIG. 23a). The data indicated that about 20% free radicals scavenging capacity was contributed by the carotenoids produced by Cz30 in Trolox Equivalent Antioxidant Capacity (TEAC) assay and it was equal to 1.95 mg Trolox (a water-soluble analog of vitamin E) in one-gram cell dry weight, although WT also possessed antioxidant capacity (FIG. 23b).

The above data indicated that the medium containing 20% glycerol provided the optimal circumstance for the production of carotenoids. Further, the results also demonstrated that the produced carotenoids possessed antioxidant efficacy.

Example 3 Improvement of Astaxanthin Production

As β-carotene ketolase and β-carotene hydroxylase are two key regulated enzymes in astaxanthin production pathway, the astaxanthin synthesis gene cassettes (ie., crtI-crtE-HpChYb-Kan-HpChYb-CrBKT-crtYB-tHMG1) were integrated with the extra ChYb gene cassette into the host genome to generate the CA6 strain (FIG. 24a). The transformant after culture produced a significant red color change in the cultured broth.

In order to increase the copy number of key enzymes for astaxanthin production, the astaxanthin synthase genes, bkt (encoding the β-carotene ketolase) and chYb (encoding the β-carotene hydroxylase), were further integrated into the internal transcribed spacer (ITS) region of the rDNA of the CA6 strain, and the thus generated strain was designated as CA6-ITS. The gene cassette included aur-HpChYb-CrBKT and a promoter (FIG. 24b). The expression levels of the HpChYb and CrBKT genes were proportionally increased as the copy number of key enzymes increased (FIG. 24c).

To investigate the carbon source for cell growth, the engineered strain CA6-ITS was cultivated in YPG medium with or without the addition of 10% glycerol. After culturing at 25° C. for 2 days, the CA6-ITS strain cultivated in YPG medium with 10% glycerol obviously produced a stronger red color change, compared with that cultivated in YPG medium without glycerol (FIG. 21b). The data of Table 11 further indicated that 10% glycerol is sufficient to induce the astaxanthin production in CA6-ITS strain.

TABLE 10

The carotenoids concentration produced by the WT, Cz5, and Cz30 strains.

| | Specific amount (μg/g [dw]) of carotenoids | | | | | | | | | | |
|---|---|---|---|---|---|---|---|---|---|---|---|
| | YPG | | | YPG + 20% gal | | | YPG + 20% glu | | | YPG + 20% gly | | |
| Carotenoids | WT | Cz5 | Cz30 | WT | Cz5 | Cz30 | WT | Cz5 | Cz30 | WT | Cz5 | Cz30 |
| β-carotene | —$^a$ | 110.24 | 131.27 | — | 15.78 | 243.68 | — | — | 0.2 | — | 148.8 | 366.98 |
| Canthaxanthin | — | 17.39 | 123.53 | — | — | 10.86 | — | — | — | — | 17.46 | 19.47 |

(1) gal: galactose; glu: glucose; gly: glycerol.
(2) $^a$ —, not detected.

TABLE 11

The carotenoids concentration produced by the CA6-ITS strain

| | Specific amount (μg/g [dw]) of carotenoids | |
|---|---|---|
| Medium | β-carotene | Astaxanthin |
| YPG | 432.16 | 0.16 |
| YPG + 10% glycerol | 241.23 | 5.49 |

Furthermore, the astaxanthin synthesis gene cassettes were introduced together with a high copy expression plasmid RS426 to the CA6-plasmid strain (FIG. 24*d*). The gene cassettes would be spontaneously assembled to the plasmid in vivo; and the transformant could produce orange to red colonies. With the high copy number of plasmids, the host cell has potential to express high amounts of proteins, and to convert the precursor to astaxanthin more efficiently.

Based on the results on the HPLC spectrometry assay, the engineered CA6-ITS strain can produce the free-form astaxanthin, zeaxanthin, cantaxanthin, β-carotene at retention times of 7.76, 9.9, 12.25, and 31.40 min, respectively (FIG. 24*e*). The yield of the astaxanthin, zeaxanthin, cantaxanthin, β-carotene is about 19.48, 21.7, 4.40, and 501.57 μg/g, respectively (Table 12). The data revealed that increasing the copy number of the chYb, which encoded β-carotene hydroxylase, can improve the productivity of carotenoids.

TABLE 12

The carotenoids concentration of the engineered strains.

| | Specific amount (μg/g [dw]) of carotenoids | | | |
|---|---|---|---|---|
| Strains | β-carotene | Zeaxanthin | Canthaxanthin | Astaxanthin |
| WT | —[a] | — | — | — |
| Cz30 | 429.51 | 13 | 0.85 | — |
| CA6 | 411.05 | 18.3 | 1.42 | 1.72 |
| CA6-ITS | 501.57 | 21.7 | 4.04 | 19.48 |

[a]—, not detected.

Thus, the two engineered strains, CA6 and CA6-ITS of the present example can efficiently convert the astaxanthin precursor to astaxanthin. Furthermore, high copy number of associated gene expression is crucial for astaxanthin production.

Example 4 Production of New Combinations of Natural Carotenoids with Monoester or Diester Forms The polar ends in free astaxanthin can be absorbed better by the animals (e.g., human) than non-polar carotenoids, but it is particularly susceptible to oxidation. Astaxanthin is largely present as fatty acid-esters in nature, such as in green algae, with one or two fatty acids to form a monoester and diester forms, and these esterified molecules are more stable. Cholesterol esterase is a likely candidate to hydrolyze esterified astaxanthin, which is subsequently incorporated into micelles to allow astaxanthin being absorbed by intestinal cells.

In this example, carotenoid esters and their geometric isomers in the engineered strain were identified. The Crabtree negative yeast, *Kluyveromyces marxianus*, was chosen to be the host cell for its high growth rate and high cell mass production abilities, as well as the potential to convert the hydroxy groups to a monoester or a diester with fatty acids of various length, such as octanoic acid-ethyl ester, acetic acid-2-phenylethyl ester, and decanoic acid-ethyl ester.

Natural astaxanthin from algae is usually paired with fatty acids attached to the end of its hydroxy groups, which results in an esterified astaxanthin. The esterified astaxanthin has been shown to be more stable and more bioactive than those of the non-esterified forms found in the synthetic and bacteria-produced astaxanthin, which is called "free" astaxanthin. To generate the monoester or diesterified astaxanthin, the fatty acid (0.01% or 0.1% octanoic acid) was added to the cultured CA6-ITS strain together with or after galactose induction. The cell color started to convert to red when the octanoic acid was added simultaneously with the galactose induction (FIGS. 25*a* and 25*b*).

The possibility of new combinations of saturated fatty acids in the diesters was examined using data collected from mass spectrometry assay (LC-MS/MS). Further, the LC MS/MS analysis was used to confirm the structures of the thus produced compounds; the data indicated that the thus produced carotenoids included, phenicoxanthin, canthaxanthin, echinenone, (3-cryptoxanthin, esterified adonixanthin, lycopene, phytoene, β-carotene, and esterified astaxanthin (FIGS. 26*a* and 26*b*).

Example 5 Characterization of Engineered Strain that Comprised a Recombinant Polynucleotide Sequence As the carotenoid compound possesses two ring structures, which are respectively located at or near the two terminals of the carotenoid compound, they could neutralize singlet and triplet oxygen molecules inside or outside the cell. It might also help Cz30 to counteract UV damage, solvent stress, and/or the reactive oxygen species (ROS) effects. Moreover, the carotenoid-producing yeasts might be more tolerant to environmental stresses due to the reduced lipid peroxidation of the growing cell. Accordingly, the engineered strains described in the present disclosure can be used to produce other value-added metabolites and improve the productivity.

5.1 Enhancing the Degree of Tolerance of a Host to a Stress

The data of FIG. 23 revealed that the cell extract of Cz30 exhibited an antioxidant activity in comparison to that of wild-type (WT) control. In this example, the anti-stress capability of Cz30 was further confirmed by UV, furfural, ethanol, or isobutanol treatment.

Figure 27A:
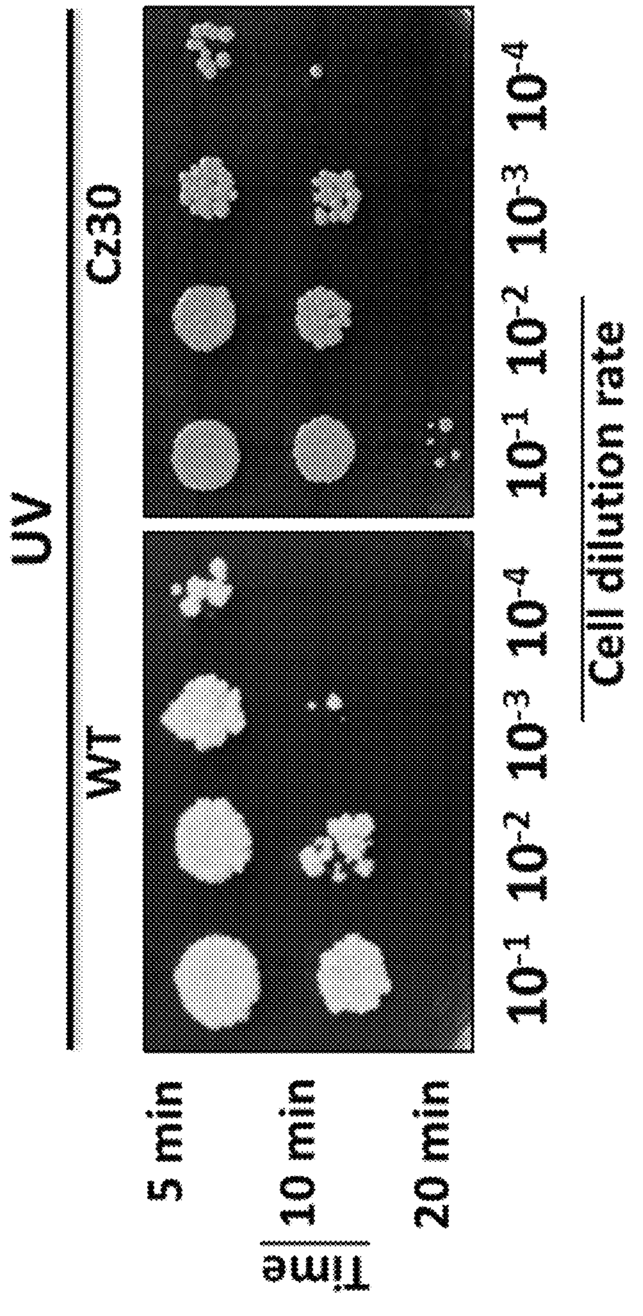

The WT and Cz30 were separately exposed to UV for 5, 10, or 20 minutes, and then inoculated in the YPG plate with a series dilution and cultivated for 48 hours. Only some Cz30 colonies could grow on the YPG plate after being exposed to UV light for 20 minutes (FIG. 27*a*). This observation suggested that the carotenoid products of Cz30 could reduce UV damage, resulting in faster cell growth as compared to that of the WT.

Figure 27B:
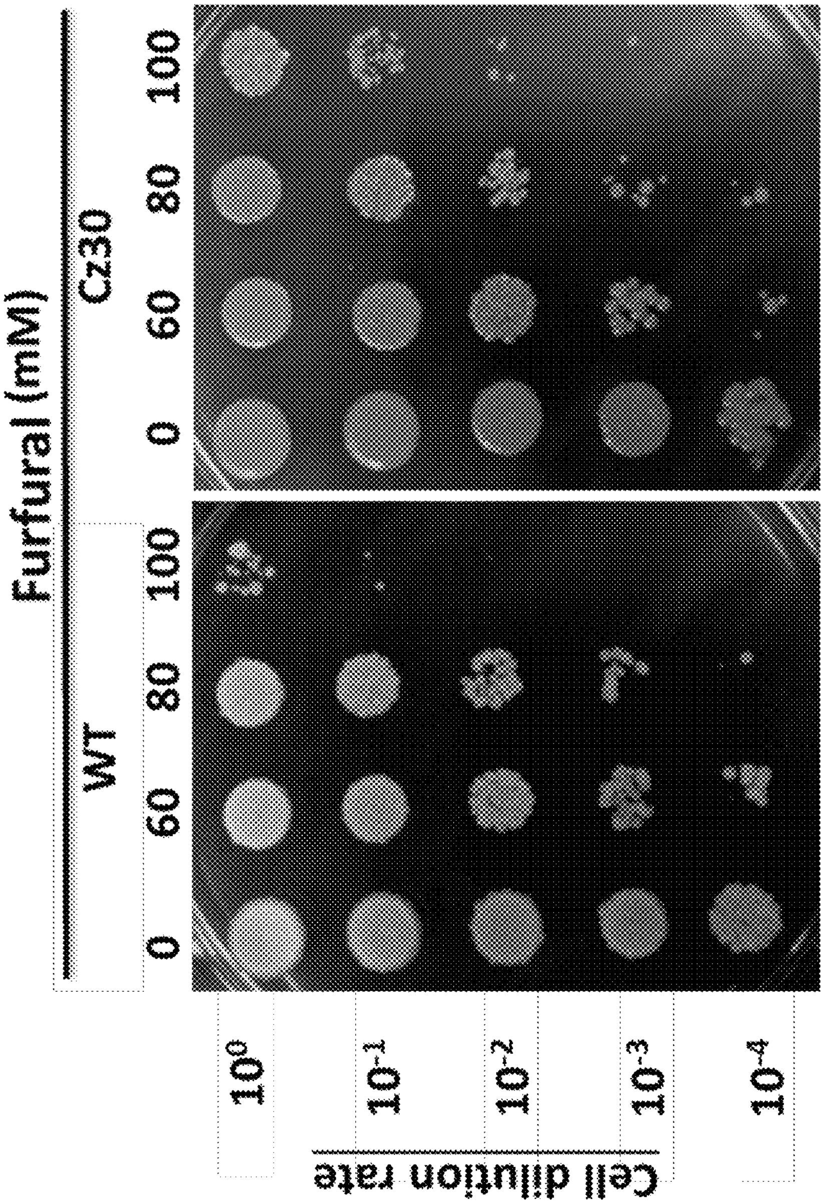
Figure 27C:
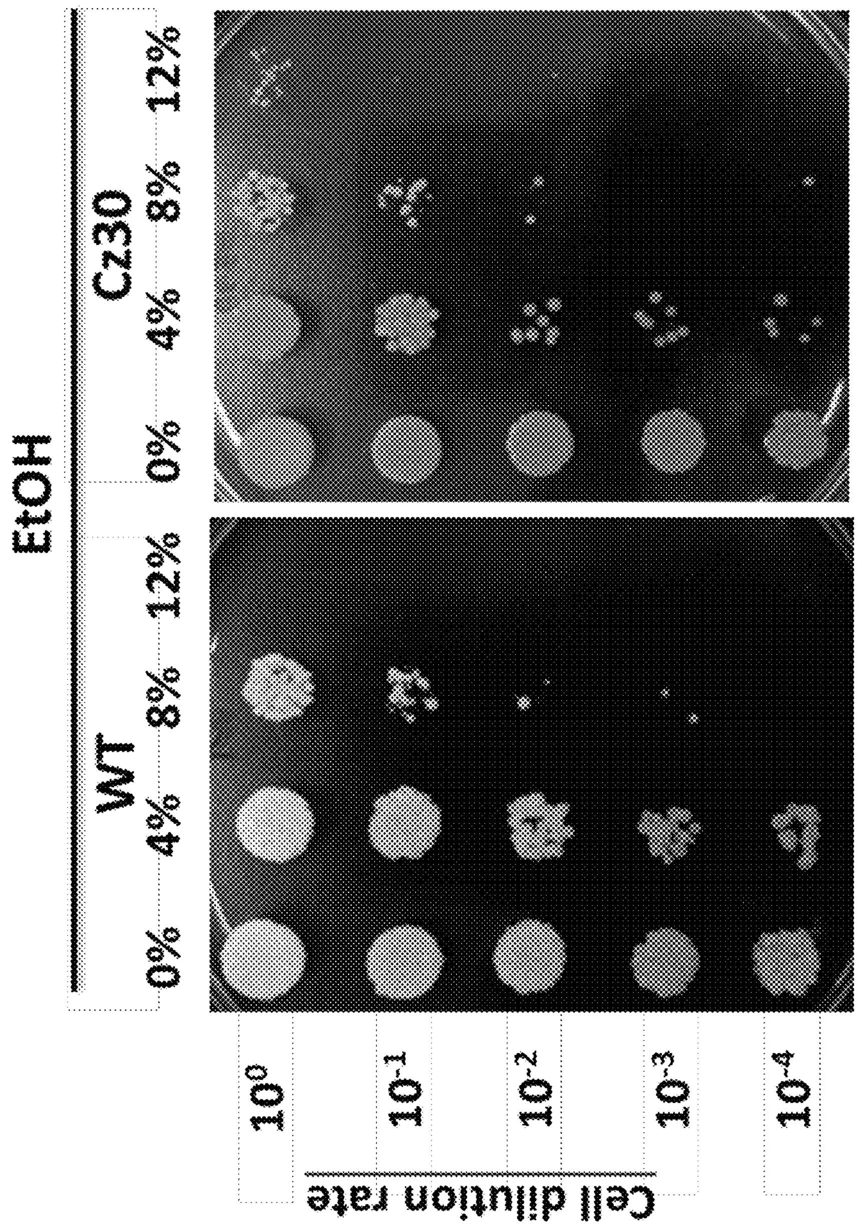

For the biorefinery application, plant biomass is one of the most abundant renewable resources on earth and is considered an essential building block for developing a sustainable society. Renewable biological resources from plant can be converted into bioproducts, such as biofuels, biochemicals, biolubricants, and biodegradable materials. To utilize the sugars contained in plant biomass, many available treatment techniques, including acid hydrolysis, steam explosion, ammonia fiber expansion, organosolv, sulfite pretreatment, alkaline wet oxidation, ozone pretreatment, and enzyme treatment, are employed for lignocellulose destruction. Toxins produced during acid and steam pretreatment of lignocellulose cover a large range of substances, such as furfural and hydroxymethylfurfural from hemicellulose and cellulose, alcohols and aldehydes from lignin, and heavy metals from bioreactor. Accordingly, the second stress factor examined was furfural treatment. In FIG. 27*b*, the Cz30 strain could tolerate the treatment of 100 mM furfural, whereas the WT strain could only tolerate the treatment with 80 mM furfural.

Figure 27D:
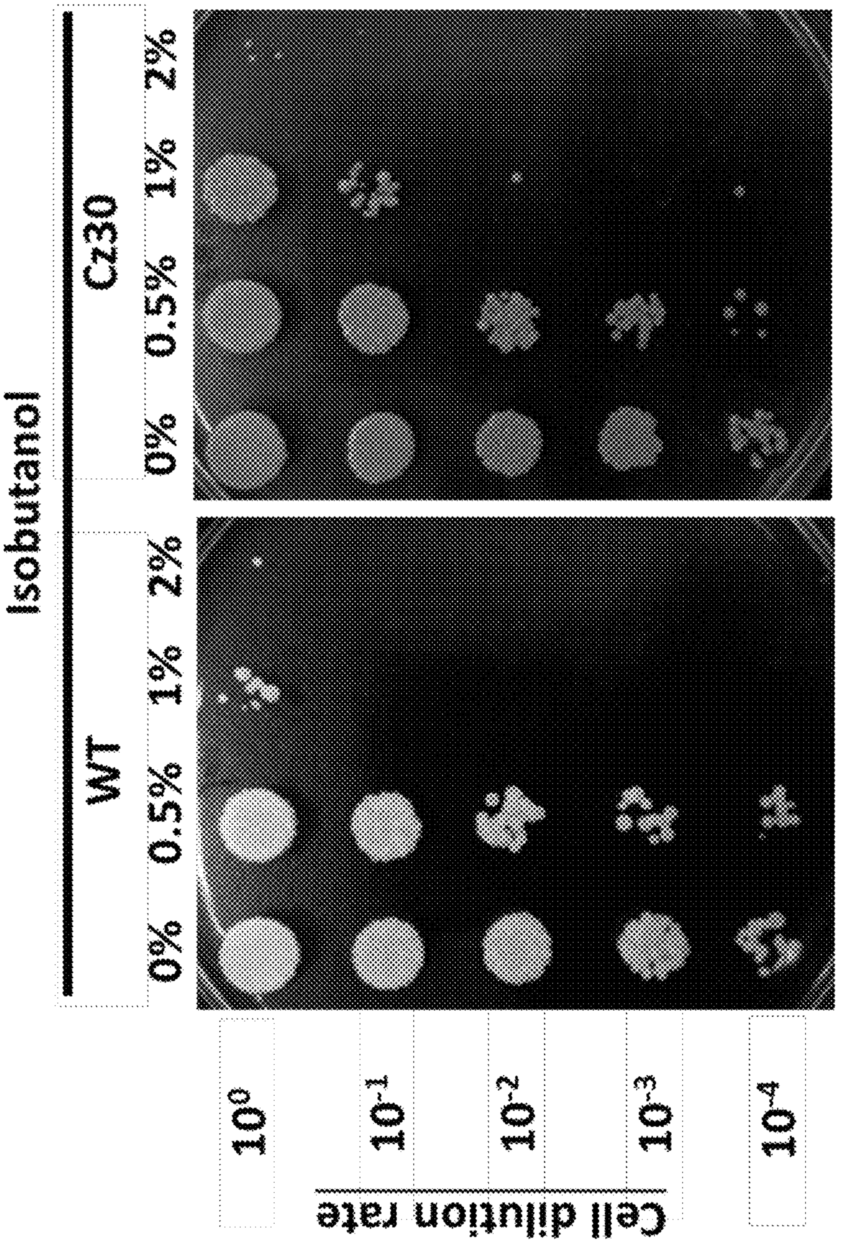

WT and Cz30 strains were further tested for ethanol and butanol treatments. The cell pellet was harvested and exposed to 0, 4, 8 or 12% ethanol for 24 hours; or to 0, 0.5, 1 or 2% isobutanol for 24 hours; and then inoculated in the YPG plate with a series dilution and cultivated for 48 hours. Only some Cz30 colonies could grow on the YPG plate after being treated with 12% ethanol (FIG. 27*c*) or 2% isobutanol for 24 hours (FIG. 27*d*). Thus, the antioxidant capability of the Cz30 strain rendered by the incorporated carotenoids pathway there within improves the Cz30 strain's tolerance to ethanol and butanol as well.

All these data indicated that the antioxidation activity of carotenoids could protect the host cell (i.e., Cz30) from the damage of different environmental stresses, including UV, furfural, ethanol, and isobutanol exposure.

5.2 Enhancing Degrees of Ethanol-Tolerance and/or Productivity of a Host During Fermentation Process In a fermentation process, the accumulation of some end products, such as ethanol, can be highly toxic to the host, thereby creating a bottleneck in the production process. The increases in reactive oxygen species (ROS) is a response of the cell to extracellular stress, under which, the free radicals may directly attack the membrane by lipid peroxidation. The cellular membrane is an important barrier allowing cells to acclimate to external stresses and is also one of the components highly affected by organic solvents.

The wild-type (WT) and the engineered strain Cz30 were subjected to the ethanol tolerance test in YPG medium with the addition of various concentrations of ethanol (FIG. 28*a*). In the 0% ethanol test, the cell growth rate was comparable between the WT strain and the Cz30 strain. In the 2, 4, or 6% ethanol test, the cell growth of WT was significantly repressed by the ethanol, while the growth of Cz30 was weakly affected; that is, compared with WT, Cz30 exhibited a higher cell density after 24 hours of cultivation in the presence of indicated concentrations of ethanol (FIG. 28*a*). This observation suggested that the carotenoid products of Cz30 could reduce the solvent damage, resulting in faster cell growth than that of WT.

To test the ethanol productivity, the WT and Cz30 strains were cultivated in YPG medium with the addition of 20% galactose. After 72 hours, Cz30 produced more ethanol (3.5%) than WT (2.5%) (FIG. 28*b*). Thus, the carotenoid products of Cz30 apparently conferred an antioxidant effect.

The data indicated that the carotenoids can protect the host from the damage of ethanol during the fermentation process, while improving the productivity.

5.3 Enhancing Toxin-Tolerance and Productivity of a Host

The yield of a secondary metabolite is less than its precursor in nature. In order to obtain a sufficient amount of a compound, semi-synthesis provides a reliable way to convert an intermediate to the final product or analogs chemically. However, the chemical process often incurs laborious manipulations and organic pollution. Both the secondary metabolite and their precursor can be highly toxic to the host, creating a bottleneck for their production in a more economic manner.

Baccatin III is a very important precursor in the medical industry for paclitaxel semi-synthesis. Furthermore, a precursor compound of baccatin III, 10-deacetyl baccatin III (10DB), which has a high yield in needle extracts of the common ornamental yew (*Taxus baccata*), has been considered a cheaper precursor and an eco-friendly source. Moreover, ethanol is a very important solvent for dissolving and extracting those precursors and/or end-products In this example, the anti-toxin efficacy of Cz30 was analyzed by treatment of 10-deacetyl baccatin III, which was dissolved in ethanol. The cell pellets of wild-type (WT) and Cz30 were separately harvested and exposed to 0, 0.8, 1.6 or 3.2 mM of 10-deacetyl baccatin III that were dissolved in 0, 4, 8 or 12% ethanol. After 24 hours, the cells were inoculated into the YPG plate with a series dilution and cultivated for another 48 hours. FIG. 29*a* showed that the Cz30 colonies grew better than WT on the YPG plate after a pretreatment with 3.2 mM 10-deacetyl baccatin III in 12% ethanol. Furthermore, the engineered yeasts were also subjected to the 10-deacetyl baccatin III tolerance test in YPG medium with different initial concentrations of 10-deacetyl baccatin III and/or ethanol (FIG. 29*b*). The data revealed that Cz30 grew better than WT in the medium containing 0.4-1.2 mM of 10-deacetyl baccatin III. The effects of the culturing in 0.8 mM of 10-deacetylbaccatin III with 4% ethanol or 1.2 mM of 10-deacetylbaccatin III with 6% ethanol exhibited a higher degree of damage than that culturing in 4% ethanol or 6% ethanol (FIG. 29*b*). These results were confirmed by the growth curve assay of the engineered yeasts under 0.8 mM of 10-deacetylbaccatin III with 4% ethanol (FIG. 30*a*) and 1.2 mM of 10-deacetylbaccatin III with 6% ethanol (FIG. 30*b*).

These data suggested that the carotenoids can protect the host cell from the damage of the precursor of bio-medical drug (e.g., 10-deacetylbaccatin III). Furthermore, a test of baccatin III bio-conversion from 10-deacetylbaccatin III was been achieved by the engineered strains (FIG. 31). The data showed that the YD8 strain containing a higher carotenoids concentration can convert more baccatin III bio-conversion from 10-deacetylbaccatin III compared with the other strains (Table 13). The results indicated that the strains containing carotenoids can improve its ability of bio-conversion.

TABLE 13

The baccatin III bio-conversion by the engineered strains.

| | Specific amounts (μg/g [dw]) of carotenoids and baccatin III | |
|---|---|---|
| Strains | Total carotenoid | Baccatin III |
| YD7 | 2.2 ± 0.2 | — |
| YD6 | 3.0 ± 0.1 | 0.72 |
| YD8 | 16.4 ± 0.4 | 5.37 |

not detect

In sum, the present disclosure provides different recombinant polynucleotide sequences, all of which can be employed to produce carotenoids in vivo. Based on the high production capacity, the present disclosure also established several engineered stains that comprised recombinant polynucleotide sequences that are different from one another. Further, an optimal condition for the expression of the present recombinant polynucleotide/engineered strain was elucidated; under the condition, the productivity can be greatly enhanced, providing a means to biosynthesize astaxanthin for scientific and industrial applications. The product expressed by the present recombinant polynucleotide sequences would protect the engineered cell from various damages caused by environmental stress, fermentation product, or precursor of bio-medical drug, rendering the engineered cell a cost-effective biorefinery.

It should be understood that the above description of embodiments is given by way of examples only and that various modifications may be made by those with ordinary skills in the art. The above specification, examples and data provide a complete description of the structure and use of exemplary embodiments of the invention. Although various embodiments of the invention have been described above with a certain degree of particularity, or with reference to one or more individual embodiments, those with ordinary skills in the art could make numerous alterations to the disclosed embodiments without departing from the spirit or scope of this invention.

What is claimed is:

1. A method for producing astaxanthin, or a precursor or a derivative thereof, wherein the derivative of astaxanthin is an astaxanthin monoester or an astaxanthin diester; the method comprising, (1) introducing a recombinant polynucleotide sequence into a host cell, wherein the recombinant polynucleotide sequence comprises, a first gene cassette comprising a first promoter, and a first nucleic acid sequence operatively linked to the first promoter and encoding a geranylgeranyl pyrophosphate synthase;

a second gene cassette comprising a second promoter, and a second nucleic acid sequence operatively linked to the second promoter and encoding a 3-hydroxy-3-methylglutaryl-coenzyme A reductase;

a third gene cassette comprising a third promoter, and a third nucleic acid sequence operatively linked to the third promoter and encoding a phytoene desaturase; and a fourth gene cassette comprising a fourth promoter, and a fourth nucleic acid sequence operatively linked to the fourth promoter and encoding a bi-functional enzyme that possesses the respective functions of a phytoene synthase and a lycopene cyclase;

wherein, the 3'-end of each gene cassette of the recombinant polynucleotide sequence is homologous to the 5'-end of the next gene cassette downstream thereto;

the first, second, third, and fourth nucleic acid sequences respectively comprise the sequences of SEQ ID NOs: 1, 2, 3 and 4; and the host cell is *Kluveromyces marxianus*; and (2) cultivating the host cell in a medium that comprises a material selected from the group consisting of glucose, galactose, glycerol, and fatty acid.

2. The method of claim 1, wherein the astaxanthin is 3S, 3'S-astaxanthin or 3R, 3'R-astaxanthin; and the precursor of astaxanthin is geranylgeranyl-pyrophosphate, phenicoxanthin, lycopene, echinenone, canthaxanthin, phytoene, zeaxanthin, β-cryptoxanthin, or β-carotene.

3. The method of claim 1, wherein the recombinant polynucleotide sequence further comprises, a fifth gene cassette comprising a fifth promoter, and a fifth nucleic acid sequence operatively linked to the fifth promoter and encoding a β-carotene hydroxylase; and a sixth gene cassette comprising a sixth promoter and a sixth nucleic acid sequence operatively linked to the sixth promoter and encoding a β-carotene ketolase.

4. The method of claim 3, wherein the fifth nucleic acid sequence comprises any of the sequence of SEQ ID NO: 5, 6 or 7, and the sixth nucleic acid sequence comprises the sequence of SEQ ID NO: 8.

5. The method of claim 3, wherein the recombinant polynucleotide sequence further comprises, a seventh gene cassette comprising a seventh promoter, and a seventh nucleic acid sequence operatively linked to the seventh promoter and encoding a P450 reductase; and an eighth gene cassette comprising an eighth promoter, and an eighth nucleic acid sequence operatively linked to the eighth promoter and encoding a β-carotene oxygenase.

6. The method of claim 5, wherein the seventh nucleic acid sequence comprises the sequence of SEQ ID NO: 9, and the eighth nucleic acid sequence comprises the sequence of SEQ ID NO: 10.

7. A method for improving the tolerance of a host cell to a stress, comprising introducing a recombinant polynucleotide sequence into the host cell, wherein the recombinant polynucleotide sequence comprises, a first gene cassette comprising a first promoter, and a first nucleic acid sequence operatively linked to the first promoter and encoding a geranylgeranyl pyrophosphate synthase;

a second gene cassette comprising a second promoter, and a second nucleic acid sequence operatively linked to the second promoter and encoding a 3-hydroxy-3-methylglutaryl-coenzyme A reductase;

a third gene cassette comprising a third promoter, and a third nucleic acid sequence operatively linked to the third promoter and encoding a phytoene desaturase; and a fourth gene cassette comprising a fourth promoter, and a fourth nucleic acid sequence operatively linked to the fourth promoter and encoding a bi-functional enzyme that possesses the respective functions of a phytoene synthase and a lycopene cyclase;

wherein, the 3'-end of each gene cassette of the recombinant polynucleotide sequence is homologous to the 5'-end of the next gene cassette downstream thereto;

the first, second, third, and fourth nucleic acid sequences respectively comprise the sequences of SEQ ID NOs: 1, 2, 3 and 4; and the host cell is *Kluveromyces marxianus*.

8. The method of claim 7, wherein the recombinant polynucleotide sequence further comprises, a fifth gene cassette comprising a fifth promoter, and a fifth nucleic acid sequence operatively linked to the fifth promoter and encoding a β-carotene hydroxylase; and a sixth gene cassette comprising a sixth promoter and a sixth nucleic acid sequence operatively linked to the sixth promoter and encoding a β-carotene ketolase.

9. The method of claim 8, wherein the fifth nucleic acid sequence comprises any of the sequence of SEQ ID NO: 5, 6 or 7, and the sixth nucleic acid sequence comprises the sequence of SEQ ID NO: 8.

10. The method of claim 7, wherein the recombinant polynucleotide sequence further comprises, a seventh gene cassette comprising a seventh promoter, and a seventh nucleic acid sequence operatively linked to the seventh promoter and encoding a P450 reductase; and an eighth gene cassette comprising an eighth promoter, and an eighth nucleic acid sequence operatively linked to the eighth promoter and encoding a β-carotene oxygenase.

11. The method of claim 10, wherein the seventh nucleic acid sequence comprises the sequence of SEQ ID NO: 9, and the eighth nucleic acid sequence comprises the sequence of SEQ ID NO: 10.

12. The method of claim 7, wherein the stress to the host cell is caused from being exposed to ethanol, butanol, UV exposure, furfural, or a drug precursor.

13. The method of claim 12, wherein the drug precursor is 10-deacetyl baccatin III.

14. A method for improving the productivity of a host cell in producing ethanol or baccatin III, comprising introducing a recombinant polynucleotide sequence into the host cell, wherein the recombinant polynucleotide sequence comprises, a first gene cassette comprising a first promoter, and a first nucleic acid sequence operatively linked to the first promoter and encoding a geranylgeranyl pyrophosphate synthase;

a second gene cassette comprising a second promoter, and a second nucleic acid sequence operatively linked to the second promoter and encoding a 3-hydroxy-3-methylglutaryl-coenzyme A reductase;

a third gene cassette comprising a third promoter, and a third nucleic acid sequence operatively linked to the third promoter and encoding a phytoene desaturase; and a fourth gene cassette comprising a fourth promoter, and a fourth nucleic acid sequence operatively linked to the fourth promoter and encoding a bi-functional enzyme that possesses the respective functions of a phytoene synthase and a lycopene cyclase;

wherein, the 3'-end of each gene cassette of the recombinant polynucleotide sequence is homologous to the 5'-end of the next gene cassette downstream thereto;

the first, second, third, and fourth nucleic acid sequences respectively comprise the sequences of SEQ ID NOs: 1, 2, 3 and 4; and the host cell is *Kluveromyces marxianus*.

15. The method of claim 14, wherein the recombinant polynucleotide sequence further comprises, a fifth gene cassette comprising a fifth promoter, and a fifth nucleic acid sequence operatively linked to the fifth promoter and encoding a β-carotene hydroxylase; and a sixth gene cassette comprising a sixth promoter and a sixth nucleic acid sequence operatively linked to the sixth promoter and encoding a β-carotene ketolase.

16. The method of claim 15, wherein the fifth nucleic acid sequence comprises any of the sequence of SEQ ID NO: 5, 6 or 7, and the sixth nucleic acid sequence comprises the sequence of SEQ ID NO: 8.

17. The method of claim 14, wherein the recombinant polynucleotide sequence further comprises, a seventh gene cassette comprising a seventh promoter, and a seventh nucleic acid sequence operatively linked to the seventh promoter and encoding a P450 reductase; and an eighth gene cassette comprising an eighth promoter, and an eighth nucleic acid sequence operatively linked to the eighth promoter and encoding a β-carotene oxygenase.

18. The method of claim 17, wherein the seventh nucleic acid sequence comprises the sequence of SEQ ID NO: 9, and the eighth nucleic acid sequence comprises the sequence of SEQ ID NO: 10.

* * * * *

SEQUENCE LISTING

<160> NUMBER OF SEQ ID NOS: 110

<210> SEQ ID NO 1
<211> LENGTH: 1128
<212> TYPE: DNA
<213> ORGANISM: Artificial Sequence
<220> FEATURE:
<223> OTHER INFORMATION: crtE gene

<400> SEQUENCE: 1
atggactacg ccaacatcct caccgccatc cccctcgagt tcaccccccca ggacgacatc 60 gtcctcctcg agccctacca ctacctcggc aagaaccccg gcaaggagat ccgctcccag 120
ctcatcgagg ccttcaacta ctggctcgac gtcaagaagg aggacctcga ggtcatccag 180
aacgtcgtcg gcatgctcca caccgcctcc ctcctcatgg acgacgtcga ggactcctcc 240
gtcctccgcc gcggctcccc cgtcgcccac ctcatctacg gcatccccca gaccatcaac 300
accgccaact acgtctactt cctcgcctac caggagatct tcaagctccg ccccaccccc 360
atccccatgc ccgtcatccc cccctcctcc gcctccctcc agtcctccgt ctcctccgcc 420
tcctcctcct cctccgcctc ctccgagaac ggcggcacct ccacccccaa ctcccagatc 480
cccttctcca aggacaccta cctcgacaag gtcatcaccg acgagatgct ctccctccac 540
cgcggccagg gcctcgagct cttctggcgc gactccctca cctgccccctc cgaggaggag 600 tacgtcaaga tggtcctcgg caagaccggc ggcctcttcc gcatcgccgt ccgcctcatg 660
atggccaagt ccgagtgcga catcgacttc gtccagctcg tcaacctcat ctccatctac 720
ttccagatcc gcgacgacta catgaacctc cagtcctccg agtacgccca caacaagaac 780
ttcgccgagg acctcaccga gggcaagttc tccttcccca ccatccactc catccacgcc 840
aacccctcct cccgcctcgt catcaacacc ctccagaaga agtccacctc ccccgagatc 900
ctccaccact gcgtcaacta catgcgcacc gagacccact ccttcgagta cacccaggag 960
gtcctcaaca ccctctccgg cgccctcgag cgcgagctcg gccgcctcca gggcgagttc 1020
gccgaggcca actccaagat cgacctcggc gacgtcgagt ccgagggccg caccggcaag 1080
aacgtcaagc tcgaggccat cctcaagaag ctcgccgaca tccccctc 1128

<210> SEQ ID NO 2
<211> LENGTH: 1638
<212> TYPE: DNA
<213> ORGANISM: Artificial Sequence
<220> FEATURE:
<223> OTHER INFORMATION: HMG1 gene

<400> SEQUENCE: 2
atggagctca ccgccaacga catccagaag aagcgcgccg ccaagctcgt ccccaagccc 60
tactccaacc acaacgagaa gcagtccccc tcctcctccg cctccaacga gaccaaggtc 120
gagaccatca ccgagcgcat gcccgtcgtc gcctccatcc agcacgagat cgacaccgag 180
tccgactccg acaacggccc ctccgaggtc cgcccccgtcg aggagctcgt cgaggtcctc 240
aagggcggcg acgtcaagtc cctctccaac cgcgaggtcg tctccctcgt cgtcgccaac 300
aagctccccc tctacgccct cgagaagcag ctcggcgaca ccacccgcgc cgtcgtcgtc 360
cgccgcaagg ccctcgccat cctcgccgac gcccccgtcc tcaccaccga gcgcctcccc 420
tacaagaact acgactacaa ccgcgtcttc ggcgcctgct gcgagaacgt catcggctac 480
atgcccctcc ccgtcggcgt catcggcccc ctcatgatcg acggcgtcta ctaccacatc 540
cccatggcca ccaccgaggg ctgcctcgtc gcctccgcca tgcgcggctg caaggccatc 600

-continued

```
aactccggcg gcggcgtcac caccgtcctc accaaggacg gcatgacccg cggcccctgc    660

gtccgcttcc cctccctcaa gcgcgccggc gcctgcaaga tctggctcga ctccgaggag    720

ggccagaaca agatcaagaa ggccttcaac tccacctccc gcttcgcccg cctccagcac    780

gtccagaccg ccctcgccgg cgacctcctc ttcatccgct tccgcaccac caccggcgac    840

gccatgggca tgaacatgat ctccaagggc gtcgagttct ccctccacca gatggtcgag    900

gagtacggct ggaaggacat ggagatcgtc tccgtctccg gcaactactg catggacaag    960

aagcccgccg ccatcaactg gatcgagggc cgcggcaagt ccgtcgtcgc cgaggccaac   1020

atccccggcg acgtcgtccg caaggtcctc aagtccgacg tcaaggccct cgtcgacctc   1080

aacatctcca agaacctcat cggctccgcc atggccggct ccatcggcgg cttcaacgcc   1140

cacgcctcca acctcgtcac cgccgtctac ctcgccctcg gccaggaccc cgcccagaac   1200

gtcgagtcct ccaactgcat gaccctcatg aaggaggtcg acggcgacct ccgcatctcc   1260

gtctccatgc cctccatcga ggtcggcacc atcggcggcg gcaccatcct cgagccccag   1320

tccgccatgc tcgacctcct cggcgtccgc ggcccccacc ccaccgagcc cggcaagaac   1380

gcccgccagc tcgccaagat cgtcgcctcc gccgtcatgg ccggcgagct ctccctctgc   1440

tccgccctcg ccgccggcca cctcgtccag tcccacatgg tccacaaccg cgccaagcag   1500

cccgtcgcca ccggcgccgg cgcccccgtc tccggccccg gccccgtctc cacccccgcc   1560

atggccacca acggcaagga gctctccgcc gagcagctca agaccctcaa ggagggctcc   1620

gtcatctgca tcaagtcc                                                 1638
```

<210> SEQ ID NO 3
<211> LENGTH: 1746
<212> TYPE: DNA
<213> ORGANISM: Artificial Sequence
<220> FEATURE:
<223> OTHER INFORMATION: crtI gene

<400> SEQUENCE: 3

```
atgggcaagg agcaggacca ggacaagccc accgccatca tcgtcggctg cggcatcggc     60

ggcatcgcca ccgccgcccg cctcgccaag gagggcttcc aggtcaccgt cttcgagaag    120

aacgactact ccggcggccg ctgctccctc atcgagcgcg acggctaccg cttcgaccag    180

ggcccctccc tcctcctcct ccccgacctc ttcaagcaga ccttcgagga cctcggcgag    240

aagatggagg actgggtcga cctcatcaag tgcgagccca actacgtctg ccacttccac    300

gacgaggaga ccttcaccct ctccaccgac atggccctcc tcaagcgcga ggtcgagcgc    360

ttcgagggca aggacggctt cgaccgcttc ctctccttca tccaggaggc ccaccgccac    420

tacgagctcg ccgtcgtcca cgtcctccag aagaacttcc ccggcttcgc cgccttcctc    480

cgcctccagt tcatcggcca gatcctcgcc ctccacccct tcgagtccat ctggacccgc    540

gtctgccgct acttcaagac cgaccgcctc cgccgcgtct tctccttcgc cgtcatgtac    600

atgggccagt cccccctactc cgcccccggc acctactccc tcctccagta caccgagctc    660

accgagggca tctggtaccc ccgcggcggc ttctggcagg tccccaacac cctcctccag    720

atcgtcaagc gcaacaaccc ctccgccaag ttcaacttca acgcccccgt ctcccaggtc    780

ctcctctccc ccgccaagga ccgcgccacc ggcgtccgcc tcgagtccgg cgaggagcac    840

cacgccgacg tcgtcatcgt caacgccgac ctcgtctacg cctccgagca cctcatcccc    900

gacgacgccc gcaacaagat cggccagctc ggcgaggtca agcgctcctg gtgggccgac    960
```

```
ctcgtcggcg gcaagaagct caagggctcc tgctcctccc tctccttcta ctggtccatg   1020

gaccgcatcg tcgacggcct cggcggccac aacatcttcc tcgccgagga cttcaagggc   1080

tccttcgaca ccatcttcga ggagctcggc ctccccgccg acccctcctt ctacgtcaac   1140

gtcccctccc gcatcgaccc ctccgccgcc cccgagggca aggacgccat cgtcatcctc   1200

gtcccctgcg gccacatcga cgcctccaac ccccaggact acaacaagct cgtcgcccgc   1260

gcccgcaagt tcgtcatcca caccctctcc gccaagctcg gcctccccga cttcgagaag   1320

atgatcgtcg ccgagaaggt ccacgacgcc ccctcctggg agaaggagtt caacctcaag   1380

gacggctcca tcctcggcct cgcccacaac ttcatgcagg tcctcggctt ccgcccctcc   1440

acccgccacc ccaagtacga caagctcttc ttcgtcggcg cctccaccca ccccggcacc   1500

ggcgtcccca tcgtcctcgc cggcgccaag ctcaccgcca accaggtcct cgagtccttc   1560

gaccgctccc ccgcccccga ccccaacatg tccctctccg tcccctacgg caagcccctc   1620

aagtccaacg gcaccggcat cgactcccag gtccagctca agttcatgga cctcgagcgc   1680

tgggtctacc tcctcgtcct cctcatcggc gccgtcatcg cccgctccgt cggcgtcctc   1740

gccttc                                                              1746
```

<210> SEQ ID NO 4
<211> LENGTH: 2019
<212> TYPE: DNA
<213> ORGANISM: Artificial Sequence
<220> FEATURE:
<223> OTHER INFORMATION: crtYB gene

<400> SEQUENCE: 4

```
atgaccgccc tcgcctacta ccagatccac ctcatctaca ccctccccat cctcggcctc     60

ctcggcctcc tcacctcccc catcctcacc aagttcgaca tctacaagat ctccatcctc    120

gtcttcatcg ccttctccgc caccaccccc tgggactcct ggatcatccg caacggcgcc    180

tggacctacc cctccgccga gtccggccag ggcgtcttcg gcaccttcct cgacgtcccc    240

tacgaggagt acgccttctt cgtcatccag accgtcatca ccggcctcgt ctacgtcctc    300

gccacccgcc acctcctccc ctccctcgcc ctccccaaga cccgctcctc cgccctctcc    360

ctcgccctca aggccctcat cccccctccc atcatctacc tcttcaccgc ccacccctcc    420

ccctcccccg accccctcgt caccgaccac tacttctaca tgcgcgccct ctccctcctc    480

atcacccccc ccaccatgct cctcgccgcc ctctccggcg agtacgcctt cgactggaag    540

tccggccgcg ccaagtccac catcgccgcc atcatgatcc ccaccgtcta cctcatctgg    600

gtcgactacg tcgccgtcgg ccaggactcc tggtccatca acgacgagaa gatcgtcggc    660

tggcgcctcg gcggcgtcct ccccatcgag gaggccatgt tcttcctcct caccaacctc    720

atgatcgtcc tcggcctctc cgcctgcgac cacacccagg ccctctacct cctccacggc    780

cgcaccatct acggcaacaa gaagatgccc tcctccttcc ccctcatcac cccccccgtc    840

ctctccctct tcttctcctc ccgcccctac tcctcccagc ccaagcgcga cctcgagctc    900

gccgtcaagc tcctcgagaa gaagtcccgc tccttcttcg tcgcctccgc cggcttcccc    960

tccgaggtcc gcgagcgcct cgtcggcctc tacgccttct gccgcgtcac cgacgacctc   1020

atcgactccc ccgaggtctc ctccaacccc cacgccacca tcgacatggt ctccgacttc   1080

ctcaccctcc tcttcggccc ccccctccac ccctcccagc ccgacaagat cctctcctcc   1140

cccctcctcc ccccctccca cccctcccgc cccaccggca tgtaccccct cccccccccc   1200

ccctccctct cccccgccga gctcgtccag ttcctcaccg agcgcgtccc cgtccagtac   1260
```

```
cacttcgcct tccgcctcct cgccaagctc cagggcctca tcccccgcta cccccctcgac   1320
gagctcctcc gcggctacac caccgacctc atcttccccc tctccaccga ggccgtccag   1380
gcccgcaaga cccccatcga gaccaccgcc gacctcctcg actacggcct ctgcgtcgcc   1440
ggctccgtcg ccgagctcct cgtctacgtc tcctgggcct ccgccccctc ccaggtcccc   1500
gccaccatcg aggagcgcga ggccgtcctc gtcgcctccc gcgagatggg caccgccctc   1560
cagctcgtca acatcgcccg cgacatcaag ggcgacgcca ccgagggccg cttctacctc   1620
cccctctcct tcttcggcct ccgcgacgag tccaagctcg ccatccccac cgactggacc   1680
gagccccgcc cccaggactt cgacaagctc ctctccctct ccccctcctc caccctcccc   1740
tcctccaacg cctccgagtc cttccgcttc gagtggaaga cctactccct cccccctcgtc   1800
gcctacgccg aggacctcgc caagcactcc tacaagggca tcgaccgcct ccccaccgag   1860
gtccaggccg gcatgcgcgc cgcctgcgcc tcctacctcc tcatcggccg cgagatcaag   1920
gtcgtctgga agggcgacgt cggcgagcgc cgcaccgtcg ccggctggcg ccgcgtccgc   1980
aaggtcctct ccgtcgtcat gtccggctgg gagggccag                           2019
```

```
<210> SEQ ID NO 5
<211> LENGTH: 891
<212> TYPE: DNA
<213> ORGANISM: Artificial Sequence
<220> FEATURE:
<223> OTHER INFORMATION: CrChYb gene

<400> SEQUENCE: 5

atgatgctcg cctcccgccc cgccgtcgcc ctcggcgccc gcgcccagcc ccaggtcctc     60
cgccccaccc tcgtcccccg ccccggcatg gtctccaacc tccgcctcca gcccgtcaag    120
gtcgccgacc ccatcgtcgc ctccgagacc tcccaggtca tggaggcccc ccaggagaag    180
aagctctccg agttcgagct caagcgcctc gagcgcaagc agcagcgcgc ccaggaggcc    240
gccacctaca agttctccgc catcgccgcc accgtcctcg tcctctccat cgccgtcgtc    300
gccacctact accgcttcgc ctggcacttc gccgaggacg gcgacctccc cgtcgacgag    360
atggccgcca ccctcctcct cgtcttcggc ggcatgttcg gcatggagat gtacgcccgc    420
ttcgcccaca aggtcctctg gcacgacttc gagcccggct gggccctcca caagtcccac    480
cacgagcccc gcaccggccc cttcgagctc aacgacatct acgccgtcgc caacgccctc    540
cccgccatgg ccctctgcgc ctacggcttc ttcacccccc acgtcatcgg cggcgtctgc    600
ttcggcgccg gcctcggcat caccctcttc ggcatcgcct acatgttctt ccacgacggc    660
ctcgtccacc gccgcttccc cgtcggcccc atcgccaacc tcccctacat gaagcgcatc    720
atggtcgccc accagatcca ccacaccaac aagttcggcg gcgtcccctt cggcatgttc    780
ctcggcgtcc aggagctcga ggccgtcccc ggcggcaagg aggagctcga caagctcatg    840
gccgacctcg aggcccgcga ggccgccgcc gccaaggccg ccggctcctc c             891
```

```
<210> SEQ ID NO 6
<211> LENGTH: 897
<212> TYPE: DNA
<213> ORGANISM: Artificial Sequence
<220> FEATURE:
<223> OTHER INFORMATION: CzChYb gene

<400> SEQUENCE: 6

atgcagaccg tcttccagcc ctcctccgtc tggcacctcc gcaaccgcca cgtcctcggc     60
```

-continued

```
gaccgcacct gcgtcccctg ccgcacctcc ctctccacct gccgccacgc cgtccgcctc    120

gtccgcgcca acgtcgccga gacccaggcc acccccacca cctcccagat gctcgaggag    180

gtccacgacg agtcccacgc cgcctccgcc tcctcccaga tcttcgagct cgccgtcaag    240

acctccatca agcgccagca gcgcaaccgc cagcagctca cctaccaggg ctccgccatc    300

gccgcctccc tcggcgtcgg cgccctcgcc gtcgccgcca cccactacaa gttctcctac    360

cacatgccct ccgagtcccc cttcccctgg ctcgacatgg ccggcaccct cgccctcgtc    420

atcggcggcg tcttcggcat ggagatgtgg gcccgctacg cccacaaggc cctctggcac    480

gacttccagc ccggctgggc cctccacaag tcccaccacg agccccgcat cggccccttc    540

gaggccaacg acatcttcgc cgtcatcaac gccgtccccg ccttctccct ctgcctctac    600

ggcttcctca cccccaacct cgtcggctcc ctctgcttcg gcgccggcct cggcatcacc    660

ctcttcggca tcatgtacat gttcatccac gacggcctcg tccacaagcg cttccccgtc    720

ggccccatcg cccagatgcc cgccatgaag cgcgtcgcca tcgcccacaa gctccaccac    780

tccgagaagt acggcggcgt cccctggggc atgttcttcg gcccccagga gctcgaggcc    840

atcggcgccg gccccgagct cgaccgcctc tgcgccgagc tcgactccaa gtcctcc       897
```

<210> SEQ ID NO 7
<211> LENGTH: 879
<212> TYPE: DNA
<213> ORGANISM: Artificial Sequence
<220> FEATURE:
<223> OTHER INFORMATION: HpChYb gene

<400> SEQUENCE: 7

```
atgctctcca agctccagtc catctccgtc aaggcccgcc gcgtcgagct cgcccgcgac     60

atcacccgcc ccaaggtctg cctccacgcc cagcgctgct ccctcgtccg cctccgcgtc    120

gccgcccccc agaccgagga ggccctcggc accgtccagg ccgccggcgc cggcgacgag    180

cactccgccg acgtcgccct ccagcagctc gaccgcgcca tcgccgagcg ccgcgcccgc    240

cgcaagcgcg agcagctctc ctaccaggcc gccgccatcg ccgcctccat cggcgtctcc    300

ggcatcgcca tcttcgccac ctacctccgc ttcgccatgc acatgaccgt cggcggcgcc    360

gtcccctggg gcgaggtcgc cggcaccctc ctcctcgtcg tcggcggcgc cctcggcatg    420

gagatgtacg cccgctacgc ccacaaggcc atctggcacg agtccccccct cggctggctc    480

ctccacaagt cccaccacac cccccgcacc ggccccttcg aggccaacga cctcttcgcc    540

atcatcaacg gcctccccgc catgctcctc tgcaccttcg gcttctggct ccccaacgtc    600

ctcggcgccg cctgcttcgg cgccggcctc ggcatcaccc tctacggcat ggcctacatg    660

ttcgtccacg acggcctcgt ccaccgccgc ttccccaccg gccccatcgc cggcctcccc    720

tacatgaagc gcctcaccgt cgcccaccag ctccaccact ccggcaagta cggcggcgcc    780

ccctggggca tgttcctcgg cccccaggag ctccagcaca tccccggcgc cgccgaggag    840

gtcgagcgcc tcgtcctcga gctcgactgg tccaagcgc                           879
```

<210> SEQ ID NO 8
<211> LENGTH: 1332
<212> TYPE: DNA
<213> ORGANISM: Artificial Sequence
<220> FEATURE:
<223> OTHER INFORMATION: bkt gene

<400> SEQUENCE: 8

```
atgggccccg gcatccagcc cacctccgcc cgcccctgct cccgcaccaa gcactcccgc     60
```

```
ttcgccctcc tcgccgccgc cctcaccgcc cgccgcgtca agcagttcac caagcagttc    120
cgctcccgcc gcatggccga ggacatcctc aagctctggc agcgccagta ccacctcccc    180
cgcgaggact ccgacaagcg caccctccgc gagcgcgtcc acctctaccg cccccccgc    240
tccgacctcg gcggcatcgc cgtcgccgtc accgtcatcg ccctctgggc caccctcttc    300
gtctacggcc tctggttcgt caagctcccc tgggccctca aggtcggcga gaccgccacc    360
tcctgggcca ccatcgccgc cgtcttcttc tccctcgagt tcctctacac cggcctcttc    420
atcaccaccc acgacgccat gcacggcacc atcgccctcc gcaaccgccg cctcaacgac    480
ttcctcggcc agctcgccat ctccctctac gcctggttcg actactccgt cctccaccgc    540
aagcactggg agcaccacaa ccacaccggc gagccccgcg tcgaccccga cttccaccgc    600
ggcaacccca acctcgccgt ctggttcgcc cagttcatgg tctcctacat gaccctctcc    660
cagttcctca agatcgccgt ctggtccaac ctcctcctcc tcgccggcgc ccccctcgcc    720
aaccagctcc tcttcatgac cgccgccccc atcctctccg ccttccgcct cttctactac    780
ggcacctacg tcccccacca ccccgagaag ggccacaccg gcgccatgcc ctggcaggtc    840
tcccgcacct cctccgcctc ccgcctccag tccttcctca cctgctacca cttcgacctc    900
cactgggagc accaccgctg gccctacgcc ccctggtggg agctccccaa gtgccgccag    960
atcgcccgcg gcgccgccct cgcccccggc cccctccccg tccccgccgc cgccgccgcc   1020
accgccgcca ccgccgccgc cgccgccgcc gccaccggct cccccgcccc cgcctcccgc   1080
gccggctccg cctcctccgc ctccgccgcc gcctccggct tcggctccgg ccactccggc   1140
tccgtcgccg cccagcccct ctcctccctc cccctcctct ccgagggcgt caagggcctc   1200
gtcgagggcg ccatggagct cgtcgccggc ggctcctcct ccggcggcgg cggcgagggc   1260
ggcaagcccg gcgccggcga gcacggcctc ctccagcgcc agcgccagct cgcccccgtc   1320
ggcgtcatgg cc                                                      1332
```

<210> SEQ ID NO 9
<211> LENGTH: 2238
<212> TYPE: DNA
<213> ORGANISM: Artificial Sequence
<220> FEATURE:
<223> OTHER INFORMATION: crtR gene

<400> SEQUENCE: 9

```
atggccaccc tctccgacct cgtcatcctc ctcctcggcg ccctcctcgc cctcggcttc     60
tacaacaagg accgcctcct cggctcctcc tcctcctccg cctccaccac ctccggctcc    120
tccgccgcca ccgccaacgg ctccaagccc acctactcca acggcaacgg caacgccttc    180
aagggcgacc cccgcgactt cgtcgcccgc atgaaggacc agaagaagcg cctcgccgtc    240
ttctacggct cccagaccgg caccgccgag gagtacgcca cccgcatcgc caaggaggcc    300
aagtcccgct tcggcgtctc ctccctcgtc tgcgacatcg aggagtacga cttcgagaag    360
ctcgaccagg tccccgagga ctgcgccatc gtcttctgca tggccaccta cggcgagggc    420
gagcccaccg acaacgccgt ccagttcatc gagatgatct cccaggacga ccccgagttc    480
tccgagggct ccaccctcga cggcctcaag tacgtcgtct tcggcctcgg caacaagacc    540
tacgagcagt acaacgtcgt cggccgccag ctcgacgccc gcctcaccgc cctcggcgcc    600
acccgcgtcg gcgagcgcgg cgagggcgac gacgacaagt ccatggagga ggactacctc    660
gcctggaagg acgacatgtt cgccgccctc gccaccaccc tctccttcga ggagggcgcc    720
```

```
tccggcgaga cccccgactt cgtcgtcacc gaggtcccca accaccccat cgagaaggtc    780
ttccagggcg agctctcctc ccgcgccctc ctcggctcca agggcgtcca cgacgccaag    840
aacccctacg cctcccccgt cctcgcctgc cgcgagctct tcaccggcgg cgaccgcaac    900
tgcatccacc tcgagttcga catcaccggc tccggcatca cctaccagac cggcgaccac    960
gtcgccgtct ggccctccaa ccccgacgtc gaggtcgagc gcctcctcgc cgtcctcggc   1020
ctcacctccc ccgagaagcg ccgcatgatc atccaggtcg tctccctcga ccccaccctc   1080
gccaaggtcc ccttccccac ccccaccacc tacgacgccg tcttccgcca ctacctcgac   1140
atctccgccg tcgcctcccg ccagaccctc gccgtcctcg ccaagtacgc cccctccgag   1200
caggccgccg agttcctcac ccgcctcggc accgacaagc aggcctacca caccgaggtc   1260
gtcggcggcc acctccgcct cgccgaggtc ctccagctcg ccgccggcaa cgacatcacc   1320
gtcatgccca ccgccgagaa caccaccgtc tggaacatcc ccttcgacca cgtcgtctcc   1380
gacgtctccc gcctccagcc ccgcttctac tccatctcct cctcccccaa gctccacccc   1440
aactccatcc acgtcaccgc cgtcatcctc aagtacgagt cccaggccac cgaccgccac   1500
cccgcccgct gggtcttcgg cctcggcacc aactacctcc tcaacgtcaa gcaggccgcc   1560
aacaacgaga ccacccccat gatctccgac ggccaggacg acgtccccga gcacgtctcc   1620
gcccccaagt acaccctcga gggcccccgc ggctcctaca agcacgacga ccagctcttc   1680
aaggtcccca tccacgtccg ccgctccacc ttccgcctcc ccacctcccc caagatcccc   1740
gtcatcatga tcggccccgg caccggcgtc gccccettcc gcggcttcat ccaggagcgc   1800
atcgccctcg cccgccgctc catcgccaag aacggccccg acgccctcgc cgactgggcc   1860
cccatctacc tcttctacgg ctcccgcgac gagcaggact tcctctacgc cgaggagtgg   1920
cccgcctacg aggccgagct ccagggcaag ttcaagatcc acgtcgcctt ctcccgctcc   1980
ggcccccgca agcccgacgg ctccaagatc tacgtccagg acctcctctg ggaccagaag   2040
gaggtcatca agtccgccat cgtcgagaag cgcgcctccg tctacatctg cggcgacggc   2100
cgcaacatgt ccaaggacgt cgagcagaag ctcgccgcca tgctcgccga gtccaagaac   2160
ggctccgccg ccgtcgaggg cgccgccgag gtcaagtccc tcaaggagcg ctcccgcctc   2220
ctcatggacg tctggtcc                                                 2238
```

<210> SEQ ID NO 10
<211> LENGTH: 1671
<212> TYPE: DNA
<213> ORGANISM: Artificial Sequence
<220> FEATURE:
<223> OTHER INFORMATION: crtS gene

<400> SEQUENCE: 10

```
atgttcatcc tcgtcctcct caccggcgcc ctcggcctcg ccgccttctc ctgggcctcc     60
atcgccttct tctccctcta cctcgccccc cgccgctcct ccctctacaa cctccagggc    120
cccaaccaca ccaactactt caccggcaac ttcctcgaca tcctctccgc ccgcaccggc    180
gaggagcacg ccaagtaccg cgagaagtac ggctccaccc tccgcttcgc cggcatcgcc    240
ggcgcccccg tcctcaactc caccgacccc aaggtcttca accacgtcat gaaggaggcc    300
tacgactacc ccaagcccgg catggccgcc cgcgtcctcc gcatcgccac cggcgacggc    360
gtcgtcaccg ccgagggcga ggcccacaag cgccaccgcc gcatcatgat cccctccctc    420
tccgcccagg ccgtcaagtc catggtcccc atcttcctcg agaagggcat ggagctcgtc    480
gacaagatga tggaggacgc cgccgagaag gacatggccg tcggcgagtc cgccggcgag    540
```

aagaaggcca cccgcctcga gaccgagggc gtcgacgtca aggactgggt cggccgcgcc 600
accctcgacg tcatggccct cgccggcttc gactacaagt ccgactccct ccagaacaag 660
accaacgagc tctacgtcgc cttcgtcggc ctcaccgacg gcttcgcccc caccctcgac 720
tccttcaagg ccatcatgtg ggacttcgtc ccctacttcc gcaccatgaa gcgccgccac 780
gagatccccc tcacccaggg cctcgccgtc tcccgccgcg tcggcatcga gctcatggag 840
cagaagaagc aggccgtcct cggctccgcc tccgaccagg ccgtcgacaa gaaggacgtc 900
cagggccgcg acatcctctc cctcctcgtc cgcgccaaca tcgccgccaa cctccccgag 960
tcccagaagc tctccgacga ggaggtcctc gcccagatct ccaacctcct cttcgccggc 1020
tacgagacct cctccaccgt cctcacctgg atgttccacc gcctctccga ggacaaggcc 1080
gtccaggaca agctccgcga ggagatctgc cagatcgaca ccgacatgcc caccctcgac 1140
gagctcaacg ccctccccta cctcgaggcc ttcgtcaagg agtccctccg cctcgacccc 1200
ccctccccct acgccaaccg cgagtgcctc aaggacgagg acttcatccc cctcgccgag 1260
cccgtcatcg gccgcgacgg ctccgtcatc aacgaggtcc gcatcaccaa gggcaccatg 1320
gtcatgctcc ccctcttcaa catcaaccgc tccaagttca tctacggcga ggacgccgag 1380
gagttccgcc ccgagcgctg gctcgaggac gtcaccgact ccctcaactc catcgaggcc 1440
ccctacggcc accaggcctc cttcatctcc ggcccccgcg cctgcttcgg ctggcgcttc 1500
gccgtcgccg agatgaaggc cttcctcttc gtcaccctcc gccgcgtcca gttcgagccc 1560
atcatctccc accccgagta cgagcacatc accctcatca tctcccgccc ccgcatcgtc 1620
ggccgcgaga aggagggcta ccagatgcgc ctccaggtca agcccgtcga g 1671

<210> SEQ ID NO 11
<211> LENGTH: 26
<212> TYPE: DNA
<213> ORGANISM: Artificial Sequence
<220> FEATURE:
<223> OTHER INFORMATION: Forward Primer-crtE gene-AgeI

<400> SEQUENCE: 11
accggtatgg attacgcgaa catcct 26

<210> SEQ ID NO 12
<211> LENGTH: 26
<212> TYPE: DNA
<213> ORGANISM: Artificial Sequence
<220> FEATURE:
<223> OTHER INFORMATION: Reverse Primer-crtE gene-NcoI

<400> SEQUENCE: 12
ccatggtcac agagggatat cggcta 26

<210> SEQ ID NO 13
<211> LENGTH: 28
<212> TYPE: DNA
<213> ORGANISM: Artificial Sequence
<220> FEATURE:
<223> OTHER INFORMATION: Forward Primer-HMG1 gene-NotI

<400> SEQUENCE: 13
gcggccgcat ggaactaact gctaatga 28

<210> SEQ ID NO 14
<211> LENGTH: 26
<212> TYPE: DNA

<213> ORGANISM: Artificial Sequence
<220> FEATURE:
<223> OTHER INFORMATION: Reverse Primer-HMG1 gene-XhoI

<400> SEQUENCE: 14
ctcgagtcac gatttgatgc aaatca 26

<210> SEQ ID NO 15
<211> LENGTH: 26
<212> TYPE: DNA
<213> ORGANISM: Artificial Sequence
<220> FEATURE:
<223> OTHER INFORMATION: Forward Primer-crtI gene-AgeI

<400> SEQUENCE: 15
accggtatgg gaaaagaaca agatca 26

<210> SEQ ID NO 16
<211> LENGTH: 26
<212> TYPE: DNA
<213> ORGANISM: Artificial Sequence
<220> FEATURE:
<223> OTHER INFORMATION: Reverse Primer-crtI gene-NcoI

<400> SEQUENCE: 16
ccatggtcag aaagcaagaa caccaa 26

<210> SEQ ID NO 17
<211> LENGTH: 26
<212> TYPE: DNA
<213> ORGANISM: Artificial Sequence
<220> FEATURE:
<223> OTHER INFORMATION: Forward Primer-crtYB gene-AgeI

<400> SEQUENCE: 17
accggtatga cggctctcgc atatta 26

<210> SEQ ID NO 18
<211> LENGTH: 28
<212> TYPE: DNA
<213> ORGANISM: Artificial Sequence
<220> FEATURE:
<223> OTHER INFORMATION: Reverse Primer-crtYB gene-NotI

<400> SEQUENCE: 18
gcggccgctt actgcccttc ccatccgc 28

<210> SEQ ID NO 19
<211> LENGTH: 26
<212> TYPE: DNA
<213> ORGANISM: Artificial Sequence
<220> FEATURE:
<223> OTHER INFORMATION: Forward Primer-crtR gene-NcoI

<400> SEQUENCE: 19
ccatggatgg ccacactctc cgatct 26

<210> SEQ ID NO 20
<211> LENGTH: 33
<212> TYPE: DNA
<213> ORGANISM: Artificial Sequence
<220> FEATURE:
<223> OTHER INFORMATION: Reverse Primer-crtR gene-SfiI

<400> SEQUENCE: 20
ggcccaacag gccctacgac cagacgtcca tca 33

<210> SEQ ID NO 21
<211> LENGTH: 26
<212> TYPE: DNA
<213> ORGANISM: Artificial Sequence
<220> FEATURE:
<223> OTHER INFORMATION: Forward Primer-crtS gene-AgeI

<400> SEQUENCE: 21
accggtatgt tcatcttggt cttgct 26

<210> SEQ ID NO 22
<211> LENGTH: 26
<212> TYPE: DNA
<213> ORGANISM: Artificial Sequence
<220> FEATURE:
<223> OTHER INFORMATION: Reverse Primer-crtS gene-NcoI

<400> SEQUENCE: 22
ccatggtcat tcgaccggct tgacct 26

<210> SEQ ID NO 23
<211> LENGTH: 25
<212> TYPE: DNA
<213> ORGANISM: Artificial Sequence
<220> FEATURE:
<223> OTHER INFORMATION: primer-KlPLac4

<400> SEQUENCE: 23
ccgcggggat cgactcataa aatag 25

<210> SEQ ID NO 24
<211> LENGTH: 82
<212> TYPE: DNA
<213> ORGANISM: Artificial Sequence
<220> FEATURE:
<223> OTHER INFORMATION: primer-ScTTPGK-KlPGapDH

<400> SEQUENCE: 24
ggactccagc ttttccattt gccttcgcgc ttgcctgtac ggtcgttacc atactaagct 60
ttttcgaaac gcagaatttt cg 82

<210> SEQ ID NO 25
<211> LENGTH: 25
<212> TYPE: DNA
<213> ORGANISM: Artificial Sequence
<220> FEATURE:
<223> OTHER INFORMATION: primer-KlPGapDH

<400> SEQUENCE: 25
agtatggtaa cgaccgtaca ggcaa 25

<210> SEQ ID NO 26
<211> LENGTH: 78
<212> TYPE: DNA
<213> ORGANISM: Artificial Sequence
<220> FEATURE:
<223> OTHER INFORMATION: primer-ScTTGap-ScPADHI

<400> SEQUENCE: 26
ggaatcccga tgtatgggtt tggttgccag aaaagaggaa gtccatattg tacactggcg 60
gaaaaaattc atttgtaa 78

<210> SEQ ID NO 27

-continued

<211> LENGTH: 26
<212> TYPE: DNA
<213> ORGANISM: Artificial Sequence
<220> FEATURE:
<223> OTHER INFORMATION: primer-ScPADHI

<400> SEQUENCE: 27
gtgtacaata tggacttcct cttttc 26

<210> SEQ ID NO 28
<211> LENGTH: 23
<212> TYPE: DNA
<213> ORGANISM: Artificial Sequence
<220> FEATURE:
<223> OTHER INFORMATION: primer-ScTTADHI-KlPLac4

<400> SEQUENCE: 28
gaaatttagg aattttaaac ttg 23

<210> SEQ ID NO 29
<211> LENGTH: 78
<212> TYPE: DNA
<213> ORGANISM: Artificial Sequence
<220> FEATURE:
<223> OTHER INFORMATION: primer-ScTTGap-ScPGK

<400> SEQUENCE: 29
ggactccagc ttttccattt gccttcgcgc ttgcctgtac ggtcgttacc atacttggcg 60
gaaaaaattc atttgtaa 78

<210> SEQ ID NO 30
<211> LENGTH: 25
<212> TYPE: DNA
<213> ORGANISM: Artificial Sequence
<220> FEATURE:
<223> OTHER INFORMATION: primer-ScPGK

<400> SEQUENCE: 30
actgtaattg cttttagttg tgtat 25

<210> SEQ ID NO 31
<211> LENGTH: 80
<212> TYPE: DNA
<213> ORGANISM: Artificial Sequence
<220> FEATURE:
<223> OTHER INFORMATION: primer-ScTTPGK-KlPADHI

<400> SEQUENCE: 31
aggtaagtat ggtaacgacc gtacaggcaa gcgcgaaggc aaatggaaaa gctggaagct 60
ttttcgaaac gcagaatttt 80

<210> SEQ ID NO 32
<211> LENGTH: 30
<212> TYPE: DNA
<213> ORGANISM: Artificial Sequence
<220> FEATURE:
<223> OTHER INFORMATION: primer-KlPADHI

<400> SEQUENCE: 32
ccagcttttc catttgcctt cgcgcttgcc 30

<210> SEQ ID NO 33
<211> LENGTH: 78
<212> TYPE: DNA
<213> ORGANISM: Artificial Sequence -continued
<220> FEATURE:
<223> OTHER INFORMATION: primer-KlTTLac4-ScPGapDH

<400> SEQUENCE: 33
ctactattaa ttatttacgt attctttgaa atggcagtat tgataatgat aaacttatac 60
aacatcgaag aagagtct 78

<210> SEQ ID NO 34
<211> LENGTH: 25
<212> TYPE: DNA
<213> ORGANISM: Artificial Sequence
<220> FEATURE:
<223> OTHER INFORMATION: primer-ScPGapDH

<400> SEQUENCE: 34
agtttatcat tatcaatact gccat 25

<210> SEQ ID NO 35
<211> LENGTH: 81
<212> TYPE: DNA
<213> ORGANISM: Artificial Sequence
<220> FEATURE:
<223> OTHER INFORMATION: primer-ScTTGap-KlPGK

<400> SEQUENCE: 35
catatacctt tgataccata aaaacaagca aatattctta cttcaaacac acccgtggcg 60
gaaaaaattc atttgtaaac t 81

<210> SEQ ID NO 36
<211> LENGTH: 25
<212> TYPE: DNA
<213> ORGANISM: Artificial Sequence
<220> FEATURE:
<223> OTHER INFORMATION: primer-KlPGK

<400> SEQUENCE: 36
cgggtgtgtt tgaagtaaga atatt 25

<210> SEQ ID NO 37
<211> LENGTH: 20
<212> TYPE: DNA
<213> ORGANISM: Artificial Sequence
<220> FEATURE:
<223> OTHER INFORMATION: primer-crtE-UPL 1-F

<400> SEQUENCE: 37
cgagatgctt tccctccata 20

<210> SEQ ID NO 38
<211> LENGTH: 21
<212> TYPE: DNA
<213> ORGANISM: Artificial Sequence
<220> FEATURE:
<223> OTHER INFORMATION: primer-crtE-UPL 1-R

<400> SEQUENCE: 38
ttcgctagga cacgtcagac t 21

<210> SEQ ID NO 39
<211> LENGTH: 20
<212> TYPE: DNA
<213> ORGANISM: Artificial Sequence
<220> FEATURE:
<223> OTHER INFORMATION: primer-crtI-UPL 155-F

<400> SEQUENCE: 39
ccgatccttc cttttacgtg 20

<210> SEQ ID NO 40
<211> LENGTH: 20
<212> TYPE: DNA
<213> ORGANISM: Artificial Sequence
<220> FEATURE:
<223> OTHER INFORMATION: primer-crtI-UPL 155-R

<400> SEQUENCE: 40
cggcacaaga atgacgatag 20

<210> SEQ ID NO 41
<211> LENGTH: 20
<212> TYPE: DNA
<213> ORGANISM: Artificial Sequence
<220> FEATURE:
<223> OTHER INFORMATION: primer-crtR-UPL 41-F

<400> SEQUENCE: 41
acgtcgtctc tgacgtttcc 20

<210> SEQ ID NO 42
<211> LENGTH: 20
<212> TYPE: DNA
<213> ORGANISM: Artificial Sequence
<220> FEATURE:
<223> OTHER INFORMATION: primer-crtR-UPL 41-R

<400> SEQUENCE: 42
ttgggtgaag tttcggagaa 20

<210> SEQ ID NO 43
<211> LENGTH: 20
<212> TYPE: DNA
<213> ORGANISM: Artificial Sequence
<220> FEATURE:
<223> OTHER INFORMATION: primer-crtS-UPL 149-F

<400> SEQUENCE: 43
ggatgttcaa ggtcgggata 20

<210> SEQ ID NO 44
<211> LENGTH: 21
<212> TYPE: DNA
<213> ORGANISM: Artificial Sequence
<220> FEATURE:
<223> OTHER INFORMATION: primer-crtS-UPL 149-R

<400> SEQUENCE: 44
cggacagctt ttgagattca g 21

<210> SEQ ID NO 45
<211> LENGTH: 25
<212> TYPE: DNA
<213> ORGANISM: Artificial Sequence
<220> FEATURE:
<223> OTHER INFORMATION: primer-crtYB-UPL 34-F

<400> SEQUENCE: 45
cactgatctt atctttccct tatcg 25

<210> SEQ ID NO 46
<211> LENGTH: 20

-continued

<212> TYPE: DNA
<213> ORGANISM: Artificial Sequence
<220> FEATURE:
<223> OTHER INFORMATION: primer-crtYB-UPL 34-R

<400> SEQUENCE: 46
gtggtctcga taggcgtctt 20

<210> SEQ ID NO 47
<211> LENGTH: 18
<212> TYPE: DNA
<213> ORGANISM: Artificial Sequence
<220> FEATURE:
<223> OTHER INFORMATION: primer-tHMG-UPL 119-F

<400> SEQUENCE: 47
ttctgctatg gcgggttc 18

<210> SEQ ID NO 48
<211> LENGTH: 21
<212> TYPE: DNA
<213> ORGANISM: Artificial Sequence
<220> FEATURE:
<223> OTHER INFORMATION: primer-tHMG-UPL 119-R

<400> SEQUENCE: 48
gctgtaacca aattcgaagc a 21

<210> SEQ ID NO 49
<211> LENGTH: 19
<212> TYPE: DNA
<213> ORGANISM: Artificial Sequence
<220> FEATURE:
<223> OTHER INFORMATION: primer-CrBKT-UPL 159-F

<400> SEQUENCE: 49
gctgctgcaa ctggttcac 19

<210> SEQ ID NO 50
<211> LENGTH: 21
<212> TYPE: DNA
<213> ORGANISM: Artificial Sequence
<220> FEATURE:
<223> OTHER INFORMATION: primer-CrBKT-UPL 159-R

<400> SEQUENCE: 50
gcactagcgg aactagcaga a 21

<210> SEQ ID NO 51
<211> LENGTH: 21
<212> TYPE: DNA
<213> ORGANISM: Artificial Sequence
<220> FEATURE:
<223> OTHER INFORMATION: primer-CrChYb-UPL 48-F

<400> SEQUENCE: 51
ttctttcacg atggattggt c 21

<210> SEQ ID NO 52
<211> LENGTH: 22
<212> TYPE: DNA
<213> ORGANISM: Artificial Sequence
<220> FEATURE:
<223> OTHER INFORMATION: primer-CrChYb-UPL 48-R

<400> SEQUENCE: 52
tgtatggtaa gttggcgata gg 22

<210> SEQ ID NO 53
<211> LENGTH: 20
<212> TYPE: DNA
<213> ORGANISM: Artificial Sequence
<220> FEATURE:
<223> OTHER INFORMATION: primer-CZChYb-UPL 157-F

<400> SEQUENCE: 53
cgcccacaaa ttacaccatt 20

<210> SEQ ID NO 54
<211> LENGTH: 20
<212> TYPE: DNA
<213> ORGANISM: Artificial Sequence
<220> FEATURE:
<223> OTHER INFORMATION: primer-CZChYb-UPL 157-R

<400> SEQUENCE: 54
tccgaaaaac ataccccaag 20

<210> SEQ ID NO 55
<211> LENGTH: 22
<212> TYPE: DNA
<213> ORGANISM: Artificial Sequence
<220> FEATURE:
<223> OTHER INFORMATION: primer-HpChYb 139-F

<400> SEQUENCE: 55
aacgacttgt tcgcaatcat ta 22

<210> SEQ ID NO 56
<211> LENGTH: 18
<212> TYPE: DNA
<213> ORGANISM: Artificial Sequence
<220> FEATURE:
<223> OTHER INFORMATION: primer-HpChYb 139-R

<400> SEQUENCE: 56
cccaacacgt ttggcaac 18

<210> SEQ ID NO 57
<211> LENGTH: 22
<212> TYPE: DNA
<213> ORGANISM: Artificial Sequence
<220> FEATURE:
<223> OTHER INFORMATION: primer-Kan-UPL 144-F

<400> SEQUENCE: 57
agactaaact ggctgacgga at 22

<210> SEQ ID NO 58
<211> LENGTH: 23
<212> TYPE: DNA
<213> ORGANISM: Artificial Sequence
<220> FEATURE:
<223> OTHER INFORMATION: primer-Kan-UPL 144-R

<400> SEQUENCE: 58
catcaggagt acggataaaa tgc 23

<210> SEQ ID NO 59
<211> LENGTH: 20
<212> TYPE: DNA
<213> ORGANISM: Artificial Sequence -continued
<220> FEATURE:
<223> OTHER INFORMATION: primer-Actin-UPL 9-F

<400> SEQUENCE: 59
gcgtagattg gaacaacgtg 20

<210> SEQ ID NO 60
<211> LENGTH: 23
<212> TYPE: DNA
<213> ORGANISM: Artificial Sequence
<220> FEATURE:
<223> OTHER INFORMATION: primer-Actin-UPL 9-R

<400> SEQUENCE: 60
agaactaccg gtattgtgtt gga 23

<210> SEQ ID NO 61
<211> LENGTH: 20
<212> TYPE: DNA
<213> ORGANISM: Artificial Sequence
<220> FEATURE:
<223> OTHER INFORMATION: primer-alg9-UPL 132-F

<400> SEQUENCE: 61
caatcaatgg cccgtatcat 20

<210> SEQ ID NO 62
<211> LENGTH: 21
<212> TYPE: DNA
<213> ORGANISM: Artificial Sequence
<220> FEATURE:
<223> OTHER INFORMATION: primer-alg9-UPL 132-R

<400> SEQUENCE: 62
tgtctcagaa gcacagtttg g 21

<210> SEQ ID NO 63
<211> LENGTH: 2292
<212> TYPE: DNA
<213> ORGANISM: Artificial Sequence
<220> FEATURE:
<223> OTHER INFORMATION: KlLac4 promoter

<400> SEQUENCE: 63
ccgcggggat cgactcataa aatagtaacc ttctaatgcg tatctattga ctaccaacca 60
ttagtgtggt tgcagaaggc ggaattttcc cttcttcgaa tttagcttgc tttttcattt 120
tttattttcc atttttcagt ttttgtttgt gtcgaattta gccagttgct tctccaagat 180
gaaaaaaacc cctgcgcagt ttctgtgctg caagatccta atcgactttt ccacccccca 240
caaaagtaaa tgttcttttg ttacattcgc gtgggtagct agctccccga atcttcaaag 300
gacttaggga ctgcactaca tcagagtgtg ttcacctggt ttgctgcctg gtttgaaaga 360
aaagagcagg gaactcgcgg gttcccggcg aataatcatg cgatagtcct ttggccttcc 420
aagtcgcatg tagagtagac aacagacagg gagggcagga aggatctttc actgagatcc 480
tgtatcttgt tgggtaagtc ggatgaaagg ggaatcgtat gagattggag aggatgcgga 540
agaggtaacg ccttttgtta acttgtttaa ttattatggg gcaggcgaga gggggaggaa 600
tgtatgtgtg tgaggcgggc gagacggagc catccaggcc aggtagaaat agagaaagcc 660
gaatgttaga caatatggca gcgtagtaga gtaggtaggt aggcaagtac tgctagcaaa 720
gaggagaagg gtaagctcac tcttcgcatt ccacaccgtt agtgtgtcag tttgaacaaa 780

-continued

```
aaaacaatca tcataccaat tgatggactg tggactggct tttggaacgg cttttcggac    840

tgcgattatt cgtgaggaat caaggtagga atttggtcat atttacggac aacagtgggt    900

gattcccata tcgagtagga aaacgagatc atggtatcct cagatatgtt gcggaaatct    960

gttcaccgca aagttcaggg tgctctggtg ggtttcggtt ggtctttgct ttgcttctcc   1020

cttgtcttgc atgttaataa tagcctagcc tgtgagccga aacttagggt aggcttagtg   1080

ttggaacgta catatctatc acgttgactt ggtttaacca ggcgacctgg tagccagcca   1140

tacccacaca cgtttttttgt atcttcagta tagttgtgaa aagtgtagcg gaaatttgtg   1200

gtccgagcaa cagcgtcttt ttctagtagt gcggtcggtt acttggttga cattggtatt   1260

tggactttgt tgctacacca ttcactactt gaagtcgagt gtgaagggta tgatttctag   1320

tggtgaacac ctttagttac gtaatgtttt cattgctgtt ttacttgaga tttcgattga   1380

gaaaaaggta tttaatagct cgaatcaatg tgagaacaga gagaagatgt tcttccctaa   1440

ctcgaaaggt atatgaggct tgtgtttctt aggagaatta ttattctttt gttatgttgc   1500

gcttgtagtt ggaaaaggtg aagagacaaa agctggaatt gtgagcggat aacaagctca   1560

acacttgaaa tttaggaaag agcagaattt ggcaaaaaaa ataaaaaaaa aataaacaca   1620

catactcatc gagaccggtg gcgcgcccct aggggccggc cacgcgtcca tgggcggccg   1680

cttaattaag gcctgttggg ccctcgagat ttatacttag ataagtatgt acttacaggt   1740

atatttctat gagatactga tgtatacatg catgataata tttaaacggt tattagtgcc   1800

gattgtcttg tgcgataatg acgttcctat caaagcaata cacttaccac ctattacatg   1860

ggccaagaaa atattttcga acttgtttag aatattagca cagagtatat gatgttatcc   1920

gttagattat gcatgattca ttcctacaac tttttcgtag cataaggatt aattacttgg   1980

atgccaataa aaaaaaaaaa catcgagaaa atttcagcat gctcagaaac aattgcagtg   2040

tatcaaagta aaaaaaagat tttcactaca tgttcctttt gaagaaagaa aatcatggaa   2100

cattagattt acaaaaattt aaccaccgct gattaacgat tagaccgtta agcgcacaac   2160

aggttattag tacagagaaa gcattctgtg gtgttgcccc ggactttctt ttgcgacata   2220

ggtaaatcga ataccatcat actatctttt ccaatgactc cctaaagaaa gactcttctt   2280

cgatgttgta ta                                                       2292
```

<210> SEQ ID NO 64
<211> LENGTH: 1047
<212> TYPE: DNA
<213> ORGANISM: Artificial Sequence
<220> FEATURE:
<223> OTHER INFORMATION: ScGapDH promoter

<400> SEQUENCE: 64

```
agtttatcat tatcaatact gccatttcaa agaatacgta aataattaat agtagtgatt     60

ttcctaactt tatttagtca aaaaattagc cttttaattc tgctgtaacc cgtacatgcc    120

caaaataggg ggcgggttac acagaatata taacatcgta ggtgtctggg tgaacagttt    180

attcctggca tccactaaat ataatggagc ccgcttttta agctggcatc cagaaaaaaa    240

aagaatccca gcaccaaaat attgttttct tcaccaacca tcagttcata ggtccattct    300

cttagcgcaa ctacagagaa caggggcaca aacaggcaaa aaacgggcac aacctcaatg    360

gagtgatgca acctgcctgg agtaaatgat gacacaaggc aattgaccca cgcatgtatc    420

tatctcattt tcttacacct tctattacct tctgctctct ctgatttgga aaaagctgaa    480

aaaaaaggtt gaaaccagtt ccctgaaatt attcccctac ttgactaata agtatataaa    540
```

```
gacggtaggt attgattgta attctgtaaa tctatttctt aaacttctta aattctactt    600

ttatagttag tcttttttt agttttaaaa caccaagaac ttagtttcga ataaacacac    660

ataaacaaac aaaaaaaccg gtggcgcgcc cctaggggcc ggccacgcgt ccatgggcgg    720

ccgcttaatt aaggcctgtt gggccctcga ggtgaattta ctttaaatct tgcatttaaa    780

taaattttct ttttatagct ttatgactta gtttcaattt atatactatt ttaatgacat    840

tttcgattca ttgattgaaa gctttgtgtt ttttcttgat gcgctattgc attgttcttg    900

tctttttcgc cacatgtaat atctgtagta gatacctgat acattgtgga tgctgagtga    960

aattttagtt aataatggag gcgctcttaa taattttggg gatattggct ttttttttta   1020

aagtttacaa atgaattttt tccgcca                                       1047
```

<210> SEQ ID NO 65
<211> LENGTH: 1239
<212> TYPE: DNA
<213> ORGANISM: Artificial Sequence
<220> FEATURE:
<223> OTHER INFORMATION: ScPGK promoter

<400> SEQUENCE: 65

```
actgtaattg cttttagttg tgtattttta gtgtgcaagt ttctgtaaat cgattaattt     60

tttttcttt cctcttttta ttaaccttaa tttttatttt agattcctga cttcaactca    120

agacgcacag atattataac atctgcataa taggcatttg caagaattac tcgtgagtaa    180

ggaaagagtg aggaactatc gcatacctgc atttaaagat gccgatttgg gcgcgaatcc    240

tttattttgg cttcaccctc atactattat cagggccaga aaaaggaagt gtttccctcc    300

ttcttgaatt gatgttaccc tcataaagca cgtggcctct tatcgagaaa gaaattaccg    360

tcgctcgtga tttgtttgca aaaagaacaa aactgaaaaa acccagacac gctcgacttc    420

ctgtcttcct attgattgca gcttccaatt tcgtcacaca acaaggtcct agcgacggct    480

cacaggtttt gtaacaagca atcgaaggtt ctggaatggc gggaaagggt ttagtaccac    540

atgctatgat gcccactgtg atctccagag caaagttcgt tcgatcgtac tgttactctc    600

tctctttcaa acagaattgt ccgaatcgtg tgacaacaac agcctgttct cacacactct    660

tttcttctaa ccaagggggt ggtttagttt agtagaacct cgtgaaactt acatttacat    720

atatataaac ttgcataaat tggtcaatgc aagaaataca tatttggtct tttctaattc    780

gtagtttttc aagttcttag atgctttctt tttctctttt ttacagatca tcaaggaagt    840

aattatctac tttttacaac aaatataaaa caaaaaaaac cggtggcgcg cccctagggg    900

ccggccacgc gtccatgggc ggccgcttaa ttaaggcctg ttgggccctc gagattgaat    960

tgaattgaaa tcgatagatc aattttttc ttttctcttt ccccatcctt tacgctaaaa   1020

taatagttta ttttattttt tgaatatttt ttatttatat acgtatatat agactattat   1080

ttacttttaa tagattatta agatttttat taaaaaaaaa ttcgtccctc tttttaatgc   1140

cttttatgca gttttttttt cccattcgat atttctatgt tcgggtttca gcgtatttta   1200

agtttaataa ctcgaaaatt ctgcgtttcg aaaaagctt                          1239
```

<210> SEQ ID NO 66
<211> LENGTH: 1090
<212> TYPE: DNA
<213> ORGANISM: Artificial Sequence
<220> FEATURE:
<223> OTHER INFORMATION: KlGapDH promoter

<400> SEQUENCE: 66

```
agtatggtaa cgaccgtaca ggcaagcgcg aaggcaaatg gaaaagctgg agtccggaag      60
ataatcattt catcttcttt tgttagaaca gaacagtgga tgtccctcat ctcggtaacg     120
tattgtccat gccctagaac tctctgtccc taaaaagagg acaaaaaccc aatggtttcc     180
ccagcttcca gtggagccac cgatcccact ggaaaccact ggacaggaag agaaaatcac     240
ggacttcctc tattgaagga taattcaaca ctttcaccag atcccaaatg tcccgcccct     300
attcccgtgt tccatcacgt accataactt accatttcat cacgttctct atggcacact     360
ggtactgctt cgactgcttt gcttcatctt ctctatgggc caatgagcta atgagcacaa     420
tgtgctgcga aataaaggga tatctaattt atattattac attataatat gtactagtgt     480
ggttattggt aattgtactt aattttgata tataaagggt ggatcttttt cattttgaat     540
cagaattgga attgcaactt gtctcttgtc actattactt aatagtaatt atatttctta     600
ttaacctttt ttttaagtca aaacaccaag gacaagaact actcttcaaa ggtatttcaa     660
gttatcatac gtctcacaca cgcttcacag tttcaagtaa aaaaaaagaa tattacacaa     720
ccggtggcgc gcccctaggg gccggccacg cgtccatggg cggccgctta attaaggcct     780
gttgggccct cgaggtgaat ttactttaaa tcttgcattt aaataaattt tctttttata     840
gctttatgac ttagtttcaa tttatatact attttaatga cattttcgat tcattgattg     900
aaagctttgt gtttttttctt gatgcgctat tgcattgttc ttgtcttttt cgccacatgt    960
aatatctgta gtagatacct gatacattgt ggatgctgag tgaaatttta gttaataatg    1020
gaggcgctct taataatttt ggggatattg gcttttttttt ttaaagttta caaatgaatt  1080
ttttccgcca                                                           1090
```

<210> SEQ ID NO 67
<211> LENGTH: 1236
<212> TYPE: DNA
<213> ORGANISM: Artificial Sequence
<220> FEATURE:
<223> OTHER INFORMATION: KlPGK promoter

<400> SEQUENCE: 67

```
cgggtgtgtt tgaagtaaga atatttgctt gtttttatgg tatcaaaggt atatgttgta      60
gaagacaatt tccggtaatc caattgtctg tctgctcagt ttagcacatg tatagtacgt     120
tgcacatagt ctacaatatt cagcattcag cattcagtat acagcatatg gctaaatgat     180
cacaaatgtg attgatgatt tgacacgact agaaaagaga acgaaaaagg gaaattccat     240
gtcacgtgcg ttggcacgtg acatggaata tcgaagaaag aaaaaaaaaa cgatctcgtc     300
ctagtggaag cccagagtct ggtccccccg gagtcttccc aaaacaagaa gctgacacat     360
gttgacacag aacaccccac agcaaatgca ccacgctacg tagatcagga agcttaactc     420
tagcgacctg tcgctcgccc cacagaacct cacccgagaa ccacacatta cacgccgcca     480
gctcccacta tactcatctt gcttccctta agcgttctca cgattcgttc gctgcccttc     540
ttcaagagtc ttctgattct aattctcatt cgaaatcctc tacagttaat gaattgcttg     600
acatgacatt cattgtctca tggttttggc tttttggctt ttgtctttta aagctatatc     660
aactttacat ataaatatac gtcaaaaggg gattcattaa ttagaaaatt ctctttttca     720
atagttgcta ttcattatca atctattcaa ctcaattggt tattattttc atctttttgt     780
catcctaaac catcaacaat atttaaatat atctgttgct acattaagag ttacttcaga     840
aataacaaaa aaatcgatca agaattaata aaaaaaccgg tggcgcgccc ctaggggccg     900
```

-continued

```
gccacgcgtc catgggcggc cgcttaatta aggcctgttg ggccctcgag attgaattga    960

attgaaatcg atagatcaat tttttttcttt tctctttccc catcctttac gctaaaataa   1020

tagtttattt tattttttga atatttttta tttatatacg tatatataga ctattattta   1080

cttttaatag attattaaga tttttattaa aaaaaaattc gtccctcttt ttaatgcctt   1140

ttatgcagtt ttttttttccc attcgatatt tctatgttcg ggtttcagcg tattttaagt   1200

ttaataactc gaaaattctg cgtttcgaaa aagctt                              1236
```

<210> SEQ ID NO 68
<211> LENGTH: 1246
<212> TYPE: DNA
<213> ORGANISM: Artificial Sequence
<220> FEATURE:
<223> OTHER INFORMATION: KlADHI promoter

<400> SEQUENCE: 68

```
ccagcttttc catttgcctt cgcgcttgcc tgtacggtcg ttaccatact tacctttctt      60

gcttcttctc aaaatggaat ccaggttttt agcttcgtgt ttcttttttt tttttaccat    120

ttttcaaatt tcagtcttcc attttcagct tcttgttttt tttttttttt tttttttca    180

tttcagtttt tacagcttcc agtctccctc tttccttcga tttccatctt cttgtttctg    240

tagccatctt cctatcacgt gcaagggaag aaagtggggg cccagcacct tcttttttgt    300

tctttggtgg gggctcgttt tagtttttac gtgcgtaatt gggaatcttc cgaggtagta    360

tgacatgtcc ggtggtgacc tgatactttc tgtttctccg agtaggacag aagaggaaaa    420

aaaaatagcg tgtgatgttc ttctattcta gtagtgtatt gatctattca caatcagatc    480

acaatcatat gagcagatga tgtattttgg gttgcttttc accaacccaa gtattcgatt    540

gatctttata tactgcggtt atttctaggt cttaaacggt taacacctgt tgcagggtgg    600

tatgtatttt tctcaaagtg tgctattttc acaccagcta gaaatcagct gtcttacttg    660

tatacaatta gaccagccat ttggtcttct ggaatatgta tataaacacc cggtcgattc    720

tgacaatcca tccacttttg tagtaggtct ctctatatcc atttgtacaa tgttgtttct    780

gttttgccct acatcatcat caagcaaaaa caatagtttc aattgaaaca taaacaagct    840

ttaaacacac aaactctata ctaaaaaaag ataaaaccgg tggcgcgccc ctaggggccg    900

gccacgcgtc catgggcggc cgcttaatta aggcctgttg ggccctcgag gtgaatttac    960

tttaaatctt gcatttaaat aaattttctt tttatagctt tatgacttag tttcaattta   1020

tatactattt taatgacatt ttcgattcat tgattgaaag ctttgtgttt tttcttgatg   1080

cgctattgca ttgttcttgt ctttttcgcc acatgtaata tctgtagtag atacctgata   1140

cattgtggat gctgagtgaa atttagtta ataatggagg cgctcttaat aattttgggg   1200

atattggctt tttttttaa agtttacaaa tgaatttttt ccgcca                    1246
```

<210> SEQ ID NO 69
<211> LENGTH: 2068
<212> TYPE: DNA
<213> ORGANISM: Artificial Sequence
<220> FEATURE:
<223> OTHER INFORMATION: ScADHI promoter

<400> SEQUENCE: 69

```
gtgtacaata tggacttcct cttttctggc aaccaaaccc atacatcggg attcctataa     60

taccttcgtt ggtctcccta acatgtaggt ggcggagggg agatatacaa tagaacagat    120
```

-continued

```
accagacaag acataatggg ctaaacaaga ctacaccaat tacactgcct cattgatggt    180
ggtacataac gaactaatac tgtagcccta gacttgatag ccatcatcat atcgaagttt    240
cactaccctt tttccatttg ccatctattg aagtaataat aggcgcatgc aacttctttt    300
cttttttttt cttttctctc tcccccgttg ttgtctcacc atatccgcaa tgacaaaaaa    360
atgatggaag acactaaagg aaaaaattaa cgacaaagac agcaccaaca gatgtcgttg    420
ttccagagct gatgaggggt atctcgaagc acacgaaact tttccttcc ttcattcacg    480
cacactactc tctaatgagc aacggtatac ggccttcctt ccagttactt gaatttgaaa    540
taaaaaaaag tttgctgtct tgctatcaag tataaataga cctgcaatta ttaatctttt    600
gtttcctcgt cattgttctc gttccctttc ttccttgttt ctttttctgc acaatatttc    660
aagctatacc aagcatacaa tcaagcaatt ccagatctaa aaaaaccggt ggcgcgcccc    720
taggggccgg ccacgcgtcc atgggcggcc gcttaattaa ggcctgttgg gccctcgagc    780
ccgggggggg ctcgatcccc tcgcgagttg gttcagctgc tgcctgaggc tggacgacct    840
cgcggagttc taccggcagt gcaaatccgt cggcatccag gaaaccagca gcggctatcc    900
gcgcatccat gcccccgaac tgcaggagtg gggaggcacg atggccgctt tggtcgatct    960
agattacgtg gaagaaaggt agtaaaagta gtagtataag tagtaaaaag aggtaaaaag   1020
agaaaaccgg ctacatacta gagaagcacg tacacaaaaa ctcataggca cttcatcata   1080
cgacagtttc ttgatgcatt ataatagtgt attagatatt ttcagaaata tgcatagaac   1140
ctcctcttgc ctttactttt tatacataga acattggcag atttacttac actactttgt   1200
ttctacgcca tttcttttgt tttcaacact tagacaagtt gttgagaacc ggactactaa   1260
aaagcaatgt tcccactgaa aatcatgtac ctgcagcata ataacccccct aattctgcat   1320
cgatccagta tgtttttttt tctctactca tttttacctg aagatagagc ttctaaaaca   1380
aaaaaaatca gtgattacat gcatattgtg tgttctagta accaaaggaa aggaacagat   1440
agataaaatt ccgagactgt caaattaggt tttttttcttt ttttttggcg ggagtcagtg   1500
ggccgaaata tgttcttggc ctagaactta atctggtttg atcatgccaa tacttgcctg   1560
agtgcccgac tttttgccca ccctcttgcc ttctgtcatc cttcaaaacc cacctgtttt   1620
ccagccgtat cttcgctcgc atctacacat actgtgccat atcttgtgtg tagccggacg   1680
tgactatgac caaaaacaaa caaggagaac tgttcgccga tttgtaacac tcctgcatcc   1740
atccaagtgg gtatgcgcta tgcaatgtta agctaggtca ggtcagacca ggtccaagga   1800
cagcaacttg actgtatgca acctttacca tctttgcaca gaacatactt gtagctagct   1860
agttacactt atggaccgaa aaggcacccc accatgtctg tccggcttta gagtacggcc   1920
gcagaccgct gatttgcctt gccaagcagt agtcacaatg catcgcatga gcacacgggc   1980
acgggcacgg gcacaggaac cattggcaaa aataccagat acactatacc gacgtatatc   2040
aagcccaagt ttaaaattcc taaatttc                                      2068
```

<210> SEQ ID NO 70
<211> LENGTH: 28
<212> TYPE: DNA
<213> ORGANISM: Artificial Sequence
<220> FEATURE:
<223> OTHER INFORMATION: KlPLac4-3 SalI-F

<400> SEQUENCE: 70

```
taggtcgacc cgcggggatc gactcata                                        28
```

<210> SEQ ID NO 71
<211> LENGTH: 92
<212> TYPE: DNA
<213> ORGANISM: Artificial Sequence
<220> FEATURE:
<223> OTHER INFORMATION: KlPLac4-3-R

<400> SEQUENCE: 71
aagcggccgc ccatggacgc gtggccggcc cctaggggcg cgccaccggt ctcgatgagt 60
atgtgtgttt attttttttt tattttttttt gc 92

<210> SEQ ID NO 72
<211> LENGTH: 93
<212> TYPE: DNA
<213> ORGANISM: Artificial Sequence
<220> FEATURE:
<223> OTHER INFORMATION: KlTTLac4-F

<400> SEQUENCE: 72
gccacgcgtc catgggcggc cgcttaatta aggcctgttg ggccctcgag atttatactt 60
agataagtat gtacttacag gtatatttct atg 93

<210> SEQ ID NO 73
<211> LENGTH: 46
<212> TYPE: DNA
<213> ORGANISM: Artificial Sequence
<220> FEATURE:
<223> OTHER INFORMATION: KlTTLac4-EcoRI-R

<400> SEQUENCE: 73
taggaattcc tactattaat tatttacgta ttctttgaaa tggcag 46

<210> SEQ ID NO 74
<211> LENGTH: 46
<212> TYPE: DNA
<213> ORGANISM: Artificial Sequence
<220> FEATURE:
<223> OTHER INFORMATION: ScPGapDH-SalI-F

<400> SEQUENCE: 74
taggtcgaca gtttatcatt atcaatactg ccatttcaaa gaatac 46

<210> SEQ ID NO 75
<211> LENGTH: 90
<212> TYPE: DNA
<213> ORGANISM: Artificial Sequence
<220> FEATURE:
<223> OTHER INFORMATION: ScPGapDH-R

<400> SEQUENCE: 75
aagcggccgc ccatggacgc gtggccggcc cctaggggcg cgccaccggt ttttttgttt 60
gtttatgtgt gtttattcga aactaagttc 90

<210> SEQ ID NO 76
<211> LENGTH: 104
<212> TYPE: DNA
<213> ORGANISM: Artificial Sequence
<220> FEATURE:
<223> OTHER INFORMATION: ScTTGap-F

<400> SEQUENCE: 76
gccacgcgtc catgggcggc cgcttaatta aggcctgttg ggccctcgag gtgaatttac 60
tttaaatctt gcatttaaat aaattttctt tttatagctt tatg 104

<210> SEQ ID NO 77
<211> LENGTH: 30
<212> TYPE: DNA
<213> ORGANISM: Artificial Sequence
<220> FEATURE:
<223> OTHER INFORMATION: ScTTGap-EcoRI-R

<400> SEQUENCE: 77
taggaattcg gactccagct tttccatttg 30

<210> SEQ ID NO 78
<211> LENGTH: 35
<212> TYPE: DNA
<213> ORGANISM: Artificial Sequence
<220> FEATURE:
<223> OTHER INFORMATION: ScPADHI-SalI-F

<400> SEQUENCE: 78
taggtcgacg tgtacaatat ggacttcctc ttttc 35

<210> SEQ ID NO 79
<211> LENGTH: 82
<212> TYPE: DNA
<213> ORGANISM: Artificial Sequence
<220> FEATURE:
<223> OTHER INFORMATION: ScPADHI -R

<400> SEQUENCE: 79
aagcggccgc ccatggacgc gtggccggcc cctaggggcg cgccaccggt ttttttagat 60
ctggaattgc ttgattgtat gc 82

<210> SEQ ID NO 80
<211> LENGTH: 75
<212> TYPE: DNA
<213> ORGANISM: Artificial Sequence
<220> FEATURE:
<223> OTHER INFORMATION: ScTTADHI_KlPLac4 -5 End-F

<400> SEQUENCE: 80
gccacgcgtc catgggcggc cgcttaatta aggcctgttg ggccctcgag cccggggggg 60
gctcgatccc ctcgc 75

<210> SEQ ID NO 81
<211> LENGTH: 44
<212> TYPE: DNA
<213> ORGANISM: Artificial Sequence
<220> FEATURE:
<223> OTHER INFORMATION: ScTTADHI_KlPLac4-5 End_EcoRI-R

<400> SEQUENCE: 81
taggaattcg aaatttagga attttaaact tgggcttgat atac 44

<210> SEQ ID NO 82
<211> LENGTH: 44
<212> TYPE: DNA
<213> ORGANISM: Artificial Sequence
<220> FEATURE:
<223> OTHER INFORMATION: ScPGK-SalI-F

<400> SEQUENCE: 82
taggtcgaca ctgtaattgc ttttagttgt gtatttttag tgtg 44

<210> SEQ ID NO 83
<211> LENGTH: 100

<212> TYPE: DNA
<213> ORGANISM: Artificial Sequence
<220> FEATURE:
<223> OTHER INFORMATION: ScPGK-R

<400> SEQUENCE: 83
aagcggccgc ccatggacgc gtggccggcc cctaggggcg cgccaccggt ttttttgtt 60 ttatatttgt tgtaaaaagt agataattac ttccttgatg 100

<210> SEQ ID NO 84
<211> LENGTH: 94
<212> TYPE: DNA
<213> ORGANISM: Artificial Sequence
<220> FEATURE:
<223> OTHER INFORMATION: ScTTPGK-F

<400> SEQUENCE: 84
gccacgcgtc catgggcggc cgcttaatta aggcctgttg ggccctcgag attgaattga 60
attgaaatcg atagatcaat ttttttcttt tctc 94

<210> SEQ ID NO 85
<211> LENGTH: 46
<212> TYPE: DNA
<213> ORGANISM: Artificial Sequence
<220> FEATURE:
<223> OTHER INFORMATION: ScTTPGK-EcoRI-R

<400> SEQUENCE: 85
taggaattcc atataccttt gataccataa aaacaagcaa atattc 46

<210> SEQ ID NO 86
<211> LENGTH: 30
<212> TYPE: DNA
<213> ORGANISM: Artificial Sequence
<220> FEATURE:
<223> OTHER INFORMATION: KlPGapDH-SalI-F

<400> SEQUENCE: 86
taggtcgaca gtatggtaac gaccgtacag 30

<210> SEQ ID NO 87
<211> LENGTH: 88
<212> TYPE: DNA
<213> ORGANISM: Artificial Sequence
<220> FEATURE:
<223> OTHER INFORMATION: KlPGapDH-R

<400> SEQUENCE: 87
aagcggccgc ccatggacgc gtggccggcc cctaggggcg cgccaccggt tgtgtaatat 60
tctttttttt tacttgaaac tgtgaagc 88

<210> SEQ ID NO 88
<211> LENGTH: 104
<212> TYPE: DNA
<213> ORGANISM: Artificial Sequence
<220> FEATURE:
<223> OTHER INFORMATION: ScTTGap-F

<400> SEQUENCE: 88
gccacgcgtc catgggcggc cgcttaatta aggcctgttg ggccctcgag gtgaatttac 60
tttaaatctt gcatttaaat aaattttctt tttatagctt tatg 104

<210> SEQ ID NO 89

<211> LENGTH: 49
<212> TYPE: DNA
<213> ORGANISM: Artificial Sequence
<220> FEATURE:
<223> OTHER INFORMATION: ScTTGap-EcoRI-R

<400> SEQUENCE: 89
taggaattct ggcggaaaaa attcatttgt aaactttaaa aaaaaaagc 49

<210> SEQ ID NO 90
<211> LENGTH: 36
<212> TYPE: DNA
<213> ORGANISM: Artificial Sequence
<220> FEATURE:
<223> OTHER INFORMATION: KlPGK-SalI-F

<400> SEQUENCE: 90
taggtcgacc gggtgtgttt gaagtaagaa tatttg 36

<210> SEQ ID NO 91
<211> LENGTH: 98
<212> TYPE: DNA
<213> ORGANISM: Artificial Sequence
<220> FEATURE:
<223> OTHER INFORMATION: KlPGK -R

<400> SEQUENCE: 91
aagcggccgc ccatggacgc gtggccggcc cctaggggcg cgccaccggt ttttttatta 60
attcttgatc gatttttttg ttatttctga agtaactc 98

<210> SEQ ID NO 92
<211> LENGTH: 94
<212> TYPE: DNA
<213> ORGANISM: Artificial Sequence
<220> FEATURE:
<223> OTHER INFORMATION: ScTTPGK -F

<400> SEQUENCE: 92
gccacgcgtc catgggcggc cgcttaatta aggcctgttg ggccctcgag attgaattga 60
attgaaatcg atagatcaat ttttttcttt tctc 94

<210> SEQ ID NO 93
<211> LENGTH: 36
<212> TYPE: DNA
<213> ORGANISM: Artificial Sequence
<220> FEATURE:
<223> OTHER INFORMATION: ScTTPGK-EcoRI-R

<400> SEQUENCE: 93
taggaattca agctttttcg aaacgcagaa ttttcg 36

<210> SEQ ID NO 94
<211> LENGTH: 30
<212> TYPE: DNA
<213> ORGANISM: Artificial Sequence
<220> FEATURE:
<223> OTHER INFORMATION: KlPADHI-SalI-F

<400> SEQUENCE: 94
taggtcgacc cagcttttcc atttgccttc 30

<210> SEQ ID NO 95
<211> LENGTH: 91
<212> TYPE: DNA
<213> ORGANISM: Artificial Sequence
<220> FEATURE:
<223> OTHER INFORMATION: KlPADHI -R

<400> SEQUENCE: 95
aagcggccgc ccatggacgc gtggccggcc cctaggggcg cgccaccggt tttatctttt 60
tttagtatag agtttgtgtg tttaaagctt g 91

<210> SEQ ID NO 96
<211> LENGTH: 104
<212> TYPE: DNA
<213> ORGANISM: Artificial Sequence
<220> FEATURE:
<223> OTHER INFORMATION: ScTTGap-F

<400> SEQUENCE: 96
gccacgcgtc catgggcggc cgcttaatta aggcctgttg ggccctcgag gtgaatttac 60
tttaaatctt gcatttaaat aaattttctt tttatagctt tatg 104

<210> SEQ ID NO 97
<211> LENGTH: 28
<212> TYPE: DNA
<213> ORGANISM: Artificial Sequence
<220> FEATURE:
<223> OTHER INFORMATION: ScTTGap-EcoRI-R

<400> SEQUENCE: 97
taggaattcg gaatcccgat gtatgggt 28

<210> SEQ ID NO 98
<211> LENGTH: 26
<212> TYPE: DNA
<213> ORGANISM: Artificial Sequence
<220> FEATURE:
<223> OTHER INFORMATION: Forward Primer-kan gene-AgeI

<400> SEQUENCE: 98
accggtatgg gtaaggaaaa gactca 26

<210> SEQ ID NO 99
<211> LENGTH: 26
<212> TYPE: DNA
<213> ORGANISM: Artificial Sequence
<220> FEATURE:
<223> OTHER INFORMATION: Reverse Primer-kan gene-NcoI

<400> SEQUENCE: 99
ccatggttag aaaaactcat cgagca 26

<210> SEQ ID NO 100
<211> LENGTH: 61
<212> TYPE: PRT
<213> ORGANISM: Artificial Sequence
<220> FEATURE:
<223> OTHER INFORMATION: catalytic domain 1
<220> FEATURE:
<221> NAME/KEY: VARIANT
<222> LOCATION: 2,3,4,5,6,7,8,10,11,12,13,15,18,21,24,25,30,33,37,38,41,
42,43,44,47,54,57
<223> OTHER INFORMATION: Xaa is any amino acid

<400> SEQUENCE: 100

His Xaa Xaa Xaa Xaa Xaa Xaa Xaa Pro Xaa Xaa Xaa Xaa Ala Xaa Thr
1 5 10 15

Leu Xaa Leu Val Xaa Gly Gly Xaa Xaa Gly Met Glu Met Xaa Ala Arg
20 25 30

-continued

```
Xaa Ala His Lys Xaa Xaa Trp His Xaa Xaa Xaa Xaa Gly Trp Xaa Leu
        35                  40                  45

His Lys Ser His His Xaa Pro Arg Xaa Gly Pro Phe Glu
    50                  55                  60


<210> SEQ ID NO 101
<211> LENGTH: 76
<212> TYPE: PRT
<213> ORGANISM: Artificial Sequence
<220> FEATURE:
<223> OTHER INFORMATION: catalytic domain 2
<220> FEATURE:
<221> NAME/KEY: VARIANT
<222> LOCATION: 3,4,7,8,11,12,14,15,16,18,19,30,32,33,37,44,48,53,54,56,
      60,61,62,65,66,69,70,72,75
<223> OTHER INFORMATION: Xaa is any amino acid

<400> SEQUENCE: 101

Pro Ala Xaa Xaa Leu Cys Xaa Xaa Gly Phe Xaa Xaa Pro Xaa Xaa Xaa
1               5                   10                  15

Gly Xaa Xaa Cys Phe Gly Ala Gly Leu Gly Ile Thr Leu Xaa Gly Xaa
            20                  25                  30

Xaa Tyr Met Phe Xaa His Asp Gly Leu Val His Xaa Arg Phe Pro Xaa
        35                  40                  45

Gly Pro Ile Ala Xaa Xaa Pro Xaa Met Lys Arg Xaa Xaa Xaa Ala His
    50                  55                  60

Xaa Xaa His His Xaa Xaa Lys Xaa Gly Gly Xaa Pro
65                  70                  75


<210> SEQ ID NO 102
<211> LENGTH: 61
<212> TYPE: PRT
<213> ORGANISM: Artificial Sequence
<220> FEATURE:
<223> OTHER INFORMATION: catalytic domain 1-Chlamydomonas reinhardtii

<400> SEQUENCE: 102

His Phe Ala Glu Asp Gly Asp Leu Pro Val Asp Glu Met Ala Ala Thr
1               5                   10                  15

Leu Leu Leu Val Phe Gly Gly Met Phe Gly Met Glu Met Tyr Ala Arg
            20                  25                  30

Phe Ala His Lys Val Leu Trp His Asp Phe Glu Pro Gly Trp Ala Leu
        35                  40                  45

His Lys Ser His His Glu Pro Arg Thr Gly Pro Phe Glu
    50                  55                  60


<210> SEQ ID NO 103
<211> LENGTH: 61
<212> TYPE: PRT
<213> ORGANISM: Artificial Sequence
<220> FEATURE:
<223> OTHER INFORMATION: catalytic domain 1-Chromochloris zofingiensis

<400> SEQUENCE: 103

His Met Pro Ser Glu Ser Pro Phe Pro Trp Leu Asp Met Ala Gly Thr
1               5                   10                  15

Leu Ala Leu Val Ile Gly Gly Val Phe Gly Met Glu Met Trp Ala Arg
            20                  25                  30

Tyr Ala His Lys Ala Leu Trp His Asp Phe Gln Pro Gly Trp Ala Leu
        35                  40                  45

His Lys Ser His His Glu Pro Arg Ile Gly Pro Phe Glu
```

50 55 60

<210> SEQ ID NO 104
<211> LENGTH: 61
<212> TYPE: PRT
<213> ORGANISM: Artificial Sequence
<220> FEATURE:
<223> OTHER INFORMATION: catalytic domain 1-Haematococcus pluvialis

<400> SEQUENCE: 104

His Met Thr Val Gly Gly Ala Val Pro Trp Gly Glu Val Ala Gly Thr
1 5 10 15

Leu Leu Leu Val Val Gly Gly Ala Leu Gly Met Glu Met Tyr Ala Arg
20 25 30

Tyr Ala His Lys Ala Ile Trp His Glu Ser Pro Leu Gly Trp Leu Leu
35 40 45

His Lys Ser His His Thr Pro Arg Thr Gly Pro Phe Glu
50 55 60

<210> SEQ ID NO 105
<211> LENGTH: 76
<212> TYPE: PRT
<213> ORGANISM: Artificial Sequence
<220> FEATURE:
<223> OTHER INFORMATION: catalytic domain 2-Chlamydomonas reinhardtii

<400> SEQUENCE: 105

Pro Ala Met Ala Leu Cys Ala Tyr Gly Phe Phe Thr Pro His Val Ile
1 5 10 15

Gly Gly Val Cys Phe Gly Ala Gly Leu Gly Ile Thr Leu Phe Gly Ile
20 25 30

Ala Tyr Met Phe Phe His Asp Gly Leu Val His Arg Arg Phe Pro Val
35 40 45

Gly Pro Ile Ala Asn Leu Pro Tyr Met Lys Arg Ile Met Val Ala His
50 55 60

Gln Ile His His Thr Asn Lys Phe Gly Gly Val Pro
65 70 75

<210> SEQ ID NO 106
<211> LENGTH: 76
<212> TYPE: PRT
<213> ORGANISM: Artificial Sequence
<220> FEATURE:
<223> OTHER INFORMATION: catalytic domain 2-Chromochloris zofingiensis

<400> SEQUENCE: 106

Pro Ala Phe Ser Leu Cys Leu Tyr Gly Phe Leu Thr Pro Asn Leu Val
1 5 10 15

Gly Ser Leu Cys Phe Gly Ala Gly Leu Gly Ile Thr Leu Phe Gly Ile
20 25 30

Met Tyr Met Phe Ile His Asp Gly Leu Val His Lys Arg Phe Pro Val
35 40 45

Gly Pro Ile Ala Gln Met Pro Ala Met Lys Arg Val Ala Ile Ala His
50 55 60

Lys Leu His His Ser Glu Lys Tyr Gly Gly Val Pro
65 70 75

<210> SEQ ID NO 107
<211> LENGTH: 76
<212> TYPE: PRT
<213> ORGANISM: Artificial Sequence

```
<220> FEATURE:
<223> OTHER INFORMATION: catalytic domain 2-Haematococcus pluvialis

<400> SEQUENCE: 107

Pro Ala Met Leu Leu Cys Thr Phe Gly Phe Trp Leu Pro Asn Val Leu
1               5                   10                  15

Gly Ala Ala Cys Phe Gly Ala Gly Leu Gly Ile Thr Leu Tyr Gly Met
            20                  25                  30

Ala Tyr Met Phe Val His Asp Gly Leu Val His Arg Arg Phe Pro Thr
        35                  40                  45

Gly Pro Ile Ala Gly Leu Pro Tyr Met Lys Arg Leu Thr Val Ala His
    50                  55                  60

Gln Leu His His Ser Gly Lys Tyr Gly Gly Ala Pro
65                  70                  75


<210> SEQ ID NO 108
<211> LENGTH: 497
<212> TYPE: PRT
<213> ORGANISM: Artificial Sequence
<220> FEATURE:
<223> OTHER INFORMATION: CAB51949

<400> SEQUENCE: 108

Pro Ser Pro Asp Pro Leu Val Thr Asp His Tyr Phe Tyr Met Arg Ala
1               5                   10                  15

Leu Ser Leu Leu Ile Thr Pro Pro Thr Met Leu Leu Ala Ala Leu Ser
            20                  25                  30

Gly Glu Tyr Ala Phe Asp Trp Lys Ser Gly Arg Ala Lys Ser Thr Ile
        35                  40                  45

Ala Ala Ile Met Ile Pro Thr Val Tyr Leu Ile Trp Val Asp Tyr Val
    50                  55                  60

Ala Val Gly Gln Asp Ser Trp Ser Ile Asn Asp Glu Lys Ile Val Gly
65                  70                  75                  80

Trp Arg Leu Gly Gly Val Leu Pro Ile Glu Glu Ala Met Phe Phe Leu
                85                  90                  95

Leu Thr Asn Leu Met Ile Val Leu Gly Leu Ser Ala Cys Asp His Thr
            100                 105                 110

Gln Ala Leu Tyr Leu Leu His Gly Arg Thr Ile Tyr Gly Asn Lys Lys
        115                 120                 125

Met Pro Ser Ser Phe Pro Leu Ile Thr Pro Pro Val Leu Ser Leu Phe
    130                 135                 140

Phe Ser Ser Arg Pro Tyr Ser Ser Gln Pro Lys Arg Asp Leu Glu Leu
145                 150                 155                 160

Ala Val Lys Leu Leu Glu Lys Lys Ser Arg Ser Phe Phe Val Ala Ser
                165                 170                 175

Ala Gly Phe Pro Ser Glu Val Arg Glu Arg Leu Val Gly Leu Tyr Ala
            180                 185                 190

Phe Cys Arg Val Thr Asp Asp Leu Ile Asp Ser Pro Glu Val Ser Ser
        195                 200                 205

Asn Pro His Ala Thr Ile Asp Met Val Ser Asp Phe Leu Thr Leu Leu
    210                 215                 220

Phe Gly Pro Pro Leu His Pro Ser Gln Pro Asp Lys Ile Leu Ser Ser
225                 230                 235                 240

Pro Leu Leu Pro Pro Ser His Pro Ser Arg Pro Thr Gly Met Tyr Pro
                245                 250                 255

Leu Pro Pro Pro Pro Ser Leu Ser Pro Ala Glu Leu Val Gln Phe Leu
```

```
                       260                 265                 270
Thr Glu Arg Val Pro Val Gln Tyr His Phe Ala Phe Arg Leu Leu Ala
            275                 280                 285
Lys Leu Gln Gly Leu Ile Pro Arg Tyr Pro Leu Asp Glu Leu Leu Arg
            290                 295                 300
Gly Tyr Thr Thr Asp Leu Ile Phe Pro Leu Ser Thr Glu Ala Val Gln
305                 310                 315                 320
Ala Arg Lys Thr Pro Ile Glu Thr Thr Ala Asp Leu Leu Asp Tyr Gly
            325                 330                 335
Leu Cys Val Ala Gly Ser Val Ala Glu Leu Leu Val Tyr Val Ser Trp
            340                 345                 350
Ala Ser Ala Pro Ser Gln Val Pro Ala Thr Ile Glu Glu Arg Glu Ala
            355                 360                 365
Val Leu Val Ala Ser Arg Glu Met Gly Thr Ala Leu Gln Leu Val Asn
            370                 375                 380
Ile Ala Arg Asp Ile Lys Gly Asp Ala Thr Glu Gly Arg Phe Tyr Leu
385                 390                 395                 400
Pro Leu Ser Phe Phe Gly Leu Arg Asp Glu Ser Lys Leu Ala Ile Pro
            405                 410                 415
Thr Asp Trp Thr Glu Pro Arg Pro Gln Asp Phe Asp Lys Leu Leu Ser
            420                 425                 430
Leu Ser Pro Ser Ser Thr Leu Pro Ser Ser Asn Ala Ser Glu Ser Phe
            435                 440                 445
Arg Phe Glu Trp Lys Thr Tyr Ser Leu Pro Leu Val Ala Tyr Ala Glu
            450                 455                 460
Asp Leu Ala Lys His Ser Tyr Lys Gly Ile Asp Arg Leu Pro Thr Glu
465                 470                 475                 480
Val Gln Ala Gly Met Arg Ala Ala Cys Ala Ser Tyr Leu Leu Ile Gly
            485                 490                 495
Arg

<210> SEQ ID NO 109
<211> LENGTH: 304
<212> TYPE: PRT
<213> ORGANISM: Artificial Sequence
<220> FEATURE:
<223> OTHER INFORMATION: AAO53257

<400> SEQUENCE: 109

Met Gly Lys Glu Gln Asp Gln Asp Lys Pro Thr Ala Ile Ile Val Gly
1               5                   10                  15
Cys Gly Ile Gly Gly Ile Ala Thr Ala Ala Arg Leu Ala Lys Glu Gly
            20                  25                  30
Phe Gln Val Thr Val Phe Glu Lys Asn Asp Tyr Ser Gly Gly Arg Cys
        35                  40                  45
Ser Leu Ile Glu Arg Asp Gly Tyr Arg Phe Asp Gln Gly Pro Ser Leu
    50                  55                  60
Leu Leu Leu Pro Asp Leu Phe Lys Gln Thr Phe Glu Asp Leu Gly Glu
65                  70                  75                  80
Lys Met Glu Asp Trp Val Asp Leu Ile Lys Cys Glu Pro Asn Tyr Val
                85                  90                  95
Cys His Phe His Asp Glu Glu Thr Phe Thr Leu Ser Thr Asp Met Ala
            100                 105                 110
Leu Leu Lys Arg Glu Val Glu Arg Phe Glu Gly Lys Asp Gly Phe Asp
        115                 120                 125
```

Arg Phe Leu Ser Phe Ile Gln Glu Ala His Arg His Tyr Glu Leu Ala
    130                 135                 140

Val Val His Val Leu Gln Lys Asn Phe Pro Gly Phe Ala Ala Phe Leu
145                 150                 155                 160

Arg Leu Gln Phe Ile Gly Gln Ile Leu Ala Leu His Pro Phe Glu Ser
                165                 170                 175

Ile Trp Thr Arg Val Cys Arg Tyr Phe Lys Thr Asp Arg Leu Arg Arg
            180                 185                 190

Val Phe Ser Phe Ala Val Met Tyr Met Gly Gln Ser Pro Tyr Ser Ala
        195                 200                 205

Pro Gly Thr Tyr Ser Leu Leu Gln Tyr Thr Glu Leu Thr Glu Gly Ile
    210                 215                 220

Trp Tyr Pro Arg Gly Gly Phe Trp Gln Val Pro Asn Thr Leu Leu Gln
225                 230                 235                 240

Ile Val Lys Arg Asn Asn Pro Ser Ala Lys Phe Asn Phe Asn Ala Pro
                245                 250                 255

Val Ser Gln Val Leu Leu Ser Pro Ala Lys Asp Arg Ala Thr Gly Val
            260                 265                 270

Arg Leu Glu Ser Gly Glu Glu His His Ala Asp Val Val Ile Val Asn
        275                 280                 285

Ala Asp Leu Val Tyr Ala Ser Glu His Leu Ile Pro Asp Asp Ala Arg
    290                 295                 300

<210> SEQ ID NO 110
<211> LENGTH: 314
<212> TYPE: PRT
<213> ORGANISM: Artificial Sequence
<220> FEATURE:
<223> OTHER INFORMATION: XP-001698699

<400> SEQUENCE: 110

Ser Asp Leu Gly Gly Ile Ala Val Ala Val Thr Val Ile Ala Leu Trp
1               5                   10                  15

Ala Thr Leu Phe Val Tyr Gly Leu Trp Phe Val Lys Leu Pro Trp Ala
            20                  25                  30

Leu Lys Val Gly Glu Thr Ala Thr Ser Trp Ala Thr Ile Ala Ala Val
        35                  40                  45

Phe Phe Ser Leu Glu Phe Leu Tyr Thr Gly Leu Phe Ile Thr Thr His
    50                  55                  60

Asp Ala Met His Gly Thr Ile Ala Leu Arg Asn Arg Arg Leu Asn Asp
65                  70                  75                  80

Phe Leu Gly Gln Leu Ala Ile Ser Leu Tyr Ala Trp Phe Asp Tyr Ser
                85                  90                  95

Val Leu His Arg Lys His Trp Glu His His Asn His Thr Gly Glu Pro
            100                 105                 110

Arg Val Asp Pro Asp Phe His Arg Gly Asn Pro Asn Leu Ala Val Trp
        115                 120                 125

Phe Ala Gln Phe Met Val Ser Tyr Met Thr Leu Ser Gln Phe Leu Lys
    130                 135                 140

Ile Ala Val Trp Ser Asn Leu Leu Leu Leu Ala Gly Ala Pro Leu Ala
145                 150                 155                 160

Asn Gln Leu Leu Phe Met Thr Ala Ala Pro Ile Leu Ser Ala Phe Arg
                165                 170                 175

Leu Phe Tyr Tyr Gly Thr Tyr Val Pro His His Pro Glu Lys Gly His
            180                 185                 190

-continued

```
Thr Gly Ala Met Pro Trp Gln Val Ser Arg Thr Ser Ser Ala Ser Arg
        195                 200                 205

Leu Gln Ser Phe Leu Thr Cys Tyr His Phe Asp Leu His Trp Glu His
    210                 215                 220

His Arg Trp Pro Tyr Ala Pro Trp Trp Glu Leu Pro Lys Cys Arg Gln
225                 230                 235                 240

Ile Ala Arg Gly Ala Ala Leu Ala Pro Gly Pro Leu Pro Val Pro Ala
                245                 250                 255

Ala Ala Ala Ala Thr Ala Ala Thr Ala Ala Ala Ala Ala Ala Ala Thr
            260                 265                 270

Gly Ser Pro Ala Pro Ala Ser Arg Ala Gly Ser Ala Ser Ser Ala Ser
        275                 280                 285

Ala Ala Ala Ser Gly Phe Gly Ser Gly His Ser Gly Ser Val Ala Ala
    290                 295                 300

Gln Pro Leu Ser Ser Leu Pro Leu Leu Ser
305                 310
```